US007994094B2

(12) United States Patent
Endo et al.

(10) Patent No.: US 7,994,094 B2
(45) Date of Patent: Aug. 9, 2011

(54) N-PYRIDYLPIPERIDINE COMPOUND, METHOD FOR PRODUCING THE SAME, AND PEST CONTROL AGENT

(75) Inventors: Yasuhiro Endo, Naruto (JP); Go Uenaka, Naruto (JP); Yuichi Shirai, Naruto (JP)

(73) Assignee: Otsuka Agritechno Co., Ltd., Tokyo (JP)

( * ) Notice: Subject to any disclaimer, the term of this patent is extended or adjusted under 35 U.S.C. 154(b) by 353 days.

(21) Appl. No.: 12/377,338

(22) PCT Filed: Aug. 29, 2007

(86) PCT No.: PCT/JP2007/066807

§ 371 (c)(1),
(2), (4) Date: Feb. 12, 2009

(87) PCT Pub. No.: WO2008/026658

PCT Pub. Date: Mar. 6, 2008

(65) Prior Publication Data

US 2010/0137582 A1 Jun. 3, 2010

(30) Foreign Application Priority Data

Sep. 1, 2006 (JP) ................................ 2006-237557
Apr. 6, 2007 (JP) ................................ 2007-100825

(51) Int. Cl.
*A01N 43/40* (2006.01)
*C07D 223/00* (2006.01)
*C07D 211/46* (2006.01)

(52) U.S. Cl. ......... 504/219; 504/248; 540/584; 546/193

(58) Field of Classification Search ........................ None
See application file for complete search history.

(56) References Cited

U.S. PATENT DOCUMENTS 4,742,060 A 5/1988 Shiokawa
4,845,106 A 7/1989 Shiokawa
5,001,138 A 3/1991 Shiokawa
5,204,360 A 4/1993 Shiokawa
5,298,507 A 3/1994 Shiokawa
5,428,032 A 6/1995 Shiokawa
5,461,167 A 10/1995 Shiokawa
5,569,664 A 10/1996 Silverman
5,580,889 A 12/1996 Shiokawa
5,750,704 A 5/1998 Shiokawa
6,022,967 A 2/2000 Shiokawa
6,297,374 B1 10/2001 Shiokawa

FOREIGN PATENT DOCUMENTS

EP 1 731 518 A1 12/2006
JP 61-183271 8/1986
JP 6-100560 4/1994
JP 2000-86636 3/2000
JP 2001-302662 A1 10/2001
JP 2004-331541 A1 11/2004
WO WO 96/37484 A1 11/1996
WO WO 2005/095380 A1 10/2005

OTHER PUBLICATIONS

Richard H. Wiley, Paul Wiley "The Chemistry of Heterocyclic Compounds vol. 20 Pyrazolones, Pyrazolidones and Derivatives" Interscience Publishers, London, UK, 1964 (see p. 43 of specification).

Garner, G.V. et al. "Syntheses of Heterocyclic Compounds. Part XXIV. Cyclisation Studies with *ortho*-Substituted Arylcarbene and Arylnitrene Precursors" J. Chem. Soc., C., 1971, pp. 3693-3701 (see p. 44 of specification).

Dai-Yuki-Kagaku (Comprehensive Organic Chemistry); Heterocyclic Compounds II; 6th Edition; vol. 15; 1965; pp. 258-317 (30 Sheets.)/p. 43 of specification.

E. Taylor, et al.; A Convenient Synthesis of 1-Aryl-4-piperidones; Synthesis; vol. 606; Aug. 1981; pp. 606-608 (3 Sheets.)/p. 44 of specification.

International Search Report for International Application No. PCT/JP2007/066807 dated Oct. 31, 2007.

*Primary Examiner* — Rebecca Anderson
*Assistant Examiner* — Alicia L Otton
(74) *Attorney, Agent, or Firm* — Kratz, Quintos & Hanson, LLP

(57) ABSTRACT

The N-pyridylpiperidine compound of the invention is represented by Formula (1)

(1)

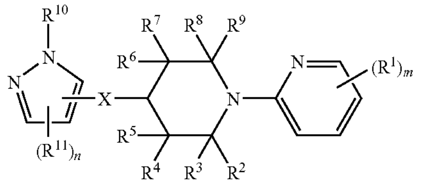

wherein $R^1$ is a halogen atom, a $C_{1-4}$ haloalkyl group, a cyano group, a nitro group, or $C_{1-4}$ alkoxycarbonyl group; $R^2$, $R^3$, $R^4$, $R^5$, $R^6$, $R^7$, $R^8$, and $R^9$ are each independently a hydrogen atom or a $C_{1-4}$ alkyl group; $R^{10}$ is a hydrogen atom, etc.; $R^{11}$ is a halogen atom, etc.; X is an oxygen atom or a sulfur atom, m is an integer of 1 to 4; and n is an integer of 1 or 2. The N-pyridylpiperidine compound of the invention has an excellent miticidal activity against spider mites and rust mites.

21 Claims, No Drawings

N-PYRIDYLPIPERIDINE COMPOUND, METHOD FOR PRODUCING THE SAME, AND PEST CONTROL AGENT

TECHNICAL FIELD

The present invention relates to an N-pyridylpiperidine compound, a method for producing the same, and a pest control agent using the same.

BACKGROUND ART

Various compounds are known in which the nitrogen atom of piperidine is substituted with a pyridyl group. Among them, compounds having a phenoxy group at the 4-position of the piperidine ring are known to have a miticidal activity (see Patent Document 1).

The compound described in Patent Document 1 exhibits an excellent miticidal effect on spider mites, but does not have a sufficient effect on rust mites (see Comparative Test 1 described below).

Generally, mites are very likely to develop resistance to chemicals. In fact, many commercially available miticides have become ineffective. In recent years, mites, particularly rust mites, have caused serious damage. However, only a few kinds of chemicals are currently known to be effective against rust mites; moreover, some of these chemicals have become ineffective due to rust mites developing resistances to them. In such circumstances, there is an urgent demand for the development of a novel chemical that exhibits an excellent miticidal activity against rust mites and spider mites.

Patent Document 1: WO2005/095380

DISCLOSURE OF THE INVENTION

Problem to be Solved by the Invention

An object of the present invention is to provide a novel chemical that exhibits an excellent miticidal activity against rust mites as well as against spider mites.

Means for Solving the Problem

The present inventor conducted extensive research to achieve the above object, and found that a piperidine compound having a pyrazole ring on the 4-position of the piperidine ring via an oxygen atom, a sulfur atom, or $SO_2$ exhibits an excellent miticidal activity against rust mites and spider mites. The present invention has been accomplished based on this finding.

The present invention provides an N-pyridylpiperidine compound, a process for producing the same, and a pest control agent using the same, as summarized below in Items 1 to 23.

Item 1. An N-pyridylpiperidine compound, an N-oxide thereof, or salts of these compounds, the N-pyridylpiperidine compound being represented by Formula (1)

(1)

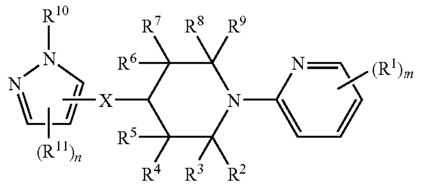

(wherein $R^1$ is a halogen atom, a $C_{1-4}$ haloalkyl group, a cyano group, a nitro group, or a $C_{1-4}$ alkoxycarbonyl group;

$R^2$, $R^3$, $R^4$, $R^5$, $R^6$, $R^7$, $R^8$, and $R^9$ are each independently a hydrogen atom or a $C_{1-4}$ alkyl group;

each pair of $R^2$ and $R^8$, and $R^4$ and $R^6$ may join to form a $C_{1-4}$ alkylene group;

$R^{10}$ is a hydrogen atom; a $C_{1-20}$ alkyl group; a $C_{3-8}$ cycloalkyl group; a $C_{2-6}$ alkenyl group; a $C_{2-6}$ alkynyl group; a $C_{1-6}$ haloalkyl group; a $C_{2-6}$ haloalkenyl group; a $C_{1-6}$ alkylcarbonyl group; a $C_{1-6}$ alkoxycarbonyl group; a benzoyl group (optionally substituted on the phenyl group with one to five halogen atoms); a phenyl group (optionally substituted on the phenyl ring with one or more substituents each independently selected from the group consisting of halogen, $C_{1-4}$ alkyl, and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group optionally substituted with one or more substituents each independently selected from the group consisting of optionally halogen-substituted $C_{3-8}$ cycloalkyl, cyano, nitro, formyl, $C_{1-6}$ alkoxy, haloalkoxy, benzyloxy, phenoxy, —CON($R^{12}$)($R^{13}$) (in which $R^{12}$ and $R^{13}$ are each independently a $C_{1-4}$ alkyl group, or $R^{12}$ and $R^{13}$ may join to form a $C_{2-7}$ alkylene group), phenyl (optionally substituted on the phenyl ring with one or more halogen atoms), and heterocyclic groups (optionally substituted on the heterocyclic ring with one or more $C_{1-4}$ alkyl groups);

$R^{11}$ is a halogen atom, a $C_{1-6}$ alkyl group, a $C_{1-4}$ haloalkyl group, a $C_{1-4}$ hydroxyalkyl group, a $C_{1-4}$ alkoxycarbonyl group, a $C_{1-4}$ alkylcarbonyl group, a mono or di($C_{1-4}$ alkyl) aminocarbonyl group, a nitro group, a cyano group, a formyl group, —C($R^{14}$)═NO($R^{15}$) (in which $R^{14}$ is a hydrogen atom or a $C_{1-4}$ alkyl group, and $R^{15}$ is a hydrogen atom, a $C_{1-4}$ alkyl group, or a benzyl group), a phenyl group (optionally substituted on the phenyl ring with one or more substituents each independently selected from the group consisting of halogen, $C_{1-6}$ alkyl, $C_{1-4}$ haloalkyl, $C_{1-6}$ alkoxy, $C_{1-4}$ haloalkoxy, alkylthio, cyano, and nitro), or a heterocyclic group (optionally substituted on the heterocyclic ring with one or more substituents each independently selected from the group consisting of halogen, $C_{1-4}$ alkyl, and $C_{1-4}$ haloalkyl);

X is an oxygen atom, a sulfur atom, or —$SO_2$—;

m is an integer of 1 to 4, and when m is an integer of 2 or more, the $R^1$'s may be the same or different; and n is an integer of 1 or 2, and when n is 2, the two $R^{11}$'s may be the same or different).

Item 2. An N-pyridylpiperidine compound, an N-oxide thereof, or salts of these compounds according to item 1, wherein the N-pyridylpiperidine compound is represented by Formula (1) in which $R^1$ is a halogen atom, a $C_{1-4}$ haloalkyl group, a cyano group, or a nitro group.

Item 3. An N-pyridylpiperidine compound, an N-oxide thereof, or salts of these compounds according to item 1 or 2, wherein the N-pyridylpiperidine compound is represented by Formula (1) in which $R^{10}$ is a hydrogen atom; a $C_{1-20}$ alkyl group; a $C_{2-6}$ alkenyl group; a $C_{1-6}$ haloalkyl group; a $C_{1-6}$ alkylcarbonyl group; a $C_{1-6}$ alkoxycarbonyl group; a benzoyl group (optionally substituted on the phenyl group with one to five halogen atoms); a phenyl group (optionally substituted on the phenyl ring with one or more substituents each independently selected from the group consisting of halogen and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of formyl, $C_{1-6}$ alkoxy, phenyl (optionally substituted on the phenyl ring with one or more halogen atoms), and heterocyclic groups.

Item 4. An N-pyridylpiperidine compound, an N-oxide thereof, or salts of these compounds according to any one of items 1 to 3, wherein the N-pyridylpiperidine compound is represented by Formula (1) in which $R^{11}$ is a halogen atom, a $C_{1-6}$ alkyl group, a $C_{1-4}$ haloalkyl group, a $C_{1-4}$ hydroxyalkyl group, a $C_{1-4}$ alkoxycarbonyl group, a formyl group, —C($R^{14}$)═NO($R^{15}$) (in which $R^{14}$ is a hydrogen atom, and $R^{15}$ is a hydrogen atom or a $C_{1-4}$ alkyl group), a phenyl group (optionally substituted on the phenyl ring with one or more substituents each independently selected from the group consisting of halogen, $C_{1-6}$ alkyl, $C_{1-4}$ haloalkyl, $C_{1-6}$ alkoxy, $C_{1-4}$ haloalkoxy, $C_{1-4}$ alkylthio, cyano, and nitro) or heterocyclic groups (optionally substituted on the heterocyclic ring with one or more halogen atoms).

Item 5. An N-pyridylpiperidine compound, an N-oxide thereof, or salts of these compounds according to any one of items 1 to 4, wherein the N-pyridylpiperidine compound is represented by Formula (1) in which X is an oxygen atom.

Item 6. An N-pyridylpiperidine compound, an N-oxide thereof, or salts of these compounds according to item 2, wherein the N-pyridylpiperidine compound is represented by Formula (1) in which $R^1$ is a $C_{1-4}$ haloalkyl group or a cyano group.

Item 7. An N-pyridylpiperidine compound, an N-oxide thereof, or salts of these compounds according to item 6, wherein the N-pyridylpiperidine compound is represented by Formula (1) in which $R^1$ is a $C_{1-4}$ haloalkyl group.

Item 8. An N-pyridylpiperidine compound, an N-oxide thereof, or salts of these compounds according to item 3, wherein the N-pyridylpiperidine compound is represented by Formula (1) in which $R^{10}$ is a $C_{1-20}$ alkyl group; a $C_{2-6}$ alkenyl group; a $C_{1-6}$ haloalkyl group; a $C_{1-6}$ alkylcarbonyl group; a phenyl group (optionally substituted on the phenyl ring with one or more substituents each independently selected from the group consisting of halogen, $C_{1-4}$ alkyl, and $C_{1-4}$ haloalkyl); a heterocyclic group (optionally substituted on the heterocyclic ring with one or more substituents each independently selected from the group consisting of $C_{1-4}$ alkyl and $C_{1-4}$ haloalkyl); or a $C_{1-4}$ alkyl group substituted with one or more substituents each independently selected from the group consisting of $C_{1-6}$ alkoxy, phenyl (optionally substituted on the phenyl ring with one or more halogen atoms), and heterocyclic groups.

Item 9. An N-pyridylpiperidine compound, an N-oxide thereof, or salts of these compounds according to item 8, wherein the N-pyridylpiperidine compound is represented by Formula (1) in which $R^{10}$ is a $C_{1-6}$ alkyl group; a $C_{2-6}$ alkenyl group; a phenyl group (optionally substituted on the phenyl group with one or more substituents selected from halogen and $C_{1-4}$ alkyl); a pyridyl group (optionally substituted on the pyridine ring with one or more $C_{1-4}$ alkyl groups); or a $C_{1-4}$ alkyl group substituted with one or two substituents each independently selected from the group consisting of $C_{1-6}$ alkoxy, phenyl (optionally substituted on the phenyl ring with one or more halogen atoms), and 1,3-dioxolan-2-yl.

Item 10. An N-pyridylpiperidine compound, an N-oxide thereof, or salts of these compounds according to item 4, wherein the N-pyridylpiperidine compound is represented by Formula (1) in which $R^{11}$ is a $C_{1-6}$ alkyl group; a $C_{1-4}$ haloalkyl group; a phenyl group (optionally substituted on the phenyl ring with one or more substituents each independently selected from the group consisting of halogen, $C_{1-6}$ alkyl, $C_{1-4}$ haloalkyl, $C_{1-4}$ haloalkoxy, and nitro); or a heterocyclic group (optionally substituted on the heterocyclic ring with one or more halogen atoms).

Item 11. An N-pyridylpiperidine compound, an N-oxide thereof, or salts of these compounds according to item 1, wherein the N-pyridylpiperidine compound is represented by Formula (1a) or (1f)

(1a)

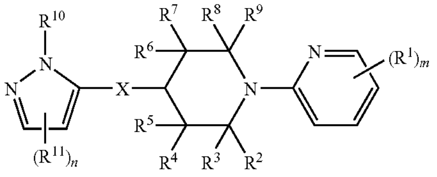

(1f)

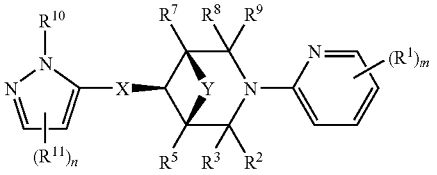

(wherein $R^1$, $R^2$, $R^3$, $R^4$, $R^5$, $R^6$, $R^7$, $R^8$, $R^9$, $R^{10}$, $R^{11}$, X, m, and n are as defined in item 1, and Y is a $C_{1-4}$ alkylene group).

Item 12. An N-pyridylpiperidine compound, an N-oxide thereof, or salts of these compounds according to item 11, wherein the N-pyridylpiperidine compound is represented by Formula (1a) or (1f) in which $R^1$ is a $C_{1-4}$ haloalkyl group or a cyano group.

Item 13. An N-pyridylpiperidine compound, an N-oxide thereof, or salts of these compounds according to item 12, wherein the N-pyridylpiperidine compound is represented by Formula (1a) or (1f) in which $R^{10}$ is a $C_{1-20}$ alkyl group; a $C_{2-6}$ alkenyl group; a $C_{1-6}$ haloalkyl group; a $C_{1-6}$ alkylcarbonyl group; a phenyl group (optionally substituted on the phenyl ring with one or more substituents each independently selected from the group consisting of halogen, $C_{1-4}$ alkyl, and $C_{1-4}$ haloalkyl); a heterocyclic group (optionally substituted on the heterocyclic ring with one or more substituents each independently selected from the group consisting of $C_{1-4}$ alkyl and $C_{1-4}$ haloalkyl); or a $C_{1-4}$ alkyl group substituted with one or more substituents each independently selected from the group consisting of $C_{1-6}$ alkoxy, phenyl (optionally substituted on the phenyl ring with one or more halogen atoms), and heterocyclic groups.

Item 14. An N-pyridylpiperidine compound, an N-oxide thereof, or salts of these compounds according to item 13, wherein the N-pyridylpiperidine compound is represented by Formula (1a) or (1f) in which $R^{11}$ is a $C_{1-6}$ alkyl group, a $C_{1-4}$ haloalkyl group, a phenyl group (optionally substituted on the phenyl ring with one or more substituents each independently selected from the group consisting of halogen, $C_{1-4}$ alkyl, $C_{1-4}$ haloalkyl, $C_{1-4}$ haloalkoxy, and nitro), or a heterocyclic group (optionally substituted on the heterocyclic ring with one or more halogen atoms).

Item 15. An N-pyridylpiperidine compound, an N-oxide thereof, or salts of these compounds according to any one of items 11 to 14, wherein the N-pyridylpiperidine compound is represented by Formula (1a) in which any one of $R^4$, $R^5$, $R^6$, and $R^7$ is a $C_{1-4}$ alkyl group which is positioned trans to the X on the 4-position of the piperidine ring.

Item 16. An N-pyridylpiperidine compound, an N-oxide thereof, or salts of these compounds according to any one of items 11 to 15, wherein the N-pyridylpiperidine compound is represented by Formula (1a) or (1f) in which X is an oxygen atom.

Item 17. A method of producing an N-pyridylpiperidine compound, an N-oxide thereof, or salts of these compounds, the N-pyridylpiperidine compound being represented by Formula (1)

(1)

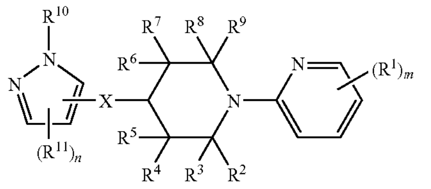

(wherein $R^1$ is a halogen atom, a $C_{1-4}$ haloalkyl group, a cyano group, a nitro group, or a $C_{1-4}$ alkoxycarbonyl group;

$R^2$, $R^3$, $R^4$, $R^5$, $R^6$, $R^7$, $R^8$, and $R^9$ are each independently a hydrogen atom or a $C_{1-4}$ alkyl group;

each pair of $R^2$ and $R^8$, and $R^4$ and $R^6$ may join to form a $C_{1-4}$ alkylene group;

$R^{10}$ is a hydrogen atom; a $C_{1-20}$ alkyl group; a $C_{3-8}$ cycloalkyl group; a $C_{2-6}$ alkenyl group; a $C_{2-6}$ alkynyl group; a $C_{1-6}$ haloalkyl group; a $C_{2-6}$ haloalkenyl group; a $C_{1-6}$ alkylcarbonyl group; a $C_{1-6}$ alkoxycarbonyl group; a benzoyl group (optionally substituted on the phenyl group with one to five halogen atoms); a phenyl group (optionally substituted on the phenyl ring with one or more substituents each independently selected from the group consisting of halogen, $C_{1-4}$ alkyl, and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of optionally halogen-substituted $C_{3-8}$ cycloalkyl, cyano, nitro, formyl, $C_{1-6}$ alkoxy, $C_{1-4}$ haloalkoxy, benzyloxy, phenoxy, —CON($R^{12}$)($R^{13}$) (in which $R^{12}$ and $R^{13}$ are each independently a $C_{1-4}$ alkyl group, or $R^{12}$ and $R^{13}$ may join to form a $C_{2-7}$ alkylene group), phenyl (optionally substituted on the phenyl ring with one or more halogen atoms), and heterocyclic groups (optionally substituted on the heterocyclic ring with one or more $C_{1-4}$ alkyl groups);

$R^{11}$ is a halogen atom, a $C_{1-6}$ alkyl group, a $C_{1-4}$ haloalkyl group, a $C_{1-4}$ hydroxyalkyl group, a $C_{1-4}$ alkoxycarbonyl group, a $C_{1-4}$ alkylcarbonyl group, a mono or di($C_{1-4}$ alkyl) aminocarbonyl group, a nitro group, a cyano group, a formyl group, —C($R^{14}$)═NO($R^{15}$) (in which $R^{14}$ is a hydrogen atom or a $C_{1-4}$ alkyl group, and $R^{15}$ is a hydrogen atom, a $C_{1-4}$ alkyl group, or a benzyl group), a phenyl group (optionally substituted on the phenyl ring with one or more substituents each independently selected from the group consisting of halogen, $C_{1-6}$ alkyl, $C_{1-4}$ haloalkyl, $C_{1-6}$ alkoxy, $C_{1-4}$ haloalkoxy, $C_{1-4}$ alkylthio, cyano, and nitro), or a heterocyclic group (optionally substituted on the heterocyclic ring with one or more substituents each independently selected from the group consisting of halogen, $C_{1-4}$ alkyl, and $C_{1-4}$ haloalkyl);

X is an oxygen atom, a sulfur atom, or —$SO_2$—;

m is an integer of 1 to 4, and when m is an integer of 2 or more, the m $R^1$'s may be the same or different;

n is an integer of 1 or 2, and when n is 2, the two $R^{11}$'s may be the same or different);

the method comprising reacting a pyrazole compound represented by Formula (2)

(2)

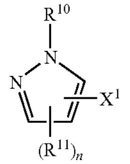

(wherein $R^{10}$, $R^{11}$, and n are as defined above, $X^1$ is a halogen atom, a methanesulfonyloxy group, a trifluoromethanesulfonyloxy group, a p-toluenesulfonyloxy group, a methylthio group, a methanesulfonyl group, a hydroxy group, or a mercapto group) with a piperidine compound represented by Formula (3)

(3)

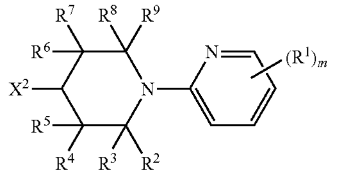

(wherein $R^1$, $R^2$, $R^3$, $R^4$, $R^5$, $R^6$, $R^7$, $R^8$, $R^9$, and m are as defined above, and $X^2$ is a hydroxy group or a mercapto group).

Item 18. A method of producing an N-pyridylpiperidine compound, an N-oxide thereof, or salts of these compounds, the N-pyridylpiperidine compound being represented by Formula (1)

(1)

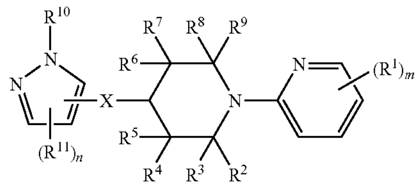

(wherein $R^1$ is a halogen atom, a $C_{1-4}$ haloalkyl group, a cyano group, a nitro group, or a $C_{1-4}$ alkoxycarbonyl group;

$R^2$, $R^3$, $R^4$, $R^5$, $R^6$, $R^7$, $R^8$, and $R^9$ are each independently a hydrogen atom or a $C_{1-4}$ alkyl group;

each pair of $R^2$ and $R^8$, and $R^4$ and $R^6$ may join to form a $C_{1-4}$ alkylene group;

$R^{10}$ is a hydrogen atom; a $C_{1-20}$ alkyl group; a $C_{3-6}$ cycloalkyl group; a $C_{2-6}$ alkenyl group; a $C_{2-6}$ alkynyl group; a $C_{1-6}$ haloalkyl group; a $C_{2-6}$ haloalkenyl group; a $C_{1-6}$ alkylcarbonyl group; a $C_{1-6}$ alkoxycarbonyl group; a benzoyl group (optionally substituted on the phenyl group with one to five halogen atoms), a phenyl group (optionally substituted on the phenyl ring with one or more substituents each independently selected from the group consisting of halogen, $C_{1-4}$ alkyl, and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of halogen-substituted $C_{3-8}$ cycloalkyl, cyano, nitro, formyl, $C_{1-8}$ alkoxy, haloalkoxy, benzyloxy, phenoxy, —CON($R^{12}$)($R^{13}$) (in which $R^{12}$ and $R^{13}$ are each independently a $C_{1-4}$ alkyl group, or $R^{12}$ and $R^{13}$ may join to form a $C_{2-7}$ alkylene group), phenyl (optionally substituted on the phenyl ring with one or more halogen atoms), and heterocyclic groups (optionally substituted on the heterocyclic ring with one or more $C_{1-4}$ alkyl groups);

$R^{11}$ is a halogen atom, a $C_{1-6}$ alkyl group, a $C_{1-4}$ haloalkyl group, a $C_{1-4}$ hydroxyalkyl group, a $C_{1-4}$ alkoxycarbonyl group, a $C_{1-4}$ alkylcarbonyl group, a mono or di($C_{1-4}$ alkyl) aminocarbonyl group, a nitro group, a cyano group, a formyl group, —C($R^{14}$)═NO($R^{15}$) (in which $R^{14}$ is a hydrogen atom or a $C_{1-4}$ alkyl group, and $R^{15}$ is a hydrogen atom, a $C_{1-4}$ alkyl group, or a benzyl group), a phenyl group (optionally substituted on the phenyl ring with one or more substituents each independently selected from the group consisting of halogen, $C_{1-6}$ alkyl, $C_{1-4}$ haloalkyl, $C_{1-6}$ alkoxy, $C_{1-4}$ haloalkoxy, $C_{1-4}$ alkylthio, cyano, and nitro), or a heterocyclic group (optionally substituted on the heterocyclic ring with one or more substituents each independently selected from the group consisting of halogen, $C_{1-4}$ alkyl, and $C_{1-4}$ haloalkyl);

X is an oxygen atom, a sulfur atom, or —$SO_2$—; and m is an integer of 1 to 4, and when m is an integer of 2 or more, the m $R^1$'s may be the same or different;

n is an integer of 1 or 2, and when n is 2, the two $R^{11}$'s may be the same or different);

the method comprising reacting a pyrazole compound represented by Formula (4)

(4)

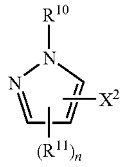

(wherein $R^{10}$, $R^{11}$, and n are as defined above, and $X^2$ is a hydroxy group or a mercapto group)

with a piperidine compound represented by Formula (5)

(5)

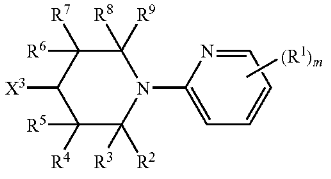

(wherein $R^1$, $R^2$, $R^3$, $R^4$, $R^5$, $R^6$, $R^7$, $R^8$, $R^9$, and m are as defined above, and $X^3$ is a halogen atom, a methanesulfonyloxy group, a trifluoromethanesulfonyloxy group, a p-toluenesulfonyloxy group, a methylthio group, or a methanesulfonyl group).

Item 19. A method of producing an N-pyridylpiperidine compound, an N-oxide thereof, or salts of these compounds, the N-pyridylpiperidine compound being represented by Formula (1)

(1)

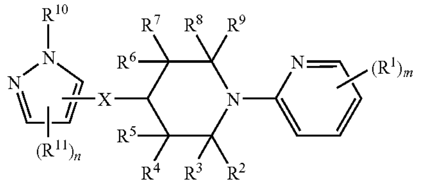

(wherein $R^1$ is a halogen atom, a $C_{1-4}$ haloalkyl group, a cyano group, a nitro group, or a $C_{1-4}$ alkoxycarbonyl group;

$R^2$, $R^3$, $R^4$, $R^5$, $R^6$, $R^7$, $R^8$, and $R^9$ are each independently a hydrogen atom or a $C_{1-4}$ alkyl group;

each pair of $R^2$ and $R^8$, and $R^4$ and $R^6$ may join to form a $C_{1-4}$ alkylene group;

$R^{10}$ is a hydrogen atom; a $C_{1-20}$ alkyl group; a $C_{3-8}$ cycloalkyl group; a $C_{2-6}$ alkenyl group; a $C_{2-6}$ alkynyl group; a $C_{1-6}$ haloalkyl group; a $C_{2-6}$ haloalkenyl group; a $C_{1-6}$ alkylcarbonyl group; a $C_{1-6}$ alkoxycarbonyl group; a benzoyl group (optionally substituted on the phenyl group with one to five halogen atoms), a phenyl group (optionally substituted on the phenyl ring with one or more substituents each independently selected from the group consisting of halogen atom, $C_{1-4}$ alkyl, and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of optionally halogen-substituted $C_{3-8}$ cycloalkyl, cyano, nitro, formyl, $C_{1-6}$ alkoxy, $C_{1-4}$ haloalkoxy, benzyloxy, phenoxy, —CON($R^{12}$)($R^{13}$) (in which $R^{12}$ and $R^{13}$ are each independently a $C_{1-4}$ alkyl group, and $R^{12}$ and $R^{13}$ may join to form a $C_{2-7}$ alkylene group), phenyl (optionally substituted on the phenyl ring with one or more halogen atoms), and heterocyclic groups (optionally substituted on the heterocyclic ring with one or more $C_{1-4}$ alkyl groups);

$R^{11}$ is a halogen atom, a $C_{1-6}$ alkyl group, a $C_{1-4}$ haloalkyl group, a $C_{1-4}$ hydroxyalkyl group, a $C_{1-4}$ alkoxycarbonyl group, a $C_{1-4}$ alkylcarbonyl group, a mono or di($C_{1-4}$ alkyl) aminocarbonyl group, a nitro group, a cyano group, a formyl group, —C($R^{14}$)═NO($R^{15}$) (in which $R^{14}$ is hydrogen or $C_{1-4}$ alkyl, and $R^{15}$ is hydrogen, $C_{1-4}$ alkyl, or benzyl), a phenyl group (optionally substituted on the phenyl ring with one or more substituents each independently selected from the group consisting of halogen, $C_{1-6}$ alkyl, $C_{1-4}$ haloalkyl, alkoxy, $C_{1-4}$ haloalkoxy, $C_{1-4}$ alkylthio, cyano, and nitro), or a heterocyclic group (optionally substituted on the heterocyclic ring with one or more substituents each independently selected from the group consisting of halogen, $C_{1-4}$ alkyl, and $C_{1-4}$ haloalkyl);

X is an oxygen atom, a sulfur atom, or —$SO_2$—;

m is an integer of 1 to 4, and when m is an integer of 2 or more, the m $R^1$'s may be the same or different;

n is an integer of 1 or 2, and when n is 2, the two $R^{11}$'s may be the same or different);

the method comprising reacting a piperidine compound represented by Formula (6)

(6)

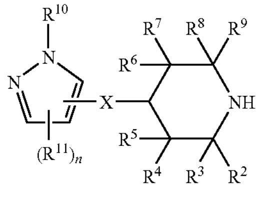

(wherein $R^2$, $R^3$, $R^4$, $R^5$, $R^6$, $R^7$, $R^8$, $R^9$, $R^{10}$, $R^{11}$, X, and n are as defined above)

with a pyridine compound represented by Formula (7)

(7)

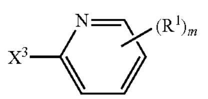

(wherein $R^1$, $X^3$, and m are as defined above).

Item 20. A method of producing an N-pyridylpiperidine compound, an N-oxide thereof, or salts of these compounds, the N-pyridylpiperidine compound being represented by Formula (1a)

(1a)

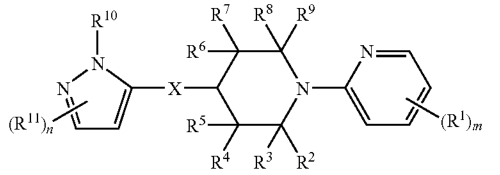

(wherein $R^1$, $R^2$, $R^3$, $R^4$, $R^5$, $R^6$, $R^7$, $R^8$, $R^9$, $R^{10}$, $R^{11}$, X, m, and n are as defined in item 1);

the method comprising reacting a pyrazolone compound represented by Formula (8)

(8)

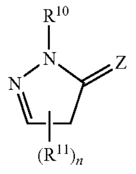

(wherein $R^{10}$, $R^{11}$ and n are as defined above, and Z is an oxygen atom or a sulfur atom)

with a piperidine compound represented by Formula (5a)

(5a)

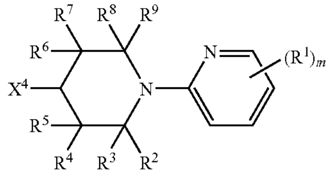

(wherein $R^2$, $R^3$, $R^4$, $R^5$, $R^6$, $R^7$, $R^8$, $R^9$, and m are as defined above, $X^4$ is $X^2$ or $X^3$, and $X^2$ and $X^3$ are as defined above).

Item 21. A method of producing an N-pyridylpiperidine compound, an N-oxide thereof, or salts of these compounds, the N-pyridylpiperidine compound being represented by Formula (1i)

(1i)

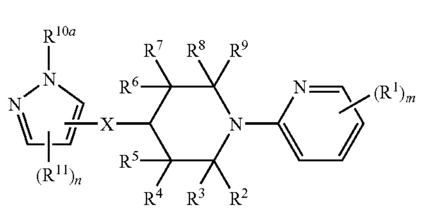

(wherein $R^1$, $R^2$, $R^3$, $R^4$, $R^5$, $R^6$, $R^7$, $R^8$, $R^9$, $R^{11}$, m, and n are as defined in item 1; $R^{10a}$ is a $C_{1-20}$ alkyl group; a $C_{3-8}$ cycloalkyl group; a $C_{2-6}$ alkenyl group; a $C_{2-6}$ alkynyl group; a $C_{1-6}$ haloalkyl group; a $C_{2-6}$ haloalkenyl group; a $C_{1-6}$ alkylcarbonyl group; a $C_{1-6}$ alkoxycarbonyl group; a benzoyl group (optionally substituted on the phenyl group with one to five halogen atoms); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of optionally halogen-substituted $C_{3-8}$ cycloalkyl, cyano, nitro, formyl, $C_{1-6}$ alkoxy, $C_{1-4}$ haloalkoxy, benzyloxy, phenoxy, —CON($R^{12}$)($R^{13}$) (in which $R^{12}$ and $R^{13}$ are each independently a $C_{1-4}$ alkyl group, and $R^{12}$ and $R^{13}$ may join to form a $C_{2-7}$ alkylene group), phenyl (optionally substituted on the phenyl ring with one or more halogen atoms), and heterocyclic groups (optionally substituted on the heterocyclic ring with one or more $C_{1-4}$ alkyl groups));

the method comprising reacting an N-pyridylpiperidine compound represented by Formula (1h)

(1h)

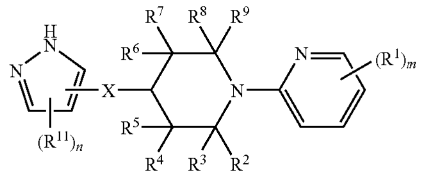

(wherein $R^1$, $R^2$, $R^3$, $R^4$, $R^5$, $R^6$, $R^7$, $R^8$, $R^9$, $R^{11}$, X, m and n are as defined in item 1)

with a compound represented by Formula (9)

$X^5—R^{10a}$ (9)

(wherein $R^{10a}$ is as defined above, and $X^5$ is a halogen atom).

Item 22. A pest control agent comprising as an active ingredient the N-pyridylpiperidine compound, N-oxide thereof, or salts of these compounds of any one of items 1 to 16.

Item 23. A pest control agent according to item 22 which is a miticide.

The groups cited in the present specification are described below.

Examples of the halogen atom are fluorine, chlorine, bromine, and iodine atoms.

Examples of the $C_{1-4}$ haloalkyl group include linear or branched alkyl groups having 1 to 4 carbon atoms and substituted with 1 to 9, preferably 1 to 5, halogen atoms. Specific examples thereof include fluoromethyl, chloromethyl, bromomethyl, iodomethyl, difluoromethyl, trifluoromethyl, chlorodifluoromethyl, bromodifluoromethyl, dichlorofluoromethyl, 1-fluoroethyl, 2-fluoroethyl, 2-chloroethyl, 2-bromoethyl, 2-iodoethyl, 2,2,2-trifluoroethyl, 2,2,2-trichloroethyl, pentafluoroethyl, 1-fluoroisopropyl, 3-fluoropropyl, 3-chloropropyl, 3-bromopropyl, 4-fluorobutyl, 4-chlorobutyl, 4,4,4-trifluorobutyl, and like groups.

Examples of the $C_{1-4}$ alkoxycarbonyl group include groups formed by the bonding of a linear or branched alkoxy group having 1 to 4 carbon atoms to a carbonyl group. Specific examples thereof include methoxycarbonyl, ethoxycarbonyl, n-propoxycarbonyl, isopropoxycarbonyl, n-butoxycarbonyl, sec-butoxycarbonyl, tert-butoxycarbonyl, and like groups.

Examples of the $C_{1-4}$ alkyl group include linear or branched alkyl groups having 1 to 4 carbon atoms, such as methyl, ethyl, n-propyl, isopropyl, n-butyl, isobutyl, sec-butyl, and tert-butyl.

Examples of the $C_{1-4}$ alkylene group include linear or branched alkylene groups having 1 to 4 carbon atoms, such as methylene, ethylene, trimethylene, tetramethylene, propylene, and ethylethylene.

Examples of the $C_{1-6}$ alkyl group include linear or branched alkylene groups having 1 to 6 carbon atoms, such as n-pentyl, isopentyl, neopentyl, tert-pentyl, n-hexyl, isohexyl, and 2-ethyl-n-butyl, in addition to those mentioned as examples of the $C_{1-4}$ alkyl group.

Examples of the $C_{1-20}$ alkyl group include linear or branched alkyl groups having 1 to 20 carbon atoms, such as n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl, and n-icosyl, in addition to those mentioned as examples of the $C_{1-4}$ alkyl group and the $C_{1-6}$ alkyl group.

Examples of the $C_{3-3}$ cycloalkyl group include cyclic alkyl groups having 4 to 8 carbon atoms, such as cyclopropyl, cyclobutyl, cyclopentyl, cyclohexyl, cycloheptyl, and cyclooctyl.

Examples of the $C_{2-6}$ alkenyl group include linear or branched alkenyl groups containing 2 to 6 carbon atoms and having at least one double bond at any position. Specific examples thereof include vinyl, 1-propenyl, allyl, isopropenyl, 2-butenyl, 3-butenyl, 1-methyl-2-propenyl, 1,3-butadienyl, 1-pentenyl, 2-pentenyl, 3-pentenyl, 4-pentenyl, 1,1-dimethyl-2-propenyl, 1-ethyl-2-propenyl, 1-methyl-2-butenyl, 1-methyl-3-butenyl, 1-hexenyl, 2-hexenyl, 3-hexenyl, 4-hexenyl, 5-hexenyl, 1,1-dimethyl-2-butenyl, 1,1-dimethyl-3-butenyl, and like groups.

Examples of the $C_{2-6}$ alkynyl group include linear or branched alkynyl groups containing 2 to 6 carbon atoms and having at least one triple bond at any position. Specific examples thereof include ethynyl, 2-propynyl, 1-methyl-2-propynyl, 1,1-dimethyl-2-propynyl, 1-butynyl, 2-butynyl, 3-butynyl, 1-pentynyl, 2-pentynyl, 3-pentynyl, 4-pentynyl, 1-methyl-2-butynyl, 1-methyl-3-butynyl, 1,1-dimethyl-2-butynyl, 1,1-dimethyl-3-butynyl, 1-methyl-3-pentynyl, 1-methyl-4-pentynyl, and like groups.

Examples of the $C_{1-6}$ haloalkyl group include linear or branched alkyl groups having 1 to 6 carbon atoms and substituted with 1 to 13, preferably 1 to 7, halogen atoms. Specific examples thereof include 5-chloropentyl, 5-fluoropentyl, 6-chlorohexyl, and 6-fluorohexyl, in addition to those mentioned as examples of the $C_{1-4}$ haloalkyl group.

Examples of the $C_{2-6}$ haloalkyl group include $C_{2-6}$ linear or branched alkenyl groups having at least one double bond at any position and substituted with 1 to 13, preferably 1 to 7, halogen atoms. Specific examples thereof include 2,2-dichlorovinyl, 2,2-dibromovinyl, 3-chloro-2-propenyl, 3,3-difluoro-2-allyl, 3,3-dichloro-2-allyl, 4-chloro-2-butenyl, 4,4,4-trifluoro-2-butenyl, 4,4,4-trichloro-3-butenyl, 5-chloro-3-pentenyl, 6-fluoro-2-hexenyl, and like groups.

Examples of the heterocyclic group include thienyl, furyl, tetrahydrofuryl, dioxolanyl, dioxanyl, pyrrolyl, pyrrolinyl, pyrrolidinyl, oxazolyl, isoxazolyl, oxazolinyl, oxazolidinyl, isoxazolinyl, thiazolyl, isothiazolyl, thiazolinyl, thiazolidinyl, isothiazolinyl, pyrazolyl, pyrazolidinyl, imidazolyl, imidazolinyl, imidazolidinyl, oxadiazolyl, oxadiazolinyl, thiadiazolinyl, triazolyl, triazolinyl, triazolidinyl, tetrazolyl, tetrazolinyl, pyridyl, dihydropyridyl, tetrahydropyridyl, piperidyl, oxazinyl, dihydroxazinyl, morpholino, thiazinyl, dihydrothiazinyl, thiamorpholino, pyridazinyl, dihydropyridazinyl, tetrahydropyridazinyl, hexahydropyridazinyl, oxadiazinyl, dihydrooxadiazinyl, tetrahydrooxadiazinyl, thiadiazolyl, thiadiazinyl, dihydrothiadiazinyl, tetrahydrothiadiazinyl, pyrimidinyl, dihydropyrimidinyl, tetrahydropyrimidinyl, hexahydropyrimidinyl, pyrazinyl, dihydropyrazinyl, tetrahydropyrazinyl, piperazinyl, triazinyl, dihydrotriazinyl, tetrahydrotriazinyl, hexahydrotriazinyl, tetrazinyl, dihydrotetrazinyl, indolyl, indolinyl, isoindolyl, indazolyl, quinazolinyl, dihydroquinazolyl, tetrahydroquinazolyl, carbazolyl, benzoxazolyl, benzoxazolinyl, benzoisoxazolyl, benzisoxazolinyl, benzothiazolyl, benzisothiazolyl, benzisothiazolinyl, benzimidazolyl, indazolinyl, quinolinyl, dihydroquinolinyl, tetrahydroquinolinyl, isoquinolinyl, dihydroisoquinolinyl, tetrahydroisoquinolinyl, pyridoindolyl, dihydrobenzoxazinyl, cinnolinyl, dihydrocinnolinyl, tetrahydrocinnolinyl, phthalazinyl, dihydrophthalazinyl, tetrahydrophthalazinyl, quinoxalinyl, dihydroquinoxalinyl, tetrahydroquinoxalinyl, purinyl, dihydrobenzotriazinyl, dihydrobenzotetrazinyl, phenothiazinyl, furanyl, benzofuranyl, benzothienyl, and like groups. These heterocyclic groups include those substituted at any substitutable position with an oxo or thioketone group. These heterocyclic groups further include those optionally substituted at any substitutable position with 1 to 5 (preferably 1 to 3) substituents, such as halogen atoms, $C_{1-4}$ alkyl groups, $C_{1-4}$ haloalkyl groups, substituted heterocyclic groups (e.g., 3-chloropyridin-2-yl, 4-trifluoromethyl-1,3-thiazol-2-yl, 5-trifluoromethylpyridin-2-yl, etc.).

Among these heterocyclic rings, thienyl, furyl, tetrahydrofuryl, dioxolanyl, dioxanyl, oxazolyl, isoxazolyl, thiazolyl, pyrazolyl, pyridyl, and piperidyl are preferable. Thienyl, tetrahydrofuryl, dioxolanyl, dioxanyl, thiazolyl, and pyridyl are particularly preferable.

Examples of the optionally halogen-substituted $C_{3-8}$ cycloalkyl group include cyclic alkyl groups having 3 to 8 carbon atoms, such as the above-mentioned $C_{3-8}$ cycloalkyl groups that are optionally substituted at any position with one to the maximum substitutable number of (preferably 1 to 5, and more preferably 1 to 3) halogen atoms.

Examples of the $C_{1-6}$ alkoxy group include linear or branched alkoxy groups having 1 to 6 carbon atoms, such as methoxy, ethoxy, n-propoxy, isopropoxy, cyclopropyloxy, n-butoxy, sec-butoxy, tert-butoxy, n-pentyloxy, isopentyloxy, neopentyloxy, tert-pentyloxy, n-hexyloxy, and isohexyloxy.

Examples of the $C_{1-4}$ haloalkoxy group include linear or branched alkoxy groups having 1 to 4 carbon atoms and substituted with 1 to 9, preferably 1 to 5, halogen atoms. Specific examples thereof include fluoromethoxy, chloromethoxy, bromomethoxy, iodomethoxy, dichloromethoxy, trichloromethoxy, difluoromethoxy, trifluoromethoxy, chlorodifluoromethoxy, bromodifluoromethoxy, dichlorofluoromethoxy, 1-fluoroethoxy, 2-fluoroethoxy, 2-chloroethoxy, 2-bromoethoxy, 2-iodoethoxy, 2,2,2-trifluoroethoxy, 2,2,2-trichloroethoxy, pentafluoroethoxy, 1-fluoroisopropoxy, 3-fluoropropoxy, 3-chloropropoxy, 3-bromopropoxy, 4-fluorobutoxy, 4-chlorobutoxy, and like groups.

Examples of the $C_{1-4}$ alkylthio group include linear or branched alkylthio groups having 1 to 4 carbon atoms, such as methylthio, ethylthio, n-propylthio, isopropylthio, and tert-butylthio.

Examples of the $C_{2-7}$ alkylene group include ethylene, trimethylene, tetramethylene, pentamethylene, hexamethylene, heptamethylene, and the like. These alkylene groups may contain an optionally substituted nitrogen, oxygen, or sulfur atom or a phenylene group. Examples of such alkylene groups include $—CH_2NHCH_2—$, $—CH_2NHCH_2CH_2—$, $—CH_2NHNHCH_2—$, $—CH_2CH_2NHCH_2CH_2—$, $—CH_2NHNHCH_2CH_2—$, $—CH_2NHCH_2NHCH_2—$, $—CH_2CH_2CH_2NHCH_2CH_2CH_2—$, $—CH_2OCH_2CH_2—$, $—CH_2CH_2OCH_2CH_2—$, $—CH_2SCH_2CH_2—$, $—CH_2CH_2SCH_2CH_2—$,

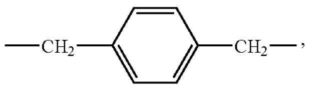

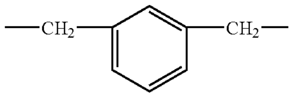

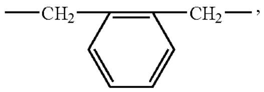

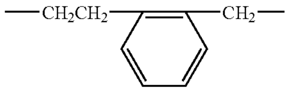

and like groups. These alkylene groups may be substituted at any position or on the nitrogen atom. Examples of such substituents include $C_{1-4}$ alkyl, $C_{1-6}$ alkoxycarbonyl, hydroxy, and like groups.

Examples of the $C_{1-4}$ alkylcarbonyl group include linear or branched alkylcarbonyl groups having 1 to 4 carbon atoms, such as methylcarbonyl (acetyl), ethylcarbonyl (propionyl), N-propylcarbonyl (butyryl), isopropylcarbonyl (isobutyryl), n-butylcarbonyl (valeryl), isobutylcarbonyl (isovaleryl), sec-butylcarbonyl, and tert-butylcarbonyl.

Examples of the mono or di($C_{1-4}$ alkyl)aminocarbonyl group include alkylaminocarbonyl groups in which nitrogen atoms of the aminocarbonyl groups are mono- or disubstituted with linear or branched alkyl groups having 1 to 4 carbon atoms, such as methylaminocarbonyl, dimethylaminocarbonyl, ethylaminocarbonyl, methylethylaminocarbonyl, diethylaminocarbonyl, n-propylaminocarbonyl, isopropylaminocarbonyl, n-butylaminocarbonyl, sec-butylaminocarbonyl, tert-butylaminocarbonyl, and dibutylaminocarbonyl.

Examples of the $C_{1-4}$ hydroxyalkyl group include linear or branched alkyl groups having 1 to 4 carbon atoms and substituted with 1 or 2 hydroxy groups, such as hydroxymethyl, 2-hydroxyethyl, 1-hydroxy-2-propyl, 3-hydroxypropyl, 4-hydroxybutyl, and 3,4-dihydroxybutyl.

N-pyridylpiperidine Compound

The N-pyridylpiperidine compound of the invention represented by Formula (1) is a structurally novel compound that has a pyrazole bonded to the 4-position of the piperidine ring via an oxygen or sulfur atom.

(1)

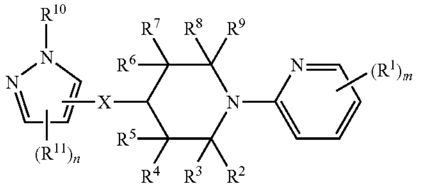

(wherein $R^1$, $R^2$, $R^3$, $R^4$, $R^5$, $R^6$, $R^7$, $R^8$, $R^9$, $R^{10}$, $R^{11}$, X, m, and n are as defined above).

The N-pyridylpiperidine compound represented by Formula (1) includes N-pyridylpiperidine compounds represented by the following Formulas (1a), (1b), and (1c).

(1a)

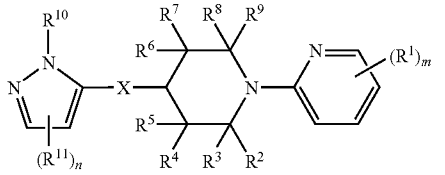

(1b)

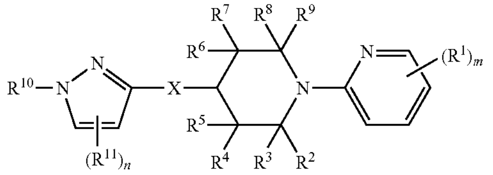

(1c)

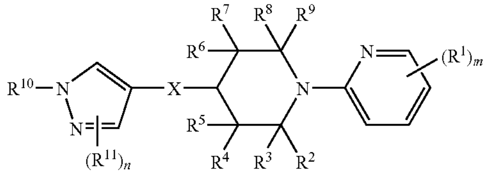

(wherein $R^1$, $R^2$, $R^3$, $R^4$, $R^5$, $R^6$, $R^7$, $R^8$, $R^9$, $R^{10}$, $R^{11}$, X, m, and n are as defined above).

The N-pyridylpiperidine compound of Formula (1) wherein $R^2$ and $R^8$ join to form a $C_{1-4}$ alkylene group may exist as cis-trans isomers represented by the following Formulas (1d) and (1e). The N-pyridylpiperidine compound of the invention represented by Formula (1) includes such isomers.

(1d)

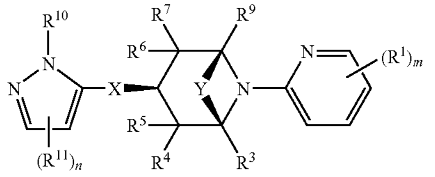

(1e)

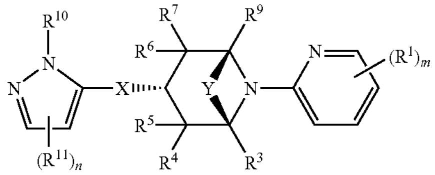

(wherein $R^1$, $R^3$, $R^4$, $R^5$, $R^6$, $R^7$, $R^9$, $R^{10}$, $R^{11}$, X, m, and n are as defined above, and Y is a $C_{1-4}$ alkylene group).

The N-pyridylpiperidine compound represented by Formula (1) wherein $R^4$ and $R^6$ join to form a $C_{1-4}$ alkylene group may exist as cis-trans isomers represented by Formulas (1f) and (1g) below. The N-pyridylpiperidine compound of the invention represented by Formula (1) includes such isomers.

(1f)

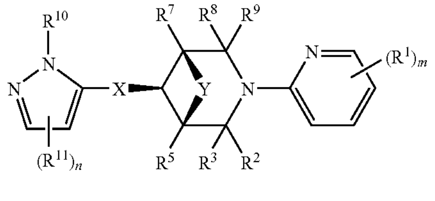

-continued

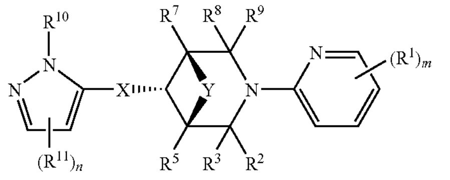

(1g)

(wherein $R^1$, $R^2$, $R^3$, $R^5$, $R^7$, $R^8$, $R^9$, $R^{10}$, $R^{11}$, X, Y, m and n are as defined above).

The N-pyridylpiperidine compound of Formula (1) wherein at least one of $R^2$, $R^3$, $R^5$, $R^6$, $R^7$, $R^8$, and $R^9$ is a $C_{1-4}$ alkyl group may exist as stereoisomers in relation to the 4-position of the piperidine ring. The N-pyridylpiperidine compound of the invention represented by Formula (1) includes such isomers.

The N-pyridylpiperidine compound represented by Formula (1) may exist as N-oxides formed by oxidation of the nitrogen of the pyridine ring or piperidine ring of the N-pyridylpiperidine compound. The N-pyridylpiperidine compound of the invention represented by Formula (1) includes these N-oxides.

In this specification, for convenience, N-oxide formed by oxidation of the nitrogen on the pyridine ring is called N-pyridyl oxide, whereas N-oxide formed by oxidation of the nitrogen atom on the piperidine ring is called N-piperidyl oxide.

The N-pyridylpiperidine compound represented by Formula (1) has basic properties, and therefore can form salts with: inorganic acids such as hydrochloric acid, sulfuric acid, and phosphoric acid; organic acids such as formic acid, acetic acid, fumaric acid, and oxalic acid; and acid salts such as sodium hydrogen sulfate, and potassium hydrogen sulfate. The N-pyridylpiperidine compound of the invention represented by Formula (1) includes these salts.

Among the N-pyridylpiperidine compounds of the invention represented by Formula (1), those wherein $R^1$ is a $C_{1-4}$ haloalkyl group or a cyano group are preferable, and those wherein $R^1$ is a $C_{1-4}$ haloalkyl group are more preferable. Specifically, those wherein $R^1$ is a trifluoromethyl group are particularly preferable.

Preferable among the N-pyridylpiperidine compounds of the invention represented by Formula (1) are those wherein $R^{10}$ is a $C_{1-20}$ alkyl group; a $C_{2-6}$ alkenyl group; a $C_{1-6}$ haloalkyl group; a $C_{1-6}$ alkylcarbonyl group; a phenyl group (optionally substituted on the phenyl ring with one or more, and preferably one or two substituents each independently selected from the group consisting of halogen, $C_{1-4}$ alkyl, and $C_{1-4}$ haloalkyl); a heterocyclic group (optionally substituted on the heterocyclic ring with one or more, and preferably one or two substituents each independently selected from the group consisting of $C_{1-4}$ alkyl and $C_{1-4}$ haloalkyl); or a $C_{1-4}$ alkyl group substituted with one or more, and preferably one or two substituents each independently selected from the group consisting of $C_{1-6}$ alkoxy, phenyl (optionally substituted on the phenyl ring with one or more, and preferably one or two halogen atoms), and heterocyclic groups. More preferable are those wherein $R^{10}$ is a $C_{1-6}$ alkyl group; a $C_{2-6}$ alkenyl group; a phenyl group (optionally substituted on the phenyl ring with one or more, and preferably one or two halogen atoms or $C_{1-4}$ alkyl groups); a pyridyl group (optionally substituted on the pyridine ring with one or more, and preferably one or two $C_{1-4}$ alkyl groups); or a $C_{1-4}$ alkyl group substituted with one or two substituents each independently selected from the group consisting of $C_{1-6}$ alkoxy, phenyl (optionally substituted on the phenyl ring with one or more, and preferably one or two halogen atoms), and 1,3-dioxolane-2-yl. Particularly preferable are the compounds wherein $R^{10}$ is a $C_{1-6}$ alkyl group, a pyridyl group, a 2,2-dimethoxyethyl group, or a (1,3-dioxolan-2-yl)methyl group.

Among the N-pyridylpiperidine compounds of the invention represented by Formula (1), preferable are those wherein $R^{11}$ is a $C_{1-6}$ alkyl group, a $C_{1-4}$ haloalkyl group, a phenyl group (optionally substituted on the phenyl ring with one or more, and preferably one to three substituents each independently selected from the group consisting of halogen, $C_{1-4}$ alkyl, nitro, $C_{1-4}$ haloalkyl, and $C_{1-4}$ haloalkoxy), or a heterocyclic group (optionally substituted on the heterocyclic ring with one or more, and preferably one or two halogen atoms). The compounds wherein $R^{11}$ is a trifluoromethyl group or a phenyl group (optionally substituted on the phenyl ring with one to three halogen atoms) are more preferable.

Among the N-pyridylpiperidine compounds of the invention represented by Formula (1), those wherein X is an oxygen atom are preferable.

More preferable are compounds of Formula (1) wherein $R^1$ is a $C_{1-4}$ haloalkyl group or a cyano group, $R^{10}$ is a $C_{1-20}$ alkyl group; a $C_{2-6}$ alkenyl group; a $C_{1-6}$ haloalkyl group; a $C_{1-6}$ alkylcarbonyl group; a phenyl group (optionally substituted on the phenyl ring with one or more, and preferably one or two substituents each independently selected from the group consisting of halogen, $C_{1-4}$ alkyl, and $C_{1-4}$ haloalkyl; a heterocyclic group (optionally substituted on the heterocyclic ring with one or more, and preferably one or two substituents each independently, selected from the group consisting of $C_{1-4}$ alkyl and $C_{1-4}$ haloalkyl; or a $C_{1-4}$ alkyl group substituted with one or more, and preferably one or two substituents each independently selected from the group consisting of $C_{1-6}$ alkoxy, phenyl (optionally substituted on the phenyl ring with one or more, and preferably one or two halogen atoms), and heterocyclic groups, and $R^{11}$ is a $C_{1-6}$ alkyl group, a $C_{1-4}$ haloalkyl group, and a phenyl group (optionally substituted on the phenyl ring with one or more, and preferably one to three substituents each independently selected from the group consisting of halogen, $C_{1-4}$ alkyl, nitro, $C_{1-4}$ haloalkyl, and $C_{1-4}$ haloalkoxy); or a heterocyclic group (optionally substituted on the heterocyclic ring with one or more, and preferably one or two halogen atoms), and X is an oxygen atom.

Among the preferable compounds, particularly preferable are those wherein $R^1$ is a $C_{1-4}$ haloalkyl group, $R^{10}$ is a $C_{1-6}$ alkyl group; a $C_{2-6}$ alkenyl group; a phenyl group (optionally substituted on the phenyl ring with one or more, and preferably one or two halogen atoms or $C_{1-4}$ alkyl groups), a pyridyl group (optionally substituted on the pyridine ring with one or more $C_{1-4}$ alkyl groups); or a $C_{1-4}$ alkyl group substituted with one or more, and preferably one or two substituents each independently selected from the group consisting of $C_{1-4}$ alkoxy, phenyl (optionally substituted on the phenyl ring with one or more, and preferably one or two halogen atoms), and 1,3-dioxolane-2-yl; $R^{11}$ is a trifluoromethyl group or a phenyl group (optionally substituted on the phenyl ring with one to three halogen atoms); and X is an oxygen atom.

Among the N-pyridylpiperidine compound of the invention represented by Formula (1), those represented by Formulas (1a), (1b), and (1f) are preferable, and those represented by Formulas (1a) and (1f) are more preferable.

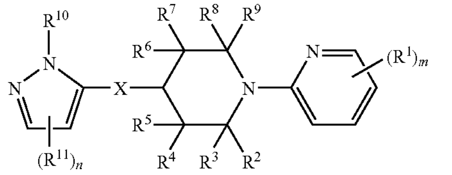

(1a)

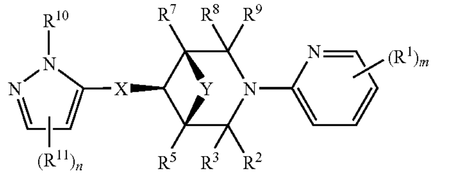

(1f)

wherein $R^1$, $R^2$, $R^3$, $R^5$, $R^7$, $R^8$, $R^9$, $R^{10}$, $R^{11}$, m, and n are as defined above.

Among the N-pyridylpiperidine compounds of the invention represented by Formulas (1a) and (1f), those wherein $R^1$ is a $C_{1-4}$ haloalkyl group or a cyano group are preferable, and those wherein $R^1$ is a $C_{1-4}$ haloalkyl group are more preferable. Specifically, the compounds wherein $R^1$ is a trifluoromethyl group are particularly preferable.

Among the N-pyridylpiperidine compounds of the invention represented by Formulas (1a) and (1f), preferable are those wherein $R^{10}$ is a $C_{1-20}$ alkyl group; a $C_{2-6}$ alkenyl group; a $C_{1-6}$ haloalkyl group; a $C_{1-6}$ alkylcarbonyl group; a phenyl group (optionally substituted on the phenyl ring with one or more, and preferably one or two substituents each independently selected from the group consisting of halogen, $C_{1-4}$ alkyl, and $C_{1-4}$ haloalkyl; a heterocyclic group (optionally substituted on the heterocyclic ring with one or more, and preferably one or two substituents each independently selected from the group consisting of $C_{1-4}$ alkyl and $C_{1-4}$ haloalkyl); or a $C_{1-4}$ alkyl group substituted with one or more, and preferably one or two substituents each independently selected from the group consisting of $C_{1-6}$ alkoxy, phenyl (optionally substituted on the phenyl ring with one or more, and preferably one or two halogen atoms), and heterocyclic groups. More preferable are those wherein $R^{10}$ is a $C_{1-6}$ alkyl group; a $C_{2-6}$ alkenyl group; a phenyl group (optionally substituted on the phenyl ring with one or more, and preferably one or two halogen atoms or $C_{1-4}$ alkyl groups); a pyridyl group (optionally substituted on the pyridine ring with one or more, and preferably one or two $C_{1-4}$ alkyl groups); or a $C_{1-4}$ alkyl group substituted with one or two substituents each independently selected from the group consisting of $C_{1-6}$ alkoxy, phenyl (optionally substituted on the phenyl ring with one or more, and preferably one or two halogen atoms), and 1,3-dioxolane-2-yl. The compounds wherein $R^{10}$ is a $C_{1-6}$ alkyl group, a pyridyl group, a 2,2-dimethoxyethyl group, or a (1,3-dioxolan-2-yl)methyl group are particularly preferable.

Among the N-pyridylpiperidine compounds of the invention represented by Formulas (1a) and (1f), preferable are those wherein $R^{11}$ is $C_{1-6}$ alkyl group, a $C_{1-4}$ haloalkyl group, and a phenyl group (optionally substituted on the phenyl ring with one or more, and preferably 1 or 3, substituents each independently selected from the group consisting of halogen, $C_{1-4}$ alkyl, nitro, $C_{1-4}$ haloalkyl, and $C_{1-4}$ haloalkoxy); or a heterocyclic group (optionally substituted on the heterocyclic ring with one or more, and preferably one or two halogen atoms). The compounds wherein $R^{11}$ is a trifluoromethyl group or a phenyl group (optionally substituted on the phenyl ring with one to three halogen atoms) are more preferable.

Among the N-pyridylpiperidine compounds of the invention represented by Formulas (1a) and (1f), those wherein X is an oxygen atom are preferable.

More preferable are the compounds of Formulas (1a) and (1f) wherein $R^1$ is a $C_{1-4}$ haloalkyl group or a cyano group, $R^{10}$ is a $C_{1-20}$ alkyl group; a $C_{2-6}$ alkenyl group; a $C_{1-6}$ haloalkyl group; a $C_{1-6}$ alkylcarbonyl group; a phenyl group (optionally substituted on the phenyl ring with one or more, and preferably one or two substituents each independently selected from the group consisting of halogen, $C_{1-4}$ alkyl, and $C_{1-4}$ haloalkyl; a heterocyclic group (optionally substituted on the heterocyclic ring with one or more, and preferably one or two substituents each independently selected from the group consisting of $C_{1-4}$ alkyl and $C_{1-4}$ haloalkyl); or a $C_{1-4}$ alkyl group substituted with one or more, and preferably one or two substituents each independently selected from the group consisting of $C_{1-6}$ alkoxy, phenyl (optionally substituted on the phenyl ring with one or more, and preferably one or two halogen atoms), and heterocyclic groups, $R^{11}$ is a $C_{1-6}$ alkyl group, a $C_{1-4}$ haloalkyl group, a phenyl group (optionally substituted on the phenyl ring with one or more, and preferably one to three substituents each independently selected from the group consisting of halogen, $C_{1-4}$ alkyl, nitro, $C_{1-4}$ haloalkyl, and $C_{1-4}$ haloalkoxy); or a heterocyclic group (optionally substituted on the heterocyclic ring with one or more, and preferably one or two halogen atoms), and X is an oxygen atom.

Among the preferable compounds, particularly preferable are those wherein $R^1$ is a $C_{1-4}$ haloalkyl group, $R^{10}$ is a $C_{1-6}$ alkyl group; a $C_{2-6}$ alkenyl group; a phenyl group (optionally substituted on the phenyl ring with one or more, and preferably one or two halogen atoms or $C_{1-4}$ alkyl groups); a pyridyl group (optionally substituted on the pyridine ring with one or more, and preferably one or two $C_{1-4}$ alkyl groups); or a $C_{1-4}$ alkyl group substituted with one or more, and preferably one or two substituents each independently selected from the group consisting of $C_{1-6}$ alkoxy, phenyl (optionally substituted on the phenyl ring with one or more, and preferably one or two halogen atoms), and 1,3-dioxolan-2-yl, $R^{11}$ is a trifluoromethyl group or a phenyl group (optionally substituted on the phenyl ring with one to three halogen atoms), and X is an oxygen atom.

Among the N-pyridylpiperidine compounds of the invention represented by Formula (1a), those wherein any one of $R^4$, $R^5$, $R^6$, and $R^7$ is a $C_{1-4}$ alkyl group that is positioned trans to the X on the 4-position of the piperidine ring are preferable. The compounds wherein the $C_{1-4}$ alkyl group is a methyl group are particularly preferable.

Method of Producing the N-pyridylpiperidine Compound

The N-pyridylpiperidine compound represented by Formula (1) can be produced, for example, by any one of the methods shown in Reaction Schemes-1 to -5 below.

Reaction Scheme-1

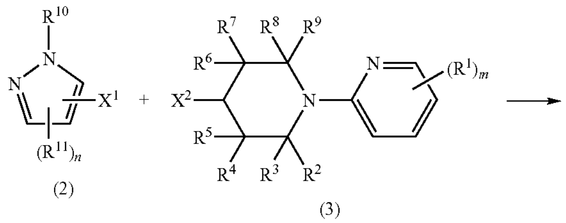

(2)

(3)

-continued

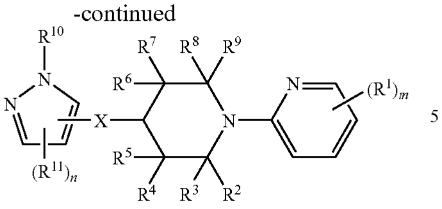

(1)

wherein $R^1$, $R^2$, $R^3$, $R^5$, $R^6$, $R^7$, $R^8$, $R^9$, $R^{10}$, $R^{11}$, X, $X^1$, $X^2$, m, and n as defined above.

In the method shown in Reaction Scheme-1, a pyrazole compound of Formula (2) and a piperidine compound of Formula (3) are reacted in a solvent in the presence of a base to produce an N-pyridylpiperidine compound represented by Formula (1).

The solvent used in the reaction of the compound of Formula (2) and the compound of Formula (3) may be any of a wide variety of known solvents that are inert to this reaction. Examples of such solvents include aliphatic or alicyclic hydrocarbons such as hexane, cyclohexane, and heptane; aromatic hydrocarbons such as benzene, chlorobenzene, toluene, and xylene; halogenated hydrocarbons such as methylene chloride, 1,2-dichloroethane, chloroform, and carbon tetrachloride; ethers such as diethyl ether, tetrahydrofuran, and 1,4-dioxane; esters such as methyl acetate and ethyl acetate; ketones such as acetone and methyl ethyl ketone; amides such as N,N-dimethylformamide; nitriles such as acetonitrile and propionitrile; aprotic polar solvents such as dimethyl sulfoxide, N-methylpyrrolidone, and N,N'-dimethylimidazolinone; and the like. Such solvents can be used singly or as a mixture of two or more.

The solvent is usually used in an amount of 1 to 500 part by weight, and preferably 5 to 100 parts by weight, per part by weight of the piperidine compound of Formula (3).

The base used for the reaction of the compound of Formula (2) and the compound of Formula (3) may be any known inorganic or organic base. Examples of the inorganic base include alkali metals such as sodium and potassium; alkali metal carbonates such as sodium carbonate, potassium carbonate, and sodium bicarbonate; alkali metal hydroxides such as sodium hydroxide and potassium hydroxide; alkali metal hydrides such as sodium hydride and potassium hydride; and the like. Examples of such organic bases include alkali metal alkoxides such as sodium methoxide, sodium ethoxide, and potassium tert-butoxide; amines such as triethylamine, diisopropylamine, and pyridine; and the like. Such bases can be used singly or as a mixture of two or more.

The base is usually used in an amount of 0.1 to 100 equivalents, preferably 0.5 to 5 equivalents, and more preferably 1 to 1.5 equivalents, per equivalent of the piperidine compound represented by Formula (3).

The ratio of the pyrazole compound represented by Formula (2) to the piperidine compound represented by Formula (3) can be suitably selected from a wide range. The pyrazole compound of Formula (2) is preferably used in an amount of at least 0.5 moles, and more preferably 0.8 to 1.5 moles, per mole of the piperidine compound of Formula (3).

The reaction can usually be carried out at a temperature in the range of −78° C. to the boiling point of the solvent used. The reaction temperature is preferably 0° C. to the boiling point temperature of the solvent used. The reaction is more preferably carried out while heating under reflux.

The reaction time varies depending on the reaction temperature, etc., and thus cannot be completely specified. However, the reaction is usually completed in about 0.5 to about 24 hours.

Reaction Scheme-2

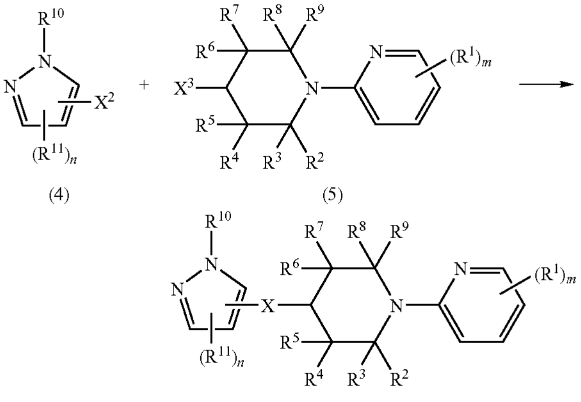

(4) (5) (1)

(wherein $R^1$, $R^2$, $R^3$, $R^4$, $R^5$, $R^6$, $R^7$, $R^8$, $R^9$, $R^{10}$, $R^{11}$, X, $X^2$, $X^3$, m and n are as defined above).

In the method shown in Reaction Scheme-2, a pyrazole compound of Formula (4) and a piperidine compound of Formula (5) are reacted in the presence of a base in a solvent to produce an N-pyridylpiperidine compound represented by Formula (1).

The solvent used for the reaction of the compound of Formula (4) and the compound of Formula (5) may be any of a wide variety of known solvents that are inert to this reaction. For example, any solvent that can be used for the reaction of the compound of Formula (2) and the compound of Formula (3) can be used. Such solvents can be used singly or as a mixture of two or more.

The solvent is usually used in an amount of about 1 to about 500 part by weight, and preferably about 5 to about 100 parts by weight, per part by weight of the piperidine compound of Formula (5).

The base used for the reaction of the compound of Formula (4) and the compound of Formula (5) may be any known inorganic or organic base. For example, any base that can be used for the reaction of the compound of Formula (2) and the compound of Formula (3) can be used. Such bases can be used singly or as a mixture of two or more.

The base is usually used in an amount of 0.1 to 100 equivalents, preferably 0.5 to 5 equivalents, and more preferably 1 to 1.5 equivalents, relative to the piperidine compound of Formula (5).

The proportion of the pyrazole compound of Formula (4) to the piperidine compound of Formula (5) can be suitably selected from a wide range. The pyrazole compound of Formula (4) is preferably used in an amount of at least 0.5 moles, and more preferably 0.8 to 1.5 moles, per mole of the piperidine compound of Formula (5).

The reaction can usually be carried out at a temperature in the range of −78° C. to the boiling point of the solvent used. The reaction temperature is preferably 0° C. to the boiling point temperature of the solvent used. The reaction is more preferably carried out while heating under reflux.

The reaction time varies depending on the reaction temperature, etc., and thus cannot be completely specified. The reaction is usually completed in about 0.5 to about 24 hours.

Reaction Scheme-3

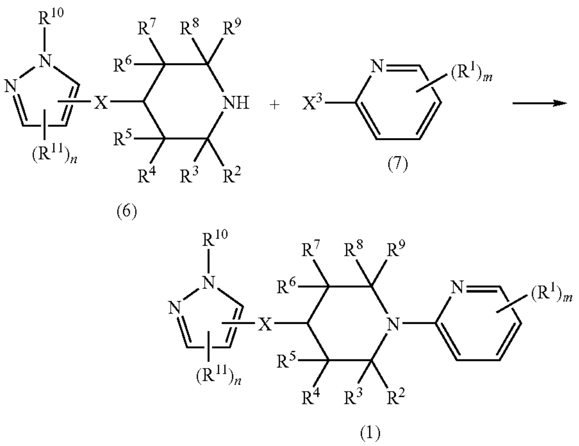

(6) (7) (1)

wherein $R^1$, $R^2$, $R^3$, $R^4$, $R^5$, $R^6$, $R^7$, $R^8$, $R^9$, $R^{10}$, X, $X^3$, m, and n are as defined above.

In the method shown in Reaction Scheme-3, a piperidine compound of Formula (6) and a pyridine compound of Formula (7) are reacted in a solvent in the presence of a base to produce an N-pyridylpiperidine compound represented by Formula (1).

The solvent used for the reaction of the compound of Formula (6) and the compound of Formula (7) may be any of a wide variety of known solvents that are inert to this reaction. For example, any solvent that can be used for the reaction of the compound of Formula (2) and the compound of Formula (3) can be used. Such solvents can be used singly or as a mixture of two or more.

The amount of solvent is usually 1 to 500 parts by weight, and preferably 5 to 100 parts by weight, per part by weight of the piperidine compound of Formula (6).

The base used in the reaction of the compound of Formula (6) and the compound of Formula (7) may be any known inorganic or organic base. For example, any solvent that can be used for the reaction of the compound of Formula (2) and the compound of Formula (3) can be used. Such solvents can be used singly or as a mixture of two or more.

The base is usually used in an amount of 0.1 to 100 equivalents, preferably 0.5 to 5 equivalents, and more preferably 1 to 1.5 equivalents, per equivalent of the piperidine compound of Formula (6).

The ratio of the pyrazole compound of Formula (6) to the piperidine compound of Formula (7) can be suitably selected from a wide range. The piperidine compound of Formula (7) is preferably used in an amount of at least 0.5 moles, and more preferably 0.8 to 1.5 moles, per mole of the pyrazole compound of Formula (6).

The reaction can usually be carried out at a temperature in the range of −78° C. to the boiling point of the solvent used. The reaction temperature is preferably 0° C. to the boiling point temperature of the solvent used. The reaction is more preferably carried out while heating under reflux.

The reaction time varies depending on the reaction temperature, etc. and thus cannot be completely specified. The reaction is usually completed in about 0.5 to about 24 hours.

The N-pyridylpiperidine compound represented by Formula (1a) can also be produced by the method shown in Reaction Scheme-4 below.

Reaction Scheme-4

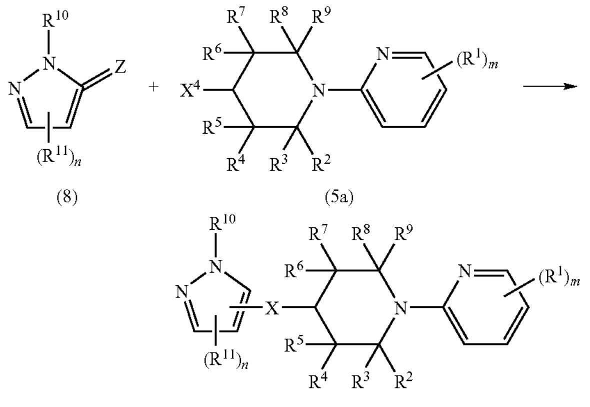

(8) (5a) (1a)

wherein $R^1$, $R^2$, $R^3$, $R^4$, $R^5$, $R^6$, $R^7$, $R^8$, $R^9$, $R^{10}$, $R^{11}$, X, $X^1$, $X^2$, $X^3$, m and n are as defined above, Z is an oxygen atom or a sulfur atom, $X^4$ is $X^2$ or $X^3$, and $X^2$ and $X^3$ are as defined above.

In the method shown in Reaction Scheme-4, a pyrazolone compound of Formula (8) and a piperidine compound of Formula (5a) are reacted in a solvent in the presence of a base to produce an N-pyridylpiperidine compound represented by Formula (1a).

The piperidine compound of Formula (5a) is a compound represented by Formula (3) or a compound represented by Formula (5).

The solvent used for the reaction of the compound of Formula (8) and the compound of Formula (5a) may be any of a wide variety of known solvents that are inert to this reaction. For example, any solvent that can be used for the reaction of the compound of Formula (2) and the compound of Formula (3) can be used. Such solvents can be used singly or as a mixture of two or more.

The solvent is usually used in an amount of 1 to 500 parts by weight, and preferably 5 to 100 parts by weight, per part by weight of the piperidine compound of Formula (5a).

The base used for the reaction of the compound of Formula (8) and the compound of Formula (5a) may be any known inorganic or organic base. For example, all solvents that can be used for the reaction of the compound of Formula (2) and the compound of Formula (3) can be used. Such solvents can be used singly or as a mixture of two or more.

The base is usually used in an amount of 0.1 to 100 equivalents, preferably 0.5 to 5 equivalents, and more preferably 1 to 1.5 equivalents, per equivalent of the piperidine compound of Formula (5a).

The ratio of the pyrazolone compound represented by Formula (8) to the piperidine compound of Formula (5a) can be suitably selected from a wide range. The pyrazolone compound of Formula (8) is preferably used in an amount of 0.5 moles or more, and more preferably 0.8 to 1.5 moles, per mole of the piperidine compound of Formula (5a).

The reaction can usually be carried out at a temperature in the range of −78° C. to the boiling point of the solvent used. The reaction temperature is preferably 0° C. to the boiling point temperature of the solvent used. The reaction is more preferably carried out while heating under reflux.

The reaction time varies depending on the reaction temperature, etc., and thus cannot be completely specified. The reaction is usually completed in about 0.5 to about 24 hours.

Among the N-pyridylpiperidine compounds represented by Formula (1), Compound (1i) wherein $R^{10}$ is $R^{10a}$ can be produced by the method shown in Reaction Scheme-5 below using the corresponding Compound (1h) wherein $R^{10}$ is a hydrogen atom.

Reaction Scheme-5

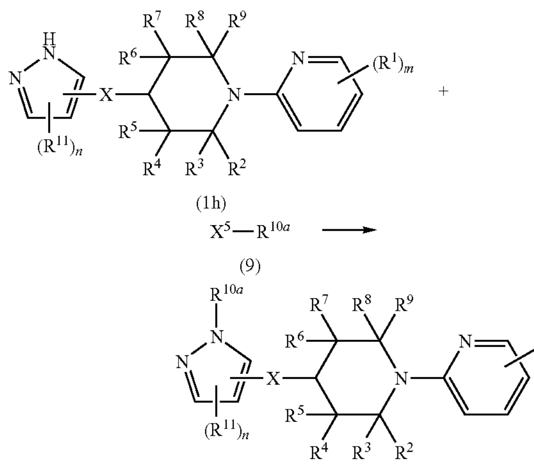

(1h) (9) (1i)

wherein $R^1$, $R^2$, $R^3$, $R^4$, $R^5$, $R^6$, $R^7$, $R^8$, $R^9$, $R^{10a}$, $R^{11}$, X, $X^5$, m and n are as defined above.

In Reaction Scheme-5, an N-pyridylpiperidine compound of Formula (1h) is substituted on the 1-position of the pyrazole ring with a compound of Formula (9) in a solvent in the presence of a base to produce an N-pyridylpiperidine compound represented by Formula (1i).

The solvent used for the reaction of the N-pyridylpiperidine compound of Formula (1h) and the compound of Formula (9) may be any of a wide variety of known solvents that are inert to this reaction. For example, any solvent that can be used for the reaction of the compound of Formula (2) and the compound of Formula (3) can be used. Such solvents can be used singly or as a mixture of two or more.

The solvent is usually used in an amount of about 1 to about 500 part by weight, and preferably about 5 to about 100 parts by weight, per part by weight of the N-pyridylpiperidine compound of Formula (1h).

The base used for the reaction of the compound of Formula (1h) and the compound of Formula (9) may be any known inorganic or organic base. For example, all bases that can be used for the reaction of the compound of Formula (2) and the compound of Formula (3) can be used. Such bases can be used singly or as a mixture of two or more.

The base is usually used in an amount of 0.1 to 100 equivalents, preferably 0.5 to 5 equivalents, and more preferably 1 to 1.5 equivalents, per equivalent of the N-pyridylpiperidine compound of Formula (1h).

The proportion of the compound of Formula (9) to the N-pyridylpiperidine compound of Formula (1h) can be suitably selected from a wide range. The pyrazole compound of Formula (9) is preferably used in an amount of 0.5 moles or more, and more preferably 0.8 to 1.5 moles, per mole of the N-pyridylpiperidine compound of Formula (1h).

The reaction can usually be carried out at a temperature in the range of −78° C. to the boiling point of the solvent used. The reaction temperature is preferably 0° C. to the boiling point temperature of the solvent used. The reaction is more preferably carried out while heating under reflux.

The reaction time may vary depending on the reaction temperature, etc., and thus cannot be completely specified. The reaction is usually completed in about 0.5 to about 24 hours.

In the reaction, the N-pyridylpiperidine compound of Formula (1h) may exist as tautomers that have different arrangements on the pyrazole ring. For example, an N-pyridylpiperidine compound of Formula (1a) and an N-pyridylpiperidine compound of Formula (1b) that is isomeric therewith may be formed. These isomers can be easily isolated by purification means, such as column chromatography.

In Reaction Scheme-5, the piperidine compound used as a starting material of Formula (1h) can be produced by any one of the methods described in Reaction Schemes-1 to -4. The compound of Formula (9) to be used may be a commercially available product or can be easily produced by a known method.

In the above Reaction Schemes-1, -2, and -4, all the pyrazole compounds of Formulas (2) and (4) and pyrazolone compound of Formula (8) used as starting materials are known compounds that are easily available, or can be easily produced according to known methods, such as the methods described in "Dai-yukikagaku, vol. 15, Heterocyclic Compounds II", 6th Edition, 1965, pages 258 to 317, and "The Chemistry of Heterocyclic Compounds Vol. 20. Pyrazolones, Pyrazolidones and Derivatives", Richard H. Wiley, Paul Wiley, Interscience Publishers, London UK, 1964.

A pyrazolone compound of Formula (8) and a pyrazole compound represented by Formula (4a) below may exist as keto-enol tautomers.

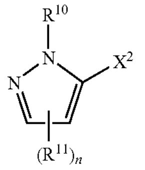

(4a)

wherein $R^{10}$, $R^{11}$, $X^2$, and n are as defined above.

The piperidine compound of Formula (3) and the piperidine compound of Formula (5) are known compounds, or can be easily produced by known methods. The piperidine compound of Formula (3) and the piperidine compound of Formula (5) can be produced, for example, by reacting the pyridine compound of Formula (7) with the piperidine compound of Formula (10)

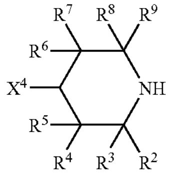

(10)

wherein $R^2$, $R^3$, $R^4$, $R^5$, $R^6$, $R^7$, $R^8$, $R^9$, and $X^4$ may be as defined above. This reaction can be carried out, for example, according to the method described in Synthesis, 606 (1981), J. Chem. Soc., C., 3693 (1971).

The piperidine compound of Formula (10) and the pyridine compound represented by Formula (7) are known compounds, or can be easily produced by known methods.

The piperidine compound of Formula (6) can be easily produced, for example, by the method shown in Reaction Scheme-6.

Reaction Scheme-6

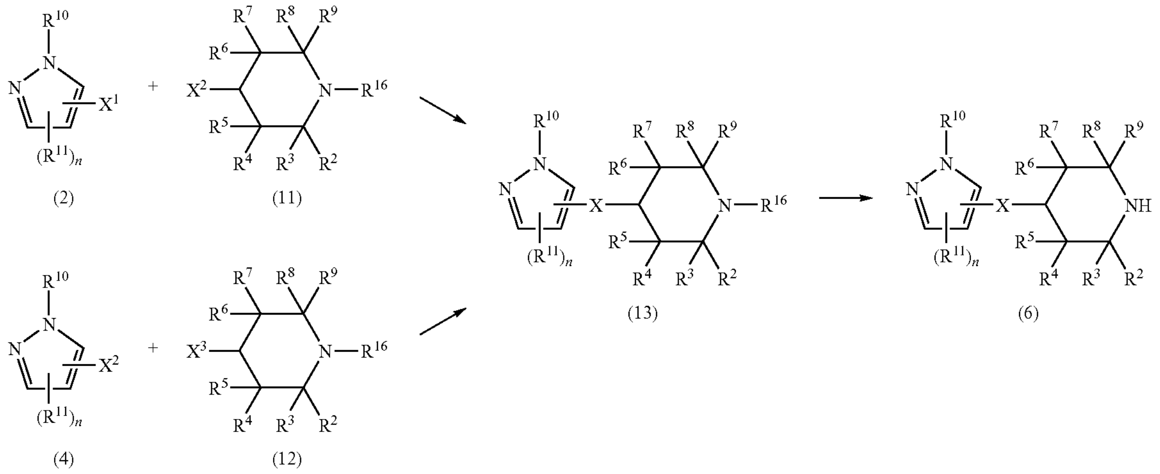

(wherein $R^2$, $R^3$, $R^4$, $R^5$, $R^6$, $R^7$, $R^8$, $R^9$, $R^{10}$, $R^{11}$, X, $X^1$, $X^2$, $X^3$, and n are as defined above, and $R^{16}$ is a methyl group or a benzyl group.)

According to the method shown in Reaction Scheme-5, a pyrazole compound of Formula (2) and a piperidine compound of Formula (11), or a pyrazole compound of Formula (4) and a piperidine compound of Formula (12) are reacted to produce a piperidine compound of Formula (13). Subsequently, the substituent $R^{16}$ is removed from the piperidine skeleton of the piperidine compound of Formula (13) to produce a piperidine compound of Formula (6).

The piperidine compounds of Formulas (11) and (12) are known compounds, or can be easily produced by known methods.

The reaction of the pyrazole compound of Formula (2) and the piperidine compound of Formula (11) can be carried out under the same reaction conditions as the reaction of the compounds of Formulas (2) and (3) shown in Reaction Scheme-1.

The reaction of the pyrazole compound of Formula (4) and the piperidine compound of Formula (12) can be carried out under the same reaction conditions as the reaction of the compounds of Formulas (4) and (5) shown in Reaction Scheme-2.

The reaction for removing the substituent $R^{16}$ from the piperidine skeleton of the piperidine compound of Formula (13) can be carried out under known demethylation or debenzylation conditions, such as the reaction conditions described in WO 2005/095380, WO96/37484, U.S. Pat. No. 5,569,664, etc.

The compounds obtained in the above reactions can be easily isolated by usual isolation means, such as organic solvent extraction, chromatography, recrystallization, distillation, and like methods, and can be further purified by usual purification means.

The N-pyridylpiperidine compound of the invention represented by Formula (1) can be used for control of agricultural pests, and preferably used for control of insect pests and mites, such as Lepidoptera, Hemiptera, Thysanoptera, and Coleoptera.

The N-pyridylpiperidine compound of the invention represented by Formula (1) exhibits excellent mite-control effects, even when used in a small amount. Examples of the mite include plant parasitic mites in various fields of agriculture and horticulture. Specific examples thereof include spider mites such as *Tetranychus urticae* (two-spotted spider mite), *Panonychus citri* (citrus red mite), *Tetranychus kanzawai* (Kanzawa spider mite), and *Panonychus ulmi* (European red mite); rust mites such as *Aculops pelekassi* (pink citrus rust mite), *Phyllocoptruta citri* Soliman et Abou-Awad, *Aculops lycopersici* (tomato russet mite), and *Eriophyes chibaensis* (Japanese pear rust mite); dust mites such as *Polyphagotarsonemus latus* (broad mite) and *Phytonemus pallidus* (cyclamen mite); flour mites such as *Tyrophagus putrescentiae* (mold mite), and *Rhizoglyphus robini* (bulb mite).

Miticide

Miticides are described below as examples of the pest control agents of the invention.

The N-pyridylpiperidine compound of the invention represented by Formula (1) may be used as a miticide without adding any other ingredient. The N-pyridylpiperidine compound is usually mixed with various carriers in the form of solids, liquids, or gases, optionally followed by addition of surfactants and/or other auxiliary materials for preparation of formulations, and then formulated into various forms, such as oil solutions, emulsifiable concentrates, wettable powders, dry flowables, flowables, water soluble powders, granules, fine granules, powders, dusts, sprays, aerosols, microcapsules, fumingants, and the like.

The N-pyridylpiperidine compound of Formula (1) may be incorporated into such formulations in a suitable amount that can be selected from a wide range according to various conditions, such as the type of formulation, place of application, etc. Such formulations usually contain the N-pyridylpiperidine compound in an amount of about 0.01 to about 95 wt. %, and preferably about 0.1 to about 50 wt. %.

Examples of solid carriers used for preparation of such formulations include clays such as kaolin clay, diatomaceous earth, bentonite, Fubasami clay, and acid clay; talcs; inorganic minerals such as ceramics, celite, quartz, sulfur, activated carbon, silica carbonate, and hydrated silica; fine powders and granules such as chemical fertilizers; and the like.

Examples of liquid carriers include water; alcohols such as methanol, and ethanol; ketones such as acetone, and methyl ethyl ketone; aliphatic and alicyclic hydrocarbons such as n-hexane, cyclohexane, kerosene, and light oil; aromatic hydrocarbons such as benzene, toluene, xylene, and naphthalene; esters such as ethyl acetate, and butyl acetate; nitriles such as acetonitrile, and isobutyronitrile; ethers such as diisopropyl ether, and dioxane; acid amides such as N,N-dimethylformamide, N,N-dimethylacetamide, N-methylpyrrolidone, and N,N'-dimethylimidazolinone; halogenated hydrocarbons such as dichloromethane, trichloroethane, and carbon tetrachloride; dimethylsulfoxide; vegetable oils such as soybean oil, and cottonseed oil; and the like.

Examples of gaseous carriers include those generally used in propellants, such as butane gas, LPG (liquefied petroleum gas), dimethyl ether, and carbon dioxide.

Examples of the surfactant include nonionic surfactants and anionic surfactants.

Specific examples of nonionic surfactants include sugar ester nonionic surfactants such as sorbitan fatty acid esters, and polyoxyethylene sorbitan fatty acid esters; fatty acid ester nonionic surfactants such as polyoxyethylene fatty acid esters; vegetable oil nonionic surfactants such as polyoxyethylene castor oil; alcohol nonionic surfactants such as polyoxyethylene alkyl ether; alkylphenol nonionic surfactants such as polyoxyethylene alkyl ($C_{8-12}$) phenyl ether-formalin condensate; polyoxyethylene-polyoxypropylene block polymer nonionic surfactants such as polyoxyethylene-polyoxypropylene block polymers; aromatic nonionic surfactants such as phenyl phenyl ether; and the like.

Specific examples of anionic surfactants include sulfonate anionic surfactants such as alkylbenzene sulfonate, alkyl sulfosuccinate, and allyl sulfonate; sulfate anionic surfactants such as alkyl sulfate, and polyoxyethylene alkyl sulfate; lignin sulfite; and the like.

Examples of auxiliary materials for preparation of formulations include fixing agents, dispersing agents, thickeners, preservatives, anti-freezing agents, stabilizers, adjuvants, and the like.

Examples of fixing agents and dispersing agents include casein, gelatin, polysaccharides (e.g., starch, gum arabic, cellulose derivatives, alginic acid), lignin derivatives, bentonite, sugars, water-soluble synthetic polymers (e.g., polyvinyl alcohol, polyvinylpyrrolidone, polyacrylic acids), and the like.

Examples of thickeners include water-soluble polymer compounds, such as xanthane gum, carboxymethyl cellulose, high purity bentonite, white carbon, and the like.

Examples of preservatives include sodium benzoate, p-hydroxybenzoic acid ester, and the like.

Examples of anti-freezing agents include ethylene glycol, diethylene glycol, and the like.

Examples of stabilizers include PAP (acidic isopropyl phosphate), BHT (2,6-di-tert-butyl-4-methylphenol), BHA (a mixture of 2-tert-butyl-4-methoxyphenol and 3-tert-butyl-4-methoxyphenol), vegetable oils, mineral oils, surfactants, fatty acids and esters thereof, and the like.

Examples of adjuvants include soybean oil, corn oil, and like vegetable oils, machine oil, glycerol, polyethylene glycol, and the like.

Such pharmaceutical preparations may be colored with an organic or inorganic dye.

The compound of the invention may be mixed with other agents such as insecticides, nematocides, acaricides, fungicides, herbicides, plant growth regulators, synergists (e.g., piperonyl butoxide), or soil conditioners and formulated in advance as a mixture. Alternatively, the miticide of the invention and such other agents may be used together without mixing them in advance.

The compound of the invention may be used as an agricultural miticide in any suitable amount that can be appropriately selected from a wide range according to various conditions, such as the type of formulation, method of application, time of application, place of application, kind of crop to be protected, and kind of mite to be controlled. The compound is usually used in an amount of about 0.1 to about 1,000 g, and preferably about 10 to about 500 g, per 100 $m^2$ of the area. When the compound of the invention in the form of an emulsifiable concentrate, wettable powder, flowable, or the like is diluted with water, the compound is usually used at a concentration of about 1 to about 1,000 ppm, and preferably about 10 to about 500 ppm. The granules, dusts, and like formulations can be used as is without being diluted.

Effect of the Invention

The N-pyridylpiperidine compounds of the invention represented by Formula (1), N-oxides thereof, or salts of these compounds have pest control activity, such as high miticidal activity against rust mites as well as against spider mites.

Therefore, the N-pyridylpiperidine compounds of the invention represented by Formula (1), N-oxides thereof, or salts of these compounds are suitably used as pest control agents, and particularly preferable for use as miticides.

BEST MODE FOR CARRYING OUT THE INVENTION

The present invention is described in more detail with reference to Production Examples, Formulation Examples, and Test Examples of the compounds of the invention. However, the invention is not limited thereto or thereby.

Production Example 1

Production of 4-[3-(3,5-dichlorophenyl)-1-methylpyrazol-5-yloxy]-1-[5-(trifluoromethyl)-2-pyridyl]-piperidine (Compound No.: 1a-107)

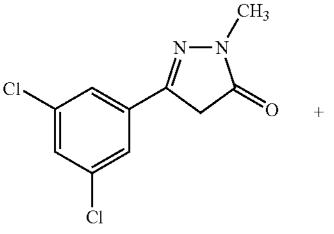

(8-1)

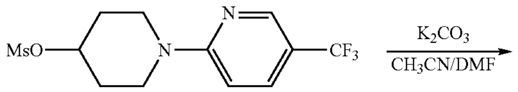

(5-1)

-continued

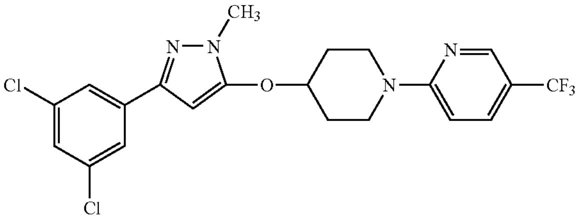

(1a-107)

(wherein MsO is a methanesulfonyloxy group.)

0.58 g of 3-(3,5-dichlorophenyl)-1-methylpyrazolin-5-one (8-1), 0.70 g of 1-[5-(trifluoromethyl)-2-pyridyl]-piperidin-4-ylmethanesulfonate (5-1), and 0.45 g of potassium carbonate were suspended in a mixture of 50 ml of acetonitrile and 20 ml of N,N-dimethylformamide (DMF). The resulting mixture was heated under reflux overnight, cooled to room temperature, and then filtered through celite. After saline was added to the filtrate, the mixture was extracted with diethyl ether. The organic layer was concentrated under reduced pressure. The residue was purified by silica gel column chromatography (n-hexane:ethyl acetate 9:1→4:1) to produce 0.64 g of Compound (1a-107).

Production Example 2

Production of 4-[1-(3-chlorophenyl)-3-(trifluoromethyl)pyrazol-5-yloxy]-1-[5-(trifluoromethyl)-2-pyridyl]-piperidine (Compound No. 1a-62)

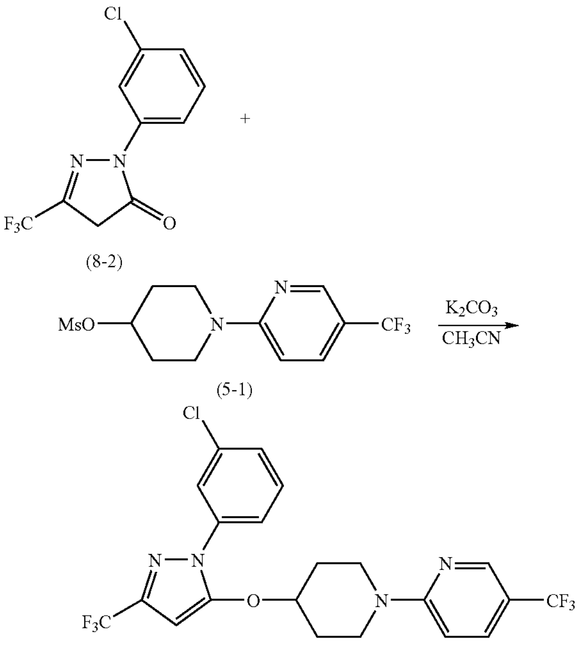

(8-2)

(5-1)

(1a-62)

(wherein MsO is as defined above.)

0.50 g of 1-(3-chlorophenyl)-3-(trifluoromethyl)pyrazolin-5-one (8-2), 0.62 g of compound (5-1), and 0.52 g of potassium carbonate were suspended in 20 ml of acetonitrile. The resulting mixture was heated under reflux overnight, cooled to room temperature, and then filtered through celite.

The filtrate was concentrated under reduced pressure. After water was added to the residue, the mixture was extracted with ethyl acetate. The organic layer was concentrated under reduced pressure. The residue was purified by silica gel column chromatography (n-hexane:ethyl acetate=9:1→4:1) to produce 0.20 g of Compound (1a-62).

Production Example 3

Production of 4-[1-butyl-3-(trifluoromethyl)pyrazol-5-yloxy]-1-[5-(trifluoromethyl)-2-pyridyl]-piperidine (Compound No. 1a-17)

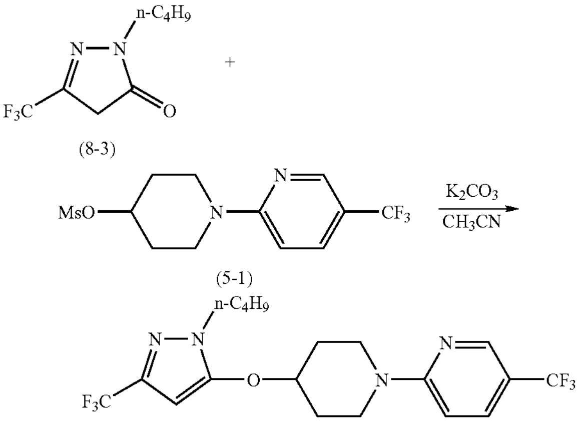

(8-3)

(5-1)

(1a-17)

(wherein MsO is as defined above.)

0.31 g of 1-butyl-3-(trifluoromethyl)pyrazolin-5-one (8-3), 0.49 g of Compound (5-1), and 0.41 g of potassium carbonate were suspended in 20 ml of acetonitrile. The resulting mixture was heated under reflux overnight, cooled to room temperature, and then filtered through celite. The filtrate was concentrated under reduced pressure. The residue was purified by silica gel column chromatography (n-hexane:ethyl acetate=1:0→8:1) to produce 0.42 g of Compound (1a-17).

Production Example 4

Production of 8β-[1-butyl-3-(trifluoromethyl)pyrazol-5-yloxy]-1-[5-(trifluoromethyl)-2-pyridyl]-3-azabicyclo[3.2.1]octane (Compound No. 1f-6)

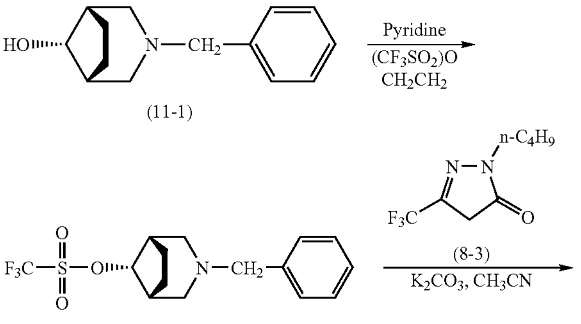

(11-1)

(12-1)

-continued

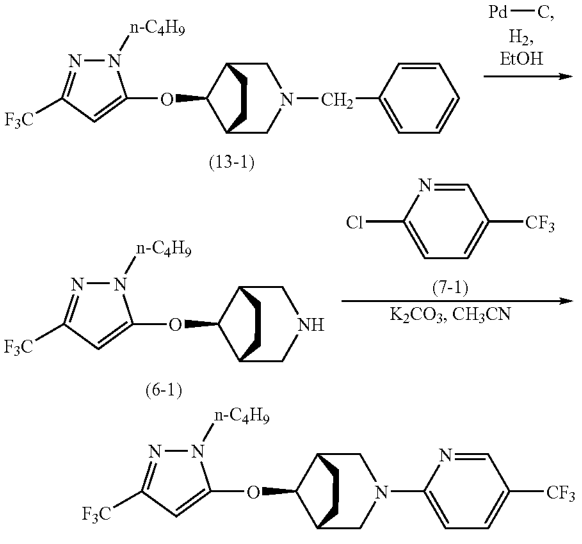

(13-1)

(6-1)

(1f-6)

(1) Production of Compound (12-1)

N-benzyl-3-azabicyclo[3.2.1]octane-8α-ol (10-1) was synthesized according to the method described in J. Med. Chem., 2003, 46, 1456-1464. 5.05 g of compound (11-1) was dissolved in 35 ml of methylene chloride. While the solution was stirred under ice-cooling, 10 ml of a methylene chloride solution containing 13.11 g of trifluoromethanesulfonic anhydride was added dropwise. Subsequently, 10 ml of a methylene chloride solution containing 16.54 g of pyridine was added dropwise, and the mixture was stirred for 1 hour. The reaction mixture was added to a saturated sodium hydrogen carbonate solution, and the mixture was extracted three times with methylene chloride. The organic layer was dried over magnesium sulfate, and filtered. The filtrate was concentrated under reduced pressure. The residue was purified by silica gel column chromatography (n-hexane:ethyl acetate=20:1) to produce 8.29 g of N-benzyl-3-azabicyclo[3.2.1]octane-8α-yl trifluoromethanesulfonate (12-1).

(2) Production of Compound (13-1)

0.89 g of Compound (8-3), a catalytic amount of 18-crown-6, and 2.76 g of potassium carbonate were suspended in 20 ml of DMF. The suspension was stirred at room temperature for 10 minutes. 15 ml of a DMF solution containing 1.00 g of compound (12-1) was added dropwise thereto, and the mixture was stirred at 50° C. for 2 hours. The resulting mixture was poured into 100 ml of water, and extracted three times with 50 ml of ethyl acetate. The organic layer was washed with saline, dried over magnesium sulfate, and then filtered. The filtrate was concentrated under reduced pressure. The residue was purified by silica gel column chromatography (n-hexane:ethyl acetate=50:1→20:1) to produce 0.83 g of 1-benzyl-8,3-[1-butyl-3-(trifluoromethyl)pyrazol-5-yloxy]-3-azabicyclo[3.2.1]octane (13-1).

(3) Production of Compound (1f-6)

Palladium-activated carbon (Pd 10%) (0.1 g) was added to a solution of 0.80 g of Compound (13-1) in 50 ml of ethanol. The mixture was stirred in a hydrogen atmosphere at 50° C. for 15 hours to produce 813-[1-butyl-3-(trifluoromethyl)pyrazol-5-yloxy]-3-azabicyclo[3.2.1]octane (6-1). The reaction solution was filtered through celite, and concentrated under reduced pressure. Water was added to the residue, and the mixture was extracted with ethyl acetate. The organic layer was washed with saline, dried over magnesium sulfate, and then filtered. The filtrate was concentrated under reduced pressure. The residue was dissolved in 50 ml of DMF. Thereto were added 1.36 g of potassium carbonate and 0.71 g of 2-chloro-5-trifluoromethylpyridine (7-1), followed by stirring at 70° C. for 4 hours. The mixture was poured into 100 ml of water, and extracted twice with 50 ml of ethyl acetate. The organic layer was washed with saline, dried over magnesium sulfate, and then filtered. The filtrate was concentrated under reduced pressure. The residue was purified by silica gel column chromatography (n-hexane:ethyl acetate=9:1) to produce 0.10 g of Compound (1f-6).

Production Example 5

Production of 4-[1-methyl-3-(trifluoromethyl)pyrazol-5-yloxy]-1-[5-(trifluoromethyl)-2-pyridyl]-piperidine (Compound No. 1a-14)

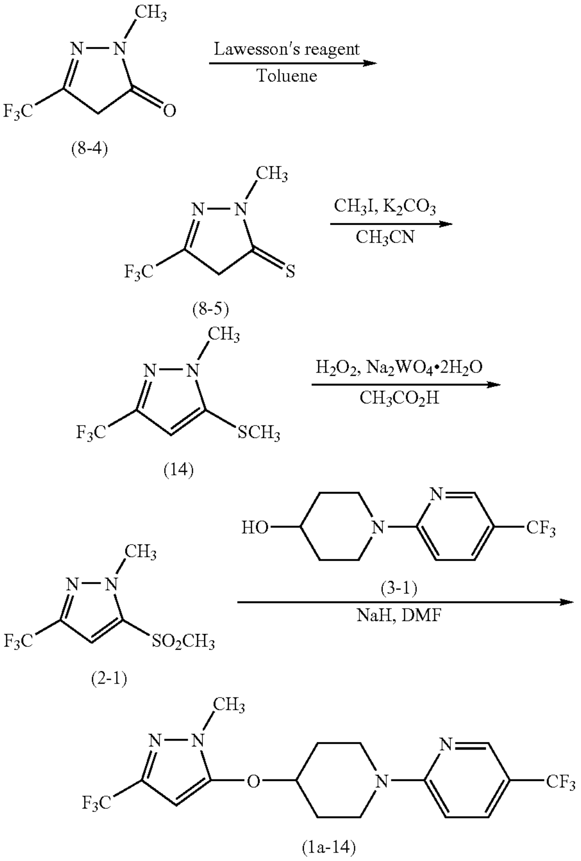

(8-4)

(8-5)

(14)

(2-1)

(1a-14)

(1) Production of Compound (8-5)

5.25 g of 1-methyl-3-(trifluoromethyl)pyrazol-5-one (8-4) and 10.23 g of Lawesson's reagent were suspended in 300 ml of anhydrous toluene. The suspension was heated under reflux for 6 hours. The reaction solution was concentrated under reduced pressure. The residue was purified by silica gel column chromatography (n-hexane:ethyl acetate=2:1) to produce 4.87 g of 1-methyl-3-(trifluoromethyl)pyrazol-5-thione (8-5).

(2) Production of compound (14)

3.87 g of compound (8-5) and 4.40 g of potassium carbonate were suspended in 100 ml of acetonitrile. The suspension was stirred at room temperature for 15 minutes. A solution of 3.62 g of methyl iodide in 10 ml of acetonitrile was added dropwise, and the mixture was stirred at room temperature for 12 hours. The reaction solution was concentrated under reduced pressure. After water was added to the residue, the mixture was extracted with ethyl acetate. The organic layer was dried over magnesium sulfate, and filtered. The filtrate was concentrated under reduced pressure to produce 3.60 g of 1-methyl-5-methylthio-3-(trifluoromethyl)pyrazole (14).

(3) Production of Compound (2-1)

0.25 g of Compounds (14) was dissolved in 20 ml of acetic acid. While stirring, 0.44 g of 30% hydrogen peroxide solution, and 0.04 g of sodium tungstate dihydrate were added sequentially. The mixture was stirred at room temperature for 12 hours, then poured into water, and extracted with ethyl acetate. The organic layer was washed with saturated sodium hydrogencarbonate, dried over magnesium sulfate, and then filtered. The filtrate was concentrated under reduced pressure to produce 0.29 g of 5-methanesulfonyl-1-methyl-3-(trifluoromethyl)pyrazole (2-1).

(4) Production of Compound (1a-14)

0.08 g of 60% sodium hydride was suspended in 1 ml of anhydrous DMF. Thereto was added 5 ml of anhydrous DMF containing 0.39 g of 1-[5-(trifluoromethyl)-2-pyridyl]-piperidin-1-ol (3-1). The mixture was stirred at room temperature for 20 minutes. A solution of 0.29 g of Compound (2-1) in 1 ml of DMF was added dropwise, and the mixture was stirred at 100° C. for 7 hours. The reaction mixture was poured into water, and extracted twice with ethyl acetate. The organic layer was washed with a saline solution, dried over magnesium sulfate, and then filtered. The filtrate was concentrated under reduced pressure. The residue was purified by silica gel column chromatography (n-hexane:ethyl acetate=5:1) to produce 0.20 g of 4-[1-methyl-3-(trifluoromethyl)pyrazol-5-yloxy]-1-[5-(trifluoromethyl)-2-pyridyl]-piperidine (1a-14).

Production Example 6

Production of 3,3-dimethyl-4-[1-methyl-3-(trifluoromethyl)pyrazol-5-yloxy]-1-[5-(trifluoromethyl)-2-pyridyl]-piperidine (Compound No. 1a-215)

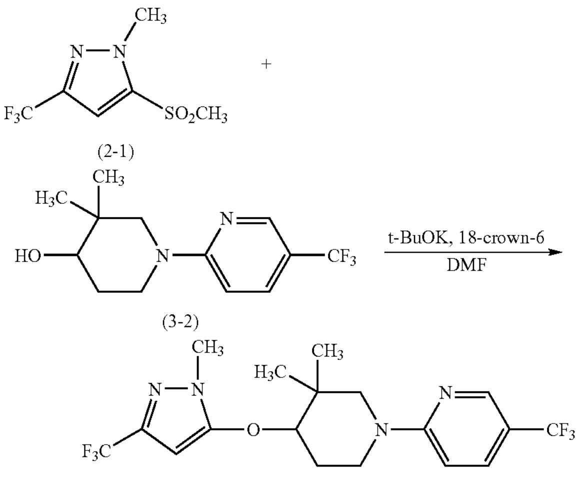

(2-1) (3-2) (1a-215)

0.66 g of Compound (2-1), 0.80 g of 3,3-dimethyl-1-[5-(trifluoromethyl)-2-pyridyl]-piperidin-1-ol (3-2), 0.65 g of t-butoxypotassium, and a catalytic amount of 18-crown-6 were suspended in 10 ml of anhydrous DMF. The suspension was stirred at 100° C. for 15 hours. The reaction mixture was poured into water, and extracted twice with ethyl acetate. The organic layer was washed with water and saline, dried over magnesium sulfate, and then filtered. The filtrate was concentrated under reduced pressure. The residue was purified by silica gel column chromatography (n-hexane:ethyl acetate=5:1) to produce 0.41 g of 3,3-dimethyl-4-[1-methyl-3-(trifluoromethyl)pyrazol-5-yloxy]-1-[5-(trifluoromethyl)-2-pyridyl]-piperidine (1a-215).

Production Example 7

Production of 8β-[1-butyl-3-(trifluoromethyl)pyrazol-5-yloxy]-1-[5-(trifluoromethyl)-2-pyridyl]-3-azabicyclo[3.2.1]octane (Compound No. 1f-6)

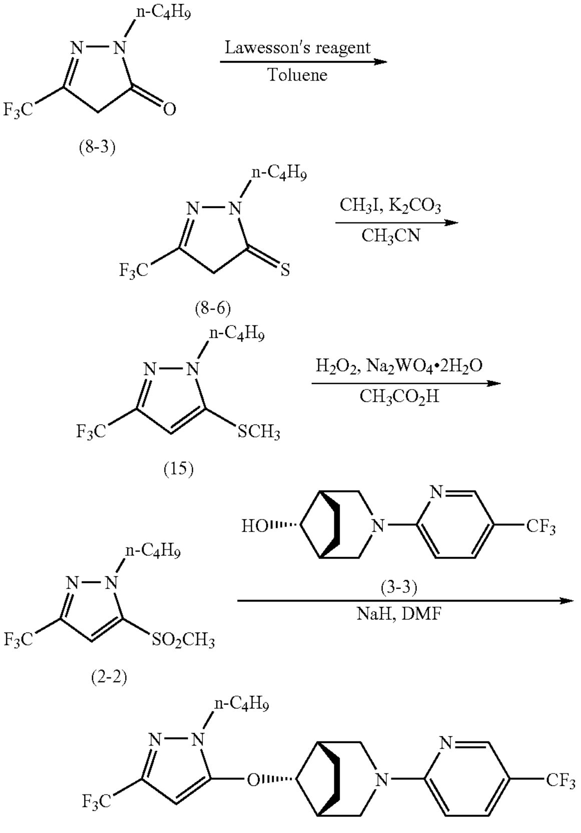

(8-3) (8-6) (15) (3-3) (2-2) (1g-6)

(1) Production of Compound (8-6)

5.00 g of 1-butyl-3-(trifluoromethyl)pyrazol-5-one (8-3), and 7.88 g of Lawesson's reagent were suspended in 300 ml of anhydrous toluene. The suspension was heated under reflux with stirring for 6 hours. The reaction solution was concentrated under reduced pressure. The residue was purified by silica gel column chromatography (n-hexane:ethyl acetate=3:1) to produce 4.35 g of 1-butyl-3-(trifluoromethyl) pyrazol-5-thione (8-6).

(2) Production of Compound (15)

3.35 g of compound (8-6) and 4.07 g of potassium carbonate were suspended in 100 ml of acetonitrile. The suspension was stirred at room temperature for 15 minutes. A solution of 3.35 g of methyl iodide in 10 ml of acetonitrile was added dropwise. The mixture was stirred at room temperature for 12 hours. The reaction solution was concentrated under reduced pressure. After water was added to the residue, the mixture was extracted with ethyl acetate. The organic layer was dried over magnesium sulfate, and filtered. The filtrate was concentrated under reduced pressure to produce 4.40 g of 1-butyl-5-methylthio-3-(trifluoromethyl)pyrazole (15).

(3) Production of Compound (2-2)

4.40 g of Compound (15) was dissolved in 20 ml of acetic acid. While stirring, 6.36 g of a 30% hydrogen peroxide solution and 0.62 g of sodium tungstate dihydrate were added sequentially. The mixture was stirred at room temperature for 4 hours, then poured into water, and extracted with ethyl acetate. The organic layer was washed with saturated sodium hydrogencarbonate, dried over magnesium sulfate, and then filtered. The filtrate was concentrated under reduced pressure to produce 5.00 g of 1-butyl-5-methanesulfonyl-3-(trifluoromethyl)pyrazole (2-2).

(4) Production of Compound (1g-6)

0.08 g of 60% sodium hydride was suspended in 1 ml of anhydrous DMF. 5 ml of anhydrous DMF containing 0.45 g of Compound (3-3) was added to this suspension. The suspension was stirred at room temperature for 15 minutes. A solution of 0.42 g of Compound (2-2) in 1 ml of DMF was added, and the mixture was stirred at 100° C. for 15 hours. The reaction mixture was poured into water, and extracted three times with ethyl acetate. The organic layer was washed with water and saline, dried over magnesium sulfate, and then filtered. The filtrate was concentrated under reduced pressure. The residue was purified by silica gel column chromatography (n-hexane:ethyl acetate=9:1→1:1) to produce 0.23 g of Compound (1g-6).

Production Example 8

Production of trans-3-methyl-4-[4-formyl-1-methyl-3-(trifluoromethyl)pyrazol-5-yloxy]-1-[5-(trifluoromethyl)-2-pyridyl]-piperidine (Compound No. 1a-222)

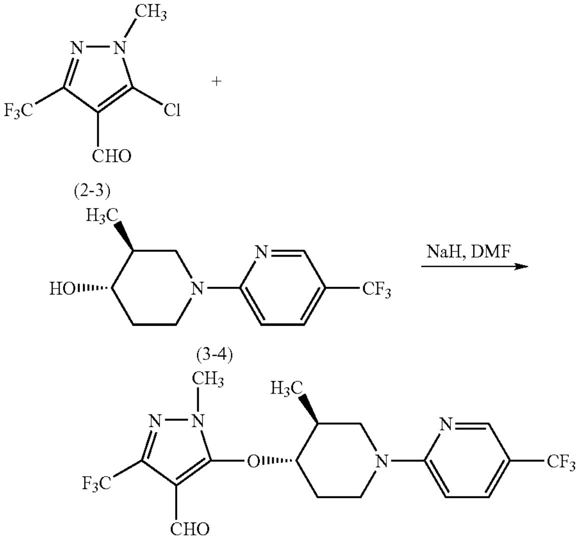

(2-3) (3-4) (1a-222)

A solution of 0.50 g of trans-3-methyl-1-[5-(trifluoromethyl)-2-pyridyl]-piperidin-4-ol (3-4) in 5 ml of anhydrous DMF was added dropwise to 0.08 g of 60% sodium hydride. The mixture was stirred at room temperature for 30 minutes. Thereto was added a solution of 0.41 g of 5-chloro-1-methyl-3-(trifluoromethyl)pyrazol-4-carbaldehyde (2-3) in 5 ml of anhydrous DMF. The mixture was stirred at 100° C. for 15 hours. The reaction mixture was poured into 100 ml of water, and the mixture was extracted twice with 50 ml of ethyl acetate. The organic layer was washed with saline, dried over magnesium sulfate, and then filtered. The filtrate was concentrated under reduced pressure. The residue was purified by silica gel column chromatography (n-hexane:ethyl acetate=5:1) to produce 0.30 g of Compound (1a-222).

Production Example 9

Production of 4-[1-butyl-4-formyl-3-(trifluoromethyl)pyrazol-5-yloxy]-1-[5-(trifluoromethyl)-2-pyridyl]-piperidine (Compound No. 1a-93)

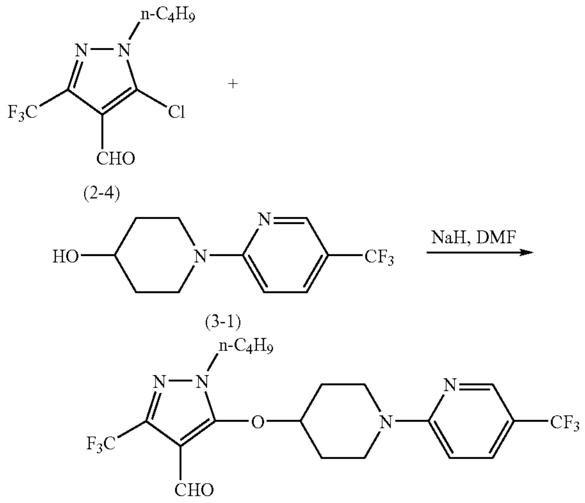

(2-4) (3-1) (1a-93)

0.22 g of 60% sodium hydride was added to a solution of 1.12 g of 1-[5-(trifluoromethyl)-2-pyridyl]-piperidin-1-ol (3-1) in 5 ml of anhydrous DMF. The mixture was stirred at room temperature for 15 minutes. Thereto was added a solution of 1.12 g of 5-chloro-1-butyl-3-(trifluoromethyl)pyrazol-4-carbaldehyde (2-4) in 5 ml of anhydrous DMF. The mixture was stirred at 100° C. for 3 hours. The reaction mixture was poured into 100 ml of water, and extracted twice with 50 ml of ethyl acetate. The organic layer was washed with saline, dried over magnesium sulfate, and then filtered. The filtrate was concentrated under reduced pressure. The residue was purified by silica gel column chromatography (n-hexane:ethyl acetate=5:1) to produce 0.56 g of Compound (1a-93).

Production Example 10

Production of 4-[1-butyl-3-(trifluoromethyl)pyrazol-5-yloxy]-1-[5-(trifluoromethyl)-2-pyridyl]-piperidine (Compound No. 1a-17)

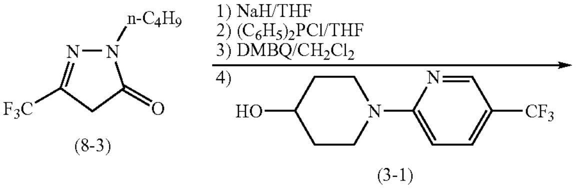

(8-3) (3-1)

-continued

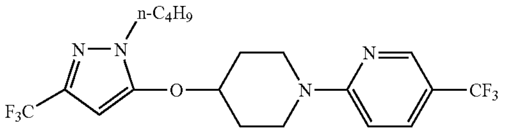

(1a-17)

0.02 g of 60% sodium hydride was added to a solution of 0.10 g of 1-butyl-3-(trifluoromethyl)pyrazol-5-one (8-3) in 3 ml of anhydrous tetrahydrofuran (THF). The mixture was stirred at room temperature for 1 hour, and then cooled to 0° C. A solution of 0.09 g of chlorodiphenylphosphine in 3 ml of anhydrous THF was added dropwise. After stirring the mixture at room temperature for 1 hour, the reaction mixture was concentrated under reduced pressure. The residue was dissolved in 3 ml of dichloromethane. Thereto were added 0.06 g of 2,6-dimethyl-1,4-benzoquinone (DMBQ) and 0.10 g of compound (3-1). The mixture was stirred at room temperature for 18 hours. The reaction solution was concentrated under reduced pressure. The residue was purified by silica gel column chromatography (n-hexane:ethyl acetate=10:1) to produce 0.06 g of Compound (1a-17).

Production Example 11

Production of 4-[1-butyl-3-(trifluoromethyl)pyrazol-5-ylthio]-1-[5-(trifluoromethyl)-2-pyridyl]-piperidine (Compound No. 1a-77)

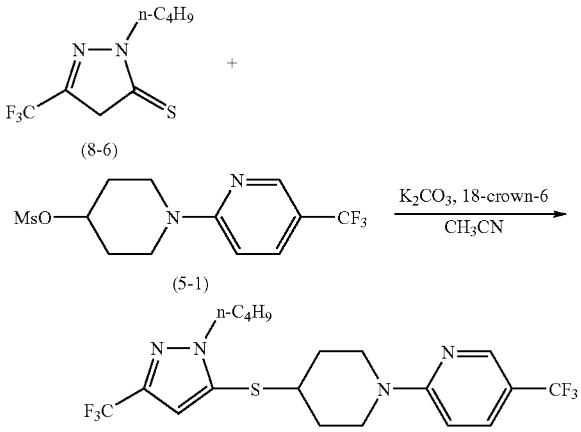

(1a-77)

(wherein MsO is as defined above.)

0.73 g of Compound (8-6), 1.27 g of Compound (5-1), 1.35 g of potassium carbonate, and a catalytic amount of 18-crown-6 were suspended in 20 ml of acetonitrile. The suspension was stirred for 1 hour at room temperature, and then heated under reflux for two and a half hours. The reaction mixture was concentrated under reduced pressure. After water was added to the residue, the mixture was extracted with ethyl acetate. The organic layer was washed with saline, dried over magnesium sulfate, and then filtered. The filtrate was concentrated under reduced pressure. The residue was purified by silica gel column chromatography (n-hexane:ethyl acetate=9:1→6:1) to produce 0.51 g of Compound (1a-77).

Production Example 12

Production of 4-[1-butyl-3-(trifluoromethyl)pyrazol-5-ylsulfonyl]-1-[5-(trifluoromethyl)-2-pyridyl]-piperidine (Compound No. 1a-218)

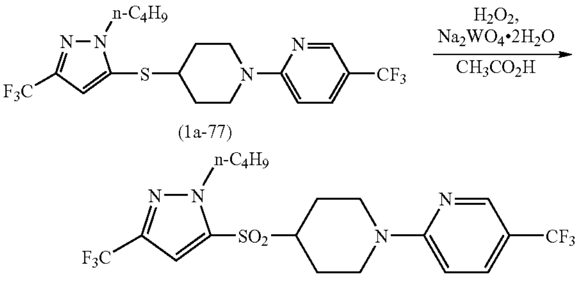

(1a-218)

0.40 g of Compound (1a-77) was dissolved in 20 ml of acetic acid. While stirring, 0.40 g of a 30% hydrogen peroxide solution and 0.03 g of sodium tungstate dihydrate were added sequentially. After stirring the mixture at room temperature for 7 hours, the reaction mixture was poured into water and extracted with ethyl acetate. The organic layer was washed with saturated sodium hydrogencarbonate, dried over magnesium sulfate, and then filtered. The filtrate was concentrated under reduced pressure.

The residue was purified by silica gel column chromatography (n-hexane:ethyl acetate=9:1→3:1) to produce 0.10 g of Compound (1a-218).

Example 13

Production of 4-[3-(trifluoromethyl)pyrazol-5-yloxy]-1-[5-(trifluoromethyl)-2-pyridyl]-piperidine (Compound No.: 1a-245)

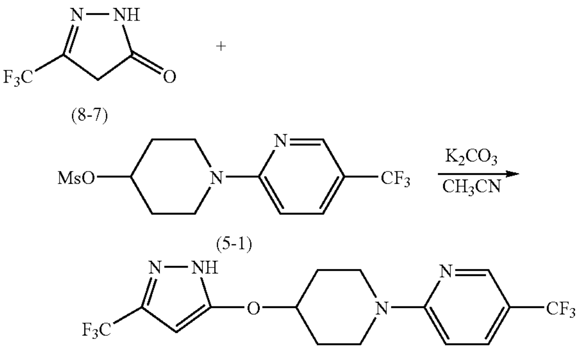

(1a-245)

(wherein MsO is as defined above.)

7.10 g of 3-(trifluoromethyl)pyrazol-5-one (8-7), 10.1 g of 1-[5-(trifluoromethyl)-2-pyridyl]-piperidin-4-yl methanesulfonate (5-1), and 8.61 g of potassium carbonate were suspended in 50 ml of acetonitrile. While heating under reflux, the suspension was stirred for 20 hours. The reaction mixture was concentrated under reduced pressure. After ethyl acetate was added to the residue, the mixture was washed with water and saturated saline. The organic layer was dried over magnesium sulfate, and filtered. The filtrate was concentrated under reduced pressure. The obtained residue was purified by silica gel column chromatography (n-hexane:ethyl acetate=7:1→4:1) to produce 6.05 g of Compound (1a-245).

Example 14

Production of 4-[1-ethoxymethyl-3-(trifluoromethyl)pyrazol-5-yloxy]-1-[5-(trifluoromethyl)-2-pyridyl]-piperidine (Compound No. 1a-262), and 4-[1-ethoxymethyl-5-(trifluoromethyl)pyrazol-3-yloxy]-1-[5-(trifluoromethyl)-2-pyridyl]-piperidine (Compound No. 1b-35)

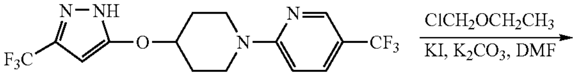

(1a-245)

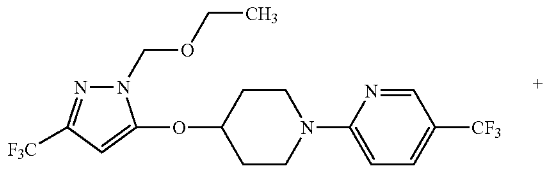

(1a-262)

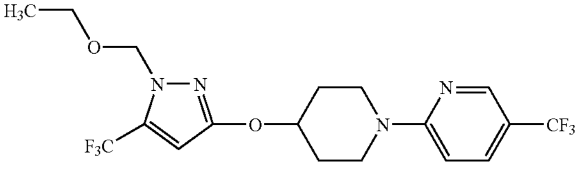

(1b-35)

0.5 g of chloromethyl ethyl ether, 0.73 g of potassium carbonate, and 0.09 g of potassium iodides were added to a solution of 1.0 g of compound (1a-245) in 5 ml of DMF. The mixture was stirred at 100° C. for one day. The reaction mixture was poured into water, and extracted twice with ethyl acetate. The organic layers were combined, washed with water and saturated saline, then dried over magnesium sulfate, and filtered. The filtrate was concentrated under reduced pressure. The residue was purified by column chromatography (n-hexane:ethyl acetate=6:1→4:1) to produce 0.17 g of Compound (1a-262) and 0.30 g of Compound (1b-35).

Example 15

Production of 4-[1-butyryl-3-(trifluoromethyl)pyrazol-5-yloxy]-1-[5-(trifluoromethyl)-2-pyridyl]-piperidine (Compound No. 1a-281)

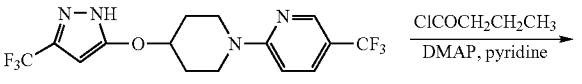

(1a-245)

-continued

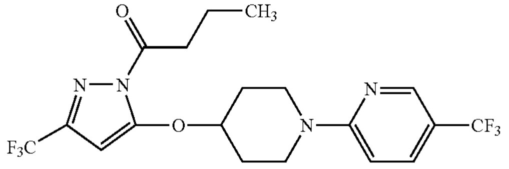

(1a-281)

0.02 g of dimethylaminopyridine (DMAP) was added to a solution of 0.5 g of Compound (1a-245) in 5 ml of pyridine. While cooling with ice, 0.17 g of butyryl chloride was added dropwise. The mixture was stirred at room temperature for 2 hours, and concentrated under reduced pressure. After water was added to the residue, the mixture was extracted with ethyl acetate. The organic layer was washed with water and saturated saline, then dried over magnesium sulfate, and filtered. The filtrate was concentrated under reduced pressure. The residue was purified by gel column chromatography (n-hexane:ethyl acetate=9:1→4:1) to produce 0.30 g of Compound (1a-281).

Example 16

Production of 4-[1-ethoxycarbonyl-3-(trifluoromethyl)pyrazol-5-yloxy]-1-[5-(trifluoromethyl)-2-pyridyl]-piperidine (Compound No.: 1a-288)

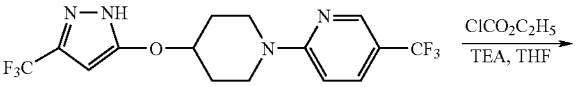

(1a-245)

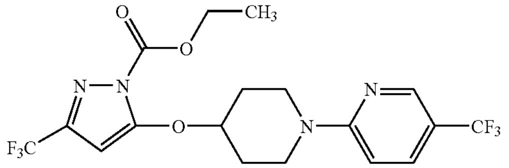

(1a-288)

0.18 g of ethyl chloroformate was added to a solution of 0.5 g of Compound (1a-245) in 10 ml of THF. While cooling with ice, 0.2 g of triethylamine (TEA) was added dropwise. The obtained mixture was stirred at 0° C. for 1 hour. Subsequently, the mixture was poured into water, and extracted with ethyl acetate. The organic layer was washed with water and saturated saline, dried over magnesium sulfate, and then filtered. The filtrate was concentrated under reduced pressure. The residue was purified by silica gel column chromatography (n-hexane:ethyl acetate=4:1→2:1) to produce 0.56 g of Compound (1a-288).

Example 17

Production of trans-4-[3-(3,5-difluorophenyl)pyrazol-5-yloxy]-3-methyl-1-[5-(trifluoromethyl)-2-pyridyl]-piperidine (Compound No. 1a-296)

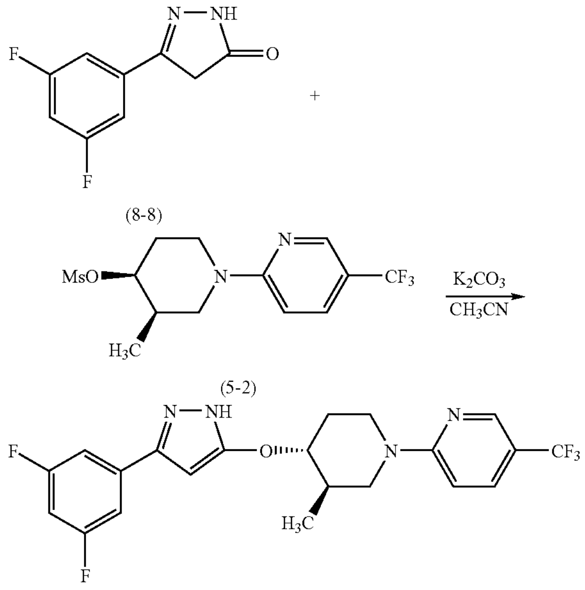

(8-8)

(5-2)

(1a-296)

(wherein MsO is as defined above.)

3.22 g of 3-(3,5-difluorophenyl)pyrazol-5-one (8-8), 4.55 g of trans-3-methyl-1-[5-(trifluoromethyl)-2-pyridyl]-piperidin-4-ylmethanesulfonate (5-2), and 3.63 g of potassium carbonate were suspended in 650 ml of acetonitrile. While heating under reflux, the suspension was stirred for 7 hours. The reaction mixture was concentrated under reduced pressure. After ethyl acetate was added to the residue, the mixture was washed with water and saturated saline. The organic layer was dried over magnesium sulfate, and then filtered. The filtrate was concentrated under reduced pressure. The residue was purified by column chromatography (n-hexane:ethyl acetate=4:1→3:1) to produce 1.51 g of Compound (1a-296).

Example 18

Production of trans-4-[1-(1,3-dioxolan-2-yl)methyl-3-(3,5-difluorophenyl)pyrazol-5-yloxy]-3-methyl-1-[5-(trifluoromethyl)-2-pyridyl]-piperidine (Compound No.: 1a-301), and trans-4-[1-(1,3-dioxolan-2-yl)methyl-5-(3,5-difluorophenyl)pyrazol-3-yloxy]-3-methyl-1-[5-(trifluoromethyl)-2-pyridyl]-piperidine (Compound No. 1b-55)

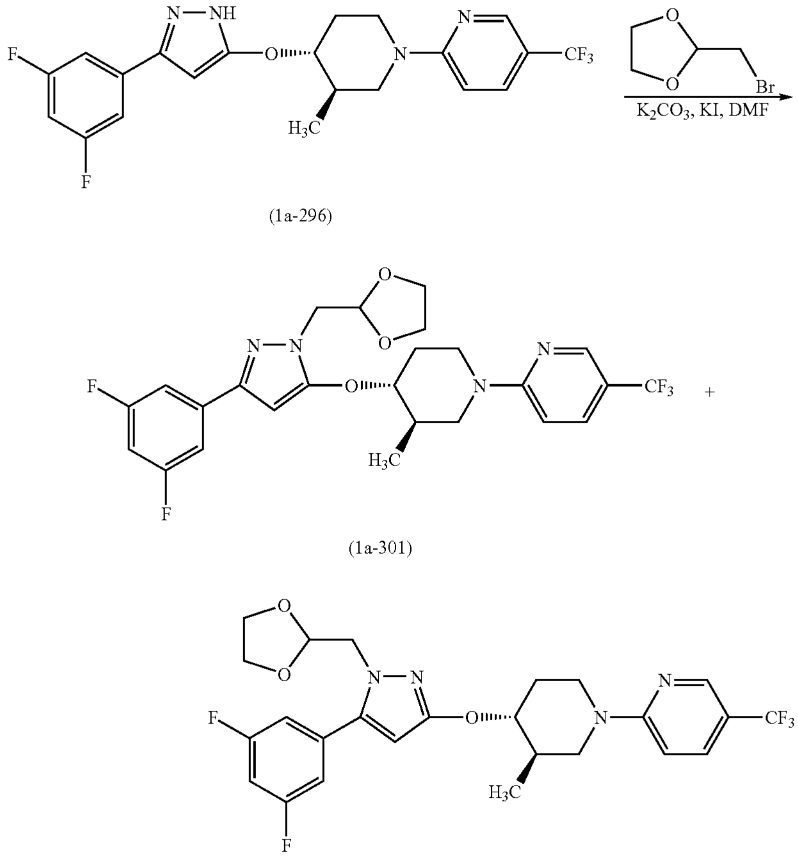

(1a-296)

(1a-301)

(1b-55)

1.4 g of potassium carbonate and 0.2 g of potassium iodide were added to a solution of 0.46 g of compound (1a-296) in 30 ml of DMF. The mixture was stirred at 100° C. for 30 minutes. The obtained mixture was cooled with ice, and a solution of 1.4 g of 2-bromomethyl-1,3-dioxolane in 10 ml of DMF was added. The mixture was stirred at 110° C. for 12 hours. The reaction mixture was poured into water, and extracted 3 times with diethyl ether. The organic layers were combined, washed with water and saturated saline, dried over magnesium sulfate, and filtered. The filtrate was concentrated under reduced pressure. The residue was purified by flash column chromatography (chloroform:n-hexane:ethyl acetate=5:4:1) to produce 0.17 g of Compound (1a-301) and 0.31 g of Compound (1b-55).

Example 19

Production of 8β-[3-(trifluoromethyl)pyrazol-5-yloxy]-1-[5-(trifluoromethyl)-2-pyridyl]-3-azabicyclo[3.2.1]octane (Compound No. 1f-37)

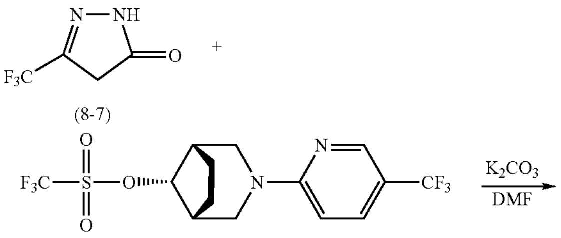

(8-7)

(5-3)

-continued

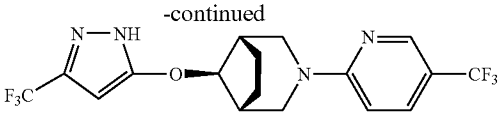

(1f-37)

0.79 g of 3-(trifluoromethyl)pyrazol-5-one (8-7), and a solution of 1.43 g of potassium carbonate in 30 ml of DMF were stirred at room temperature for 5 minutes. To this mixture was added a solution of 1.40 g of 1-[5-(trifluoromethyl)-2-pyridyl]-3-azabicyclo[3.2.1]octane-8α-yl trifluoromethanesulfonate (5-3) in 10 ml of DMF. The mixture was stirred at 50° C. for 16 hours. The reaction mixture was poured into water, and extracted twice with ethyl acetate. The organic layers were combined, washed twice with water, and then washed with saturated saline. The organic layer was dried over magnesium sulfate, and filtered. The filtrate was concentrated under reduced pressure. The residue was purified by silica gel column chromatography (n-hexane:ethyl acetate=4:1) to produce 0.61 g of Compound (1f-37).

Example 20

Production of 8β-[1-(2,2-dimethoxy)ethyl-3-(trifluoromethyl)pyrazol-5-yloxy]-1-[5-(trifluoromethyl)-2-pyridyl]-3-azabicyclo[3.2.1]octane (Compound No. 1f-38) and 8β-[1-(2,2-dimethoxy)ethyl-5-(trifluoromethyl)pyrazol-3-yloxy]-1-[5-(trifluoromethyl)-2-pyridyl]-3-azabicyclo[3.2.1]octane (Compound No. 1b-52)

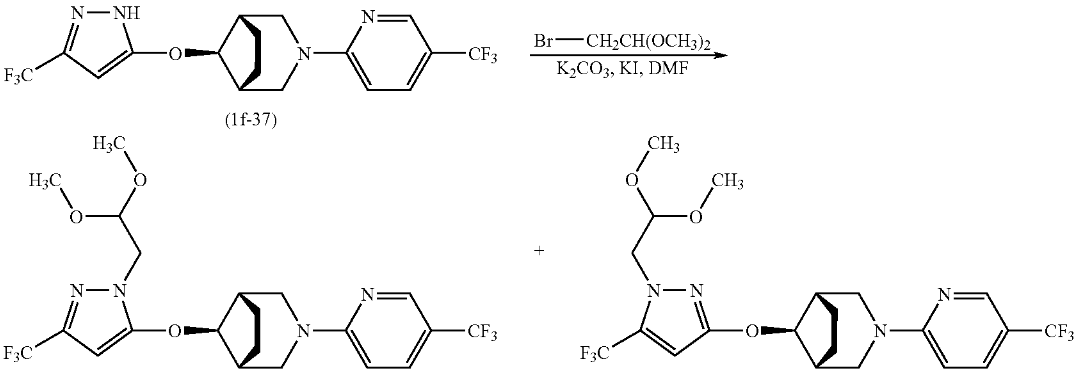

(1f-37)

(1f-38)

(1b-52)

0.58 g of potassium carbonate and 0.1 g of potassium iodides were added to a solution of 0.57 g of Compound (1f-37) in 30 ml of DMF. The mixture was stirred at 100° C. for 30 minutes. The mixture was cooled with ice, and a solution of 0.71 g of 2-bromoacetaldehyde in 10 ml of DMF was added. The mixture was stirred at 100° C. for 7 hours. The reaction mixture was poured into water, and extracted twice with ethyl acetate. The organic layers were combined, washed twice with water, and then washed with saturated saline. The organic layer was dried over magnesium sulfate, and filtered. The filtrate was concentrated under reduced pressure. The residue was purified by column chromatography (n-hexane:ethyl acetate=4:1→3:1) to produce 0.32 g of Compound (1f-38) and 0.19 g of Compound (1b-52).

Example 21

Production of 3α-[3-(3,5-difluorophenyl)pyrazol-5-yloxy]-N-[5-(trifluoromethyl)-2-pyridyl]-8-azabicyclo[3.2.1]octane (Compound No. 1d-40)

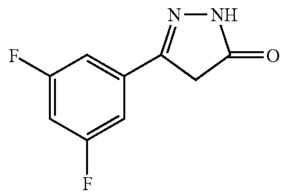

(8-8)

+

-continued

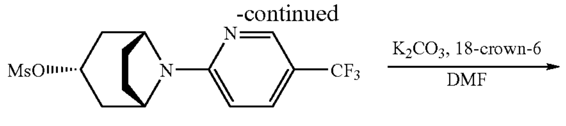

(5-4)

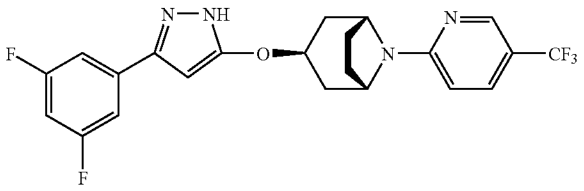

(1d-40)

(wherein MsO is as defined above.)

2.5 g of N-[5-(trifluoromethyl)-2-pyridyl]-8-azabicyclo[3.2.1]octane-3,3-yl methanesulfonate (5-4), 1.5 g of 3-(3,5-difluorophenyl)pyrazol-5-one (8-8), 1.5 g of potassium carbonate, and a catalytic amount of 18-crown-6 were suspended in 50 ml of DMF. The suspension was heated under reflux overnight. An aqueous ammonium chloride solution was added to the reaction mixture, and the mixture was extracted twice with ethyl acetate. The organic layers were combined, washed twice with water, and then washed with saturated saline. The organic layer was dried over magnesium sulfate, and filtered. The filtrate was concentrated under reduced pressure. The residue was purified by silica gel column chromatography (n-hexane:ethyl acetate=2:1) to produce 2.0 g of Compound (1d-40).

Example 22

Production of 3α-[1-(1,3-dioxolan-2-yl)methyl-3-(3,5-difluorophenyl)pyrazol-5-yloxy]-N-[5-(trifluoromethyl)-2-pyridyl]-8-azabicyclo[3.2.1]octane (Compound No. 1d-42)

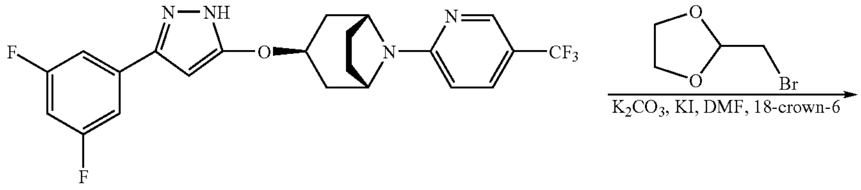

(1d-40)

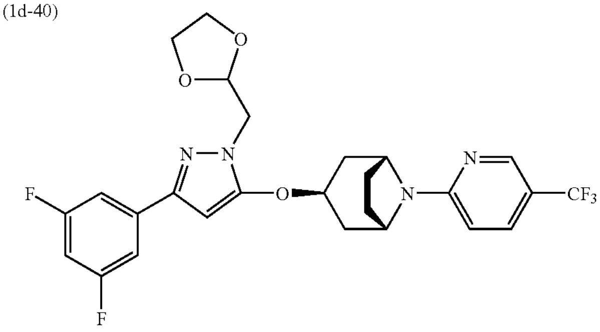

(1d-42)

A solution of 0.93 g of 2-bromomethyl-1,3-dioxolane in 10 ml of DMF was added to a solution of 0.5 g of Compound (1d-40), 0.23 g of potassium carbonate, 0.20 g of potassium iodide, and a catalytic amount of 18-crown-6 in 30 ml of DMF. While heating under reflux, the mixture was stirred overnight. An aqueous ammonium chloride solution was added to the reaction mixture, and the mixture was extracted twice with ethyl acetate. The organic layers were combined, washed twice with water, and then washed with saturated saline. The organic layer was dried over magnesium sulfate, and filtered. The filtrate was concentrated under reduced pressure. The residue was purified by flash column chromatography (n-hexane:ethyl acetate=5:1) to produce 0.25 g of Compound (1d-42).

Tables 1 to 66 below show compounds produced according to the methods described in the above Production Examples, and physical properties of the compounds. The abbreviations used in Tables 1 to 66 are explained below.

Me: methyl, Et: ethyl, n-Pr: n-propyl, i-Pr: isopropyl, c-Pr: cyclopropyl, n-Bu: n-butyl, i-Bu: isobutyl, s-Bu: sec-butyl, t-Bu: text-butyl, c-Bu: cyclobutyl, n-Pen: n-pentyl, i-Pen: isopentyl, c-Pen: cyclopentyl, n-Hex: n-hexyl, c-Hex: cyclohexyl, n-Hept: N-heptyl, c-Hept: cycloheptyl, n-Oct: n-octyl, c-Oct: cyclooctyl, n-Non: n-nonyl, n-Dec: n-decyl, Ph: phenyl, Bn: benzyl, Py: pyridyl.

The $^1$H-NMR spectra were determined using tetramethylsilane (TMS) as a reference material.

TABLE 1

(1a)

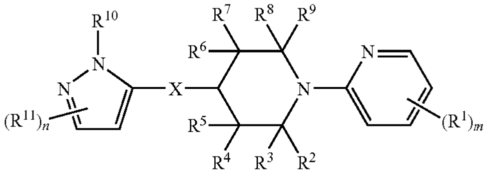

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-1 | 5-$CF_3$ | H | H | H | H | H | H | H | H | Me | 3-Me | O | |
| 1a-2 | 5-$CF_3$ | H | H | H | H | H | H | H | H | n-Bu | 3-Me | O | |
| 1a-3 | 5-$CF_3$ | H | H | H | H | H | H | H | H | 3-Cl-Ph | 3-Me | O | |
| 1a-4 | 5-$CF_3$ | H | H | H | H | H | H | H | H | 3-$CF_3$-Ph | 3-Me | O | |
| 1a-5 | 5-$CF_3$ | H | H | H | H | H | H | H | H | 3-Me-Ph | 3-Me | O | |
| 1a-6 | 5-$CF_3$ | H | H | H | H | H | H | H | H | n-Bu | 3-Me<br>4-Cl | O | |
| 1a-7 | 5-$CF_3$ | H | H | H | H | H | H | H | H | n-Bu | 3-Me<br>4-Br | O | |
| 1a-8 | 5-$CF_3$ | H | H | H | H | H | H | H | H | n-Bu | 3-Me<br>4-CN | O | |
| 1a-9 | 5-$CF_3$ | H | H | H | H | H | H | H | H | n-Bu | 3-Me<br>4-$CO_2$Et | O | |
| 1a-10 | 5-$CF_3$ | H | H | H | H | H | H | H | H | n-Bu | 3-Me<br>4-$CONEt_2$ | O | |
| 1a-11 | 5-$CF_3$ | H | H | H | H | H | H | H | H | n-Bu | 3-Me<br>4-CHO | O | |
| 1a-12 | 5-$CF_3$ | H | H | H | H | H | H | H | H | n-Bu | 3-Me<br>4-CHNOMe | O | |
| 1a-13 | 5-$CF_3$ | H | H | H | H | H | H | H | H | n-Bu | 3-Me<br>4-CHNOBn | O | |
| 1a-14 | 5-$CF_3$ | H | H | H | H | H | H | H | H | Me | 3-$CF_3$ | O | |
| 1a-14 | 5-$CF_3$ | H | H | H | H | H | H | H | H | Et | 3-$CF_3$ | O | |
| 1a-16 | 5-$CF_3$ | H | H | H | H | H | H | H | H | n-Pr | 3-$CF_3$ | O | |
| 1a-17 | 5-$CF_3$ | H | H | H | H | H | H | H | H | n-Bu | 3-$CF_3$ | O | |

TABLE 2

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-18 | 5-$CF_3$ | H | H | H | H | H | H | H | H | n-Pen | 3-$CF_3$ | O | |
| 1a-19 | 5-$CF_3$ | H | H | H | H | H | H | H | H | n-Hex | 3-$CF_3$ | O | |
| 1a-20 | 5-$CF_3$ | H | H | H | H | H | H | H | H | n-Hept | 3-$CF_3$ | O | |
| 1a-21 | 5-$CF_3$ | H | H | H | H | H | H | H | H | n-Oct | 3-$CF_3$ | O | |
| 1a-22 | 5-$CF_3$ | H | H | H | H | H | H | H | H | n-Non | 3-$CF_3$ | O | |
| 1a-23 | 5-$CF_3$ | H | H | H | H | H | H | H | H | n-Dec | 3-$CF_3$ | O | |
| 1a-24 | 5-$CF_3$ | H | H | H | H | H | H | H | H | i-Pr | 3-$CF_3$ | O | |
| 1a-25 | 5-$CF_3$ | H | H | H | H | H | H | H | H | i-Bu | 3-$CF_3$ | O | |
| 1a-26 | 5-$CF_3$ | H | H | H | H | H | H | H | H | t-Bu | 3-$CF_3$ | O | |
| 1a-27 | 5-$CF_3$ | H | H | H | H | H | H | H | H | s-Bu | 3-$CF_3$ | O | |
| 1a-28 | 5-$CF_3$ | H | H | H | H | H | H | H | H | $—CH_2CH{=}CH_2$ | 3-$CF_3$ | O | |
| 1a-29 | 5-$CF_3$ | H | H | H | H | H | H | H | H | $—CH_2C{\equiv}CH$ | 3-$CF_3$ | O | |
| 1a-30 | 5-$CF_3$ | H | H | H | H | H | H | H | H | $—CH_2C{\equiv}CCH_3$ | 3-$CF_3$ | O | |
| 1a-31 | 5-$CF_3$ | H | H | H | H | H | H | H | H | $—CH_2CONMe_2$ | 3-$CF_3$ | O | |
| 1a-32 | 5-$CF_3$ | H | H | H | H | H | H | H | H | $—CH_2NO_2$ | 3-$CF_3$ | O | |
| 1a-33 | 5-$CF_3$ | H | H | H | H | H | H | H | H | $—CH_2CN$ | 3-$CF_3$ | O | |
| 1a-34 | 5-$CF_3$ | H | H | H | H | H | H | H | H | $—CH_2CH_2OMe$ | 3-$CF_3$ | O | |
| 1a-35 | 5-$CF_3$ | H | H | H | H | H | H | H | H | $—CH_2CH_2OEt$ | 3-$CF_3$ | O | |
| 1a-36 | 5-$CF_3$ | H | H | H | H | H | H | H | H | $—CH_2CH_2OBn$ | 3-$CF_3$ | O | |
| 1a-37 | 5-$CF_3$ | H | H | H | H | H | H | H | H | $—CH_2$(2-Py) | 3-$CF_3$ | O | |
| 1a-38 | 5-$CF_3$ | H | H | H | H | H | H | H | H | $—CH_2$(3-Py) | 3-$CF_3$ | O | |
| 1a-39 | 5-$CF_3$ | H | H | H | H | H | H | H | H | $—CH_2$(4-Py) | 3-$CF_3$ | O | |
| 1a-40 | 5-$CF_3$ | H | H | H | H | H | H | H | H | 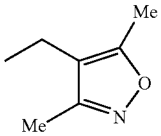 | 3-$CF_3$ | O | |
| 1a-41 | 5-$CF_3$ | H | H | H | H | H | H | H | H | 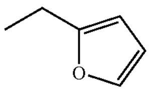 | 3-$CF_3$ | O | |

TABLE 2-continued

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-42 | 5-$CF_3$ | H | H | H | H | H | H | H | H | 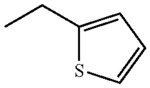 | 3-$CF_3$ | O | |
| 1a-43 | 5-$CF_3$ | H | H | H | H | H | H | H | H | $—CH_2$(c-Pr) | 3-$CF_3$ | O | |

TABLE 3

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-44 | 5-$CF_3$ | H | H | H | H | H | H | H | H | $—CH_2$(c-Hex) | 3-$CF_3$ | O | |
| 1a-45 | 5-$CF_3$ | H | H | H | H | H | H | H | H | $—CH_2CF_3$ | 3-$CF_3$ | O | |
| 1a-46 | 5-$CF_3$ | H | H | H | H | H | H | H | H | $—(CH_2)_3CF_3$ | 3-$CF_3$ | O | |
| 1a-47 | 5-$CF_3$ | H | H | H | H | H | H | H | H | $—(CH_2)_2CH{=}CF_2$ | 3-$CF_3$ | O | |
| 1a-48 | 5-$CF_3$ | H | H | H | H | H | H | H | H | $—(CH_2)_2CF{=}CF_2$ | 3-$CF_3$ | O | |
| 1a-49 | 5-$CF_3$ | H | H | H | H | H | H | H | H | 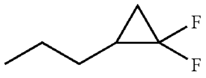 | 3-$CF_3$ | O | |
| 1a-50 | 5-$CF_3$ | H | H | H | H | H | H | H | H | Bn | 3-$CF_3$ | O | |
| 1a-51 | 5-$CF_3$ | H | H | H | H | H | H | H | H | 2-Cl-Bn | 3-$CF_3$ | O | |
| 1a-52 | 5-$CF_3$ | H | H | H | H | H | H | H | H | 3-Cl-Bn | 3-$CF_3$ | O | |
| 1a-53 | 5-$CF_3$ | H | H | H | H | H | H | H | H | 4-Cl-Bn | 3-$CF_3$ | O | |
| 1a-54 | 5-$CF_3$ | H | H | H | H | H | H | H | H | 2,3-$Cl_2$-Bn | 3-$CF_3$ | O | |
| 1a-55 | 5-$CF_3$ | H | H | H | H | H | H | H | H | 2,4-$Cl_2$-Bn | 3-$CF_3$ | O | |
| 1a-56 | 5-$CF_3$ | H | H | H | H | H | H | H | H | 2,5-$Cl_2$-Bn | 3-$CF_3$ | O | |
| 1a-57 | 5-$CF_3$ | H | H | H | H | H | H | H | H | 2,6-$Cl_2$-Bn | 3-$CF_3$ | O | |
| 1a-58 | 5-$CF_3$ | H | H | H | H | H | H | H | H | 3,4-$Cl_2$-Bn | 3-$CF_3$ | O | |
| 1a-59 | 5-$CF_3$ | H | H | H | H | H | H | H | H | 3,5-$Cl_2$-Bn | 3-$CF_3$ | O | |
| 1a-60 | 5-$CF_3$ | H | H | H | H | H | H | H | H | Ph | 3-$CF_3$ | O | |
| 1a-61 | 5-$CF_3$ | H | H | H | H | H | H | H | H | 2-Cl-Ph | 3-$CF_3$ | O | |
| 1a-62 | 5-$CF_3$ | H | H | H | H | H | H | H | H | 3-Cl-Ph | 3-$CF_3$ | O | |
| 1a-63 | 5-$CF_3$ | H | H | H | H | H | H | H | H | 4-Cl-Ph | 3-$CF_3$ | O | |
| 1a-64 | 5-$CF_3$ | H | H | H | H | H | H | H | H | 2,3-$Cl_2$-Ph | 3-$CF_3$ | O | |
| 1a-65 | 5-$CF_3$ | H | H | H | H | H | H | H | H | 2,4-$Cl_2$-Ph | 3-$CF_3$ | O | |
| 1a-66 | 5-$CF_3$ | H | H | H | H | H | H | H | H | 2,5-$Cl_2$-Ph | 3-$CF_3$ | O | |
| 1a-67 | 5-$CF_3$ | H | H | H | H | H | H | H | H | 2,6-$Cl_2$-Ph | 3-$CF_3$ | O | |
| 1a-68 | 5-$CF_3$ | H | H | H | H | H | H | H | H | 3,4-$Cl_2$-Ph | 3-$CF_3$ | O | |
| 1a-69 | 5-$CF_3$ | H | H | H | H | H | H | H | H | 3,5-$Cl_2$-Ph | 3-$CF_3$ | O | |
| 1a-70 | 5-$CF_3$ | H | H | H | H | H | H | H | H | 2-Py | 3-$CF_3$ | O | |
| 1a-71 | 5-$CF_3$ | H | H | H | H | H | H | H | H | 6-Cl-2-Py | 3-$CF_3$ | O | |
| 1a-72 | 5-$CF_3$ | H | H | H | H | H | H | H | H | 3-Py | 3-$CF_3$ | O | |

TABLE 4

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-73 | 5-$CF_3$ | H | H | H | H | H | H | H | H | 4-Py | 3-$CF_3$ | O | |
| 1a-74 | 5-$CF_3$ | Me | H | H | H | H | H | H | H | n-Bu | 3-$CF_3$ | O | |
| 1a-75 | 5-$CF_3$ | H | H | Me | H | H | H | H | H | n-Bu | 3-$CF_3$ | O | Note 1 |
| 1a-76 | 5-$CF_3$ | H | H | Me | H | H | H | H | H | n-Bu | 3-$CF_3$ | O | Note 2 |
| 1a-77 | 5-$CF_3$ | H | H | H | H | H | H | H | H | n-Bu | 3-$CF_3$ | S | |
| 1a-78 | 5-$CF_3$ | H | H | H | H | H | H | H | H | Me | 3-$CF_3$ 4-Cl | O | |
| 1a-79 | 5-$CF_3$ | H | H | H | H | H | H | H | H | n-Bu | 3-$CF_3$ 4-Cl | O | |
| 1a-80 | 5-$CF_3$ | H | H | H | H | H | H | H | H | Me | 3-$CF_3$ 4-Br | O | |
| 1a-81 | 5-$CF_3$ | H | H | H | H | H | H | H | H | n-Bu | 3-$CF_3$ 4-Br | O | |
| 1a-82 | 5-$CF_3$ | H | H | H | H | H | H | H | H | n-Bu | 3-$CF_3$ 4-Ph | O | |
| 1a-83 | 5-$CF_3$ | H | H | H | H | H | H | H | H | Me | 3-$CF_3$ 4-CN | O | |
| 1a-84 | 5-$CF_3$ | H | H | H | H | H | H | H | H | Me | 3-$CF_3$ 4-$CO_2$Et | O | |
| 1a-85 | 5-$CF_3$ | H | H | H | H | H | H | H | H | Me | 3-$CF_3$ 4-$CONEt_2$ | O | |
| 1a-86 | 5-$CF_3$ | H | H | H | H | H | H | H | H | Me | 3-$CF_3$ 4-CHO | O | |

TABLE 4-continued

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-87 | 5-$CF_3$ | H | H | H | H | H | H | H | H | Me | 3-$CF_3$ 4-CHNOMe | O | |
| 1a-88 | 5-$CF_3$ | H | H | H | H | H | H | H | H | Me | 3-$CF_3$ 4-CHNOBn | O | |
| 1a-89 | 5-$CF_3$ | H | H | H | H | H | H | H | H | Me | 3-$CF_3$ 4-Ph | O | |

Note 1: A cis relationship between the substituent (methyl group) of $R^4$ and X = O.
Note 2: A trans relationship between the substituent (methyl group) of $R^4$ and X = O.

TABLE 5

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-90 | 5-$CF_3$ | H | H | H | H | H | H | H | H | n-Bu | 3-$CF_3$ 4-CN | O | |
| 1a-91 | 5-$CF_3$ | H | H | H | H | H | H | H | H | n-Bu | 3-$CF_3$ 4-$CO_2$Et | O | |
| 1a-92 | 5-$CF_3$ | H | H | H | H | H | H | H | H | n-Bu | 3-$CF_3$ 4-$CONEt_2$ | O | |
| 1a-93 | 5-$CF_3$ | H | H | H | H | H | H | H | H | n-Bu | 3-$CF_3$ 4-CHO | O | |
| 1a-94 | 5-$CF_3$ | H | H | H | H | H | H | H | H | n-Bu | 3-$CF_3$ 4-CHNOMe | O | |
| 1a-95 | 5-$CF_3$ | H | H | H | H | H | H | H | H | n-Bu | 3-$CF_3$ 4-CHNOBn | O | |
| 1a-96 | 5-$CF_3$ | H | H | H | H | H | H | H | H | n-Bu | 3-Ph | O | |
| 1a-97 | 5-$CF_3$ | H | H | H | H | H | H | H | H | n-Bu | 3-(2-Cl-Ph) | O | |
| 1a-98 | 5-$CF_3$ | H | H | H | H | H | H | H | H | Me | 3-(3-Cl-Ph) | O | |
| 1a-99 | 5-$CF_3$ | H | H | H | H | H | H | H | H | n-Bu | 3-(3-Cl-Ph) | O | |
| 1a-100 | 5-$CF_3$ | H | H | H | H | H | H | H | H | n-Bu | 3-(4-Cl-Ph) | O | |
| 1a-101 | 5-$CF_3$ | H | H | H | H | H | H | H | H | n-Bu | 3-(2,3-$Cl_2$-Ph) | O | |
| 1a-102 | 5-$CF_3$ | H | H | H | H | H | H | H | H | Me | 3-(2,4-$Cl_2$-Ph) | O | |
| 1a-103 | 5-$CF_3$ | H | H | H | H | H | H | H | H | n-Bu | 3-(2,4-$Cl_2$-Ph) | O | |
| 1a-104 | 5-$CF_3$ | H | H | H | H | H | H | H | H | n-Bu | 3-(2,5-$Cl_2$-Ph) | O | |
| 1a-105 | 5-$CF_3$ | H | H | H | H | H | H | H | H | n-Bu | 3-(2,6-$Cl_2$-Ph) | O | |
| 1a-106 | 5-$CF_3$ | H | H | H | H | H | H | H | H | n-Bu | 3-(3,4-$Cl_2$-Ph) | O | |
| 1a-107 | 5-$CF_3$ | H | H | H | H | H | H | H | H | Me | 3-(3,5-$Cl_2$-Ph) | O | |
| 1a-108 | 5-$CF_3$ | H | H | H | H | H | H | H | H | n-Bu | 3(3,5-Cl2-Ph) | O | |
| 1a-109 | 5-$CF_3$ | H | H | H | H | H | H | H | H | Me | 3-(3,5-$Cl_2$-Ph) 4-Cl | O | |
| 1a-110 | 5-$CF_3$ | H | H | H | H | H | H | H | H | Me | 3-(3,5-$Cl_2$-Ph) 4-Br | O | |

TABLE 6

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-111 | 5-$CF_3$ | H | H | H | H | H | H | H | H | Me | 3-(3,5-$Cl_2$-Ph) 4-CN | O | |
| 1a-112 | 5-$CF_3$ | H | H | H | H | H | H | H | H | Me | 3-(3,5-$Cl_2$-Ph) 4-$CO_2$Et | O | |
| 1a-113 | 5-$CF_3$ | H | H | H | H | H | H | H | H | Me | 3-(3,5-Cl2-Ph) 4-$CONEt_2$ | O | |
| 1a-114 | 5-$CF_3$ | H | H | H | H | H | H | H | H | Me | 3-(3,5-$Cl_2$-Ph) 4-CHO | O | |
| 1a-115 | 5-$CF_3$ | H | H | H | H | H | H | H | H | Me | 3-(3,5-$Cl_2$-Ph) 4-CHNOMe | O | |
| 1a-116 | 5-$CF_3$ | H | H | H | H | H | H | H | H | Me | 3-(3,5-$Cl_2$-Ph) 4-CHNOBn | O | |
| 1a-117 | 5-$CF_3$ | H | H | H | H | H | H | H | H | n-Bu | 3-(3,5-$Cl_2$-Ph) 4-Cl | O | |
| 1a-118 | 5-$CF_3$ | H | H | H | H | H | H | H | H | n-Bu | 3-(3,5-$Cl_2$-Ph) 4-Br | O | |
| 1a-119 | 5-$CF_3$ | H | H | H | H | H | H | H | H | n-Bu | 3-(3,5-$Cl_2$-Ph) 4-CN | O | |
| 1a-120 | 5-$CF_3$ | H | H | H | H | H | H | H | H | n-Bu | 3-(3,5-$Cl_2$-Ph) 4-$CO_2$Et | O | |
| 1a-121 | 5-$CF_3$ | H | H | H | H | H | H | H | H | n-Bu | 3-(3,5-$Cl_2$-Ph) 4-$CONEt_2$ | O | |
| 1a-122 | 5-$CF_3$ | H | H | H | H | H | H | H | H | n-Bu | 3-(3,5-$Cl_2$-Ph) 4-CHO | O | |

TABLE 6-continued

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-123 | 5-$CF_3$ | H | H | H | H | H | H | H | H | n-Bu | 3-(3,5-$Cl_2$-Ph) 4-CHNOMe | O | |
| 1a-124 | 5-$CF_3$ | H | H | H | H | H | H | H | H | n-Bu | 3-(3,5-$Cl_2$-Ph) 4-CHNOBn | O | |
| 1a-125 | 5-$CF_3$ | H | H | H | H | H | H | H | H | Me | t-Bu | O | |
| 1a-126 | 5-$CF_3$ | H | H | H | H | H | H | H | H | n-Bu | t-Bu | O | |

TABLE 7

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-127 | 5-CN | H | H | H | H | H | H | H | H | n-Bu | 3-$CF_3$ | O | |
| 1a-128 | 5-CN | H | H | H | H | H | H | H | H | n-Pen | 3-$CF_3$ | O | |
| 1a-129 | 5-CN | H | H | H | H | H | H | H | H | n-Hex | 3-$CF_3$ | O | |
| 1a-130 | 5-CN | H | H | H | H | H | H | H | H | 3-Cl-Ph | 3-$CF_3$ | O | |
| 1a-131 | 5-CN | H | H | H | H | H | H | H | H | —$(CH_2)_2$OMe | 3-$CF_3$ | O | |
| 1a-132 | 5-CN | H | H | H | H | H | H | H | H | —$(CH_2)_2$OEt | 3-$CF_3$ | O | |
| 1a-133 | 3-Cl 5-$CF_3$ | H | H | H | H | H | H | H | H | Me | 3-$CF_3$ | O | |
| 1a-134 | 3-Cl 5-$CF_3$ | H | H | H | H | H | H | H | H | Et | 3-$CF_3$ | O | |
| 1a-135 | 3-Cl 5-$CF_3$ | H | H | H | H | H | H | H | H | n-Pr | 3-$CF_3$ | O | |
| 1a-136 | 3-Cl 5-$CF_3$ | H | H | H | H | H | H | H | H | n-Bu | 3-$CF_3$ | O | |
| 1a-137 | 3-Cl 5-$CF_3$ | H | H | H | H | H | H | H | H | n-Pen | 3-$CF_3$ | O | |
| 1a-138 | 3-Cl 5-$CF_3$ | H | H | H | H | H | H | H | H | n-Hex | 3-$CF_3$ | O | |
| 1a-139 | 3-Cl 5-$CF_3$ | H | H | H | H | H | H | H | H | 3-Cl-Ph | 3-$CF_3$ | O | |
| 1a-140 | 3-Cl 5-$CF_3$ | H | H | H | H | H | H | H | H | —$(CH_2)_2$OMe | 3-$CF_3$ | O | |
| 1a-141 | 3-Cl 5-$CF_3$ | H | H | H | H | H | H | H | H | —$(CH_2)_2$OEt | 3-$CF_3$ | O | |
| 1a-142 | 5-$NO_2$ | H | H | H | H | H | H | H | H | Me | 3-$CF_3$ | O | |
| 1a-143 | 5-$NO_2$ | H | H | H | H | H | H | H | H | Et | 3-$CF_3$ | O | |
| 1a-144 | 5-$NO_2$ | H | H | H | H | H | H | H | H | n-Pr | 3-$CF_3$ | O | |
| 1a-145 | 5-$NO_2$ | H | H | H | H | H | H | H | H | n-Bu | 3-$CF_3$ | O | |
| 1a-146 | 5-$NO_2$ | H | H | H | H | H | H | H | H | n-Pen | 3-$CF_3$ | O | |
| 1a-147 | 5-$NO_2$ | H | H | H | H | H | H | H | H | n-Hex | 3-$CF_3$ | O | |

TABLE 8

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-148 | 5-$NO_2$ | H | H | H | H | H | H | H | H | 3-ClPh | 3-$CF_3$ | O | |
| 1a-149 | 5-$NO_2$ | H | H | H | H | H | H | H | H | —$(CH_2)_2$OMe | 3-$CF_3$ | O | |
| 1a-150 | 5-$NO_2$ | H | H | H | H | H | H | H | H | —$(CH_3)_2$OEt | 3-$CF_3$ | O | |
| 1a-151 | 5-$CF_3$ | H | H | H | H | H | H | H | H | n-Bu | 3-(2-Py) | O | |
| 1a-152 | 5-$CF_3$ | H | H | H | H | H | H | H | H | n-Bu | 3-(3-Py) | O | |
| 1a-153 | 5-$CF_3$ | H | H | H | H | H | H | H | H | n-Bu | 3-(4-Py) | O | |
| 1a-154 | 5-$CF_3$ | H | H | H | H | H | H | H | H | n-Bu | 3-(2-$CF_3$-Ph) | O | |
| 1a-155 | 5-$CF_3$ | H | H | H | H | H | H | H | H | n-Bu | 3-(3-$CF_3$-Ph) | O | |
| 1a-156 | 5-$CF_3$ | H | H | H | H | H | H | H | H | n-Bu | 3-(4-$CF_3$-Ph) | O | |
| 1a-157 | 5-$CF_3$ | H | H | H | H | H | H | H | H | n-Bu | 3- 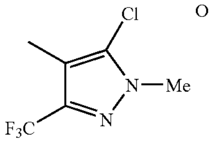 | O | |
| 1a-158 | 5-$CF_3$ | H | H | H | H | H | H | H | H | n-Bu | 3- 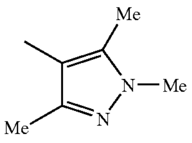 | O | |

TABLE 8-continued

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-159 | 5-$CF_3$ | H | H | H | H | H | H | H | H | n-Bu | 3- 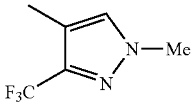 | O | |
| 1a-160 | 5-$CF_3$ | H | H | H | H | H | H | H | H | n-Bu | 3- 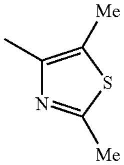 | O | |
| 1a-161 | 5-$CF_3$ | H | H | H | H | H | H | H | H | n-Bu | 3- 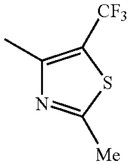 | O | |
| 1a-162 | 5-$CF_3$ | H | H | H | H | H | H | H | H | n-Bu | 3- 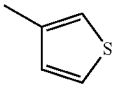 | O | |
| 1a-163 | 5-$CF_3$ | H | H | H | H | H | H | H | H | n-Bu | 3- 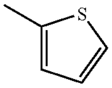 | O | |

TABLE 9

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-164 | 5-$CF_3$ | H | H | H | H | H | H | H | H | n-Bu | 3- 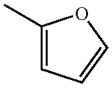 | O | |
| 1a-165 | 5-$CF_3$ | H | H | H | H | H | H | H | H | n-Bu | 3- 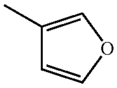 | O | |
| 1a-166 | 5-$CF_3$ | H | H | H | H | H | H | H | H | n-Bu | 3- 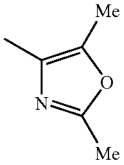 | O | |
| 1a-167 | 5-$CF_3$ | H | H | H | H | H | H | H | H | n-Bu | 3- 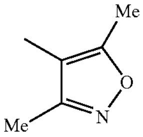 | O | |
| 1a-168 | 5-$CF_3$ | H | H | H | H | H | H | H | H | c-Bu | 3-$CF_3$ | O | |
| 1a-169 | 5-$CF_3$ | H | H | H | H | H | H | H | H | c-Pen | 3-$CF_3$ | O | |
| 1a-170 | 5-$CF_3$ | H | H | H | H | H | H | H | H | c-Hex | 3-$CF_3$ | O | |
| 1a-171 | 5-$CF_3$ | H | H | H | H | H | H | H | H | c-Hept | 3-$CF_3$ | O | |
| 1a-172 | 5-$CF_3$ | H | H | H | H | H | H | H | H | c-Oct | 3-$CF_3$ | O | |
| 1a-173 | 5-$CF_3$ | H | H | H | H | H | H | H | H | 3-$CF_3$-Ph | 3-$CF_3$ | O | |
| 1a-174 | 5-$CF_3$ | H | H | H | H | H | H | H | H | 3-Me-Ph | 3-$CF_3$ | O | |
| 1a-175 | 5-$CO_2$Et | H | H | H | H | H | H | H | H | Me | 3-$CF_3$ | O | |
| 1a-176 | 5-$CO_2$Et | H | H | H | H | H | H | H | H | Et | 3-$CF_3$ | O | |
| 1a-177 | 5-$CO_2$Et | H | H | H | H | H | H | H | H | n-Pr | 3-$CF_3$ | O | |
| 1a-178 | 5-$CO_2$Et | H | H | H | H | H | H | H | H | n-Bu | 3-$CF_3$ | O | |
| 1a-179 | 5-$CO_2$Et | H | H | H | H | H | H | H | H | n-Pen | 3-$CF_3$ | O | |

TABLE 9-continued

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-180 | 5-$CO_2$Et | H | H | H | H | H | H | H | H | n-Hex | 3-$CF_3$ | O | |
| 1a-181 | 5-$CO_2$Et | H | H | H | H | H | H | H | H | 3-Cl-Ph | 3-$CF_3$ | O | |
| 1a-182 | 5-$CO_2$Et | H | H | H | H | H | H | H | H | —$(CH_2)_2$OMe | 3-$CF_3$ | O | |
| 1a-183 | 5-$CO_2$Et | H | H | H | H | H | H | H | H | —$(CH_2)_2$OEt | 3-$CF_3$ | O | |
| 1a-184 | 5-$CF_3$ | H | H | H | H | H | H | H | H | Me | 3-$CF_3$ 4-COMe | O | |

TABLE 10

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-185 | 5-$CF_3$ | H | H | H | H | H | H | H | H | n-Bu | 3-$CF_3$ 4-COMe | O | |
| 1a-186 | 5-$CF_3$ | H | H | H | H | H | H | H | H | Me | 3-$CF_3$ 4-CONHEt | O | |
| 1a-187 | 5-$CF_3$ | H | H | H | H | H | H | H | H | n-Bu | 3-$CF_3$ 4-CONHEt | O | |
| 1a-188 | 5-$CF_3$ | H | H | H | H | H | H | H | H | Me | 3-$CF_3$ 4-$NO_2$ | O | |
| 1a-189 | 5-$CF_3$ | H | H | H | H | H | H | H | H | n-Bu | 3-$CF_3$ 4-$NO_2$ | O | |
| 1a-190 | 5-$CF_3$ | H | H | H | H | H | H | H | H | Me | 3-$CF_3$ 4-C(Me)NOMe | O | |
| 1a-191 | 5-$CF_3$ | H | H | H | H | H | H | H | H | Me | 3-$CF_3$ 4-C(Me)NOBn | O | |
| 1a-192 | 5-$CF_3$ | H | H | H | H | H | H | H | H | n-Bu | 3-$CF_3$ 4-C(Me)NOMe | O | |
| 1a-193 | 5-$CF_3$ | H | H | H | H | H | H | H | H | n-Bu | 3-$CF_3$ 4-C(Me)NOBn | O | |
| 1a-194 | 5-$CF_3$ | H | H | H | H | H | H | H | H | —$(CH_2)_2OCH_2CF_3$ | 3-$CF_3$ | O | |
| 1a-195 | 5-$CF_3$ | H | H | H | H | H | H | H | H | —$(CH_2)_2$OPh | 3-$CF_3$ | O | |
| 1a-196 | 5-$CF_3$ | H | H | H | H | H | H | H | H | 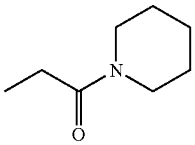 | O | | |
| 1a-197 | 5-$CF_3$ | H | H | H | H | H | H | H | H | n-Bu | 3-$CF_3$ | O | Note 3 |
| 1a-198 | 5-$CF_3$ | H | H | H | H | H | H | H | H | n-Bu | 3-$CF_3$ | O | Note 4 |
| 1a-199 | 5-$CF_3$ | H | H | H | H | H | H | H | H | n-Bu | 3-$CF_3$ | O | Note 5 |

Note 3:
Hydrochloride compound
Note 4:
N-piperidyl oxide
Note 5:
N-pyridyl oxide

TABLE 11

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-200 | 5-$CF_3$ | H | H | Me | H | H | H | H | H | 2-Py | 3-$CF_3$ | O | Note 1 |
| 1a-201 | 5-$CF_3$ | H | H | Me | H | H | H | H | H | 2-Py | 3-$CF_3$ | O | Note 2 |
| 1a-202 | 5-$CF_3$ | H | H | Et | H | H | H | H | H | 2-Py | 3-$CF_3$ | O | Note 1 |
| 1a-203 | 5-$CF_3$ | H | H | Et | H | H | H | H | H | 2-Py | 3-$CF_3$ | O | Note 2 |
| 1a-204 | 5-$CF_3$ | H | H | n-Pr | H | H | H | H | H | 2-Py | 3-$CF_3$ | O | Note 1 |
| 1a-205 | 5-$CF_3$ | H | H | H | H | H | H | H | H | 2-Py | 3-(3,4,5-$F_2$-Ph) | O | |
| 1a-206 | 5-$CF_3$ | H | H | H | H | H | H | H | H | 2-Py | 3-(3,5-$F_2$-Ph) | O | |
| 1a-207 | 5-$CF_3$ | H | H | Me | H | H | H | H | H | 2-Py | 3-(3,5-$F_2$-Ph) | O | Note 1 |
| 1a-208 | 5-$CF_3$ | H | H | Me | H | H | H | H | H | 2-Py | 3-(3,5-$F_2$-Ph) | O | Note 2 |
| 1a-209 | 5-$CF_3$ | H | H | H | H | H | H | H | H | 3-Cl-2-Py | 3-$CF_3$ | O | |
| 1a-210 | 5-$CF_3$ | H | H | H | H | H | H | H | H | 6-Me-2-Py | 3-$CF_3$ | O | |
| 1a-211 | 5-$CF_3$ | H | H | H | H | H | H | H | H | 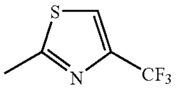 | 3-$CF_3$ | O | |

TABLE 11-continued

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-212 | 5-$CF_3$ | H | H | Et | H | H | H | H | H | n-Bu | 3-$CF_3$ | O | Note 1 |
| 1a-213 | 5-$CF_3$ | H | H | Et | H | H | H | H | H | n-Bu | 3-$CF_3$ | O | Note 2 |
| 1a-214 | 5-$CF_3$ | H | H | n-Pr | H | H | H | H | H | n-Bu | 3-$CF_3$ | O | Note 1 |
| 1a-215 | 5-$CF_3$ | H | H | Me | Me | H | H | H | H | Me | 3-$CF_3$ | O | |
| 1a-216 | 5-$CF_3$ | H | H | Me | Me | H | H | H | H | n-Bu | 3-$CF_3$ | O | |
| 1a-217 | 5-$CF_3$ | H | H | H | H | H | H | H | H | Me | 3-$CF_3$ | S | |
| 1a-218 | 5-$CF_3$ | H | H | H | H | H | H | H | H | n-Bu | 3-$CF_3$ | $SO_2$ | |
| 1a-219 | 5-$CF_3$ | H | H | H | H | H | H | H | H | Me | 3-$CF_3$ 4-Me | O | |
| 1a-220 | 5-$CF_3$ | H | H | H | H | H | H | H | H | Me | 3-$CF_3$ 4-$CH_2OH$ | O | |
| 1a-221 | 5-$CF_3$ | H | H | H | H | H | H | H | H | n-Bu | 3-$CF_3$ 4-Me | O | |
| 1a-222 | 5-$CF_3$ | H | H | Me | H | H | H | H | H | Me | 3-$CF_3$ 4-CHO | O | Note 2 |

Note 1:
A cis relationship between the substituent (alkyl group) of $R^4$ and X = O.
Note 2:
A trans relationship between the substituent (alkyl group) of $R^4$ and X = O.

TABLE 12

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-223 | 5-$CF_3$ | H | H | H | H | H | H | H | H | n-Bu | 3-(3,5-$(CF_3)_2$-Ph) | O | |
| 1a-224 | 5-$CF_3$ | H | H | H | H | H | H | H | H | n-Bu | 3-(3,5-$F_2$-Ph) | O | |
| 1a-225 | 5-$CF_3$ | H | H | Me | H | H | H | H | H | n-Bu | 3-(3,5-$F_2$-Ph) | O | Note 1 |
| 1a-226 | 5-$CF_3$ | H | H | Me | H | H | H | H | H | n-Bu | 3-(3,5-$F_2$-Ph) | O | Note 2 |
| 1a-227 | 5-$CF_3$ | H | H | Et | H | H | H | H | H | n-Bu | 3-(3,5-$F_2$-Ph) | O | Note 1 |
| 1a-228 | 5-$CF_3$ | H | H | Et | H | H | H | H | H | n-Bu | 3-(3,5-$F_2$-Ph) | O | Note 2 |
| 1a-229 | 5-$CF_3$ | H | H | n-Pr | H | H | H | H | H | n-Bu | 3-(3,5-$F_2$-Ph) | O | Note 1 |
| 1a-230 | 5-$CF_3$ | H | H | H | H | H | H | H | H | n-Hex | 3-(3,5-$F_2$-Ph) | O | |
| 1a-231 | 5-$CF_3$ | H | H | Me | H | H | H | H | H | n-Hex | 3-(3,5-$F_2$-Ph) | O | Note 1 |
| 1a-232 | 5-$CF_3$ | H | H | Me | H | H | H | H | H | n-Hex | 3-(3,5-$F_2$-Ph) | O | Note 2 |
| 1a-233 | 5-$CF_3$ | H | H | H | H | H | H | H | H | n-Bu | 3-(3,4,5-$F_3$-Ph) | O | |
| 1a-234 | 5-$CF_3$ | H | H | Me | H | H | H | H | H | n-Bu | 3-(3,4,5-$F_3$-Ph) | O | Note 2 |
| 1a-235 | 5-$CF_3$ | H | H | H | H | H | H | H | H | n-Bu | 3-(4-CN-Ph) | O | |
| 1a-236 | 5-$CF_3$ | H | H | H | H | H | H | H | H | n-Bu | 3-(4-F-Ph) | O | |
| 1a-237 | 5-$CF_3$ | H | H | H | H | H | H | H | H | n-Bu | 3-(4-t-Bu-Ph) | O | |
| 1a-238 | 5-$CF_3$ | H | H | H | H | H | H | H | H | n-Bu | 3-(4-MeS-Ph) | O | |
| 1a-239 | 5-$CF_3$ | H | H | H | H | H | H | H | H | n-Bu | 3-(4-$NO_2$-Ph) | O | |
| 1a-240 | 5-$CF_3$ | H | H | H | H | H | H | H | H | n-Bu | 3-(4-$CF_3$-Ph) | O | |
| 1a-241 | 5-$CF_3$ | H | H | H | H | H | H | H | H | n-Bu | 3-(4-MeO-Ph) | O | |
| 1a-242 | 5-$CF_3$ | H | H | H | H | H | H | H | H | n-Bu | 3-(4-$CF_3O$-Ph) | O | |
| 1a-243 | 5-$CF_3$ | H | H | H | H | H | H | H | H | Me | 3-$CO_2Et$ 4-Me | O | |
| 1a-244 | 3-Cl 5-$CF_3$ | H | H | H | H | H | H | H | H | Me | 3-$CF_3$ 4-Cl | O | |

Note 1: A cis relationship between the substituent (alkyl group) of $R^4$ and X = O.
Note 2: A trans relationship between the substituent (alkyl group) of $R^4$ and X = O.

TABLE 13

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-245 | 5-$CF_3$ | H | H | H | H | H | H | H | H | H | 3-$CF_3$ | O | |
| 1a-246 | 5-$CF_3$ | H | H | Me | H | H | H | H | H | H | 3-$CF_3$ | O | Note 2 |
| 1a-247 | 5-$CF_3$ | H | H | H | H | H | H | H | H | 5-Me-2-Py | 3-$CF_3$ | O | |
| 1a-248 | 5-$CF_3$ | H | H | H | H | H | H | H | H | n-Bu | 3-(3,4,5-$Me_2$-Ph) | O | |
| 1a-249 | 5-$CF_3$ | H | H | H | H | H | H | H | H | n-Bu | 3-(3,6-$Cl_2$-4-Py) | O | |
| 1a-250 | 5-$CF_3$ | H | H | H | H | H | H | H | H | —CO(t-Bu) | 3-$CF_3$ | O | |
| 1a-251 | 5-$CF_3$ | H | H | Me | H | H | H | H | H | Ph | 3-$CF_3$ | O | Note 2 |
| 1a-252 | 5-$CF_3$ | H | H | Me | H | H | H | H | H | 3-Me-Ph | 3-$CF_3$ | O | Note 2 |
| 1a-253 | 5-$CF_3$ | H | H | H | H | H | H | H | H | n-Bu | 3-(3-F-5-$CF_3$-Ph) | O | |
| 1a-254 | 5-$CF_3$ | H | H | H | H | H | H | H | H | n-Bu | 3-(3-F-Ph) | O | |
| 1a-255 | 5-$CF_3$ | H | H | H | H | H | H | H | H | n-Bu | 3-(4-Me-Ph) | O | |

TABLE 13-continued

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-256 | 5-$CF_3$ | H | H | H | H | H | H | H | H | 2-Py | 3-(3,5-$Cl_2$-Ph) | O | |
| 1a-257 | 5-$CF_3$ | H | H | Me | H | H | H | H | H | 2-Py | 3-(3,5-$Cl_2$-Ph) | O | Note 2 |
| 1a-258 | 5-$CF_3$ | H | H | H | H | H | H | H | H | n-Bu | 3-(4-I-Ph) | O | |
| 1a-259 | 3-Cl<br>5-$CF_3$ | H | H | H | H | H | H | H | H | n-Bu | 3-(3,5-$F_2$-Ph) | O | |
| 1a-260 | 5-$CF_3$ | H | H | H | H | H | H | H | H | 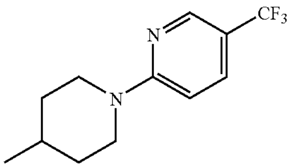 | 3-$CF_3$ | O | |
| 1a-261 | 5-$CF_3$ | H | H | H | H | H | H | H | H | —$CH_2OMe$ | 3-$CF_3$ | O | |
| 1a-262 | 5-$CF_3$ | H | H | H | H | H | H | H | H | —$CH_2OEt$ | 3-$CF_3$ | O | |
| 1a-263 | 5-$CF_3$ | H | H | Me | H | H | H | H | H | —$CH_2OEt$ | 3-$CF_3$ | O | Note 2 |
| 1a-264 | 5-$CF_3$ | H | H | H | H | H | H | H | H | —$CH_2CH_2OMe$ | 3-$CF_3$ | O | |
| 1a-265 | 5-$CF_3$ | H | H | H | H | H | H | H | H | —$CH_2CH_2OEt$ | 3-$CF_3$ | O | |
| 1a-266 | 5-$CF_3$ | H | H | H | H | H | H | H | H | —$CH_2CH(OMe)_2$ | 3-$CF_3$ | O | |
| 1a-267 | 5-$CF_3$ | H | H | Me | H | H | H | H | H | —$CH_2CH(OMe)_2$ | 3-$CF_3$ | O | Note 2 |
| 1a-268 | 5-$CF_3$ | H | H | Me | H | H | H | H | H | —$CH_2CH(OMe)_2$ | 3-$CF_3$ | O | Note 1 |

Note 1:
A cis relationship between the substituent (methyl group) of $R^4$ and X = O.
Note 2:
A trans relationship between the substituent (methyl group) of $R^4$ and X = O.

TABLE 14

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-269 | 5-$CF_3$ | H | H | H | H | H | H | H | H | —$CH_2CH(OEt)_2$ | 3-$CF_3$ | O | |
| 1a-270 | 5-$CF_3$ | H | H | Me | H | H | H | H | H | —$CH_2CH(OEt)_2$ | 3-$CF_3$ | O | Note 2 |
| 1a-271 | 5-$CF_3$ | H | H | H | H | H | H | H | H | —$(CH_2)_2CH(OMe)_2$ | 3-$CF_3$ | O | |
| 1a-272 | 5-$CF_3$ | H | H | H | H | H | H | H | H | —$(CH_2)_2CH(OEt)_2$ | 3-$CF_3$ | O | |
| 1a-273 | 5-$CF_3$ | H | H | H | H | H | H | H | H | 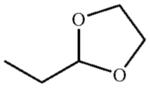 | 3-$CF_3$ | O | |
| 1a-274 | 5-$CF_3$ | H | H | Me | H | H | H | H | H | 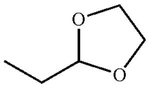 | 3-$CF_3$ | O | Note 2 |
| 1a-275 | 5-$CF_3$ | H | H | Me | H | H | H | H | H | 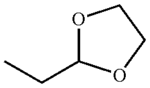 | 3-$CF_3$ | O | Note 1 |
| 1a-276 | 5-$CF_3$ | H | H | H | H | H | H | H | H | 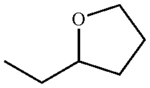 | 3-$CF_3$ | O | |
| 1a-277 | 5-$CF_3$ | H | H | H | H | H | H | H | H | 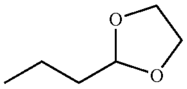 | 3-$CF_3$ | O | |
| 1a-278 | 5-$CF_3$ | H | H | H | H | H | H | H | H | 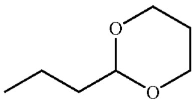 | 3-$CF_3$ | O | |
| 1a-279 | 5-$CF_3$ | H | H | H | H | H | H | H | H | —COMe | 3-$CF_3$ | O | |
| 1a-280 | 5-$CF_3$ | H | H | H | H | H | H | H | H | —COEt | 3-$CF_3$ | O | |
| 1a-281 | 5-$CF_3$ | H | H | H | H | H | H | H | H | —CO(n-Pr) | 3-$CF_3$ | O | |
| 1a-282 | 5-$CF_3$ | H | H | H | H | H | H | H | H | —CO(n-Bu) | 3-$CF_3$ | O | |
| 1a-283 | 5-$CF_3$ | H | H | H | H | H | H | H | H | —COPh | 3-$CF_3$ | O | |
| 1a-284 | 5-$CF_3$ | H | H | H | H | H | H | H | H | —CO(2-Cl-Ph) | 3-$CF_3$ | O | |
| 1a-285 | 5-$CF_3$ | H | H | H | H | H | H | H | H | —CO(3-Cl-Ph) | 3-$CF_3$ | O | |

TABLE 14-continued

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-286 | 5-$CF_3$ | H | H | H | H | H | H | H | H | —CO(4-Cl-Ph) | 3-$CF_3$ | O | |
| 1a-287 | 5-$CF_3$ | H | H | H | H | H | H | H | H | —$CO_2$Me | 3-$CF_3$ | O | |
| 1a-288 | 5-$CF_3$ | H | H | H | H | H | H | H | H | —$CO_2$Et | 3-$CF_3$ | O | |
| 1a-289 | 5-$CF_3$ | H | H | H | H | H | H | H | H | —$CO_2$(n-Pr) | 3-$CF_3$ | O | |
| 1a-290 | 5-$CF_3$ | H | H | H | H | H | H | H | H | —$CO_2$(n-Bu) | 3-$CF_3$ | O | |

Note 1:
A cis relationship between the substituent (methyl group) of $R^4$ and X = O.
Note 2:
A trans relationship between the substituent (methyl group) of $R^4$ and X = O.

TABLE 15

| No. | $(R^1)_m$ | $R^2$ | $R^3$ | $R^4$ | $R^5$ | $R^6$ | $R^7$ | $R^8$ | $R^9$ | $R^{10}$ | $(R^{11})_n$ | X | Remarks |
|---|---|---|---|---|---|---|---|---|---|---|---|---|---|
| 1a-291 | 5-$CF_3$ | H | H | H | H | H | H | H | H | —$CH_2$CHO | 3-$CF_3$ | O | |
| 1a-292 | 5-$CF_3$ | H | H | H | H | H | H | H | H | —$(CH_2)_2$CHO | 3-$CF_3$ | O | |
| 1a-293 | 5-$CF_3$ | H | H | H | H | H | H | H | H | Me | 3-$CF_3$<br>4-CHNOH | O | |
| 1a-294 | 5-$CF_3$ | H | H | H | H | H | H | H | H | Me | 3-$CF_3$<br>4-CHNOEt | O | |
| 1a-295 | 5-$CF_3$ | H | H | H | H | H | H | H | H | H | 3-(3,5-$F_2$-Ph) | O | |
| 1a-296 | 5-$CF_3$ | H | H | Me | H | H | H | H | H | H | 3-(3,5-$F_2$-Ph) | O | Note 2 |
| 1a-297 | 5-$CF_3$ | H | H | H | H | H | H | H | H | —$CH_2CH(OMe)_2$ | 3-(3,5-$F_2$-Ph) | O | |
| 1a-298 | 5-$CF_3$ | H | H | Me | H | H | H | H | H | —$CH_2CH(OMe)_2$ | 3-(3,5-$F_2$-Ph) | O | Note 2 |
| 1a-299 | 5-$CF_3$ | H | H | Me | H | H | H | H | H | —$CH_2CH(OMe)_2$ | 3-(3,5-$F_2$-Ph) | O | Note 1 |
| 1a-300 | 5-$CF_3$ | H | H | H | H | H | H | H | H | 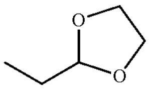 | 3-(3,5-$F_2$-Ph) | O | |
| 1a-301 | 5-$CF_3$ | H | H | Me | H | H | H | H | H | 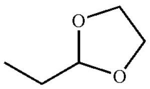 | 3-(3,5-$F_2$-Ph) | O | Note 2 |
| 1a-302 | 5-$CF_3$ | H | H | Me | H | H | H | H | H | 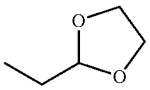 | 3-(3,5-$F_2$-Ph) | O | Note 1 |
| 1a-303 | 5-$CF_3$ | H | H | H | H | H | H | H | H | 2-Py | 3- 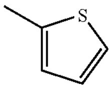 | O | |
| 1a-304 | 5-$CF_3$ | H | H | H | H | H | H | H | H | —$(CH_2)_2CH{=}CH_2$ | 3-$CF_3$ | O | |
| 1a-305 | 5-$CF_3$ | H | H | H | H | H | H | H | H | —$CH_2CH(Et)_2$ | 3-$CF_3$ | O | |
| 1a-306 | 5-$CF_3$ | H | H | H | H | H | H | H | H | i-Pen | 3-$CF_3$ | O | |

Note 1:
A cis relationship between the substituent (methyl group) of $R^4$ and X = O.
Note 2:
A trans relationship between the substituent (methyl group) of $R^4$ and X = O.

TABLE 16

(1b)

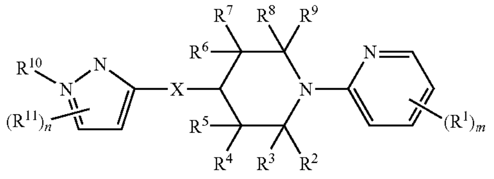

| No. | $(R^1)_m$ | $R^2$ | $R^8$ | $R^3$ | $R^5$ | $R^4$ | $R^6$ | $R^7$ | $R^9$ | $R^{10}$ | $(R^{11})_n$ | X | Remarks |
|---|---|---|---|---|---|---|---|---|---|---|---|---|---|
| 1b-1 | 5-$CF_3$ | H | H | H | H | H | H | H | H | Me | 5-Me | O | |
| 1b-2 | 5-$CF_3$ | H | H | H | H | H | H | H | H | Me | 5-$CF_3$ | O | |
| 1b-3 | 5-$CF_3$ | H | H | H | H | H | H | H | H | Et | 5-$CF_3$ | O | |
| 1b-4 | 5-$CF_3$ | H | H | H | H | H | H | H | H | n-Bu | 5-$CF_3$ | O | |
| 1b-5 | 5-$CF_3$ | H | H | H | H | H | H | H | H | t-Bu | 5-$CF_3$ | O | |

TABLE 16-continued (1b)

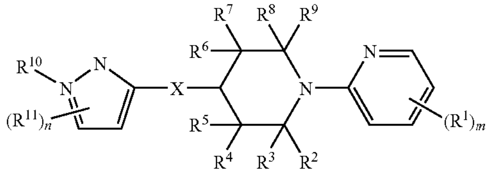

| No. | $(R^1)_m$ | $R^2$ | $R^8$ | $R^3$ | $R^5$ | $R^4$ | $R^6$ | $R^7$ | $R^9$ | $R^{10}$ | $(R^{11})_n$ | X | Remarks |
|---|---|---|---|---|---|---|---|---|---|---|---|---|---|
| 1b-6 | 5-$CF_3$ | H | H | H | H | H | H | H | H | Bn | 5-$CF_3$ | O | |
| 1b-7 | 5-$CF_3$ | H | H | H | H | H | H | H | H | Ph | 5-$CF_3$ | O | |
| 1b-8 | 5-$CF_3$ | H | H | H | H | H | H | H | H | 2-Cl-Ph | 5-$CF_3$ | O | |
| 1b-9 | 5-$CF_3$ | H | H | H | H | H | H | H | H | 3-Cl-Ph | 5-$CF_3$ | O | |
| 1b-10 | 5-$CF_3$ | H | H | H | H | H | H | H | H | 4-Cl-Ph | 5-$CF_3$ | O | |
| 1b-11 | 5-$CF_3$ | H | H | H | H | H | H | H | H | 2-Py | 5-$CF_3$ | O | |
| 1b-12 | 5-$CF_3$ | H | H | H | H | H | Me | H | H | Me | 5-$CF_3$ | O | Note 6 |
| 1b-13 | 5-$CF_3$ | H | H | H | H | H | Me | H | H | Me | 5-$CF_3$ | O | Note 7 |
| 1b-14 | 5-$CF_3$ | $—CH_2CH_2—$ | | H | H | H | H | H | H | Me | 5-$CF_3$ | O | Note 8 |
| 1b-15 | 5-$CF_3$ | $—CH_2CH_2—$ | | H | H | H | H | H | H | Me | 5-$CF_3$ | O | Note 9 |
| 1b-16 | 5-$CF_3$ | H | H | H | H | $—CH_2CH_2—$ | | H | H | Me | 5-$CF_3$ | O | Note 10 |
| 1b-17 | 5-$CF_3$ | H | H | H | H | $—CH_2CH_2—$ | | H | H | Me | 5-$CF_3$ | O | Note 11 |
| 1b-18 | 5-$CF_3$ | H | H | H | H | H | H | H | H | Me | 5-$CF_3$ | S | |

Note 6:

A cis relationship between the methyl group of $R^6$ and X = O.

Note 7:

A trans relationship between the methyl group of $R^6$ and X = O.

Note 8:

A cis relationship between the ethylene groups of $R^2$ and $R^8$ and X = O.

Note 9:

A trans relationship between the ethylene groups of $R^2$ and $R^8$ and X = O.

Note 10:

A cis relationship between the ethylene groups of $R^4$ and $R^6$ and X = O.

Note 11:

A cis relationship between the ethylene groups of $R^4$ and $R^6$ and X = O.

TABLE 17

| No. | $(R^1)_m$ | $R^2$ | $R^8$ | $R^3$ | $R^5$ | $R^4$ | $R^6$ | $R^7$ | $R^9$ | $R^{10}$ | $(R^{11})_n$ | X | Remarks |
|---|---|---|---|---|---|---|---|---|---|---|---|---|---|
| 1b-19 | 5-$CF_3$ | H | H | H | H | H | H | H | H | Me | 5-$CF_3$ 4-Cl | O | |
| 1b-20 | 5-$CF_3$ | H | H | H | H | H | H | H | H | Me | 5-$CF_3$ | O | |
| 1b-21 | 5-$CF_3$ | H | H | H | H | H | H | H | H | Me | 5-Ph | O | |
| 1b-22 | 5-$CF_3$ | H | H | H | H | H | H | H | H | Me | 5-(2-Cl-Ph) | O | |
| 1b-23 | 5-$CF_3$ | H | H | H | H | H | H | H | H | Me | 5-(3-Cl-Ph) | O | |
| 1b-24 | 5-$CF_3$ | H | H | H | H | H | H | H | H | Me | 5-(4-Cl-Ph) | O | |
| 1b-25 | 5-$CF_3$ | H | H | H | H | H | H | H | H | Me | 5-(3,5-$Cl_2$-Ph) | O | |
| 1b-26 | 5-$CF_3$ | H | H | H | H | H | H | H | H | Me | 5-t-Bu | O | |
| 1b-27 | 5-CN | H | H | H | H | H | H | H | H | Me | 5-$CF_3$ | O | |
| 1b-28 | 5-Cl 5-$CF_3$ | H | H | H | H | H | H | H | H | Me | 5-$CF_3$ | O | |
| 1b-29 | 5-$NO_2$ | H | H | H | H | H | H | H | H | Me | 5-$CF_3$ | O | |
| 1b-30 | 5-$CF_3$ | H | H | H | H | H | H | H | H | c-Hex | 5-$CF_3$ | O | |
| 1b-31 | 5-$CF_3$ | H | H | H | H | H | H | H | H | $—CH_2OMe$ | 5-$CF_3$ | O | |
| 1b-32 | 5-$CF_3$ | H | H | H | H | H | H | H | H | $—CH_2OEt$ | 5-$CF_3$ | O | |
| 1b-33 | 5-$CF_3$ | H | H | H | H | H | Me | H | H | $—CH_2OEt$ | 5-$CF_3$ | O | Note 7 |
| 1b-34 | 5-$CF_3$ | H | H | H | H | H | H | H | H | $—(CH_2)_2OMe$ | 5-$CF_3$ | O | |
| 1b-35 | 5-$CF_3$ | H | H | H | H | H | H | H | H | $—(CH_2)_2OEt$ | 5-$CF_3$ | O | |
| 1b-36 | 5-$CF_3$ | H | H | H | H | H | H | H | H | $—CH_2CH(OMe)_2$ | 5-$CF_3$ | O | |
| 1b-37 | 5-$CF_3$ | H | H | H | H | H | Me | H | H | $—CH_2CH(OMe)_2$ | 5-$CF_3$ | O | Note 7 |
| 1b-38 | 5-$CF_3$ | H | H | H | H | H | Me | H | H | $—CH_2CH(OMe)_2$ | 5-$CF_3$ | O | Note 6 |
| 1b-39 | 5-$CF_3$ | H | H | H | H | H | H | H | H | $—CH_2CH(OEt)_2$ | 5-$CF_3$ | O | |
| 1b-40 | 5-$CF_3$ | H | H | H | H | H | Me | H | H | $—CH_2CH(OEt)_2$ | 5-$CF_3$ | O | Note 7 |
| 1b-41 | 5-$CF_3$ | H | H | H | H | H | H | H | H | $—(CH_2)_2CH(OMe)_2$ | 5-$CF_3$ | O | |
| 1b-42 | 5-$CF_3$ | H | H | H | H | H | H | H | H | $—(CH_2)_2CH(OEt)_2$ | 5-$CF_3$ | O | |

TABLE 17-continued

| No. | $(R^1)_m$ | $R^2$ | $R^8$ | $R^3$ | $R^5$ | $R^4$ | $R^6$ | $R^7$ | $R^9$ | $R^{10}$ | $(R^{11})_n$ | X | Remarks |
|---|---|---|---|---|---|---|---|---|---|---|---|---|---|
| 1b-43 | 5-$CF_3$ | H | H | H | H | H | H | H | H | 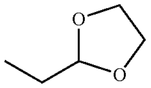 | 5-$CF_3$ | O | |

Note 6:

A cis relationship between the methyl group of $R^6$ and X = O.

Note 7:

A trans relationship between the methyl group of $R^6$ and X = O.

TABLE 18

| No. | $(R^1)_m$ | $R^2$ | $R^8$ | $R^3$ | $R^5$ | $R^4$ | $R^6$ | $R^7$ | $R^9$ | $R^{10}$ | $(R^{11})_n$ | X | Remarks |
|---|---|---|---|---|---|---|---|---|---|---|---|---|---|
| 1b-44 | 5-$CF_3$ | H | H | H | H | H | Me | H | H | 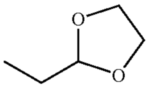 | 5-$CF_3$ | O | Note 7 |
| 1b-45 | 5-$CF_3$ | H | H | H | H | H | Me | H | H | 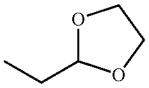 | 5-$CF_3$ | O | Note 6 |
| 1b-46 | 5-$CF_3$ | H | H | H | H | H | H | H | H | 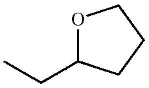 | 5-$CF_3$ | O | |
| 1b-47 | 5-$CF_3$ | H | H | H | H | H | H | H | H | 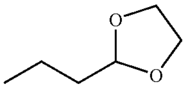 | 5-$CF_3$ | O | |
| 1b-48 | 5-$CF_3$ | H | H | H | H | H | H | H | H | 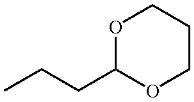 | 5-$CF_3$ | O | |
| 1b-49 | 5-$CF_3$ | H | H | H | H | H | H | H | H | $-(CH_2)_3CF_3$ | 5-$CF_3$ | O | |
| 1b-50 | 5-$CF_3$ | $-CH_2CH_2-$ | | H | H | H | H | H | H | $-CH_2CH(OMe)_2$ | 5-$CF_3$ | O | Note 9 |
| 1b-51 | 5-$CF_3$ | $-CH_2CH_2-$ | | H | H | H | H | H | H | 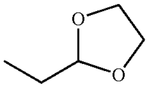 | 5-$CF_3$ | O | Note 9 |
| 1b-52 | 5-$CF_3$ | H | H | H | H | $-CH_2CH_2-$ | | H | H | $-CH_2CH(OMe)_2$ | 5-$CF_3$ | O | Note 10 |
| 1b-53 | 5-$CF_3$ | H | H | H | H | $-CH_2CH_2-$ | | H | H | 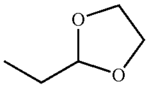 | 5-$CF_3$ | O | Note 10 |
| 1b-54 | 5-$CF_3$ | H | H | H | H | H | H | H | H | 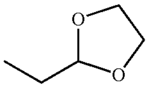 | 5-(3,5-$F_2$-Ph) | O | |
| 1b-55 | 5-$CF_3$ | H | H | H | H | Me | H | H | H | 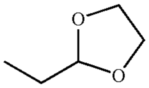 | 5-(3,5-$F_2$-Ph) | O | Note 7 |
| 1b-56 | 5-$CF_3$ | H | H | H | H | $-CH_2CH_2-$ | | H | H | $-CH_2CH(OMe)_2$ | 5-(3,5-$F_2$-Ph) | O | Note 10 |
| 1b-57 | 5-$CF_3$ | $-CH_2CH_2-$ | | H | H | H | H | H | H | $-CH_2CH(OMe)_2$ | 5-(3,5-$F_2$-Ph) | O | Note 9 |
| 1b-58 | 5-$CF_3$ | $-CH_2CH_2-$ | | H | H | H | H | H | H | 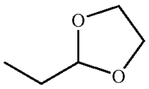 | 5-(3,5-$F_2$-Ph) | O | Note 9 |
| 1b-59 | 5-$CF_3$ | H | H | H | H | H | H | H | H | $-(CH_2)_2CH{=}CH_2$ | 5-$CF_3$ | O | |

TABLE 18-continued

| No. | $(R^1)_m$ | $R^2$ | $R^8$ | $R^3$ | $R^5$ | $R^4$ | $R^6$ | $R^7$ | $R^9$ | $R^{10}$ | $(R^{11})_n$ | X | Remarks |
|---|---|---|---|---|---|---|---|---|---|---|---|---|---|
| 1b-60 | 5-$CF_3$ | H | H | H | H | H | H | H | H | —$CH_2CH(Et)_2$ | 5-$CF_3$ | O | |
| 1b-61 | 5-$CF_3$ | H | H | H | H | H | H | H | H | i-Pen | 5-$CF_3$ | O | |

Note 6:
A cis relationship between the methyl group of $R^6$ and X = O.
Note 7:
A trans relationship between the methyl group of $R^6$ and X = O.
Note 9:
A trans relationship between the ethylene groups of $R^2$ and $R^8$ and X = O.
Note 10:
A cis relationship between the ethylene groups of $R^4$ and $R^6$ and X = O.

TABLE 19

(1c)

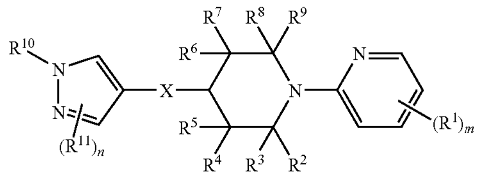

| No. | $(R^1)_m$ | $R^2$ | $R^8$ | $R^3$ | $R^4$ | $R^6$ | $R^5$ | $R^7$ | $R^9$ | $R^{10}$ | $(R^{11})_n$ | X | Remarks |
|---|---|---|---|---|---|---|---|---|---|---|---|---|---|
| 1c-1 | 5-$CF_3$ | H | H | H | H | H | H | H | H | Me | 3-COMe | O | |
| 1c-2 | 5-$CF_3$ | H | H | H | H | H | H | H | H | Ph | 3-COMe | O | |
| 1c-3 | 5-$CF_3$ | H | H | H | H | H | H | H | H | 2-Cl-Ph | 3-COMe | O | |
| 1c-4 | 5-$CF_3$ | H | H | H | H | H | H | H | H | 3-Cl-Ph | 3-COMe | O | |
| 1c-5 | 5-$CF_3$ | H | H | H | H | H | H | H | H | 4-Cl-Ph | 3-COMe | O | |
| 1c-6 | 5-$CF_3$ | H | H | H | H | H | H | H | H | 2,4-$Cl_2$-Ph | 3-COMe | O | |
| 1c-7 | 5-$CF_3$ | H | H | H | H | H | H | H | H | 3,5-$Cl_2$-Ph | 3-COMe | O | |
| 1c-8 | 5-$CF_3$ | H | H | H | H | H | H | H | H | Me | 3-$CO_2$Me | O | |
| 1c-9 | 5-$CF_3$ | H | H | H | H | H | H | H | H | Ph | 3-$CO_2$Me | O | |
| 1c-10 | 5-$CF_3$ | H | H | H | H | H | H | H | H | 2-Cl-Ph | 3-$CO_2$Me | O | |
| 1c-11 | 5-$CF_3$ | H | H | H | H | H | H | H | H | 3-Cl-Ph | 3-$CO_2$Me | O | |
| 1c-12 | 5-$CF_3$ | H | H | H | H | H | H | H | H | 4-Cl-Ph | 3-$CO_2$Me | O | |
| 1c-13 | 5-$CF_3$ | H | H | H | H | H | H | H | H | 2,4-$Cl_2$-Ph | 3-$CO_2$Me | O | |
| 1c-14 | 5-$CF_3$ | H | H | H | H | H | H | H | H | 3,5-$Cl_2$-Ph | 3-$CO_2$Me | O | |
| 1c-15 | 5-$CF_3$ | H | H | H | H | H | H | H | H | Me | 3-$CO_2$Et | O | |
| 1c-16 | 5-$CF_3$ | H | H | H | H | H | H | H | H | Ph | 3-$CO_2$Et | O | |
| 1c-17 | 5-$CF_3$ | H | H | H | H | H | H | H | H | 2-Cl-Ph | 3-$CO_2$Et | O | |
| 1c-18 | 5-$CF_3$ | H | H | H | H | H | H | H | H | 3-Cl-Ph | 3-$CO_2$Et | O | |
| 1c-19 | 5-$CF_3$ | H | H | H | H | H | H | H | H | 4-Cl-Ph | 3-$CO_2$Et | O | |
| 1c-20 | 5-$CF_3$ | H | H | H | H | H | H | H | H | 2,4-$Cl_2$-Ph | 3-$CO_2$Et | O | |
| 1c-21 | 5-$CF_3$ | H | H | H | H | H | H | H | H | 3,5-$Cl_2$-Ph | 3-$CO_2$Et | O | |
| 1c-22 | 5-CN | H | H | H | H | H | H | H | H | Me | 3-$CO_2$Et | O | |
| 1c-23 | 5-CN | H | H | H | H | H | H | H | H | Ph | 3-$CO_2$Et | O | |
| 1c-24 | 5-CN | H | H | H | H | H | H | H | H | 2-Cl-Ph | 3-$CO_2$Et | O | |
| 1c-25 | 5-CN | H | H | H | H | H | H | H | H | 3-Cl-Ph | 3-$CO_2$Et | O | |

TABLE 20

| No. | $(R^1)_m$ | $R^2$ | $R^8$ | $R^3$ | $R^4$ | $R^6$ | $R^5$ | $R^7$ | $R^9$ | $R^{10}$ | $(R^{11})_n$ | X | Remarks |
|---|---|---|---|---|---|---|---|---|---|---|---|---|---|
| 1c-26 | 5-CN | H | H | H | H | H | H | H | H | 4-Cl-Ph | 3-$CO_2$Et | O | |
| 1c-27 | 5-CN | H | H | H | H | H | H | H | H | 2,4-$Cl_2$-Ph | 3-$CO_2$Et | O | |
| 1c-28 | 5-CN | H | H | H | H | H | H | H | H | 3,5-$Cl_2$-Ph | 3-$CO_2$Et | O | |
| 1c-29 | 3-Cl 5-$CF_3$ | H | H | H | H | H | H | H | H | Me | 3-$CO_2$Et | O | |
| 1c-30 | 3-Cl 5-$CF_3$ | H | H | H | H | H | H | H | H | Ph | 3-$CO_2$Et | O | |
| 1c-31 | 3-Cl 5-$CF_3$ | H | H | H | H | H | H | H | H | 2-Cl-Ph | 3-$CO_2$Et | O | |
| 1c-32 | 3-Cl 5-$CF_3$ | H | H | H | H | H | H | H | H | 3-Cl-Ph | 3-$CO_2$Et | O | |
| 1c-33 | 3-Cl 5-$CF_3$ | H | H | H | H | H | H | H | H | 4-Cl-Ph | 3-$CO_2$Et | O | |
| 1c-34 | 3-Cl 5-$CF_3$ | H | H | H | H | H | H | H | H | 2,4-$Cl_2$-Ph | 3-$CO_2$Et | O | |
| 1c-35 | 3-Cl 5-$CF_3$ | H | H | H | H | H | H | H | H | 3,5-$Cl_2$-Ph | 3-$CO_2$Et | O | |
| 1c-36 | 5-$CF_3$ | H | H | H | H | Me | H | H | H | 3,5-$Cl_2$-Ph | 3-$CO_2$Et | O | Note 12 |

TABLE 20-continued

| No. | $(R^1)_m$ | $R^2$ | $R^8$ | $R^3$ | $R^4$ | $R^6$ | $R^5$ | $R^7$ | $R^9$ | $R^{10}$ | $(R^{11})_n$ | X | Remarks |
|---|---|---|---|---|---|---|---|---|---|---|---|---|---|
| 1c-37 | 5-$CF_3$ | H | H | H | H | Me | H | H | H | 3,5-$Cl_2$-Ph | 3-$CO_2$Et | O | Note 13 |
| 1c-38 | 5-$CF_3$ | —$CH_2CH_2$— | | H | H | H | H | H | H | 3,5-$Cl_2$-Ph | 3-$CO_2$Et | O | Note 14 |
| 1c-39 | 5-$CF_3$ | —$CH_2CH_2$— | | H | H | H | H | H | H | 3,5-$Cl_2$-Ph | 3-$CO_2$Et | O | Note 15 |
| 1c-40 | 5-$CF_3$ | H | H | H | —$CH_2CH_2$— | | H | H | H | 3,5-$Cl_2$-Ph | 3-$CO_2$Et | O | Note 16 |
| 1c-41 | 5-$CF_3$ | H | H | H | —$CH_2CH_2$— | | H | H | H | 3,5-$Cl_2$-Ph | 3-$CO_2$Et | O | Note 17 |
| 1c-42 | 5-$CF_3$ | H | H | H | H | H | H | H | H | 3,5-$Cl_2$-Ph | 3-$CO_2$Et | S | |

Note 12: A cis relationship between the methyl group of $R^6$ and X = O.

Note 13: A trans relationship between the methyl group of $R^6$ and X = O.

Note 14: A cis relationship between the ethylene groups of $R^2$ and $R^8$ and X = O.

Note 15: A trans relationship between the ethylene groups of $R^2$ and $R^8$ and X = O.

Note 16: A cis relationship between the ethylene groups of $R^4$ and $R^6$ and X = O.

Note 17: A trans relationship between the ethylene groups of $R^4$ and $R^6$ and X = O.

TABLE 21

(1d)

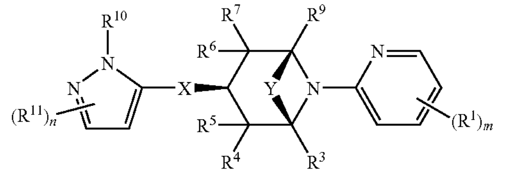

| No. | $(R^1)$m | $R^3$ | $R^4$ | $R^5$ | $R^6$ | $R^7$ | $R^9$ | $R^{10}$ | $(R^{11})_n$ | X | Y |
|---|---|---|---|---|---|---|---|---|---|---|---|
| 1d-1 | 5-$CF_3$ | H | H | H | H | H | H | Me | 3-Me | O | —$CH_2CH_2$— |
| 1d-2 | 5-$CF_3$ | H | H | H | H | H | H | n-Bu | 3-Me | O | —$CH_2CH_2$— |
| 1d-3 | 5-$CF_3$ | H | H | H | H | H | H | Me | 3-$CF_3$ | O | —$CH_2CH_2$— |
| 1d-4 | 5-$CF_3$ | H | H | H | H | H | H | Et | 3-$CF_3$ | O | —$CH_2CH_2$— |
| 1d-5 | 5-$CF_3$ | H | H | H | H | H | H | n-Pr | 3-$CF_3$ | O | —$CH_2CH_2$— |
| 1d-6 | 5-$CF_3$ | H | H | H | H | H | H | n-Bu | 3-$CF_3$ | O | —$CH_2CH_2$— |
| 1d-7 | 5-$CF_3$ | H | H | H | H | H | H | n-Pen | 3-$CF_3$ | O | —$CH_2CH_2$— |
| 1d-8 | 5-$CF_3$ | H | H | H | H | H | H | n-Hex | 3-$CF_3$ | O | —$CH_2CH_2$— |
| 1d-9 | 5-$CF_3$ | H | H | H | H | H | H | n-Hept | 3-$CF_3$ | O | —$CH_2CH_2$— |
| 1d-10 | 5-$CF_3$ | H | H | H | H | H | H | n-Oct | 3-$CF_3$ | O | —$CH_2CH_2$— |
| 1d-11 | 5-$CF_3$ | H | H | H | H | H | H | n-Non | 3-$CF_3$ | O | —$CH_2CH_2$— |
| 1d-12 | 5-$CF_3$ | H | H | H | H | H | H | n-Dec | 3-$CF_3$ | O | —$CH_2CH_2$— |
| 1d-13 | 5-$CF_3$ | H | H | H | H | H | H | i-Pr | 3-$CF_3$ | O | —$CH_2CH_2$— |
| 1d-14 | 5-$CF_3$ | H | H | H | H | H | H | i-Bu | 3-$CF_3$ | O | —$CH_2CH_2$— |
| 1d-15 | 5-$CF_3$ | H | H | H | H | H | H | t-Bu | 3-$CF_3$ | O | —$CH_2CH_2$— |
| 1d-16 | S-$CF_3$ | H | H | H | H | H | H | s-Bu | 3-$CF_3$ | O | —$CH_2CH_2$— |
| 1d-17 | 5-$CF_3$ | H | H | H | H | H | H | Ph | 3-$CF_3$ | O | —$CH_2CH_2$— |
| 1d-18 | 5-$CF_3$ | H | H | H | H | H | H | 2-Cl-Ph | 3-$CF_3$ | O | —$CH_2CH_2$— |
| 1d-19 | S-$CF_3$ | H | H | H | H | H | H | 3-Cl-Ph | 3-$CF_3$ | O | —$CH_2CH_2$— |
| 1d-20 | 5-$CF_3$ | H | H | H | H | H | H | 4-Cl-Ph | 3-$CF_3$ | O | —$CH_2CH_2$— |
| 1d-21 | 5-$CF_3$ | H | H | H | H | H | H | Bn | 3-$CF_3$ | O | —$CH_2CH_2$— |
| 1d-22 | 5-$CF_3$ | H | H | H | H | H | H | —$(CH_2)_2$OMe | 3-$CF_3$ | O | —$CH_2CH_2$— |
| 1d-23 | 5-$CF_3$ | H | H | H | H | H | H | —$(CH_2)_2$OEt | 3-$CF_3$ | O | —$CH_2CH_2$— |
| 1d-24 | 5-$CF_3$ | H | H | H | H | H | H | n-Bu | 3-$CF_3$ | S | —$CH_2CH_2$— |
| 1d-25 | 5-$CF_3$ | H | H | H | H | H | H | n-Pen | 3-$CF_3$ | S | —$CH_2CH_2$— |

TABLE 22

| No. | $(R^1)_m$ | $R^3$ | $R^4$ | $R^5$ | $R^6$ | $R^7$ | $R^9$ | $R^{10}$ | $(R^{11})_n$ | X | Y |
|---|---|---|---|---|---|---|---|---|---|---|---|
| 1d-26 | 5-$CF_3$ | H | H | H | H | H | H | 3-Cl-Ph | 3-$CF_3$ | S | —$CH_2CH_2$— |
| 1d-27 | 5-$CF_3$ | H | H | H | H | H | H | n-Bu | 3-$CF_3$<br>4-Cl | O | —$CH_2CH_2$— |
| 1d-28 | 5-$CF_3$ | H | H | H | H | H | H | n-Bu | 3-$CF_3$<br>4-Br | O | —$CH_2CH_2$— |
| 1d-29 | 5-$CF_3$ | H | H | H | H | H | H | n-Bu | 3-$CF_3$<br>4-Ph | O | —$CH_2CH_2$— |
| 1d-30 | 5-$CF_3$ | H | H | H | H | H | H | n-Bu | 3-Ph | O | —$CH_2CH_2$— |
| 1d-31 | 5-$CF_3$ | H | H | H | H | H | H | n-Bu | 3-(2-Cl-Ph) | O | —$CH_2CH_2$— |
| 1d-32 | 5-$CF_3$ | H | H | H | H | H | H | n-Bu | 3-(3-Cl-Ph) | O | —$CH_2CH_2$— |
| 1d-33 | 5-$CF_3$ | H | H | H | H | H | H | n-Bu | 3-(4-Cl-Ph) | O | —$CH_2CH_2$— |
| 1d-34 | 5-CN | H | H | H | H | H | H | n-Bu | 3-$CF_3$ | O | —$CH_2CH_2$— |
| 1d-35 | 3-Cl<br>5-$CF_3$ | H | H | H | H | H | H | n-Bu | 3-$CF_3$ | O | —$CH_2CH_2$— |
| 1d-36 | 5-$NO_2$ | H | H | H | H | H | H | n-Bu | 3-$CF_3$ | O | —$CH_2CH_2$— |
| 1d-37 | 5-$CF_3$ | H | H | H | H | H | H | H | 3-$CF_3$ | O | —$CH_2CH_2$— |

TABLE 22-continued

| No. | $(R^1)_m$ | $R^3$ | $R^4$ | $R^5$ | $R^6$ | $R^7$ | $R^9$ | $R^{10}$ | $(R^{11})_n$ | X | Y |
|---|---|---|---|---|---|---|---|---|---|---|---|
| 1d-38 | 5-CF$_3$ | H | H | H | H | H | H | —CH$_2$CH(OMe)$_2$ | 3-CF$_3$ | O | —CH$_2$CH$_2$— |
| 1d-39 | 5-CF$_3$ | H | H | H | H | H | H | 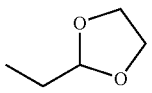 | 3-CF$_3$ | O | —CH$_2$CH$_2$— |
| 1d-40 | 5-CF$_3$ | H | H | H | H | H | H | H | 3-(3,5-F$_2$-Ph) | O | —CH$_2$CH$_2$— |
| 1d-41 | 5-CF$_3$ | H | H | H | H | H | H | —CH$_2$CH(OMe)$_2$ | 3-(3,5-F$_2$-Ph) | O | —CH$_2$CH$_2$— |
| 1d-42 | 5-CF$_3$ | H | H | H | H | H | H | 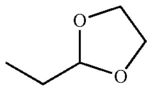 | 3-(3,5-F$_2$-Ph) | O | —CH$_2$CH$_2$— |

TABLE 23

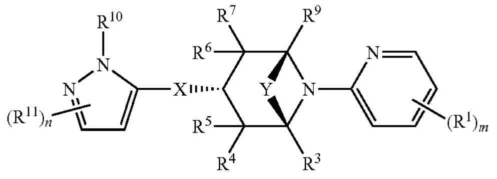

(1e)

| No. | $(R^1)_m$ | $R^3$ | $R^4$ | $R^5$ | $R^6$ | $R^7$ | $R^9$ | $R^{10}$ | $(R^{11})_n$ | X | Y |
|---|---|---|---|---|---|---|---|---|---|---|---|
| 1e-1 | 5-CF$_3$ | H | H | H | H | H | H | Me | 3-Me | O | —CH$_2$CH$_2$— |
| 1e-2 | 5-CF$_3$ | H | H | H | H | H | H | n-Bu | 3-Me | O | —CH$_2$CH$_2$— |
| 1e-3 | 5-CF$_3$ | H | H | H | H | H | H | Me | 3-CF$_3$ | O | —CH$_2$CH$_2$— |
| 1e-4 | 5-CF$_3$ | H | H | H | H | H | H | Et | 3-CF$_3$ | O | —CH$_2$CH$_2$— |
| 1e-5 | 5-CF$_3$ | H | H | H | H | H | H | n-Pr | 3-CF$_3$ | O | —CH$_2$CH$_2$— |
| 1e-6 | 5-CF$_3$ | H | H | H | H | H | H | n-Bu | 3-CF$_3$ | O | —CH$_2$CH$_2$— |
| 1e-7 | 5-CF$_3$ | H | H | H | H | H | H | n-Pen | 3-CF$_3$ | O | —CH$_2$CH$_2$— |
| 1e-8 | 5-CF$_3$ | H | H | H | H | H | H | n-Hex | 3-CF$_3$ | O | —CH$_2$CH$_2$— |
| 1e-9 | 5-CF$_3$ | H | H | H | H | H | H | n-Hept | 3-CF$_3$ | O | —CH$_2$CH$_2$— |
| 1e-10 | 5-CF$_3$ | H | H | H | H | H | H | n-Oct | 3-CF$_3$ | O | —CH$_2$CH$_2$— |
| 1e-11 | 5-CF$_3$ | H | H | H | H | H | H | n-Non | 3-CF$_3$ | O | —CH$_2$CH$_2$— |
| 1e-12 | 5-CF$_3$ | H | H | H | H | H | H | n-Dec | 3-CF$_3$ | O | —CH$_2$CH$_2$— |
| 1e-13 | 5-CF$_3$ | H | H | H | H | H | H | i-Pr | 3-CF$_3$ | O | —CH$_2$CH$_2$— |
| 1e-14 | 5-CF$_3$ | H | H | H | H | H | H | i-Bu | 3-CF$_3$ | O | —CH$_2$CH$_2$— |
| 1e-15 | 5-CF$_3$ | H | H | H | H | H | H | t-Bu | 3-CF$_3$ | O | —CH$_2$CH$_2$— |
| 1e-16 | 5-CF$_3$ | H | H | H | H | H | H | s-Bu | 3-CF$_3$ | O | —CH$_2$CH$_2$— |
| 1e-17 | 5-CF$_3$ | H | H | H | H | H | H | Ph | 3-CF$_3$ | O | —CH$_2$CH$_2$— |
| 1e-18 | 5-CF$_3$ | H | H | H | H | H | H | 2-Cl-Ph | 3-CF$_3$ | O | —CH$_2$CH$_2$— |
| 1e-19 | 5-CF$_3$ | H | H | H | H | H | H | 3-Cl-Ph | 3-CF$_3$ | O | —CH$_2$CH$_2$— |
| 1e-20 | 5-CF$_3$ | H | H | H | H | H | H | 4-Cl-Ph | 3-CF$_3$ | O | —CH$_2$CH$_2$— |
| 1e-21 | 5-CF$_3$ | H | H | H | H | H | H | Bn | 3-CF$_3$ | O | —CH$_2$CH$_2$— |
| 1e-22 | 5-CF$_3$ | H | H | H | H | H | H | —(CH$_2$)$_2$OMe | 3-CF$_3$ | O | —CH$_2$CH$_2$— |
| 1e-23 | 5-CF$_3$ | H | H | H | H | H | H | —(CH$_2$)$_2$OEt | 3-CF$_3$ | O | —CH$_2$CH$_2$— |
| 1e-24 | 5-CF$_3$ | H | H | H | H | H | H | n-Bu | 3-CF$_3$ | S | —CH$_2$CH$_2$— |
| 1e-25 | 5-CF$_3$ | H | H | H | H | H | H | n-Pen | 3-CF$_3$ | S | —CH$_2$CH$_2$— |

TABLE 24

| No. | $(R^1)_m$ | $R^3$ | $R^4$ | $R^5$ | $R^6$ | $R^7$ | $R^9$ | $R^{10}$ | $(R^{11})_n$ | X | Y |
|---|---|---|---|---|---|---|---|---|---|---|---|
| 1e-26 | 5-CF$_3$ | H | H | H | H | H | H | 3-Cl-Ph | 3-CF$_3$ | S | —CH$_2$CH$_2$— |
| 1e-27 | 5-CF$_3$ | H | H | H | H | H | H | n-Bu | 3-CF$_3$<br>4-Cl | O | —CH$_2$CH$_2$— |
| 1e-28 | 5-CF$_3$ | H | H | H | H | H | H | n-Bu | 3-CF$_3$<br>4-Br | O | —CH$_2$CH$_2$— |
| 1e-29 | 5-CF$_3$ | H | H | H | H | H | H | n-Bu | 3-CF$_3$<br>4-Ph | O | —CH$_2$CH$_2$— |
| 1e-30 | 5-CF$_3$ | H | H | H | H | H | H | n-Bu | 3-Ph | O | —CH$_2$CH$_2$— |
| 1e-31 | 5-CF$_3$ | H | H | H | H | H | H | n-Bu | 3-(2-Cl-Ph) | O | —CH$_2$CH$_2$— |
| 1e-32 | 5-CF$_3$ | H | H | H | H | H | H | n-Bu | 3-(3-Cl-Ph) | O | —CH$_2$CH$_2$— |
| 1e-33 | 5-CF$_3$ | H | H | H | H | H | H | n-Bu | 3-(4-Cl-Ph) | O | —CH$_2$CH$_2$— |
| 1e-34 | 5-CN | H | H | H | H | H | H | n-Bu | 3-CF$_3$ | O | —CH$_2$CH$_2$— |
| 1e-35 | 3-Cl<br>5-CF$_3$ | H | H | H | H | H | H | n-Bu | 3-CF$_3$ | O | —CH$_2$CH$_2$— |

TABLE 24-continued

| No. | $(R^1)_m$ | $R^3$ | $R^4$ | $R^5$ | $R^6$ | $R^7$ | $R^9$ | $R^{10}$ | $(R^{11})_n$ | X | Y |
|---|---|---|---|---|---|---|---|---|---|---|---|
| 1e-36 | 5-$NO_2$ | H | H | H | H | H | H | n-Bu | 3-$CF_3$ | O | —$CH_2CH_2$— |
| 1e-37 | 5-$CF_3$ | H | H | H | H | H | H | 2-Py | 3-$CF_3$ | O | —$CH_2CH_2$— |
| 1e-38 | 5-$CF_3$ | H | H | H | H | H | H | H | 3-$CF_3$ | O | —$CH_2CH_2$— |
| 1e-39 | 5-$CF_3$ | H | H | H | H | H | H | —$CH_2CH(OMe)_2$ | 3-$CF_3$ | O | —$CH_2CH_2$— |
| 1e-40 | 5-$CF_3$ | H | H | H | H | H | H | 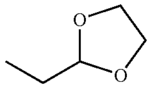 | 3-$CF_3$ | O | —$CH_2CH_2$— |
| 1e-41 | 5-$CF_3$ | H | H | H | H | H | H | H | 3-(3,5-$F_2$-Ph) | O | —$CH_2CH_2$— |
| 1e-42 | 5-$CF_3$ | H | H | H | H | H | H | —$CH_2CH(OMe)_2$ | 3-(3,5-$F_2$-Ph) | O | —$CH_2CH_2$— |
| 1e-43 | 5-$CF_3$ | H | H | H | H | H | H | 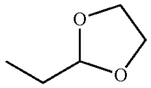 | 3-(3,5-$F_2$-Ph) | O | —$CH_2CH_2$— |

TABLE 25

(1f)

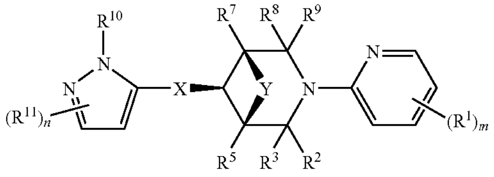

| No. | $(R^1)_m$ | $R^2$ | $R^3$ | $R^5$ | $R^7$ | $R^8$ | $R^9$ | $R^{10}$ | $(R^{11})_n$ | X | Y |
|---|---|---|---|---|---|---|---|---|---|---|---|
| 1f-1 | 5-$CF_3$ | H | H | H | H | H | H | Me | 3-Me | O | —$CH_2CH_2$— |
| 1f-2 | 5-$CF_3$ | H | H | H | H | H | H | n-Bu | 3-Me | O | —$CH_2CH_2$— |
| 1f-3 | 5-$CF_3$ | H | H | H | H | H | H | Me | 3-$CF_3$ | O | —$CH_2CH_2$— |
| 1f-4 | 5-$CF_3$ | H | H | H | H | H | H | Et | 3-$CF_3$ | O | —$CH_2CH_2$— |
| 1f-5 | 5-$CF_3$ | H | H | H | H | H | H | n-Pr | 3-$CF_3$ | O | —$CH_2CH_2$— |
| 1f-6 | 5-$CF_3$ | H | H | H | H | H | H | n-Bu | 3-$CF_3$ | O | —$CH_2CH_2$— |
| 1f-7 | 5-$CF_3$ | H | H | H | H | H | H | n-Pen | 3-$CF_3$ | O | —$CH_2CH_2$— |
| 1f-8 | 5-$CF_3$ | H | H | H | H | H | H | n-Hex | 3-$CF_3$ | O | —$CH_2CH_2$— |
| 1f-9 | 5-$CF_3$ | H | H | H | H | H | H | n-Hept | 3-$CF_3$ | O | —$CH_2CH_2$— |
| 1f-10 | 5-$CF_3$ | H | H | H | H | H | H | n-Oct | 3-$CF_3$ | O | —$CH_2CH_2$— |
| 1f-11 | 5-$CF_3$ | H | H | H | H | H | H | n-Non | 3-$CF_3$ | O | —$CH_2CH_2$— |
| 1f-12 | 5-$CF_3$ | H | H | H | H | H | H | n-Dec | 3-$CF_3$ | O | —$CH_2CH_2$— |
| 1f-13 | 5-$CF_3$ | H | H | H | H | H | H | i-Pr | 3-$CF_3$ | O | —$CH_2CH_2$— |
| 1f-14 | 5-$CF_3$ | H | H | H | H | H | H | i-Bu | 3-$CF_3$ | O | —$CH_2CH_2$— |
| 1f-15 | 5-$CF_3$ | H | H | H | H | H | H | t-Bu | 3-$CF_3$ | O | —$CH_2CH_2$— |
| 1f-16 | S-$CF_3$ | H | H | H | H | H | H | s-Bu | 3-$CF_3$ | O | —$CH_2CH_2$— |
| 1f-17 | 5-$CF_3$ | H | H | H | H | H | H | Ph | 3-$CF_3$ | O | —$CH_2CH_2$— |
| 1f-18 | 5-$CF_3$ | H | H | H | H | H | H | 2-Cl-Ph | 3-$CF_3$ | O | —$CH_2CH_2$— |
| 1f-19 | S-$CF_3$ | H | H | H | H | H | H | 3-Cl-Ph | 3-$CF_3$ | O | —$CH_2CH_2$— |
| 1f-20 | 5-$CF_3$ | H | H | H | H | H | H | n-Cl-Ph | 3-$CF_3$ | O | —$CH_2CH_2$— |
| 1f-21 | 5-$CF_3$ | H | H | H | H | H | H | Bn | 3-$CF_3$ | O | —$CH_2CH_2$— |
| 1f-22 | 5-$CF_3$ | H | H | H | H | H | H | —$(CH_2)_2$OMe | 3-$CF_3$ | O | —$CH_2CH_2$— |
| 1f-23 | 5-$CF_3$ | H | H | H | H | H | H | —$(CH_2)_2$OEt | 3-$CF_3$ | O | —$CH_2CH_2$— |
| 1f-24 | 5-$CF_3$ | H | H | H | H | H | H | n-Bu | 3-$CF_3$ | S | —$CH_2CH_2$— |
| 1f-25 | 5-$CF_3$ | H | H | H | H | H | H | n-Pen | 3-$CF_3$ | S | —$CH_2CH_2$— |

TABLE 26

| No. | $(R^1)_m$ | $R^2$ | $R^3$ | $R^5$ | $R^7$ | $R^8$ | $R^9$ | $R^{10}$ | $(R^{11})_n$ | X | Y |
|---|---|---|---|---|---|---|---|---|---|---|---|
| 1f-26 | 5-$CF_3$ | H | H | H | H | H | H | 3-Cl-Ph | 3-$CF_3$ | S | —$CH_2CH_2$— |
| 1f-27 | 5-$CF_3$ | H | H | H | H | H | H | n-Bu | 3-$CF_3$<br>4-Cl | O | —$CH_2CH_2$— |
| 1f-28 | 5-$CF_3$ | H | H | H | H | H | H | n-Bu | 3-$CF_3$<br>4-Br | O | —$CH_2CH_2$— |
| 1f-29 | 5-$CF_3$ | H | H | H | H | H | H | n-Bu | 3-$CF_3$<br>4-Ph | O | —$CH_2CH_2$— |
| 1f-30 | 5-$CF_3$ | H | H | H | H | H | H | n-Bu | 3-Ph | O | —$CH_2CH_2$— |
| 1f-31 | 5-$CF_3$ | H | H | H | H | H | H | n-Bu | 3-(2-Cl-Ph) | O | —$CH_2CH_2$— |
| 1f-32 | 5-$CF_3$ | H | H | H | H | H | H | n-Bu | 3-(3-Cl-Ph) | O | —$CH_2CH_2$— |

TABLE 26-continued

| No. | $(R^1)_m$ | $R^2$ | $R^3$ | $R^5$ | $R^7$ | $R^8$ | $R^9$ | $R^{10}$ | $(R^{11})_n$ | X | Y |
|---|---|---|---|---|---|---|---|---|---|---|---|
| 1f-33 | 5-$CF_3$ | H | H | H | H | H | H | n-Bu | 3-(4-Cl-Ph) | O | —$CH_2CH_2$— |
| 1f-34 | 5-CN | H | H | H | H | H | H | n-Bu | 3-$CF_3$ | O | —$CH_2CH_2$— |
| 1f-35 | 3-Cl 5-$CF_3$ | H | H | H | H | H | H | n-Bu | 3-$CF_3$ | O | —$CH_2CH_2$— |
| 1f-36 | 5-$NO_2$ | H | H | H | H | H | H | n-Bu | 3-$CF_3$ | O | —$CH_2CH_2$— |
| 1f-37 | 5-$CF_3$ | H | H | H | H | H | H | H | 3-$CF_3$ | O | —$CH_2CH_2$— |
| 1f-38 | 5-$CF_3$ | H | H | H | H | H | H | —$CH_2CH(OMe)_2$ | 3-$CF_3$ | O | —$CH_2CH_2$— |
| 1f-39 | 5-$CF_3$ | H | H | H | H | H | H | 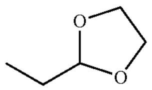 | 3-$CF_3$ | O | —$CH_2CH_2$— |
| 1f-40 | 5-$CF_3$ | H | H | H | H | H | H | —$CH_2CH(OMe)_2$ | 3-(3,5-$F_2$-Ph) | O | —$CH_2CH_2$— |
| 1f-41 | 5-$CF_3$ | H | H | H | H | H | H | H | 3-(3,5-$F_2$-Ph) | O | —$CH_2CH_2$— |

TABLE 27

(1g)

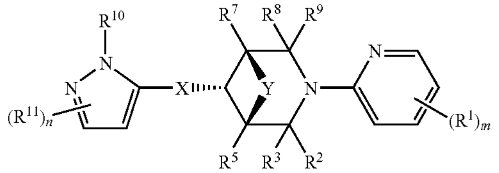

| No. | $(R^1)_m$ | $R^2$ | $R^3$ | $R^5$ | $R^7$ | $R^8$ | $R^9$ | $R^{10}$ | $(R^{11})_n$ | X | Y |
|---|---|---|---|---|---|---|---|---|---|---|---|
| 1g-1 | 5-$CF_3$ | H | H | H | H | H | H | Me | 3-Me | O | —$CH_2CH_2$— |
| 1g-2 | 5-$CF_3$ | H | H | H | H | H | H | n-Bu | 3-Me | O | —$CH_2CH_2$— |
| 1g-3 | 5-$CF_3$ | H | H | H | H | H | H | Me | 3-$CF_3$ | O | —$CH_2CH_2$— |
| 1g-4 | 5-$CF_3$ | H | H | H | H | H | H | Et | 3-$CF_3$ | O | —$CH_2CH_2$— |
| 1g-5 | 5-$CF_3$ | H | H | H | H | H | H | n-Pr | 3-$CF_3$ | O | —$CH_2CH_2$— |
| 1g-6 | 5-$CF_3$ | H | H | H | H | H | H | n-Bu | 3-$CF_3$ | O | —$CH_2CH_2$— |
| 1g-7 | 5-$CF_3$ | H | H | H | H | H | H | n-Pen | 3-$CF_3$ | O | —$CH_2CH_2$— |
| 1g-8 | 5-$CF_3$ | H | H | H | H | H | H | n-Hex | 3-$CF_3$ | O | —$CH_2CH_2$— |
| 1g-9 | 5-$CF_3$ | H | H | H | H | H | H | n-Hept | 3-$CF_3$ | O | —$CH_2CH_2$— |
| 1g-10 | 5-$CF_3$ | H | H | H | H | H | H | n-Oct | 3-$CF_3$ | O | —$CH_2CH_2$— |
| 1g-11 | 5-$CF_3$ | H | H | H | H | H | H | n-Non | 3-$CF_3$ | O | —$CH_2CH_2$— |
| 1g-12 | 5-$CF_3$ | H | H | H | H | H | H | n-Dec | 3-$CF_3$ | O | —$CH_2CH_2$— |
| 1g-13 | 5-$CF_3$ | H | H | H | H | H | H | i-Pr | 3-$CF_3$ | O | —$CH_2CH_2$— |
| 1g-14 | 5-$CF_3$ | H | H | H | H | H | H | i-Bu | 3-$CF_3$ | O | —$CH_2CH_2$— |
| 1g-15 | 5-$CF_3$ | H | H | H | H | H | H | t-Bu | 3-$CF_3$ | O | —$CH_2CH_2$— |
| 1g-16 | S-$CF_3$ | H | H | H | H | H | H | s-Bu | 3-$CF_3$ | O | —$CH_2CH_2$— |
| 1g-17 | 5-$CF_3$ | H | H | H | H | H | H | Ph | 3-$CF_3$ | O | —$CH_2CH_2$— |
| 1g-18 | 5-$CF_3$ | H | H | H | H | H | H | 2-Cl-Ph | 3-$CF_3$ | O | —$CH_2CH_2$— |
| 1g-19 | S-$CF_3$ | H | H | H | H | H | H | 3-Cl-Ph | 3-$CF_3$ | O | —$CH_2CH_2$— |
| 1g-20 | 5-$CF_3$ | H | H | H | H | H | H | 4-Cl-Ph | 3-$CF_3$ | O | —$CH_2CH_2$— |
| 1g-21 | 5-$CF_3$ | H | H | H | H | H | H | Bn | 3-$CF_3$ | O | —$CH_2CH_2$— |
| 1g-22 | 5-$CF_3$ | H | H | H | H | H | H | —$(CH_2)_2$OMe | 3-$CF_3$ | O | —$CH_2CH_2$— |
| 1g-23 | 5-$CF_3$ | H | H | H | H | H | H | —$(CH_2)_2$OEt | 3-$CF_3$ | O | —$CH_2CH_2$— |
| 1g-24 | 5-$CF_3$ | H | H | H | H | H | H | n-Bu | 3-$CF_3$ | S | —$CH_2CH_2$— |
| 1g-25 | 5-$CF_3$ | H | H | H | H | H | H | n-Pen | 3-$CF_3$ | S | —$CH_2CH_2$— |

TABLE 28

| No. | $(R^1)_m$ | $R^2$ | $R^3$ | $R^5$ | $R^7$ | $R^8$ | $R^9$ | $R^{10}$ | $(R^{11})_n$ | X | Y |
|---|---|---|---|---|---|---|---|---|---|---|---|
| 1g-26 | 5-$CF_3$ | H | H | H | H | H | H | 3-Cl-Ph | 3-$CF_3$ | S | —$CH_2CH_2$— |
| 1g-27 | 5-$CF_3$ | H | H | H | H | H | H | n-Bu | 3-$CF_3$ 4-Cl | O | —$CH_2CH_2$— |
| 1g-28 | 5-$CF_3$ | H | H | H | H | H | H | n-Bu | 3-$CF_3$ 4-Br | O | —$CH_2CH_2$— |
| 1g-29 | 5-$CF_3$ | H | H | H | H | H | H | n-Bu | 3-$CF_3$ 4-Ph | O | —$CH_2CH_2$— |
| 1g-30 | 5-$CF_3$ | H | H | H | H | H | H | n-Bu | 3-Ph | O | —$CH_2CH_2$— |
| 1g-31 | 5-$CF_3$ | H | H | H | H | H | H | n-Bu | 3-(2-Cl-Ph) | O | —$CH_2CH_2$— |
| 1g-32 | 5-$CF_3$ | H | H | H | H | H | H | n-Bu | 3-(3-Cl-Ph) | O | —$CH_2CH_2$— |
| 1g-33 | 5-$CF_3$ | H | H | H | H | H | H | n-Bu | 3-(4-Cl-Ph) | O | —$CH_2CH_2$— |
| 1g-34 | 5-CN | H | H | H | H | H | H | n-Bu | 3-$CF_3$ | O | —$CH_2CH_2$— |

TABLE 28-continued

| No. | $(R^1)_m$ | $R^2$ | $R^3$ | $R^5$ | $R^7$ | $R^8$ | $R^9$ | $R^{10}$ | $(R^{11})_n$ | X | Y |
|---|---|---|---|---|---|---|---|---|---|---|---|
| 1g-35 | 3-Cl<br>5-$CF_3$ | H | H | H | H | H | H | n-Bu | 3-$CF_3$ | O | —$CH_2CH_2$— |
| 1g-36 | 5-$NO_2$ | H | H | H | H | H | H | n-Bu | 3-$CF_3$ | O | —$CH_2CH_2$— |

TABLE 29

| No. | Properties or Melting Points (° C.) | $^1$H-NMR data |
|---|---|---|
| 1a-1 | Viscous liquid | δ8.40 (pseudo-d, J = 2.4, 1H), 7.63 (dd, J1 = 9.1, J2 = 2.4, 1H), 6.68 (d, J = 9.0, 1H), 5.34 (s, 1H), 4.46-4.35 (m, 1H), 3.96-3.85 (m, 2H), 3.68-3.59 (m, 2H), 3.58 (s, 3H), 2.19 (s, 3H), 2.09-1.99 (m, 2H), 1.94-1.83 (m, 2H) |
| 1a-2 | Viscous liquid | δ8.40 (pseudo-d, J = 2.4, 1H), 7.63 (dd, J1 = 9.0, J2 = 2.4, 1H), 6.69 (d, J = 9.0, 1H), 5.32 (s, 1H), 4.44-4.36 (m, 1H), 3.95-3.84 (m, 4H), 3.69-3.58 (m, 2H), 2.20 (s, 3H), 2.10-1.98 (m, 2H), 1.96-1.83 (m, 2H), 1.80-1.68 (m, 2H), 1.38-1.23 (m, 2H), 0.91 (t, J = 7.4, 3H) |
| 1a-14 | Viscous liquid | δ8.41 (pseudo-d, J = 2.5, 1H), 7.65 (dd, J1 = 9.0, J2 = 2.5, 1H), 6.70 (d, J = 9.0, 1H), 5.81 (s, 1H), 4.52-4.45 (m, 1H), 4.11-3.91 (m, 2H), 3.70 (s, 3H), 3.66-3.56 (m, 2H), 2.14-2.04 (m, 2H), 1.97-1.87 (m, 2H) |
| 1a-15 | Viscous liquid | δ8.41 (pseudo-d, J = 2.5, 1H), 7.65 (dd, J1 = 9.0, J2 = 2.5, 1H), 6.70 (d, J = 9.0, 1H), 5.80 (s, 1H), 4.52-4.43 (m, 1H), 4.06 (q, J = 7.2, 2H), 3.99-3.90 (m, 2H), 3.67-3.58 (m, 2H), 2.14-2.05 (m, 2H), 1.97-1.86 (m, 2H), 1.40 (t, J = 7.2, 3H) |
| 1a-16 | Viscous liquid | δ8.41 (pseudo-d, J = 2.4, 1H), 7.65 (dd, J1 = 9.0, J2 = 2.4, 1H), 6.71 (d, J = 9.0, 1H), 5.80 (s, 1H), 4.54-4.45 (m, 1H), 4.01-3.90 (m, 4H), 3.68-3.58 (m, 2H), 2.15-2.04 (m, 2H), 1.97-1.77 (m, 4H), 0.90 (t, J = 7.6, 3H) |
| 1a-17 | Viscous liquid | δ8.41 (pseudo-d, J = 2.5, 1H), 7.65 (dd, J1 = 9.0, J2 = 2.5, 1H), 6.70 (d, J = 9.0, 1H), 5.79 (s, 1H), 4.52-4.43 (m, 1H), 4.00 (t, J = 7.2, 2H), 3.98-3.90 (m, 2H), 3.67-3.59 (m, 2H), 2.13-2.04 (m, 2H), 1.95-1.85 (m, 2H), 1.83-1.73 (m, 2H), 1.36-1.26 (m, 2H), 0.92 (t, J = 7.4, 3H) |
| 1a-18 | Viscous liquid | δ8.41 (pseudo-d, J = 2.4, 1H), 7.65 (dd, J1 = 9.0, J2 = 2.4, 1H), 6.70 (d, J = 9.0, 1H), 5.79 (s, 1H), 4.53-4.44 (m, 1H), 3.99 (t, J = 7.3, 2H), 3.97-3.89 (m, 2H), 3.67-3.58 (m, 2H), 2.14-2.03 (m, 2H), 1.96-1.85 (m, 2H), 1.85-1.74 (m, 2H), 1.37-1.22 (m, 4H), 0.87 (t, J = 7.1, 3H) |

TABLE 30

| No. | Properties or Melting Points (° C.) | $^1$H-NMR data |
|---|---|---|
| 1a-19 | Viscous liquid | δ8.41 (pseudo-d, J = 2.4, 1H), 7.65 (dd, J1 = 9.0, J2 = 2.4, 1H), 6.70 (d, J = 9.0, 1H), 5.79 (s, 1H), 4.53-4.43 (m, 1H), 3.99 (t, J = 7.3, 2H), 3.97-3.87 (m, 2H), 3.68-3.59 (m, 2H), 2.14-2.05 (m, 2H), 1.96-1.87 (m, 2H), 1.86-1.72 (m, 2H), 1.34-1.20 (m, 6H), 0.86 (t, J = 6.9, 3H) |
| 1a-24 | Viscous liquid | δ8.41 (pseudo-d, J = 2.4, 1H), 7.64 (dd, J1 = 9.0, J2 = 2.4, 1H), 6.70 (d, J = 9.0, 1H), 5.78 (s, 1H), 4.62-4.44 (m, 2H), 3.97-3.88 (m, 2H), 3.68-3.59 (m, 2H), 2.15-2.05 (m, 2H), 1.97-1.87 (m, 2H), 1.45 (d, J = 6.7, 6H) |
| 1a-26 | 127.2-127.8 | δ8.41 (pseudo-d, J = 2.4, 1H), 7.65 (dd, J1 = 9.0, J2 = 2.4, 1H), 6.70 (d, J = 9.0, 1H), 5.81 (s, 1H), 4.54-4.44 (m, 1H), 3.94-3.83 (m, 2H), 3.75-3.64 (m, 2H), 2.16-2.04 (m, 2H), 2.01-1.89 (m, 2H), 1.61 (s, 9H) |
| 1a-28 | Viscous liquid | δ8.41 (pseudo-d, J = 2.3, 1H), 7.65 (dd, J1 = 9.0, J2 = 2.3, 1H), 6.69 (d, J = 9.0, 1H), 5.90-5.87 (m, 1H), 5.83 (s, 1H), 5.82 (dd, J1 = 10.3, J2 = 1.2, 1H), 5.11 (dd, J1 = 17.1, J2 = 1.2, 1H), 4.64 (d, J = 5.6, 2H), 4.54-4.44 (m, 1H), 3.94-3.84 (m, 2H), 3.70-3.60 (m, 2H), 2.13-2.02 (m, 2H), 1.96-1.85 (m, 2H) |
| 1a-45 | Viscous liquid | δ8.41 (pseudo-d, J = 2.4, 1H), 7.65 (dd, J1 = 9.0, J2 = 2.4, 1H), 6.70 (d, J = 9.0, 1H), 5.85 (s, 1H), 4.60 (q, J = 8.2, 2H), 4.59-4.51 (m, 1H), 4.00-3.90 (m, 2H), 3.67-3.57 (m, 2H), 2.16-2.06 (m, 2H), 1.98-1.87 (m, 2H) |

TABLE 30-continued

| No. | Properties or Melting Points (° C.) | $^1$H-NMR data |
|---|---|---|
| 1a-46 | Viscous liquid | δ8.41 (pseudo-d, J = 2.4, 1H), 7.65 (dd, J1 = 9.0, J2 = 2.4, 1H), 6.70 (d, J = 9.0, 1H), 5.82 (s, 1H), 4.52-4.46 (m, 1H), 4.13-4.05 (m, 2H), 4.01-3.93 (m, 2H), 3.63-3.55 (m, 2H), 2.18-2.04 (m, 6H), 1.94-1.84 (m, 2H) |

TABLE 31

| No. | Properties or Melting Points (° C.) | $^1$H-NMR data |
|---|---|---|
| 1a-50 | Viscous liquid | δ8.40 (pseudo-d, J = 2.3, 1H), 7.63 (dd, J1 = 9.0, J2 = 2.3, 1H), 7.34-7.18 (m, 5H), 6.63 (d, J = 9.0, 1H), 5.82 (s, 1H), 5.21(s, 2H), 4.48-4.42 (m, 1H), 3.68-3.55 (m, 4H), 2.00-1.93 (m, 2H), 1.86-1.77 (m, 2H) |
| 1a-51 | Viscous liquid | δ8.38 (pseudo-d, J = 2.4, 1H), 7.62 (dd, J1 = 9.0, J2 = 2.4, 1H), 7.36-7.33 (m, 1H), 7.22-7.17 (m, 2H), 6.88-6.84 (m, 1H), 6.63 (d, J = 9.0, 1H), 5.87 (s, 1H), 5.36 (s, 2H), 4.50-4.45 (m, 1H), 3.71-3.64 (m, 2H), 3.62-3.55 (m, 2H), 2.02-1.94 (m, 2H), 1.85-1.78 (m, 2H) |
| 1a-52 | Viscous liquid | δ8.40 (pseudo-d, J = 2.4, 1H), 7.64 (dd, J1 = 9.0, J2 = 2.4, 1H), 7.26-7.20 (m, 3H), 7.12-7.08 (m; 1H), 6.66 (d, J = 9.0, 1H), 5.83 (s, 1H), 5.17 (s, 2H), 4.51-4.44 (m, 1H), 3.75-3.68 (m, 2H), 3.63-3.56 (m, 2H); 2.06-1.97 (m, 2H), 1.88-1.79 (m, 2H) |
| 1a-53 | Viscous liquid | δ8.41 (pseudo-d, J = 2.4, 1H), 7.65 (dd, J1 = 9.0, J2 = 2.4, 1H), 7.28-7.24 (m, 2H), 7.16-7.13 (m, 2H), 6.65 (d, J = 9.0, 1H), 5.83 (s, 1H), 5.16 (s, 2H), 4.50-4.43 (m, 1H), 3.74-3.67 (m, 2H), 3.61-3.54 (m, 2H), 2.05-1.97 (m, 2H), 1.87-1.78 (m, 2H) |
| 1a-60 | 161.8-162.4 | δ8.40 (pseudo-d, J = 2.5, 1H), 7.72-7.66 (m, 2H), 7.63 (dd, J1 = 9.0, J2 = 2.5, 1H), 7.49-7.41 (m, 2H), 7.34 (t, J = 7.4, 1H), 6.67 (d, J = 9.0, 1H), 5.99 (s, 1H), 4.63-4.54 (m, 1H), 3.86-3.76 (m, 2H), 3.72-3.63 (m, 2H), 2.14-2.03 (m, 2H), 2.00-1.89 (m, 2H) |
| 1a-61 | Viscous liquid | δ8.37 (pseudo-d, J = 2.4, 1H), 7.61 (dd, J1 = 9.0, J2 = 2.4, 1H), 7.52 (dd, J1 = 7.7, J2 = 1.6, 1H), 7.48-7.34 (m, 3H), 6.63 (d, J = 9.0, 1H), 5.95 (s, 1H), 4.59-4.50 (m, 1H), 3.78-3.69 (m, 2H), 3.65-3.55 (m, 2H), 2.08-1.98 (m, 2H), 1.92-1.81 (m, 2H) |
| 1a-62 | 86.4-87.3 | δ8.40 (s, 1H), 7.78 (pseudo-t, J = 1.9, 1H), 7.67-7.61 (m, 2H), 7.38 (pseudo-t, J = 8.1, 1H), 7.34-7.29 (m, 1H), 6.68 (d, J = 9.0, 1H), 5.98 (s, 1H), 4.65-4.56 (m, 1H), 3.89-3.80 (m, 2H), 3.73-3.64 (m, 2H), 2.16-2.06 (m, 2H), 2.02-1.91 (m, 2H) |

TABLE 32

| No. | Properties or Melting Points (° C.) | $^1$H-NMR data |
|---|---|---|
| 1a-63 | 112.7-113.4 | δ8.40 (s, 1H), 7.68-7.61 (m, 3H), 7.45-7.39 (m, 2H), 6.68 (d, J = 9.0, 1H), 5.98 (s, 1H), 4.63-4.55 (m, 1H), 3.88-3.78 (m, 2H), 3.71-3.61 (m, 2H), 2.15-2.05 (m, 2H), 1.99-1.88 (m, 2H) |
| 1a-68 | Viscous liquid | δ8.41 (pseudo-d, J = 2.4, 1H), 7.91 (d, J = 2.4, 1H), 7.69-7.58 (m, 2H), 7.51 (d, J = 8.7, 1H), 6.69 (d, J = 9.0, 1H), 5.98 (s, 1H), 4.65-4.57 (m, 1H), 3.91-3.81 (m, 2H), 3.73-3.62 (m, 2H), 2.18-7.07 (m, 2H), 2.02-1.90 (m, 2H) |
| 1a-69 | 130.3-130.9 | δ8.41 (pseudo-d, J = 2.5, 1H), 7.73 (d, J = 1.8, 2H), 7.65 (dd, J1 = 9.0, J2 = 2.5, 1H), 7.32 (t, J = 1.8, 1H), 6.69 (d, J = 9.0, 1H), 5.98 (s, 1H), 4.67-4.58 (m, 1H), 3.92-3.81 (m, 2H), 3.75-3.65 (m, 2H), 2.19-2.08 (m, 2H), 2.04-1.92 (m, 2H) |
| 1a-70 | 123.7-123.9 | δ8.57 (pseudo-d, J = 3.8, 1H), 8.39 (pseudo-d, J = 2.5, 1H), 7.85 (pseudo-t, J = 7.8, 1H), 7.69 (pseudo-d, J = 8.2, 1H), 7.63 (dd, J1 = 9.0, J2 = 2.5, 1H), 7.33-7.29 (m, 1H), 6.67 (d, J = 9.0, 1H), 6.01 (s, 1H), 4.68-4.62 (m, 1H), 3.88-3.81 (m, 2H), 3.75-3.68 (m, 2H), 2.12-2.04 (m, 2H), 2.03-1.94 (m, 2H) |
| 1a-75 | Viscous liquid | δ8.40 (pseudo-d, J = 2.4, 1H), 7.64 (dd, J1 = 9.1, J2 = 2.4, 1H), 6.69 (d, J = 9.1, 1H), 5.77 (s, 1H), 4.44-4.41 (m, 1H), 4.12-3.95 (m, 4H), 3.43-3.32 (m, 1H), 3.30-3.20 (m, 1H), 2.20-2.06 (m, 2H), 1.92-1.66 (m, 3H), 1.40-1.28 (m, 2H), 1.09 (d, J = 6.9, 3H), 0.93 (t, J = 7.4, 3H) |

TABLE 32-continued

| No. | Properties or Melting Points (° C.) | $^1$H-NMR data |
|---|---|---|
| 1a-76 | Viscous liquid | δ8.40 (pseudo-d, J = 2.5, 1H), 7.64 (dd, J1 = 9.0, J2 = 2.5, 1H), 6.69 (d, J = 9.0, 1H), 5.78 (s, 1H), 4.34-4.24 (m, 2H), 4.23-3.94 (m, 3H), 3.28-3.18 (m, 1H), 2.97-2.87 (m, 1H), 2.28-2.19 (m, 1H), 2.07-1.97 (m, 1H), 1.82-1.64 (m, 3H), 1.37-1.21 (m, 2H), 1.12 (d, J = 6.6, 3H), 0.92 (t, J = 7.3, 3H) |

TABLE 33

| No. | Properties or Melting Points (° C.) | $^1$H-NMR data |
|---|---|---|
| 1a-77 | Viscous liquid | δ8.39 (pseudo-d, J = 2.5, 1H), 7.63 (dd, J1 = 9.0, J2 = 2.5, 1H), 6.65 (d, J = 9.0, 1H), 6.62 (s, 1H), 4.44-4.25 (m, 4H), 3.23-3.07 (m, 3H), 2.05-1.99 (m, 2H), 1.88-1.79 (m, 2H), 1.69-1.58 (m, 2H), 1.39-1.29 (m, 2H), 0.95 (t, J = 7.4, 3H) |
| 1a-79 | Viscous liquid | δ8.41 (pseudo-d, J = 2.4, 1H), 7.65 (dd, J1 = 9.1, J2 = 2.4, 1H), 6.70 (d, J = 9.1, 1H), 4.92-4.85 (m, 1H), 4.16-4.07 (m, 2H), 3.98(t, J = 7.3, 2H), 3.79-3.41 (m, 2H), 2.16-2.08 (m, 2H), 1.91-1.82 (m, 2H), 1.82-1.74 (m, 2H), 1.38-1.25 (m, 2H), 0.93 (t, J = 7.4, 3H) |
| 1a-81 | Viscous liquid | δ8.41 (pseudo-d, J = 2.5, 1H), 7.65 (dd, J1 = 9.0, J2 = 2.5, 1H), 6.70 (d, J = 9.0, 1H), 4.91-4.84 (m, 1H), 4.18-4.11 (m, 2H), 4.00 (t, J = 7.3, 2H), 3.46-3.38 (m, 2H), 2.16-2.08 (m, 2H), 1.91-1.74 (m, 4H), 1.36-1.25 (m, 2H), 0.93 (t, J = 7.4, 3H) |
| 1a-82 | Viscous liquid | δ8.35 (pseudo-d, J = 2.4, 1H), 7.59 (dd, J1 = 9.0, J2 = 2.4, 1H), 7.44-7.30 (m, 5H), 6.59 (d, J = 9.0, 1H), 4.09-4.00 (m, 3H), 3.95-3.86 (m, 2H), 3.19-3.09 (m, 2H), 1.90-1.73 (m, 4H), 1.68-1.58 (m, 2H), 1.44-1.33 (m, 2H), 0.96 (t, J = 7.4, 3H) |
| 1a-86 | 80.8-81.3 | δ9.86 (s, 1H), 8.41 (pseudo-d, J = 2.5, 1H), 7.65 (dd, J1 = 9.0, J2 = 2.5, 1H), 6.70 (d, J = 9.0, 1H), 5.34-5.26 (m, 1H), 4.19-4.11 (m, 2H), 3.73 (s, 3H), 3.45-3.37 (m, 2H), 2.18-2.10 (m, 2H), 1.87-1.77 (m, 2H) |
| 1a-87 | Viscous liquid | δ8.41 (pseudo-d, J = 2.4, 1H), 8.06 (s, 1H), 7.65 (dd, J1 = 9.0, J2 = 2.4, 1H), 6.71 (d, J = 9.0, 1H), 4.96-4.87 (m, 1H), 4.25-4.18 (m, 2H), 3.94 (s, 3H), 3.75 (s, 3H), 3.37-3.30 (m, 2H), 2.14-2.06 (m, 2H), 1.90-1.81 (m, 2H) |

TABLE 34

| No. | Properties or Melting Points (° C.) | $^1$H-NMR data |
|---|---|---|
| 1a-93 | Viscous liquid | δ9.85 (d, J = 0.9, 1H), 8.41 (pseudo-d, J = 2.4, 1H), 7.64 (dd, J1 = 9.0, J2 = 2.4, 1H), 6.70 (d, J = 9.0, 1H), 5.34-5.26 (m, 1H), 4.18-4.11 (m, 2H), 4.01 (t, J = 7.3, 2H), 3.44-3.36 (m, 2H), 2.18-2.10 (m, 2H), 1.86-1.75 (m, 4H), 1.35-1.27 (m, 2H), 0.93 (t, J = 7.4, 3H) |
| 1a-96 | 79.8-80.6 | δ8.41 (pseudo-d, J = 2.4, 1H), 7.75 (pseudo-d, J = 7.0, 2H), 7.64 (dd, J1 = 9.0, J2 = 2.4, 1H), 7.42-7.33 (m, 2H), 7.36 (t, J = 7.3, 1H), 6.70 (d, J = 9.0, 1H), 5.84 (s, 1H), 4.57-4.47 (m, 1H), 4.01 (t, J = 7.2, 2H), 3.98-3.86 (m, 2H), 3.73-3.60 (m, 2H), 2.15-2.04 (m, 2H), 1.98-1.90 (m, 2H), 1.85-1.78 (m, 2H), 1.40-1.29 (m, 2H), 0.94 (t, J = 7.4, 3H) |
| 1a-97 | 77.4-78.0 | δ8.41 (pseudo-d, J = 2.5, 1H), 7.81 (dd, J1 = 7.7, J2 = 1.8, 1H), 7.64 (dd, J1 = 9.1, J2 = 2.5, 1H), 7.41 (dd, J1 = 7.9, J2 = 1.3, 1H), 7.32-7.21 (m, 2H), 6.70 (d, J = 9.1, 1H), 6.08 (s, 1H), 4.58-4.49 (m, 1H), 4.03 (t, J = 7.2, 2H), 3.97-3.87 (m, 2H), 3.73-3.61 (m, 2H), 2.16-2.05 (m, 2H), 2.02-1.89 (m, 2H), 1.87-1.77 (m, 2H), 1.42-1.31 (m, 2H), 0.94 (t, J = 7.4, 3H) |
| 1a-98 | 97.2-97.7 | δ8.41 (s, 1H), 7.73 (d, J = 1.7, 1H), 7.68-7.61 (m, 2H), 7.34-7.22 (m, 2H), 6.70 (d, J = 9.0, 1H), 5.85 (s, 1H), 4.55-4.46 (m, 1H), 4.01-3.91 (m, 2H), 3.71 (s, 3H), 3.69-3.59 (m, 2H), 2.16-2.06 (m, 2H), 2.00-1.89 (m, 2H) |
| 1a-99 | Viscous liquid | δ8.41 (pseudo-d, J = 2.3, 1H), 7.75 (pseudo-t, J = 1.8, 1H), 7.68-7.60 (m, 2H), 7.34-7.22 (m, 2H), 6.70 (d, J = 9.0, 1H), 5.83 (s, 1H), 4.57-4.47 (m, 1H), 4.00 (t, J = 7.2, 2H), 3.99-3.89 (m, 2H), 3.70-3.61 (m, 2H), 2.14-2.02 (m, 2H), 1.99-1.88 (m, 2H), 1.86-1.76 (m, 2H), 1.40-1.30 (m, 2H), 0.94 (t, J = 7.4, 3H) |

TABLE 35

| No. | Properties or Melting Points (° C.) | $^1$H-NMR data |
|---|---|---|
| 1a-100 | Viscous liquid | δ8.41 (pseudo-d, J = 2.3, 1H), 7.71-7.61 (m, 3H), 7.34 (dd, J1 = 6.6, J2 = 1.9, 2H), 6.70 (d, J = 9.0, 1H), 5.81 (s, 1H), 4.56-4.47 (m, 1H), 4.00 (t, J = 7.1, 2H), 3.99-3.88 (m, 2H), 3.71-3.60 (m, 2H), 2.15-2.05 (m, 2H), 2.00-1.90 (m, 2H), 1.86-1.75 (m, 2H), 1.40-1.30 (m, 2H), 0.94 (t, J = 7.4, 3H) |
| 1a-101 | Viscous liquid | δ8.41 (pseudo-d, J = 2.4, 1H), 7.69 (dd, J1 = 7.8, J2 = 1.6, 1H), 7.64 (dd, J1 = 9.0, J2 = 2.4, 1H), 7.41 (dd, J1 = 8.0, J2 = 1.6, 1H), 7.25-7.18 (m, 1H), 6.69 (d, J = 9.0, 1H), 6.05 (s, 1H), 4.59-4.49 (m, 1H), 4.03 (t, J = 7.1, 2H), 3.99-3.89 (m, 2H), 3.71-3.61 (m, 2H), 2.14-2.04 (m, 2H), 2.00-1.90 (m, 2H), 1.86-1.76 (m, 2H), 1.40-1.31 (m, 2H), 0.94 (t, J = 7.4, 3H) |
| 1a-102 | 112.0-112.7 | δ8.41 (pseudo-d, J = 2.3, 1H), 7.75 (d, J = 8.5, 1H), 7.64 (dd, J1 = 9.0, J2 = 2.3, 1H), 7.44 (d, J = 2.1, 1H), 7.27 (dd, J1 = 8.5, J2 = 2.1, 1H), 6.70 (d, J = 9.0, 1H), 6.08 (s, 1H), 4.57-4.49 (m, 1H), 3.99-3.90 (m, 2H), 3.72 (s, 3H), 3.70-3.60 (m, 2H), 2.16-2.05 (m, 2H), 2.00-1.89 (m, 2H) |
| 1a-103 | Viscous liquid | δ8.41 (pseudo-d, J = 2.4, 1H), 7.78 (d, J = 8.4, 1H), 7.64 (dd, J1 = 9.0, J2 = 2.4, 1H), 7.43 (d, J = 2.1, 1H), 7.26 (dd, J1 = 8.4, J2 = 2.1, 1H), 6.69 (d, J = 9.0, 1H), 6.07 (s, 1H), 4.58-4.48 (m, 1H), 4.02 (t, J = 7.1, 2H), 3.98-3.88 (m, 2H), 3.70-3.61 (m, 2H), 2.14-2.05 (m, 2H), 2.00-1.88 (m, 2H), 1.87-1.77 (m, 2H), 1.41-1.30 (m, 2H), 0.94 (t, J = 7.4, 3H) |
| 1a-104 | Viscous liquid | δ8.41 (pseudo-d, J = 2.3, 1H), 7.84 (d, J = 2.6, 1H), 7.64 (dd, J1 = 9.0, J2 = 2.3, 1H), 7.33 (d, J = 8.5, 1H), 7.19 (dd, J1 = 8.5, J2 = 2.6, 1H), 6.69 (d, J = 9.0, 1H), 6.10 (s, 1H), 4.58-4.49 (m, 1H), 4.02 (t, J = 7.1, 2H), 3.98-3.88 (m, 2H), 3.71-3.61 (m, 2H), 2.14-2.04 (m, 2H), 1.99-1.89 (m, 2H), 1.88-1.79 (m, 2H), 1.41-1.30 (m, 2H), 0.95 (t, J = 7.4, 3H) |

TABLE 36

| No. | Properties or Melting Points (° C.) | $^1$H-NMR data |
|---|---|---|
| 1a-105 | Viscous liquid | δ8.41 (pseudo-d, J = 2.4, 1H), 7.64 (dd, J1 = 9.0, J2 = 2.4, 1H), 7.36 (d, J = 8.0, 2H), 7.21 (pseudo-t, J = 8.0, 1H), 6.70 (d, J = 9.0, 1H), 5.60 (s, 1H), 4.54-4.46 (m, 1H), 4.05 (t, J = 7.0, 2H), 4.01-3.90 (m, 2H), 3.69-3.58 (m, 2H), 2.16-2.05 (m, 2H), 2.01-1.90 (m, 2H), 1.89-1.75 (m, 2H), 1.39-1.27 (m, 2H), 0.93 (t, J = 7.4, 3H) |
| 1a-106 | 114.9-116.1 | δ8.41 (pseudo-d, J = 2.4, 1H), 7.84 (d, J = 2.0, 1H), 7.65 (dd, J1 = 9.0, J2 = 2.4, 1H), 7.58 (dd, J1 = 8.4, J2 = 2.0, 1H), 7.43 (d, J = 8.4, 1H), 6.71 (d, J = 9.0, 1H), 5.81 (s, 1H), 4.56-4.46 (m, 1H), 4.00 (t, J = 7.2, 2H), 3.99-3.90 (m, 2H), 3.70-3.60 (m, 2H), 2.15-2.06 (m, 2H), 2.00-1.89 (m, 2H), 1.86-1.75 (m, 2H), 1.40-1.24 (m, 2H), 0.94 (t, J = 7.4, 3H) |
| 1a-107 | 161.8-162.4 | δ8.41 (pseudo-d, J = 2.2, 1H), 7.68-7.61 (m, 3H), 7.26 (s, 1H), 6.70 (d, J = 9.0, 1H), 5.83 (s, 1H), 4.55-4.46 (m, 1H), 4.01-3.92 (m, 2H), 3.70 (s, 3H), 3.68-3.58 (m, 2H), 2.16-2.06 (m, 2H), 1.99-1.88 (m, 2H) |
| 1a-108 | Viscous liquid | δ8.41 (pseudo-d, J = 2.4, 1H), 7.64 (dd, J1 = 9.0, J2 = 2.4, 1H), 7.63 (pseudo-d, J = 1.9, 2H), 7.25 (t, J = 1.9, 1H), 6.70 (d, J = 9.0, 1H), 5.82 (s, 1H), 4.55-4.47 (m, 1H), 4.00 (t, J = 7.2, 2H), 3.99-3.89 (m, 2H), 3.70-3.59 (m, 2H), 2.16-2.05 (m, 2H), 2.00-1.88 (m, 2H), 1.87-1.74 (m, 2H), 1.39-1.27 (m, 2H), 0.94 (t, J = 7.4, 3H) |
| 1a-126 | Viscous liquid | δ8.4 (pseudo-d, J = 2.3, 1H), 7.65 (dd, J1 = 9.0, J2 = 2.3, 1H), 6.69 (d, J = 9.0, 1H), 5.36 (s, 1H), 4.46-4.38 (m, 1H), 3.95-3.83 (m, 4H), 3.70-3.60 (m, 2H), 2.10-2.00 (m, 2H), 1.96-1.84 (m, 2H), 1.77-1.67 (m, 2H), 1.36-1.28 (m, 2H), 1.27 (s, 9H), 0.91 (t, J = 7.4, 3H) |
| 1a-127 | Viscous liquid | δ8.43 (pseudo-d, J = 2.3, 1H), 7.64 (dd, J1 = 9.0, J2 = 2.3, 1H), 6.66 (d, J = 9.5, 1H), 5.80 (s, 1H), 4.55-4.45 (m, 1H), 4.01-3.89 (m, 4H), 3.74-3.64 (m, 2H), 2.12-2.02 (m, 2H), 1.99-1.89 (m, 2H), 1.84-1.74 (m, 2H), 1.36-1.25 (m, 2H), 0.92 (t, J = 7.4, 3H) |

TABLE 37

| No. | Properties or Melting Points (° C.) | $^1$H-NMR data |
|---|---|---|
| 1a-145 | Viscous liquid | δ9.05 (pseudo-d, J = 2.8, 1H), 8.24 (dd, J1 = 9.5, J2 = 2.8, 1H), 6.64 (d, J = 9.5, 1H), 5.80 (s, 1H), 4.58-4.48 (m, 1H), 4.05-3.93 (m, 4H), 3.86-3.74 (m, 2H), 2.17-2.06 (m, 2H), 2.02-1.91 (m, 2H), 1.84-1.73 (m, 2H), 1.36-1.26 (m, 2H), 0.93 (t, J = 7.4, 3H) |
| 1a-173 | Viscous liquid | δ8.40 (pseudo-d, J = 2.4, 1H), 8.07 (s, 1H), 7.99-7.93 (m, 1H), 7.64 (dd, J1 = 9.0, J2 = 2.4, 1H), 7.62-7.57 (m, 2H), 6.68 (d, J = 9.0, 1H), 6.00 (s, 1H), 4.68-4.59 (m, 1H), 3.87-3.77 (m, 2H), 3.76-3.66 (m, 2H), 2.17-2.06 (m, 2H), 2.03-1.92 (m, 2H) |
| 1a-174 | 144.2-145.5 | δ8.39 (pseudo-d, J = 2.4, 1H), 7.63 (dd, J1 = 9.0, J2 = 2.4, 1H), 7.51 (s, 1H), 7.47 (d, J = 8.0, 1H), 7.32 (pseudo-t, J = 7.8, 1H), 7.16 (d, J = 7.6, 1H), 6.67 (d, J = 9.0, 1H), 5.98 (s, 1H), 4.61-4.55 (m, 1H), 3.83-3.76 (m, 2H), 3.72-3.65 (m, 2H), 2.40 (s, 3H), 2.12-2.04 (m, 2H), 1.99-1.90 (m, 2H) |
| 1a-200 | 130.8-131.1 | δ8.58 (pseudo-d, J = 4.9, 1H), 8.39 (pseudo-d, J = 2.4, 1H), 7.83 (pseudo-t, J = 7.8, 1H), 7.65 (d, J = 8.2, 1H), 7.64 (dd, J1 = 9.0, J2 = 2.4, 1H), 7.30 (dd, J1 = 7.3, J2 = 4.9, 1H), 6.67 (d, J = 9.0, 1H), 6.00 (s, 1H), 4.24-4.12 (m, 3H), 3.38-3.30 (m, 1H), 3.06-2.99 (m, 1H), 2.30-2.23 (m, 1H), 2.11-2.03 (m, 1H), 1.84-1.74 (m, 1H), 1.11 (d, J = 6.7, 3H) |
| 1a-201 | Viscous liquid | δ8.57 (dd, J1 = 4.8, J2 = 1.1, 1H), 8.39 (pseudo-d, J = 2.4, 1H), 7.85 (pseudo-t, J = 7.8, 1H), 7.70 (d, J = 8.2, 1H), 7.62 (dd, J1 = 9.0, J2 = 2.4, 1H), 7.33-7.28 (m, 1H), 6.66 (d, J = 9.0, 1H), 5.98 (s, 1H), 4.58-4.52 (m, 1H), 4.10-4.05 (m, 1H), 4.04-3.99 (m, 1H), 3.45-3.37 (m, 1H), 3.25-3.18 (m, 1H), 2.24-2.16 (m, 1H), 2.14-2.04(m, 1H), 1.91-1.82 (m, 1H), 1.13 (d, J = 6.6, 3H) |

TABLE 38

| No. | Properties or Melting Points (° C.) | $^1$H-NMR data |
|---|---|---|
| 1a-202 | Viscous liquid | δ8.58-8.56 (m, 1H), 8.39 (pseudo-d, J = 2.3, 1H), 7.85 (dt, J1 = 7.8, J2 = 1.7, 1H), 7.69 (pseudo-d, J = 8.2, 1H), 7.62 (dd, J1 = 9.0, J2 = 2.3, 1H), 7.33-7.28 (m, 1H), 6.66 (d, J = 9.0, 1H), 5.99 (s, 1H), 4.69-4.64 (m, 1H), 4.19 (pseudo-d, J = 13.7, 1H), 4.10 (pseudo-d, J = 13.7, 1H), 3.33 (pseudo-t, J = 13.1, 1H), 3.15 (dd, J1 = 13.1, J2 = 11.1, 1H), 2.26-2.18 (m, 1H), 1.87-1.74 (m, 2H), 1.53-1.38 (m, 2H), 0.97 (t, J = 7.5, 3H) |
| 1a-203 | Viscous liquid | δ8.59-8.56 (m, 1H), 8.38 (pseudo-d, J = 2.4, 1H), 7.83 (dt, J1 = 7.8, J2 = 1.9, 1H), 7.66 (pseudo-d, J = 8.2, 1H), 7.61 (dd, J1 = 9.0, J2 = 2.4, 1H), 7.32-7.28 (m, 1H), 6.65 (d, J = 9.0, 1H), 5.99 (s, 1H), 4.34-4.28 (m, 1H), 4.09 (dd, J1 = 13.7, J2 = 3.5, 1H), 4.01-3.94 (m, 1H), 3.55-3.48 (m, 1H), 3.31 (dd, J1 = 13.7, J2 = 7.7, 1H), 2.23-2.15 (m, 1H), 1.93-1.80 (m, 2H), 1.69-1.60 (m, 1H), 1.41-1.31 (m, 1H), 1.01 (t, J = 7.5, 3H) |
| 1a-204 | Viscous liquid | δ8.58-8.56 (m, 1H), 8.39 (pseudo-d, J = 2.5, 1H), 7.85 (pseudo-t, J = 7.8, 1H), 7.69 (pseudo-d, J = 8.2, 1H), 7.62 (dd, J1 = 9.1, J2 = 2.5, 1H), 7.33-7.28 (m, 1H), 6.65 (d, J = 9.1, 1H), 5.98 (s, 1H), 4.64-4.60 (m, 1H), 4.17 (dd, J1 = 13.6, J2 = 3.8, 1H), 4.09 (pseudo-d, J = 13.6, 1H), 3.33 (pseudo-t, J = 13.2, 1H), 3.15 (dd, J1 = 13.2, J2 = 11.0, 1H), 2.24-2.16 (m, 1H), 1.92-1.78 (m, 2H), 1.47-1.31 (m, 4H), 0.90 (t, J = 6.7, 3H) |
| 1a-205 | 104.2-104.7 | δ8.60-8.57 (m, 1H), 8.40 (pseudo-d, J = 2.4, 1H), 7.83 (ddd, J1 = 8.2, J2 = 7.4, J3 = 1.9, 1H), 7.73 (pseudo-d, J = 8.2, 1H), 7.63 (dd, J1 = 9.0, J2 = 2.4, 1H), 7.54-7.47 (m, 2H), 7.29-7.24 (m, 1H), 6.68 (d, J = 9.0, 1H), 6.01 (s, 1H), 4.70-4.65 (m, 1H), 3.89-3.81 (m, 2H), 3.78-3.70 (m, 2H), 2.13-1.99 (m, 4H) |

TABLE 39

| No. | Properties or Melting Points (° C.) | $^1$H-NMR data |
|---|---|---|
| 1a-206 | 114.2-115.0 | δ8.60-8.57 (m, 1H), 8.40 (pseudo-d, J = 2.4, 1H), 7.83 (pseudo-t, J = 7.8, 1H), 7.75 (pseudo-d, J = 8.2, 1H), 7.63 (dd, J1 = 9.0, J2 = 2.4, 1H), 7.44-7.38 (m, 2H), 7.28-7.23 (m, 1H), 6.78 (pseudo-t, J = 8.8, 1H), 6.68 (d, J = 9.0, 1H), 6.05 (s, 1H), 4.72-4.65 (m, 1H), 3.90-3.81 (m, 2H), 3.78-3.69 (m, 2H), 2.14-1.98 (m, 4H) |

TABLE 39-continued

| No. | Properties or Melting Points (° C.) | $^1$H-NMR data |
|---|---|---|
| 1a-207 | Viscous liquid | δ8.59-8.57 (m, 1H), 8.39 (pseudo-s, 1H), 7.84 (pseudo-t, J = 7.8, 1H), 7.75 (d, J = 8.0, 1H), 7.61 (dd, J1 = 9.0, J2 = 2.4, 1H), 7.44-7.37 (m, 2H), 7.28-7.23 (m, 1H), 6.78 (pseudo-t, J = 8.8, 1H), 6.66(d, J = 9.0, 1H), 6.03 (s, 1H), 4.62-4.57 (m, 1H), 4.11-3.97 (m, 2H), 3.46-3.38 (m, 1H), 3.29-3.22 (m, 1H), 2.27-2.20 (m, 1H), 2.15-2.04 (m, 1H), 1.92-1.82 (m, 1H), 1.09 (d, J = 6.9, 3H) |
| 1a-208 | 125.0-125.6 | δ8.61-8.58 (m, 1H), 8.39 (pseudo-d, J = 2.3, 1H), 7.82 (pseudo-t, J = 7.8, 1H), 7.71 (pseudo-d, J = 8.2, 1H), 7.63 (dd, J1 = 9.0, J2 = 2.3, 1H), 7.44-7.38 (m, 2H), 7.29-7.23 (m, 1H), 6.78 (pseudo-t, J = 8.9, 1H), 6.68 (d, J = 9.0, 1H), 6.03 (s, 1H), 4.24-4.15 (m, 3H), 3.41-3.32 (m, 1H), 3.09-3.02 (m, 1H), 2.33-2.26 (m, 1H), 2.16-2.04(m, 1H), 1.87-1.77 (m, 1H), 1.13 (d, J = 6.6, 3H) |
| 1a-209 | Viscous liquid | δ8.53 (dd, J1 = 4.7, J2 = 1.6, 1H), 8.37 (pseudo-d, J = 2.4, 1H), 7.92 (dd, J1 = 8.1, J2 = 1.1, 1H), 7.61 (dd, J1 = 9.0, J2 = 2.4, 1H), 7.43 (dd, J1 = 8.1, J2 = 4.7, 1H), 6.64 (d, J = 9.0, 1H), 5.97 (s, 1H), 4.61-4.55 (m, 1H), 3.79-3.71 (m, 2H), 3.64-3.56 (m, 2H), 2.09-2.00 (m, 2H), 1.92-1.83 (m, 2H) |
| 1a-210 | 152.5-152.9 | δ8.40 (pseudo-d, J = 2.4, 1H), 7.72 (pseudo-t, J = 7.8, 1H), 7.63 (dd, J1 = 9.0, J2 = 2.4, 1H), 7.46 (d, J = 8.0, 1H), 7.16 (d, J = 7.6, 1H), 6.67 (d, J = 9.0, 1H), 6.00 (s, 1H), 4.70-4.62 (m, 1H), 3.83-3.76 (m, 4H), 2.57 (s, 3H), 2.06-1.96 (m, 4H) |

TABLE 40

| No. | Properties or Melting Points (° C.) | $^1$H-NMR data |
|---|---|---|
| 1a-211 | 100.2-100.4 | δ8.41 (pseudo-d, J = 2.5, 1H), 7.65 (dd, J1 = 9.0, J2 = 2.5, 1H), 7.63 (s, 1H), 6.70 (d, J = 9.0, 1H), 6.00 (s, 1H), 4.79-4.73 (m, 1H), 3.95-3.88 (m, 2H), 3.86-3.78 (m, 2H), 2.11-2.04 (m, 4H) |
| 1a-212 | Viscous liquid | δ8.40 (pseudo-d, J = 2.4, 1H), 7.64 (dd, J1 = 9.1, J2 = 2.4, 1H), 6.69 (d, J = 9.1, 1H), 5.78 (s, 1H), 4.56-4.52 (m, 1H), 4.23-4.17 (m, 1H), 4.17-4.11 (m, 1H), 4.02 (t, J = 7.2, 2H), 3.33-3.25 (m, 1H), 3.25-3.15 (m, 1H), 2.21-2.14 (m, 1H), 1.87-1.76 (m, 4H), 1.56-1.41 (m, 2H), 1.38-1.24 (m, 2H), 0.99 (t, J = 7.5, 3H), 0.93 (t, J = 7.4, 3H) |
| 1a-213 | Viscous liquid | δ8.40 (pseudo-d, J = 2.5, 1H), 7.64 (dd, J1 = 9.0, J2 = 2.5, 1H), 6.68 (d, J = 9.0, 1H), 5.77 (s, 1H), 4.24-4.19 (m, 1H), 4.18-4.08 (m, 2H), 3.99 (t, J = 7.2, 2H), 3.42-3.34 (m, 1H), 3.18-3.11 (m, 1H), 2.22-2.15 (m, 1H), 1.89-1.62 (m, 5H), 1.41-1.24 (m, 3H), 1.04 (t, J = 7.5, 3H), 0.92 (t, J = 7.4, 3H) |
| 1a-214 | Viscous liquid | δ8.40 (pseudo-d, J = 2.4, 1H), 7.64 (dd, J1 = 9.1, J2 = 2.4, 1H), 6.68 (d, J = 9.1, 1H), 5.77 (s, 1H), 4.53-4.47 (m, 1H), 4.22-4.11 (m, 2H), 4.03 (t, J = 7.2, 2H), 3.33-3.24 (m, 1H), 3.22-3.14 (m, 1H), 2.21-2.13 (m, 1H), 1.95-1.86 (m, 1H), 1.85-1.76 (m, 3H), 1.49-1.24 (m, 6H), 0.93 (t, J = 7.4, 3H), 0.93 (t, J = 7.4, 3H) |
| 1a-215 | 102.5-103.0 | δ8.38 (pseudo-d, J = 2.4, 1H), 7.62 (dd, J1 = 9.0, J2 = 2.4, 1H), 6.68 (d, J = 9.0, 1H), 5.80 (s, 1H), 4.05-3.94 (m, 2H), 3.78 (pseudo-d, J = 13.5, 1H), 3.71 (s, 3H), 3.56-3.48 (m, 1H), 3.28 (d, J = 13.5, 1H), 2.12-2.04 (m, 1H), 1.94-1.85 (m, 1H), 1.10 (s, 3H), 1.08 (s, 3H) |

TABLE 41

| No. | Properties or Melting Points (° C.) | $^1$H-NMR data |
|---|---|---|
| 1a-216 | Viscous liquid | δ8.38 (pseudo-d, J = 2.4, 1H), 7.62 (dd, J1 = 9.1, J2 = 2.4, 1H), 6.67 (d, J = 9.1, 1H), 5.78 (s, 1H), 4.05-3.94 (m, 2H), 4.01 (t, J = 7.2, 2H), 3.77 (pseudo-d, J = 13.5, 1H), 3.55-3.48 (m, 1H), 3.28 (d, J = 13.5, 1H), 2.11-2.04 (m, 1H), 1.93-1.85 (m, 1H), 1.84-1.75 (m, 2H), 1.36-1.25 (m, 2H), 1.10 (s, 3H), 1.08 (s, 3H), 0.93 (t, J = 7.4, 3H) |
| 1a-217 | 127.9-128.3 | δ8.39 (pseudo-d, J = 2.3, 1H), 7.63 (dd, J1 = 9.0, J2 = 2.3, 1H), 6.65 (s, 1H), 6.64 (d, J = 9.0, 1H), 4.35-4.29 (m, 2H), 3.99 (s, 3H), 3.23-3.15 (m, 1H), 3.14-3.06 (m, 2H), 2.05-1.99 (m, 2H), 1.68-1.58 (m, 2H) |

TABLE 41-continued

| No. | Properties or Melting Points (° C.) | $^1$H-NMR data |
|---|---|---|
| 1a-218 | 105.3-105.6 | δ8.40 (pseudo-d, J = 2.5, 1H), 7.66 (dd, J1 = 9.0, J2 = 2.5, 1H), 7.06 (s, 1H), 6.67 (d, J = 9.0, 1H), 4.61 (pseudo-d, J = 13.8, 2H), 4.47 (t, J = 7.5, 2H), 3.30-3.20 (m, 1H), 2.99-2.89 (m, 2H), 2.14-2.08 (m, 2H), 1.99-1.91 (m, 2H), 1.88-1.75 (m, 2H), 1.44-1.33 (m, 2H), 0.97 (t, J = 7.4, 3H) |
| 1a-219 | Viscous liquid | δ8.41 (pseudo-d, J = 2.4, 1H), 7.64 (dd, J1 = 9.0, J2 = 2.4, 1H), 6.70 (d, J = 9.0, 1H), 4.40-4.32 (m, 1H), 4.23-4.16 (m, 2H), 3.71 (s, 3H), 3.40-3.32 (m, 2H), 2.13-2.05 (m, 2H), 2.07 (s, 3H), 1.89-1.79 (m, 2H) |
| 1a-220 | Viscous liquid | δ8.41 (pseudo-d, J = 2.3, 1H), 7.65 (dd, J1 = 9.0, J2 = 2.3, 1H), 6.70 (d, J = 9.0, 1H), 4.72-4.64 (m, 1H), 4.57 (d, J = 5.9, 2H), 4.20-4.14 (m, 2H), 3.73 (s, 3H), 3.43-3.35 (m, 2H), 2.17-2.09 (m, 2H), 1.91-1.81 (m, 2H), 1.59 (t, J = 5.9, 1H) |
| 1a-221 | Viscous liquid | δ8.41 (pseudo-d, J = 2.5, 1H), 7.65 (dd, J1 = 9.0, J2 = 2.5, 1H), 6.70 (d, J = 9.0, 1H), 4.39-4.31 (m, 1H), 4.21-4.14 (m, 2H), 3.96 (t, J = 7.4, 2H), 3.40-3.32 (m, 2H), 2.12-2.05 (m, 2H), 2.07 (s, 3H), 1.88-1.74 (m, 4H), 1.36-1.27 (m, 2H), 0.92 (t, J = 7.4, 3H) |

TABLE 42

| No. | Properties or Melting Points (° C.) | $^1$H-NMR data |
|---|---|---|
| 1a-222 | Viscous liquid | δ9.84 (d, J = 1.0, 1H), 8.40 (pseudo-d, J = 2.3, 1H), 7.64 (dd, J1 = 9.0, J2 = 2.3, 1H), 6.69 (d, J = 9.0, 1H), 5.08-5.01 (m, 1H), 4.34-4.29 (m, 2H), 3.72 (s, 3H), 3.22-3.14 (m, 1H), 2.91 (dd, J1 = 13.7, J2 = 10.3, 1H), 2.12-2.05 (m, 1H), 2.04-1.94 (m, 1H), 1.69-1.61 (m, 1H), 1.15 (d, J = 6.6, 3H) |
| 1a-223 | Viscous liquid | δ8.42 (pseudo-d, J = 2.4, 1H), 8.18 (s, 2H), 7.76(s, 1H), 7.65 (dd, J1 = 9.0, J2 = 2.4, 1H), 6.71 (d, J = 9.0, 1H), 5.93 (s, 1H), 4.59-4.51 (m, 1H), 4.03 (t, J = 7.1, 2H), 4.01-3.91 (m, 2H), 3.71-3.61 (m, 2H), 2.18-2.07 (m, 2H), 2.01-1.91 (m, 2H), 1.89-1.79 (m, 2H), 1.42-1.30 (m, 2H), 0.95 (t, J = 7.4, 3H) |
| 1a-224 | Viscous liquid | δ8.41 (pseudo-d, J = 2.4, 1H), 7.65 (dd, J1 = 9.0, J2 = 2.4, 1H), 7.30-7.22 (m, 2H), 6.74-6.68 (m, 2H), 5.81 (s, 1H), 4.55-4.48 (m, 1H), 4.00 (t, J = 7.1, 2H), 3.98-3.90 (m, 2H), 3.69-3.61 (m, 2H), 2.15-2.07 (m, 2H), 1.99-1.90 (m, 2H), 1.85-1.76 (m, 2H), 1.39-1.30 (m, 2H), 0.94 (t, J = 7.4, 3H) |
| 1a-225 | Viscous liquid | δ8.41 (pseudo-d, J = 2.5, 1H), 7.64 (dd, J1 = 9.0, J2 = 2.5, 1H), 7.29-7.23 (m, 2H), 6.75-6.69 (m, 1H), 6.70 (d, J = 9.0, 1H), 5.79 (s, 1H), 4.49-4.43 (m, 1H), 4.09-4.02 (m, 2H), 4.03 (t, J = 7.1, 2H), 3.45-3.36 (m, 1H), 3.31-3.24 (m, 1H), 2.23-2.16 (m, 1H), 2.16-2.08 (m, 1H), 1.92-1.79 (m, 3H), 1.42-1.32 (m, 2H), 1.11 (d, J = 6.9, 3H), 0.95 (t, J = 7.4, 3H) |
| 1a-226 | Viscous liquid | δ8.41 (pseudo-d, J = 2.4, 1H), 7.64 (dd, J1 = 9.1, J2 = 2.4, 1H), 7.30-7.25 (m, 2H), 6.75-6.68 (m, 1H), 6.70 (d, J = 9.1, 1H), 5.79 (s, 1H), 4.32-4.26 (m, 2H), 4.06-4.00 (m, 1H), 3.98 (t, J = 7.2, 2H), 3.30-3.22 (m, 1H), 2.99-2.92 (m, 1H), 2.32-2.24 (m, 1H), 2.00-1.99 (m, 1H), 1.84-1.67 (m, 3H), 1.38-1.27 (m, 2H), 1.14 (d, J = 6.6, 3H), 0.93 (t, J = 7.4, 3H) |

TABLE 43

| No. | Properties or Melting Points (° C.) | $^1$H-NMR data |
|---|---|---|
| 1a-227 | Viscous liquid | δ8.41 (pseudo-d, J = 2.5, 1H), 7.64 (dd, J1 = 9.0, J2 = 2.5, 1H), 7.30-7.24 (m, 2H), 6.74-6.67 (m, 2H), 5.80 (s, 1H), 4.59-4.55 (m, 1H), 4.24-4.10 (m, 2H), 4.07-3.97 (m, 2H), 3.36-3.27 (m, 1H), 3.25-3.15 (m, 1H), 2.26-2.19 (m, 1H), 1.89-1.65 (m, 4H), 1.60-1.28 (m, 4H), 1.07-0.91 (m, 6H) |
| 1a-228 | Viscous liquid | δ8.40 (pseudo-d, J = 2.2, 1H), 7.64 (dd, J1 = 9.0, J2 = 2.2, 1H), 7.30-7.23 (m, 2H), 6.71 (pseudo-t, J = 8.9, 1H), 6.68 (d, J = 9.0, 1H), 5.79 (s, 1H), 4.24-4.10 (m, 3H), 3.98 (t, J = 7.1, 2H), 3.45-3.37 (m, 1H), 3.18 (dd, J1 = 13.6, J2 = 8.6, 1H), 2.25-2.19 (m, 1H), 1.90-1.67 (m, 5H), 1.43-1.24 (m, 3H), 1.05 (t, J = 7.5, 3H), 0.93 (t, J = 7.4, 3H) |

TABLE 43-continued

| No. | Properties or Melting Points (° C.) | $^1$H-NMR data |
|---|---|---|
| 1a-229 | Viscous liquid | δ8.41 (pseudo-d, J = 2.5, 1H), 7.64 (dd, J1 = 9.0, J2 = 2.5, 1H), 7.30-7.23 (m, 2H), 6.74-6.66 (m, 2H), 5.79 (s, 1H), 4.56-4.51 (m, 1H), 4.24-4.08 (m, 2H), 4.05-3.96 (m, 2H), 3.46-3.27 (m, 1H), 3.24-3.11 (m, 1H), 2.27-2.18 (m, 1H), 1.98-1.89 (m, 1H), 1.88-1.70 (m, 3H), 1.58-1.30 (m, 6H), 0.98 (m, 6H) |
| 1a-230 | Viscous liquid | δ8.42 (pseudo-d, J = 2.4, 1H), 7.65 (dd, J1 = 9.0, J2 = 2.4, 1H), 7.29-7.24 (m, 2H), 6.74-6.67 (m, 2H), 5.81 (s, 1H), 4.54-4.49 (m, 1H), 3.99 (t, J = 7.2, 2H), 3.96-3.89 (m, 2H), 3.70-3.62 (m, 2H), 2.14-2.06 (m, 2H), 1.99-1.90 (m, 2H), 1.85-1.78 (m, 2H), 1.35-1.25 (m, 6H), 0.86 (pseudo-t, J = 7.0, 3H) |
| 1a-231 | Viscous liquid | δ8.41 (pseudo-d, J = 2.5, 1H), 7.64 (dd, J1 = 9.0, J2 = 2.5, 1H), 7.29-7.23 (m, 2H), 6.75-6.68 (m, 2H), 5.79 (s, 1H), 4.47-4.45 (m, 1H), 4.12-4.04 (m, 2H), 4.01 (t, J = 7.2, 2H), 3.44-3.36 (m, 1H), 3.31-3.22 (m, 1H), 2.23-2.17 (m, 1H), 2.16-2.10 (m, 1H), 1.91-1.80 (m, 3H), 1.38-1.24 (m, 6H), 1.11 (d, J = 6.8, 3H), 0.86 (t, J = 7.0, 3H) |

TABLE 44

| No. | Properties or Melting Points (° C.) | $^1$H-NMR data |
|---|---|---|
| 1a-232 | Viscous liquid | δ8.41 (pseudo-d, J = 2.4, 1H), 7.64 (dd, J1 = 9.0, J2 = 2.4, 1H), 7.30-7.25 (m, 2H), 6.74-6.68 (m, 2H), 5.80 (s, 1H), 4.32-4.26 (m, 2H), 4.06-3.99 (m, 1H), 3.97 (t, J = 7.2, 2H), 3.30-3.22 (m, 1H), 2.98-2.92 (m, 1H), 2.31-2.24 (m, 1H), 2.07-2.00 (m, 1H), 1.84-1.67 (m, 3H), 1.34-1.23 (m, 6H), 1.14 (d, J = 6.6, 3H), 0.86 (t, J = 6.9, 3H) |
| 1a-233 | 75.0-75.6 | δ8.41 (pseudo-d, J = 2.4, 1H), 7.65 (dd, J1 = 9.0, J2 = 2.4, 1H), 7.39-7.25 (m, 2H), 6.71 (d, J = 9.0, 1H), 5.76 (s, 1H), 4.53-4.48 (m, 1H), 3.99 (t, J = 7.1, 2H), 3.98-3.90 (m, 2H), 3.69-3.61 (m, 2H), 2.14-2.06 (m, 2H), 1.98-1.89 (m, 2H), 1.84-1.76 (m, 2H), 1.39-1.29 (m, 2H), 0.94 (t, J = 7.4, 3H) |
| 1a-234 | Viscous liquid | δ8.41 (pseudo-d, J = 2.5, 1H), 7.64 (dd, J1 = 9.0, J2 = 2.5, 1H), 7.40-7.31 (m, 2H), 6.70 (d, J = 9.0, 1H), 5.75 (s, 1H), 4.32-4.25 (m, 2H), 4.06-3.99 (m, 1H), 3.97 (t, J = 7.2, 2H), 3.30-3.22 (m, 1H), 2.98-2.91 (m, 1H), 2.30-2.25 (m, 1H), 2.08-2.00 (m, 1H), 1.84-1.67 (m, 3H), 1.38-1.28 (m, 2H), 1.14 (d, J = 6.6, 3H), 0.93 (t, J = 7.4, 3H) |
| 1a-235 | 99.2-100.7 | δ8.41 (s, 1H), 7.88 (pseudo-d, J = 6.7, 2H), 7.67-7.63 (m, 3H), 6.71 (d, J = 9.0, 1H), 5.89 (s, 1H), 4.56-4.50 (m, 1H), 4.02 (t, J = 7.1, 2H), 3.98-3.90 (m, 2H), 3.70-3.62 (m, 2H), 2.16-2.07 (m, 2H), 2.00-1.90 (m, 2H), 1.87-1.77 (m, 2H), 1.40-1.30 (m, 2H), 0.94 (t, J = 7.4, 3H) |
| 1a-236 | Viscous liquid | δ8.41 (pseudo-d, J = 2.4, 1H), 7.74-7.69 (m, 2H), 7.65 (dd, J1 = 9.0, J2 = 2.4, 1H), 7.06 (pseudo-t, J = 8.8, 2H), 6.70 (d, J = 9.0, 1H), 5.79 (s, 1H), 4.55-4.48 (m, 1H), 4.00 (t, J = 7.2, 2H), 3.97-3.89 (m, 2H), 3.70-3.62 (m, 2H), 2.14-2.06 (m, 2H), 1.99-1.90 (m, 2H), 1.85-1.77 (m, 2H), 1.39-1.30 (m, 2H), 0.94 (t, J = 7.4, 3H) |

TABLE 45

| No. | Properties or Melting Points (° C.) | $^1$H-NMR data |
|---|---|---|
| 1a-237 | 133.1-134.0 | δ8.41 (pseudo-d, J = 2.4, 1H), 7.67 (pseudo-d, J = 8.5, 2H), 7.65 (dd, J1 = 9.0, J2 = 2.4, 1H), 7.39 (pseudo-d, J = 8.5, 2H), 6.70 (d, J = 9.0, 1H), 5.81 (s, 1H), 4.55-4.49 (m, 1H), 4.00 (t, J = 7.1, 2H), 3.97-3.88 (m, 2H), 3.71-3.62 (m, 2H), 2.14-2.05 (m, 2H), 1.99-1.89(m, 2H), 1.85-1.76 (m, 2H), 1.39-1.30 (m, 2H), 1.33 (s, 9H), 0.93 (t, J = 7.4, 3H) |
| 1a-238 | Viscous liquid | δ8.41 (pseudo-d, J = 2.4, 1H), 7.67 (pseudo-d, J = 8.5, 2H), 7.64 (dd, J1 = 9.0, J2 = 2.4, 1H), 7.26 (pseudo-d, J = 8.5, 2H), 6.70 (d, J = 9.0, 1H), 5.81 (s, 1H), 4.55-4.48 (m, 1H), 4.00 (t, J = 7.2, 2H), 3.96-3.88 (m, 2H), 3.70-3.62 (m, 2H), 2.50 (s, 3H), 2.13-2.04 (m, 2H), 1.98-1.90 (m, 2H), 1.85-1.76 (m, 2H), 1.39-1.30 (m, 2H), 0.93 (t, J = 7.4, 3H) |

TABLE 45-continued

| No. | Properties or Melting Points (° C.) | $^1$H-NMR data |
|---|---|---|
| 1a-239 | 86.2-86.5 | δ8.42 (pseudo-d, J = 2.3, 1H), 8.23 (d, J = 9.0, 2H), 7.91 (d, J = 9.0, 2H), 7.66 (dd, J1 = 9.0, J2 = 2.3, 1H), 6.71 (d, J = 9.0, 1H), 5.94 (s, 1H), 4.57-4.52 (m, 1H), 4.03 (t, J = 7.1, 2H), 3.99-3.91 (m, 2H), 3.70-3.62 (m, 2H), 2.17-2.08 (m, 2H), 1.99-1.90 (m, 2H), 1.88-1.79 (m, 2H), 1.41-1.31 (m, 2H), 0.95 (t, J = 7.4, 3H) |
| 1a-240 | Viscous liquid | δ8.42 (pseudo-d, J = 2.4, 1H), 7.86 (d, J = 8.0, 2H), 7.65 (dd, J1 = 9.1, J2 = 2.4, 1H), 7.62 (d, J = 8.0, 2H), 6.71 (d, J = 9.1, 1H), 5.88 (s, 1H), 4.56-4.51 (m, 1H), 4.02 (t, J = 7.1, 2H), 3.98-3.90 (m, 2H), 3.70-3.63 (m, 2H), 2.16-2.07 (m, 2H), 2.00-1.91 (m, 2H), 1.87-1.78 (m, 2H), 1.39-1.30 (m, 2H), 0.94 (t, J = 7.4, 3H) |
| 1a-241 | Viscous liquid | δ8.41 (pseudo-d, J = 2.4, 1H), 7.68 (pseudo-d, J = 8.9, 2H), 7.64 (dd, J1 = 9.0, J2 = 2.4, 1H), 6.91 (pseudo-d, J = 8.9, 2H), 6.69 (d, J = 9.0, 1H), 5.77 (s, 1H), 4.55-4.47 (m, 1H), 3.99 (t, J = 7.2, 2H), 3.96-3.88 (m, 2H), 3.83 (s, 3H), 3.69-3.62 (m, 2H), 2.13-2.05 (m, 2H), 1.98-1.90 (m, 2H), 1.85-1.76 (m, 2H), 1.39-1.30 (m, 2H), 0.93 (t, J = 7.4, 3H) |

TABLE 46

| No. | Properties or Melting Points (° C.) | $^1$H-NMR data |
|---|---|---|
| 1a-242 | Viscous liquid | δ8.41 (pseudo-d, J = 2.4, 1H), 7.76 (pseudo-d, J = 8.8, 2H), 7.65 (dd, J1 = 9.0, J2 = 2.4, 1H), 7.22 (pseudo-d, J = 8.8, 2H), 6.70 (d, J = 9.0, 1H), 5.82 (s, 1H), 4.55-4.49 (m, 1H), 4.00 (t, J = 7.1, 2H), 3.99-3.90 (m, 2H), 3.70-3.62 (m, 2H), 2.15-2.06 (m, 2H), 1.98-1.91 (m, 2H), 1.85-1.76 (m, 2H), 1.39-1.30 (m, 2H), 0.94 (t, J = 7.4, 3H) |
| 1a-243 | 98.7-99.8 | δ8.35 (pseudo-d, J = 2.5, 1H), 7.58 (dd, J1 = 9.0, J2 = 2.5, 1H), 6.60 (d, J = 9.0, 1H), 4.50-4.34 (m, 4H), 3.40 (s, 3H), 2.88-2.73 (m, 2H), 2.37-2.28 (m, 1H), 1.79-1.72 (m, 2H), 1.58-1.48 (m, 2H), 1.45 (s, 3H), 1.39 (t, J = 7.1, 3H) |
| 1a-244 | Viscous liquid | δ8.40 (s, 1H), 7.78 (s, 1H), 4.91-4.85 (m, 1H), 4.00 (t, J = 7.3, 2H), 3.88-3.81 (m, 2H), 3.37-3.29 (m, 2H), 2.22-2.14 (m, 2H), 2.05-1.94 (m, 2H), 1.84-1.75 (m, 2H), 1.38-1.28 (m, 2H), 0.94 (t, J = 7.4, 3H) |
| 1a-245 | 133.8-134.5 | δ10.04 (br-s, 1H), 8.41 (pseudo-d, J = 2.4, 1H), 7.64 (dd, J1 = 9.0, J2 = 2.4, 1H), 6.69 (d, J = 9.0, 1H), 5.93 (s, 1H), 4.67-4.58 (m, 1H), 4.00-3.92 (m, 2H), 3.64-3.56 (m, 2H), 2.14-2.04 (m, 2H), 1.95-1.85 (m, 2H) |
| 1a-246 | 136.9-137.6 | δ10.00 (br-s, 1H), 8.40 (pseudo-d, J = 2.4, 1H), 7.63 (dd, J1 = 9.0, J2 = 2.4, 1H), 6.69 (d, J = 9.0, 1H), 5.92 (s, 1H), 4.31-4.23 (m, 2H), 4.15 (br-s, 1H), 3.27-3.18 (m, 1H), 2.94-2.87 (m, 1H), 2.30-2.22 (m, 1H), 2.03-1.94 (m, 1H), 1.75-1.66 (m, 1H), 1.10 (d, J = 6.8, 3H) |
| 1a-247 | 120.0-120.8 | δ8.39 (pseudo-s, 2H), 7.66-7.60 (m, 2H), 7.55 (d, J = 8.2, 1H), 6.67 (d, J = 9.0, 1H), 6.00 (s, 1H), 4.67-4.59 (m, 1H), 3.86-3.78 (m, 2H), 3.75-3.66 (m, 2H), 2.38 (s, 3H), 2.11-2.01 (m, 2H), 2.00-1.92 (m, 2H) |

TABLE 47

| No. | Properties or Melting Points (° C.) | $^1$H-NMR data |
|---|---|---|
| 1a-248 | Viscous liquid | δ8.42 (pseudo-d, J = 2.5, 1H), 7.65 (dd, J1 = 9.0, J2 = 2.5, 1H), 7.37 (s, 2H), 6.93 (s, 1H), 6.70 (d, J = 9.0, 1H), 5.82 (s, 1H), 4.55-4.49 (m, 1H), 4.00 (t, J = 7.2, 2H), 3.98-3.89 (m, 2H), 3.70-3.61 (m, 2H), 2.34 (s, 6H), 2.15-2.05 (m, 2H), 2.20-1.90 (m, 2H), 1.86-1.76 (m, 2H), 1.38-1.29 (m, 2H), 0.93 (t, J = 7.4, 3H) |
| 1a-249 | 95.1-95.7 | δ8.42 (pseudo-d, J = 2.4, 1H), 7.66 (dd, J1 = 9.0, J2 = 2.4, 1H), 7.60 (s, 2H), 6.71 (d, J = 9.0, 1H), 5.90 (s, 1H), 4.55-4.49 (m, 1H), 4.01 (t, J = 7.1, 2H), 3.99-3.92 (m, 2H), 3.68-3.61 (m, 2H), 2.18-2.08 (m, 2H), 1.98-1.89 (m, 2H), 1.85-1.77 (m, 2H), 1.39-1.29 (m, 2H), 0.94 (t, J = 7.4, 3H) |
| 1a-250 | Viscous liquid | δ8.40 (pseudo-d, J = 2.4, 1H), 7.63 (dd, J1 = 9.0, J2 = 2.4, 1H), 6.69 (d, J = 9.0, 1H), 5.83 (s, 1H), 4.61-4.53 (m, 1H), 3.90-3.75 (m, 4H), 2.08-1.98 (m, 4H), 1.47 (s, 9H) |

TABLE 47-continued

| No. | Properties or Melting Points (° C.) | $^1$H-NMR data |
|---|---|---|
| 1a-251 | Viscous liquid | δ8.38 (pseudo-d, J = 2.4, 1H), 7.67 (pseudo-d, J = 8.8, 2H), 7.62 (dd, J1 = 9.2, J2 = 2.4, 1H), 7.44 (pseudo-t, J = 7.8, 2H), 7.34 (pseudo-t, J = 7.4, 1H), 6.66 (d, J = 9.2, 1H), 5.97 (s, 1H), 4.24-4.16 (m, 2H), 4.13-4.07 (m, 1H), 3.32-3.25 (m, 1H), 3.00-2.94 (m, 1H), 2.30-2.23 (m, 1H), 2.09-1.98 (m, 1H), 1.78-1.68 (m, 1H), 1.10 (d, J = 6.7, 3H) |
| 1a-252 | Viscous liquid | δ8.39 (pseudo-d, J = 2.4, 1H), 7.62 (dd, J1 = 9.2, J2 = 2.4, 1H), 7.49 (s, 1H), 7.44 (pseudo-d, J = 8.0, 1H), 7.30 (pseudo-t, J = 7.8, 1H), 7.15 (pseudo-d, J = 7.6, 1H), 6.66 (d, J = 9.2, 1H), 5.96 (s, 1H), 4.20-4.12 (m, 2H), 4.12-4.05 (m, 1H), 3.32-3.24 (m, 1H), 3.01-2.94 (m, 1H), 2.39 (s, 3H), 2.29-2.22 (m, 1H), 2.06-1.99 (m, 1H), 1.78-1.67 (m, 1H), 1.10 (d, J = 6.6, 3H) |

TABLE 48

| No. | Properties or Melting Points (° C.) | $^1$H-NMR data |
|---|---|---|
| 1a-253 | Viscous liquid | δ8.42 (pseudo-d, J = 2.4, 1H), 7.78 (s, 1H), 7.67-7.63 (m, 2H), 7.22 (d, J = 8.0, 1H), 6.71 (d, J = 9.0, 1H), 5.87 (s, 1H), 4.56-4.50 (m, 1H), 4.01 (t, J = 7.2, 2H), 3.99-3.92 (m, 2H), 3.69-3.62 (m, 2H), 2.16-2.08 (m, 2H), 1.99-1.90 (m, 2H), 1.85-1.78 (m, 2H), 1.40-1.30 (m, 2H), 0.95 (t, J = 7.4, 3H) |
| 1a-254 | Viscous liquid | δ8.41 (pseudo-d, J = 2.4, 1H), 7.65 (dd, J1 = 9.0, J2 = 2.4, 1H), 7.52 (pseudo-d, J = 8.0, 1H), 7.46 (pseudo-d, J = 10.0, 1H), 7.36-7.29 (m, 1H), 7.00-6.94 (m, 1H), 6.70 (d, J = 9.0, 1H), 5.83 (s, 1H), 4.55-4.49 (m, 1H), 4.00 (t, J = 7.2, 2H), 3.97-3.90 (m, 2H), 3.69-3.62 (m, 2H), 2.15-2.06 (m, 2H), 1.99-1.90 (m, 2H), 1.86-1.77 (m, 2H), 1.40-1.30 (m, 2H), 0.94 (t, J = 7.4, 3H) |
| 1a-255 | Viscous liquid | δ8.41 (pseudo-d, J = 2.4, 1H), 7.66-7.62 (m, 3H), 7.78 (pseudo-d, J = 8.0, 2H), 6.70 (d, J = 8.8, 1H), 5.81 (s, 1H), 4.55-4.48 (m, 1H), 4.00 (t, J = 7.2, 2H), 3.96-3.89 (m, 2H), 3.70-3.62 (m, 2H), 2.36 (s, 3H), 2.14-2.05 (m, 2H), 1.99-1.90 (m, 2H), 1.85-1.77 (m, 2H), 1.40-1.30 (m, 2H), 0.93 (t, J = 7.4, 3H) |
| 1a-256 | Viscous liquid | δ8.59 (pseudo-d, J = 5.6, 1H), 8.40 (pseudo-d, J = 2.4, 1H), 7.86-7.91 (m, 1H), 7.78 (d, J = 1.6, 2H), 7.75 (d, J = 8.4, 1H), 7.63 (dd, J1 = 9.2, J2 = 2.4, 1H), 7.32 (t, J = 2.0, 1H), 7.29-7.24 (m, 1H), 6.68 (d, J = 9.2, 1H), 6.07 (s, 1H), 4.70-4.66 (m, 1H), 3.90-3.83 (m, 2H), 3.76-3.69 (m, 2H), 2.13-1.99 (m, 4H) |
| 1a-257 | Viscous liquid | δ8.60(pseudo-d, J = 4.8, 1H), 8.39 (pseudo-d, J = 2.6, 1H), 7.82 (pseudo-t, J = 8.4, 1H), 7.79 (d, J = 2.0, 2H), 7.70 (d, J = 8.0, 1H), 7.63 (dd, J1 = 9.1, J2 = 2.6, 1H), 7.32 (t, J = 2.0, 1H), 7.28-7.24 (m, 1H), 6.68 (d, J = 9.1, 1H), 6.05 (s, 1H), 4.24-4.15 (m, 3H), 3.40-3.32 (m, 1H), 3.08-3.00 (m, 1H), 2.34-2.26 (m, 1H), 2.14-2.04 (m, 1H), 1.86-1.76 (m, 1H), 1.13 (d, J = 6.7, 3H) |

TABLE 49

| No. | Properties or Melting Points (° C.) | $^1$H-NMR data |
|---|---|---|
| 1a-258 | Viscous liquid | δ8.41 (pseudo-d, J = 2.4, 1H), 7.69 (d, J = 8.4, 2H), 7.64 (dd, J1 = 8.8, J2 = 2.4, 1H), 7.49 (d, J = 8.4, 2H), 6.70 (d, J = 8.8, 1H), 5.81 (s, 1H), 4.54-4.48 (m, 1H), 3.99 (t, J = 7.2, 2H), 3.97-3.89 (m, 2H), 3.69-3.62 (m, 2H), 2.14-2.06 (m, 2H), 1.98-1.89 (m, 2H), 1.85-1.76 (m, 2H), 1.40-1.29 (m, 2H), 0.93 (t, J = 7.4, 3H) |
| 1a-259 | Viscous liquid | δ8.41 (pseudo-d, J = 2.8, 1H), 7.78 (d, J = 2.0, 1H), 7.30-7.23 (m, 2H), 6.74-7.67 (m, 1H), 5.81 (s, 1H), 4.53-4.46 (m, 1H), 4.01 (t, J = 7.2, 2H), 3.78-3.70 (m, 2H), 3.51-3.44 (m, 2H), 2.23-2.15 (m, 2H), 2.08-1.99 (m, 2H), 1.86-1.78 (m, 2H), 1.41-1.31 (m, 2H), 0.95 (t, J = 7.4, 3H) |
| 1a-260 | Viscous liquid | δ8.41 (pseudo-d, J = 2.4, 1H), 8.38 (pseudo-d, J = 2.4, 1H), 7.64 (dd, J1 = 9.2, J2 = 2.4, 1H), 7.61 (dd, J1 = 9.2, J2 = 2.4, 1H), 6.70 (d, J = 9.2, 1H), 6.65 (d, J = 9.2, 1H), 5.98 (s, 1H), 4.80-4.72 (m, 1H), 4.62-4.65 (m, 2H), 4.37-4.29 (m, 1H), 3.97-3.90 (m, 2H), 3.60-3.52 (m, 2H), 3.10-3.02 (m, 2H), 2.28-2.16 (m, 2H), 2.09-2.00 (m, 4H), 1.90-1.80 (m, 2H) |

TABLE 49-continued

| No. | Properties or Melting Points (° C.) | $^1$H-NMR data |
|---|---|---|
| 1a-261 | Viscous liquid | δ8.41 (pseudo-d, J = 2.6, 1H), 7.65 (dd, J1 = 9.1, J2 = 2.6, 1H), 6.70 (d, J = 9.1, 1H), 5.85 (s, 1H), 5.32 (s, 2H), 4.56-4.51 (m, 1H), 3.98-3.91 (m, 2H), 3.67-3.60 (m, 2H), 3.39 (s, 3H), 2.13-2.07 (m, 2H), 1.97-1.91 (m, 2H) |
| 1a-262 | Viscous liquid | δ8.41 (pseudo-d, J = 2.4, 1H), 7.65 (dd, J1 = 8.8, J2 = 2.4, 1H), 6.69 (d, J = 8.8, 1H), 5.84 (s, 1H), 5.36 (s, 2H), 4.56-4.50 (m, 1H), 3.98-3.90 (m, 2H), 3.68-3.61 (m, 2H), 3.61 (q, J = 7.0, 2H), 2.12-2.04 (m, 2H), 1.98-1.91 (m, 2H), 1.17 (t, J = 7.0, 3H) |
| 1a-263 | Viscous liquid | δ8.40 (pseudo-d, J = 2.4, 1H), 7.64 (dd, J1 = 9.2, J2 = 2.4, 1H), 6.69 (d, J = 9.2, 1H), 5.83 (s, 1H), 5.35 (s, 2H), 4.31-4.26 (m, 2H), 4.07-4.00 (m, 1H), 3.59 (q, J = 7.0, 2H), 3.28-3.20 (m, 1H), 2.97-2.90 (m, 1H), 2.28-2.07 (m, 1H), 2.09-2.01 (m, 1H), 1.79-1.69 (m, 1H), 1.16 (t, J = 7.0, 3H), 1.12 (d, J = 6.4, 3H) |

TABLE 50

| No. | Properties or Melting Points (° C.) | $^1$H-NMR data |
|---|---|---|
| 1a-264 | Viscous liquid | δ8.41 (pseudo-d, J = 2.4, 1H), 7.64 (dd, J1 = 9.2, J2 = 2.4, 1H), 6.70 (d, J = 9.2, 1H), 5.81 (s, 1H), 4.53-4.48 (m, 1H), 4.18 (t, J = 5.6, 2H), 3.97-3.90 (m, 2H), 3.74 (t, J = 5.6, 2H), 3.69-3.62 (m, 2H), 3.30 (s, 3H), 2.12-2.04 (m, 2H), 1.97-1.88 (m, 2H) |
| 1a-265 | Viscous liquid | δ8.41 (pseudo-d, J = 2.4, 1H), 7.64 (dd, J1 = 9.0, J2 = 2.4, 1H), 6.70 (d, J = 9.0, 1H), 5.81 (s, 1H), 4.51-4.47 (m, 1H), 4.18 (t, J = 5.9, 2H), 3.97-3.90 (m, 2H), 3.77 (t, J = 5.9, 2H), 3.68-3.61 (m, 2H), 3.45 (q, J = 7.0, 2H), 2.11-2.03 (m, 2H), 1.97-1.88 (m, 2H), 1.12 (t, J = 7.0, 3H) |
| 1a-266 | Viscous liquid | δ8.40 (pseudo-d, J = 2.4, 1H), 7.64 (dd, J1 = 9.2, J2 = 2.4, 1H), 6.69 (d, J = 9.2, 1H), 5.81 (s, 1H), 4.77 (t, J = 5.7, 1H), 4.52-4.48 (m, 1H), 4.11 (d, J = 5.7, 2H), 3.97-3.90 (m, 2H), 3.68-3.61 (m, 2H), 3.35 (s, 6H), 2.12-2.04 (m, 2H), 1.97-1.88 (m, 2H) |
| 1a-267 | Viscous liquid | δ8.40 (pseudo-d, J = 2.4, 1H), 7.64 (dd, J1 = 9.1, J2 = 2.4, 1H), 6.69 (d, J = 9.1, 1H), 5.79 (s, 1H), 4.76 (t, J = 5.7, 1H), 4.30-4.25 (m, 2H), 4.10 (d, J = 5.7, 2H), 4.04-3.98 (m, 1H), 3.35 (s, 3H), 3.35 (s, 3H), 3.27-3.20 (m, 1H), 2.96-2.90 (m, 1H), 2.27-2.19 (m, 1H), 2.07-1.98 (m, 1H), 1.77-1.67 (m, 1H), 1.12 (d, J = 6.8, 3H) |
| 1a-268 | Viscous liquid | δ8.40 (pseudo-d, J = 2.2, 1H), 7.63 (dd, J1 = 8.9, J2 = 2.2, 1H), 6.68 (d, J = 8.9, 1H), 5.78 (s, 1H), 4.77 (t, J = 5.6, 1H), 4.46-4.41 (m, 1H), 4.13 (pseudo-d, J = 5.6, 2H), 4.10-4.01 (m, 2H), 3.46-3.37 (m, 1H), 3.38 (s, 3H), 3.36 (s, 3H), 3.30-3.23 (m, 1H), 2.18-2.04 (m, 2H), 1.89-1.79 (m, 1H), 1.09 (d, J = 6.8, 3H) |

TABLE 51

| No. | Properties or Melting Points (° C.) | $^1$H-NMR data |
|---|---|---|
| 1a-269 | Viscous liquid | δ8.40 (pseudo-d, J = 2.6, 1H), 7.64 (dd, J1 = 8.9, J2 = 2.6, 1H), 6.69 (d, J = 8.9, 1H), 5.80 (s, 1H), 4.89 (t, J = 5.7, 1H), 4.53-4.46 (m, 2H), 4.11 (pseudo-d, J = 5.7, 2H), 3.96-3.89 (m, 2H), 3.76-3.61 (m, 4H), 3.49-3.41 (m, 2H), 2.10-2.02 (m, 2H), 1.97-1.88 (m, 2H), 1.12 (t, J = 7.2, 6H) |
| 1a-270 | Viscous liquid | δ8.40 (pseudo-d, J = 2.6, 1H), 7.64 (dd, J1 = 9.1, J2 = 2.6, 1H), 6.68 (d, J = 9.1, 1H), 5.78 (s, 1H), 4.88 (t, J = 5.7, 1H), 4.29-4.24 (m, 2H), 4.09 (pseudo-d, J = 5.7, 2H), 4.06-3.97 (m, 1H), 3.75-3.66 (m, 2H), 3.48-3.40 (m, 2H), 3.27-3.19 (m, 1H), 2.97-2.90 (m, 1H), 2.25-2.17 (m, 1H), 2.05-1.98 (m, 1H), 1.77-1.67 (m, 1H), 1.14-1.09 (m, 9H) |
| 1a-271 | Viscous liquid | δ8.41 (pseudo-d, J = 2.6, 1H), 7.65 (dd, J1 = 9.1, J2 = 2.6, 1H), 6.70 (d, J = 9.1, 1H), 5.80 (s, 1H), 4.52-4.45 (m, 1H), 4.37 (t, J = 5.6, 1H), 4.08 (t, J = 7.2, 2H), 3.99-3.92 (m, 2H), 3.65-3.58 (m, 2H), 3.31 (s, 6H), 2.14-2.04 (m, 4H), 1.96-1.87 (m, 2H) |
| 1a-272 | Viscous liquid | δ8.41 (pseudo-d, J = 2.4, 1H), 7.65 (dd, J1 = 8.8, J2 = 2.4, 1H), 6.70 (d, J = 8.8, 1H), 5.80 (s, 1H), 4.52-4.46 (m, 2H), 4.14-4.08 (m, 2H), 3.98-3.90 (m, 2H), 3.67-3.58 (m, 4H), 3.51-3.43 (m, 2H), 2.15-2.04 (m, 4H), 1.96-1.87 (m, 2H), 1.17 (t, J = 7.0, 6H) |

TABLE 51-continued

| No. | Properties or Melting Points (° C.) | $^1$H-NMR data |
|---|---|---|
| 1a-273 | Viscous liquid | δ8.41 (pseudo-d, J = 2.4, 1H), 7.65 (dd, J1 = 9.2, J2 = 2.4, 1H), 6.70 (d, J = 9.2, 1H), 5.82 (s, 1H), 5.28 (t, J = 4.4, 1H), 4.54-4.48 (m, 1H), 4.16 (d, J = 4.4, 2H), 3.96-3.85 (m, 6H), 3.70-3.63 (m, 2H), 2.12-2.04 (m, 2H), 1.98-1.89 (m, 2H) |
| 1a-274 | Viscous liquid | δ8.40 (pseudo-d, J = 2.4, 1H), 7.64 (dd, J1 = 9.0, J2 = 2.4, 1H), 6.69 (d, J = 9.0, 1H), 5.80 (s, 1H), 5.27 (t, J = 4.4, 1H), 4.31-4.28 (m, 2H), 4.14 (d, J = 4.4, 2H), 4.05-3.99 (m, 1H), 3.95-3.85 (m, 4H), 3.29-3.21 (m, 1H), 2.98-2.91 (m, 1H), 2.28-2.20 (m, 1H), 2.07-1.99 (m, 1H), 1.78-1.67 (m, 1H), 1.12 (d, J = 6.4, 3H) |

TABLE 52

| No. | Properties or Melting Points (° C.) | $^1$H-NMR data |
|---|---|---|
| 1a-275 | Viscous liquid | δ8.40 (pseudo-d, J = 2.4, 1H), 7.63 (dd, J1 = 9.0, J2 = 2.4, 1H), 6.70 (d, J = 9.0, 1H), 5.81 (s, 1H), 5.28 (t, J = 4.4, 1H), 4.48-4.43 (m, 1H), 4.19 (d, J = 4.4, 2H), 4.13-4.02 (m, 2H), 3.96-3.85 (m, 4H), 3.47-3.39 (m, 1H), 3.30-3.23 (m, 1H), 2.21-2.07 (m, 2H), 1.90-1.80 (m, 1H), 1.10 (d, J = 6.8, 3H) |
| 1a-276 | Viscous liquid | δ8.41 (pseudo-d, J = 2.4, 1H), 7.65 (dd, J1 = 8.8, J2 = 2.4, 1H), 6.70 (d, J = 8.8, 1H), 5.81 (s, 1H), 4.53-4.47 (m, 1H), 4.34-4.27 (m, 1H), 4.14-4.09 (m, 1H), 4.01-3.89 (m, 3H), 3.85-3.79 (m, 1H), 3.78-3.71 (m, 1H), 3.69-3.60 (m, 2H), 2.12-2.05 (m, 2H), 2.04-1.84 (m, 5H), 1.75-1.66 (m, 1H) |
| 1a-277 | Viscous liquid | δ8.41 (pseudo-d, J = 2.4, 1H), 7.65 (dd, J1 = 9.1, J2 = 2.4, 1H), 6.70 (d, J = 9.1, 1H), 5.79 (s, 1H), 4.91 (t, J = 4.5, 1H), 4.52-4.46 (m, 1H), 4.16 (t, J = 7.3, 2H), 3.97-3.90 (m, 4H), 3.85-3.81 (m, 2H), 3.68-3.61 (m, 2H), 2.21-2.15 (m, 2H), 2.12-2.05 (m, 2H), 1.97-1.88 (m, 2H) |
| 1a-278 | Viscous liquid | δ8.41 (pseudo-d, J = 2.2, 1H), 7.65 (dd, J1 = 8.9, J2 = 2.2, 1H), 6.70 (d, J = 8.9, 1H), 5.79 (s, 1H), 4.54 (t, J = 5.0, 1H), 4.51-4.45 (m, 1H), 4.13 (t, J = 7.2, 2H), 4.09-4.04 (m, 2H), 3.98-3.90 (m, 2H), 3.75-3.68 (m, 2H), 3.67-3.59 (m, 2H), 2.21-2.03 (m, 5H), 1.96-1.87 (m, 2H), 1.32 (pseudo-d, J = 13.2, 1H) |
| 1a-279 | Viscous liquid | δ8.40 (pseudo-d, J = 2.4, 1H), 7.64 (dd, J1 = 9.2, J2 = 2.4, 1H), 6.69 (d, J = 9.2, 1H), 5.87 (s, 1H), 4.62-4.57 (m, 1H), 3.89-3.75 (m, 4H), 2.67 (s, 3H), 2.04-2.00 (m, 4H) |
| 1a-280 | Viscous liquid | δ8.40 (pseudo-d, J = 2.4, 1H), 7.63 (dd, J1 = 9.0, J2 = 2.4, 1H), 6.69 (d, J = 9.0, 1H), 5.88 (s, 1H), 4.64-4.58 (m, 1H), 3.89-3.77 (m, 4H), 3.11 (q, J = 7.4, 2H), 2.10-1.97 (m, 4H), 1.24 (t, J = 7.4, 3H) |

TABLE 53

| No. | Properties or Melting Points (° C.) | $^1$H-NMR data |
|---|---|---|
| 1a-281 | Viscous liquid | δ8.40 (pseudo-d, J = 2.4, 1H), 7.63 (dd, J1 = 9.2, J2 = 2.4, 1H), 6.69 (d, J = 9.2, 1H), 5.90 (s, 1H), 4.64-4.59 (m, 1H), 3.91-3.76 (m, 4H), 3.06 (pseudo-t, J = 7.3, 2H), 2.09-1.99 (m, 4H), 1.83-1.72 (m, 2H), 1.02 (t, J = 7.4, 3H) |
| 1a-282 | Viscous liquid | δ8.40 (pseudo-d, J = 2.6, 1H), 7.64 (dd, J1 = 9.1, J2 = 2.6, 1H), 6.69 (d, J = 9.1, 1H), 5.87 (s, 1H), 4.62-4.57 (m, 1H), 3.89-3.76 (m, 4H), 3.08 (t, J = 7.5, 2H), 2.07-1.99 (m, 4H), 1.96-1.68 (m, 2H), 1.48-1.38 (m, 2H), 0.95 (t, J = 7.4, 3H) |
| 1a-283 | 99.8-100.1 | δ8.40 (s, 1H), 7.97 (pseudo-d, J = 8.4, 2H), 7.65-7.60 (m, 2H), 7.52-7.47 (m, 2H), 6.68 (d, J = 8.8, 1H), 5.97 (s, 1H), 4.68-4.63 (m, 1H), 3.85-3.74 (m, 4H), 2.10-1.97 (m, 4H) |
| 1a-284 | Viscous liquid | δ8.40 (pseudo-d, J = 2.4, 1H), 7.63 (dd, J1 = 8.8, J2 = 2.4, 1H), 7.51 (dd, J1 = 7.4, J2 = 2.0, 1H), 7.49-7.41 (m, 2H), 7.39-7.34 (m, 1H), 6.66 (d, J = 8.8, 1H), 5.90 (s, 1H), 4.64-4.59 (m, 1H), 3.79-3.71 (m, 2H), 3.67-3.59 (m, 2H), 2.05-1.95 (m, 2H), 1.94-1.86 (m, 2H) |
| 1a-285 | Viscous liquid | δ8.40 (pseudo-d, J = 2.4, 1H), 7.94 (t, J = 2.0, 1H), 7.86 (pseudo-d, J = 8.0, 1H), 7.63 (dd, J1 = 9.2, J2 = 2.4, 1H), 7.58 (pseudo-d, J = 8.1, 1H), 7.43 (pseudo-t, J = 8.0, 1H), 6.68 (d, J = 9.2, 1H), 5.97 (s, 1H), 4.69-4.63 (m, 1H), 3.82-3.78 (m, 4H), 2.10-1.96 (m, 4H), |

TABLE 53-continued

| No. | Properties or Melting Points (° C.) | $^1$H-NMR data |
|---|---|---|
| 1a-286 | Viscous liquid | δ8.40 (pseudo-d, J = 2.6, 1H), 7.94 (pseudo-d, J = 8.8, 2H), 7.63 (dd, J1 = 9.1, J2 = 2.6, 1H), 7.46 (pseudo-d, J = 8.8, 2H), 6.69 (d, J = 9.1, 1H), 5.97 (s, 1H), 4.69-4.63 (m, 1H), 3.87-3.77 (m, 4H), 2.10-2.00 (m, 4H) |
| 1a-287 | Viscous liquid | δ8.41 (pseudo-d, J = 2.4, 1H), 7.65 (dd, J1 = 9.0, J2 = 2.4, 1H), 6.70 (d, J = 9.0, 1H), 5.89 (s, 1H), 4.67-4.61 (m, 1H), 4.06 (s, 3H), 3.87-3.79 (m, 4H), 2.09-2.00 (m, 4H) |
| 1a-288 | Viscous liquid | δ8.41 (pseudo-d, J = 2.4, 1H), 7.65 (dd, J1 = 9.0, J2 = 2.4, 1H), 6.70 (d, J = 9.0, 1H), 5.88 (s, 1H), 4.66-4.59 (m, 1H), 4.52 (q, J = 7.1, 2H), 3.88-3.79 (m, 4H), 2.11-1.98 (m, 4H), 1.45 (t, J = 7.1, 3H) |

TABLE 54

| No. | Properties or Melting Points (° C.) | $^1$H-NMR data |
|---|---|---|
| 1a-289 | Viscous liquid | δ8.41 (pseudo-d, J = 2.4, 1H), 7.64 (dd, J1 = 9.0, J2 = 2.4, 1H), 6.71 (d, J = 9.0, 1H), 5.90 (s, 1H), 4.67-4.61 (m, 1H), 4.41 (t, J = 6.8, 2H), 3.91-3.76 (m, 4H), 2.13-1.97 (m, 4H), 1.89-1.79 (m, 2H), 1.01 (t, J = 7.4, 3H) |
| 1a-290 | Viscous liquid | δ8.41 (pseudo-d, J = 2.4, 1H), 7.64 (dd, J1 = 9.2, J2 = 2.4, 1H), 6.73 (d, J = 9.2, 1H), 5.93 (s, 1H), 4.69-4.64 (m, 1H), 4.45 (t, J = 6.8, 2H), 3.92-3.77 (m, 4H), 2.16-1.97 (m, 4H), 1.83-1.74 (m, 2H), 1.50-1.39 (m, 2H), 0.94 (t, J = 7.4, 3H) |
| 1a-291 | Viscous liquid | δ9.67 (s, 1H), 8.40 (pseudo-d, J = 2.2, 1H), 7.65 (dd, J1 = 8.9, J2 = 2.2, 1H), 6.69 (d, J = 8.9, 1H), 5.90 (s, 1H), 4.83 (pseudo-s, 2H), 4.56-4.49 (m, 1H), 3.96-3.88 (m, 2H), 3.63-3.54 (m, 2H), 2.14-2.04 (m, 2H), 1.92-1.83 (m, 2H) |
| 1a-292 | Viscous liquid | δ9.81 (s, 1H), 8.41 (pseudo-d, J = 2.4, 1H), 7.65 (dd, J1 = 9.2, J2 = 2.4, 1H), 6.70 (d, J = 9.2, 1H), 5.80 (s, 1H), 4.53-4.47 (m, 1H), 4.32 (t, J = 6.7, 2H), 4.02-3.95 (m, 2H), 3.65-3.58 (m, 2H), 3.06 (pseudo-t, J = 6.7, 2H), 2.15-2.07 (m, 2H), 1.97-1.85 (m, 2H) |
| 1a-293 | 136.5-136.9 | δ8.41 (pseudo-d, J = 2.4, 1H), 8.12 (s, 1H), 7.65 (dd, J1 = 9.8, J2 = 2.4, 1H), 7.53 (s, 1H), 6.70 (d, J = 8.8, 1H), 4.86-4.81 (m, 1H), 4.23-4.16 (m, 2H), 3.75 (s, 3H), 3.45-3.27 (m, 2H), 2.10-2.01 (m, 2H), 1.85-1.75 (m, 2H) |
| 1a-294 | Viscous liquid | δ8.41 (pseudo-d, J = 2.4, 1H), 8.07 (s, 1H), 7.65 (dd, J1 = 9.2, J2 = 2.4, 1H), 6.71 (d, J = 9.2, 1H), 4.97-4.91 (m, 1H), 4.25-4.18 (m, 2H), 4.18 (q, J = 7.0, 2H), 3.74 (s, 3H), 3.36-3.28 (m, 2H), 2.13-2.06 (m, 2H), 1.88-1.81 (m, 2H), 1.32 (t, J = 7.0, 3H) |
| 1a-295 | 148.1-148.4 | δ10.04 (br-s, 1H), 8.41 (pseudo-d, J = 2.4, 1H), 7.64 (dd, J1 = 9.0, J2 = 2.4, 1H), 6.69 (d, J = 9.0, 1H), 5.93 (S, 1H), 4.67-4.58 (m, 1H), 4.00-3.92 (m, 2H), 3.64-3.56 (m, 2H), 2.14-2.04 (m, 2H), 1.95-1.85 (m, 2H) |

TABLE 55

| No. | Properties or Melting Points (° C.) | $^1$H-NMR data |
|---|---|---|
| 1a-296 | 136.9-137.6 | δ10.00 (br-s, 1H), 8.40 (pseudo-d, J = 2.4, 1H), 7.63 (dd, J1 = 9.0, J2 = 2.4, 1H), 6.69 (d, J = 9.0, 1H), 5.92 (s, 1H), 4.31-4.23 (m, 2H), 4.15 (br-s, 1H), 3.27-3.18 (m, 1H), 2.94-2.87 (m, 1H), 2.30-2.22 (m, 1H), 2.03-1.94 (m, 1H), 1.75-1.66 (m, 1H), 1.10 (d, J = 6.8, 3H) |
| 1a-297 | Viscous liquid | δ8.41 (pseudo-d, J = 2.4, 1H), 7.64 (dd, J1 = 8.8, J2 = 2.4, 1H), 7.31-7.24 (m, 2H), 6.76-6.68 (m, 2H), 5.83 (s, 1H), 4.82 (t, J = 5.6, 1H), 4.57-4.50 (m, 1H), 4.12 (d, J = 5.6, 2H), 3.98-3.91 (m, 2H), 3.70-3.63 (m, 2H), 3.37 (s, 6H), 2.14-2.04 (m, 2H), 1.99-1.91 (m, 2H) |
| 1a-298 | Viscous liquid | δ8.40 (pseudo-d, J = 2.2, 1H), 7.64 (dd, J1 = 9.0, J2 = 2.2, 1H), 7.30-7.26 (m, 2H), 6.76-6.70 (m, 1H), 6.69 (d, J = 9.0, 1H), 5.81 (s, 1H), 4.81 (t, J = 5.6, 1H), 4.31-4.26 (m, 2H), 4.10 (d, J = 5.6, 2H), 4.09-4.01 (m, 1H), 3.36 (s, 3H), 3.36(s, 3H), 3.32-3.23 (m, 1H), 2.99-2.92 (m, 1H), 2.31-2.23 (m, 1H), 2.10-2.00 (m, 1H), 1.79-1.69 (m, 1H), 1.14 (d, J = 6.8, 3H) |

TABLE 55-continued

| No. | Properties or Melting Points (° C.) | $^1$H-NMR data |
|---|---|---|
| 1a-299 | Viscous liquid | δ8.40 (pseudo-d, J = 2.6, 1H), 7.63(dd, J1 = 9.0, J2 = 2.6, 1H), 7.04-7.24 (m, 2H), 6.76-6.67 (m, 2H), 5.80 (s, 1H), 4.82 (t, J = 5.6, 1H), 4.49-4.45 (m, 1H), 4.15-4.12 (m, 2H), 4.11-4.02 (m, 2H), 3.49-3.39 (m, 1H), 3.40 (s, 3H), 3.37 (s, 3H), 3.33-3.26 (m, 1H), 2.23-2.16 (m, 1H), 2.15-2.04 (m, 1H), 1.89-1.80 (m, 1H), 1.11 (d, J = 6.8, 3H) |
| 1a-300 | Viscous liquid | δ8.41 (pseudo-d, J = 2.4, 1H), 7.65 (dd, J1 = 9.2, J2 = 2.4, 1H), 7.31-7.25 (m, 2H), 6.75-7.69 (m, 2H), 5.84 (s, 1H), 5.32 (t, J = 4.6, 1H), 4.58-4.52 (m, 1H), 4.17 (d, J = 4.6, 2H), 3.98-3.87 (m, 6H), 3.72-3.65 (m, 2H), 2.13-2.04 (m, 2H), 2.01-1.92 (m, 2H) |

TABLE 56

| No. | Properties or Melting Points (° C.) | $^1$H-NMR data |
|---|---|---|
| 1a-301 | Viscous liquid | δ8.41 (pseudo-d, J = 2.6, 1H), 7.64 (dd, J1 = 9.0, J2 = 2.6, 1H), 7.32-7.26 (m, 2H), 6.75-6.68 (m, 2H), 5.82 (s, 1H), 5.31 (t, J = 4.6, 1H), 4.31-4.24 (m, 2H), 4.15 (d, J = 4.6, 2H), 4.10-4.02 (m, 1H), 3.98-3.86 (m, 4H), 3.32-3.24 (m, 1H), 3.00-2.94 (m, 1H), 2.31-2.24 (m, 1H), 2.10-1.99 (m, 1H), 1.81-1.69 (m, 1H), 1.14 (d, J = 6.8, 3H) |
| 1a-302 | Viscous liquid | δ8.40 (pseudo-d, J = 2.4, 1H), 7.63 (dd, J1 = 9.2, J2 = 2.4, 1H), 7.30-7.25 (m, 2H), 6.75-6.68 (m, 2H), 5.81 (s, 1H), 5.32 (t, J = 4.5, 1H), 4.50-4.46 (m, 1H), 4.19 (d, J = 4.5, 2H), 4.12-4.01 (m, 2H), 3.99-3.86 (m, 4H), 3.48-3.40 (m, 1H), 3.31-3.24 (m, 1H), 2.26-2.18 (m, 1H), 2.15-2.08 (m, 1H), 1.90-1.81 (m, 1H), 1.11 (d, J = 6.8, 3H) |
| 1a-303 | Viscous liquid | δ8.56-8.54 (m, 1H), 8.40 (pseudo-d, J = 2.4, 1H), 7.80 (dt, J1 = 7.7, J2 = 2.1, 1H), 7.74 (d, J = 8.0, 1H), 7.63 (dd, J1 = 8.8, J2 = 2.4, 1H), 7.41 (dd, J1 = 3.7, J2 = 1.0, 1H), 7.30 (dd, J1 = 4.9, J2 = 1.0, 1H), 7.24-7.20 (m, 1H), 7.07 (dd, J1 = 4.5, J2 = 3.7, 1H), 6.68 (d, J = 8.8, 1H), 6.00 (s, 1H), 4.70-4.64 (m, 1H), 3.88-3.81 (m, 2H), 3.78-3.71 (m, 2H), 2.12-1.98 (m, 4H) |
| 1a-304 | Viscous liquid | δ8.41 (pseudo-d, J = 2.4, 1H), 7.65 (dd, J1 = 9.2, J2 = 2.4, 1H), 6.70 (d, J = 9.2, 1H), 5.79 (s, 1H), 5.79-5.68 (m, 1H), 5.08-5.01 (m, 2H), 4.51-4.45 (m, 1H), 4.07 (t, J = 7.2, 2H), 3.98-3.91 (m, 2H), 3.66-3.58 (m, 2H), 2.59-2.53 (m, 2H), 2.13-2.04 (m, 2H), 1.95-1.87 (m, 2H) |
| 1a-305 | Viscous liquid | δ8.41 (pseudo-d, J = 2.4, 1H), 7.65 (dd, J1 = 9.0, J2 = 2.4, 1H), 6.70 (d, J = 9.0, 1H), 5.79 (s, 1H), 4.52-4.45 (m, 1H), 3.97-3.91 (m, 2H), 3.89 (d, J = 7.2, 2H), 3.66-3.59 (m, 2H), 2.14-2.04 (m, 2H), 1.95-1.85 (m, 3H), 1.33-1.24 (m, 4H), 0.87 (t, J = 7.4, 6H) |

TABLE 57

| No. | Properties or Melting Points (° C.) | $^1$H-NMR data |
|---|---|---|
| 1a-306 | Viscous liquid | δ8.41 (pseudo-d, J = 2.4, 1H), 7.65 (dd, J1 = 9.2, J2 = 2.4, 1H), 6.70 (d, J = 9.2, 1H), 5.79 (s, 1H), 4.52-4.45 (m, 1H), 4.02 (pseudo-t, J = 7.4, 2H), 3.98-3.90 (m, 2H), 3.67-3.59 (m, 2H), 2.14-2.06 (m, 2H), 1.96-1.87 (m, 2H), 1.73-1.66 (m, 2H), 1.61-1.50 (m, 1H), 0.92 (d, J = 6.6, 6H) |
| 1b-2 | Viscous liquid | δ8.39 (pseudo-d, J = 2.5, 1H), 7.62 (dd, J1 = 9.0, J2 = 2.5, 1H), 6.67 (d, J = 9.0, 1H), 6.00 (s, 1H), 4.82-4.73 (m, 1H), 4.01-3.90 (m, 2H), 3.83 (s, 3H), 3.63-3.53 (m, 2H), 2.12-2.00 (m, 2H), 1.92-1.80 (m, 2H) |
| 1b-4 | Viscous liquid | δ8.40 (pseudo-d, J = 2.4, 1H), 7.64 (dd, J1 = 8.8, J2 = 2.4, 1H), 6.70 (d, J = 8.8, 1H), 6.40 (s, 1H), 5.04-4.97 (m, 1H), 3.99-3.92 (m, 2H), 3.67-3.60 (m, 2H), 3.01 (t, J = 7.4, 2H), 2.16-2.07 (m, 2H), 1.97-1.88 (m, 2H), 1.79-1.68 (m, 2H), 1.49-1.39 (m, 2H), 0.96 (t, J = 7.3, 3H) |
| 1b-31 | Viscous liquid | δ8.40 (pseudo-d, J = 2.6, 1H), 7.62 (dd, J1 = 8.9, J2 = 2.6, 1H), 6.68 (d, J = 8.9, 1H), 6.13 (s, 1H), 5.34 (s, 2H), 4.91-4.85 (m, 1H), 4.00-3.93 (m, 2H), 3.62-3.55 (m, 2H), 3.88 (s, 3H), 2.12-2.04 (m, 2H), 1.92-1.83 (m, 2H) |

TABLE 57-continued

| No. | Properties or Melting Points (° C.) | $^1H$-NMR data |
|---|---|---|
| 1b-32 | Viscous liquid | δ8.40 (pseudo-d, J = 2.4, 1H), 7.62 (dd, J1 = 9.2, J2 = 2.4, 1H), 6.68 (d, J = 9.2, 1H), 6.12 (s, 1H), 5.38 (s, 2H), 4.90-4.84 (m, 1H), 4.00-3.93 (m, 2H), 3.62-3.54 (m, 4H), 2.12-2.04 (m, 2H), 1.92-1.83 (m, 2H), 1.19 (t, J = 7.0, 3H) |
| 1b-33 | Viscous liquid | δ8.39 (pseudo-d, J = 2.6, 1H), 7.62 (dd, J1 = 9.0, J2 = 2.6, 1H), 6.68 (d, J = 9.0, 1H), 6.11 (s, 1H), 5.38 (s, 2H), 4.48-4.41 (m, 2H), 4.29-4.21 (m, 1H), 3.58 (q, J = 7.0, 2H), 3.28-3.20 (m, 1H), 2.94-2.87 (m, 1H), 2.33-2.26 (m, 1H), 2.02-1.90 (m, 1H), 1.70-1.60 (m, 1H), 1.19 (t, J = 7.0, 3H), 1.08 (t, J = 6.4, 3H) |

TABLE 58

| No. | Properties or Melting Points (° C.) | $^1H$-NMR data |
|---|---|---|
| 1b-34 | Viscous liquid | δ8.39 (pseudo-d, J = 2.4, 1H), 7.62 (dd, J1 = 9.2, J2 = 2.4, 1H), 6.68 (d, J = 9.2, 1H), 6.01 (s, 1H), 4.82-4.76 (m, 1H), 4.21 (t, J = 5.9, 2H), 3.99-3.92 (m, 2H), 3.77 (t, J = 5.9, 2H), 3.63-3.55 (m, 2H), 3.45 (s, 3H), 2.10-2.02 (m, 2H), 1.92-1.83 (m, 2H) |
| 1b-35 | Viscous liquid | δ8.39 (pseudo-d, J = 2.6, 1H), 7.62 (dd, J1 = 9.1, J2 = 2.6, 1H), 6.68 (d, J = 9.1, 1H), 6.00 (s, 1H), 4.82-4.76 (m, 1H), 4.21 (t, J = 6.1, 2H), 3.99-3.92 (m, 2H), 3.79 (t, J = 6.1, 2H), 3.62-3.55 (m, 2H), 3.48 (q, J = 7.0, 2H), 2.10-2.02 (m, 2H), 1.92-1.82 (m, 2H), 1.16 (t, J = 7.0, 3H) |
| 1b-36 | Viscous liquid | δ8.39 (pseudo-d, J = 2.6, 1H), 7.62 (dd, J1 = 9.1, J2 = 2.6, 1H), 6.68 (d, J = 9.1, 1H), 6.02 (s, 1H), 4.82-4.77 (m, 1H), 4.77 (t, J = 5.5, 1H), 4.14 (d, J = 5.5, 2H), 3.99-3.92 (m, 2H), 3.63-3.55 (m, 2H), 3.38 (s, 6H), 2.10-2.03 (m, 2H), 1.92-1.85 (m, 2H) |
| 1b-37 | Viscous liquid | δ8.39 (pseudo-d, J = 2.6, 1H), 7.62 (dd, J1 = 9.1, J2 = 2.6, 1H), 6.67 (d, J = 9.1, 1H), 6.01 (s, 1H), 4.77 (t, J = 5.5, 1H), 4.41-4.35 (m, 1H), 4.28-4.22 (m, 2H), 4.13 (d, J = 5.5, 2H), 3.38 (s, 6H), 3.28-3.20 (m, 1H), 2.94-2.88 (m, 1H), 2.30-2.24 (m, 1H), 2.02-1.90 (m, 1H), 1.70-1.60 (m, 1H), 1.08 (d, J = 6.4, 3H) |
| 1b-38 | Viscous liquid | δ8.38 (pseudo-d, J = 2.4, 1H), 7.60 (dd, J1 = 9.2, J2 = 2.4, 1H), 6.67 (d, J = 9.2, 1H), 6.04 (s, 1H), 4.79-4.76 (m, 2H), 4.13 (d, J = 5.4, 2H), 4.00-3.95 (m, 2H), 3.49-3.42 (m, 1H), 3.38 (s, 6H), 3.36-3.28 (m, 1H), 2.19-2.12 (m, 1H), 2.11-2.00 (m, 1H), 1.84-1.75 (m, 1H), 1.05 (d, J = 6.8, 3H) |

TABLE 59

| No. | Properties or Melting Points (° C.) | $^1H$-NMR data |
|---|---|---|
| 1b-39 | Viscous liquid | δ8.40 (pseudo-d, J = 2.4, 1H), 7.62 (dd, J1 = 9.2, J2 = 2.4, 1H), 6.68 (d, J = 9.2, 1H), 6.01 (s, 1H), 4.87 (t, J = 5.5, 1H), 4.83-4.76 (m, 1H), 4.14 (d, J = 5.5, 2H), 4.00-3.93 (m, 2H), 3.77-3.68 (m, 2H), 3.62-3.55 (m, 2H), 3.48-3.39 (m, 2H), 2.11-2.03 (m, 2H), 1.92-1.84 (m, 2H), 1.15 (t, J = 7.2, 6H) |
| 1b-40 | Viscous liquid | δ8.39 (pseudo-d, J = 2.4, 1H), 7.61 (dd, J1 = 9.2, J2 = 2.4, 1H), 6.67 (d, J = 9.2, 1H), 6.00 (s, 1H), 4.87 (t, J = 5.5, 1H), 4.41-4.34 (m, 1H), 4.29-424 (m, 2H), 4.13 (d, J = 5.5, 2H), 3.77-3.68 (m, 2H), 3.48-3.39 (m, 2H), 3.27-3.19 (m, 1H), 2.93-2.87 (m, 1H), 2.30-2.24 (m, 1H), 2.00-1.90 (m, 1H), 1.71-1.60 (m, 1H), 1.15 (t, J = 7.2, 6H), 1.08 (d, J = 6.4, 3H) |
| 1b-41 | Viscous liquid | δ8.39 (pseudo-d, J = 2.4, 1H), 7.62 (dd, J1 = 8.8, J2 = 2.4, 1H), 6.68 (d, J = 8.8, 1H), 5.98 (s, 1H), 4.82-4.75 (m, 1H), 4.44 (t, J = 5.6, 1H), 4.11 (t, J = 7.3, 2H), 3.99-3.92 (m, 2H), 3.61-3.54 (m, 2H), 3.31 (s, 6H), 2.19-2.13 (m, 2H), 2.10-2.02 (m, 2H), 1.91-1.82 (m, 2H) |
| 1b-42 | Viscous liquid | δ8.39 (pseudo-d, J = 2.4, 1H), 7.62 (dd, J1 = 9.0, J2 = 2.4, 1H), 6.68 (d, J = 9.0, 1H), 5.98 (s, 1H), 4.81-4.75 (m, 1H), 4.57 (t, J = 5.5, 1H), 4.13 (t, J = 7.3, 2H), 3.99-3.92 (m, 2H), 3.71-3.62 (m, 2H), 3.61-3.54 (m, 2H), 3.54-3.46 (m, 2H), 2.20-2.14 (m, 2H), 2.10-2.00 (m, 2H), 1.91-1.82 (m, 2H), 1.21 (t, J = 7.0, 6H) |

TABLE 59-continued

| No. | Properties or Melting Points (° C.) | $^1$H-NMR data |
|---|---|---|
| 1b-43 | Viscous liquid | δ8.39 (pseudo-d, J = 2.4, 1H), 7.62 (dd, J1 = 9.2, J2 = 2.4, 1H), 6.67 (d, J = 9.2, 1H), 6.04 (s, 1H), 5.34 (t, J = 4.6, 1H), 4.85-4.79 (m, 1H), 4.16 (d, J = 4.6, 2H), 4.01-3.89 (m, 6H), 3.63-3.55 (m, 2H), 2.10-2.00 (m, 2H), 1.91-1.82 (m, 2H) |

TABLE 60

| No. | Properties or Melting Points (° C.) | $^1$H-NMR data |
|---|---|---|
| 1b-44 | Viscous liquid | δ8.39 (pseudo-d, J = 2.6, 1H), 7.61 (dd, J1 = 8.9, J2 = 2.6, 1H), 6.67 (d, J = 8.9, 1H), 6.02 (s, 1H), 5.35 (t, J = 4.6, 1H), 4.42-4.36 (m, 1H), 4.28-4.20 (m, 2H), 4.15 (d, J = 4.6, 2H), 4.00-3.89 (m, 4H), 3.28-3.21 (m, 1H), 2.94-2.87 (m, 1H), 2.33-2.25 (m, 1H), 2.00-1.91 (m, 1H), 1.70-1.59 (m, 1H), 1.08 (d, J = 6.8, 3H) |
| 1b-45 | Viscous liquid | δ8.38 (pseudo-d, J = 2.4, 1H), 7.60 (dd, J1 = 9.0, J2 = 2.4, 1H), 6.66 (d, J = 9.0, 1H), 6.06 (s, 1H), 5.34 (t, J = 4.6, 1H), 4.79-4.75 (m, 1H), 4.16 (d, J = 4.6, 2H), 4.00-3.89 (m, 6H), 3.49-3.41 (m, 1H), 3.34-3.27 (m, 1H), 2.20-2.13 (m, 1H), 2.08-2.01 (m, 1H), 1.83-1.74 (m, 1H), 1.05 (d, J = 6.8, 3H) |
| 1b-46 | Viscous liquid | δ8.39 (pseudo-d, J = 2.4, 1H), 7.62 (dd, J1 = 9.0, J2 = 2.4, 1H), 6.67 (d, J = 9.0, 1H), 6.01 (s, 1H), 4.82-4.76 (m, 1H), 4.41-4.33 (m, 1H), 4.15-4.08 (m, 1H), 4.03-3.85 (m, 4H), 3.82-3.75 (m, 1H), 3.63-3.55 (m, 2H), 2.10-1.98 (m, 3H), 1.96-1.83 (m, 4H), 1.75-1.66 (m, 1H) |
| 1b-47 | Viscous liquid | δ8.39 (pseudo-d, J = 2.4, 1H), 7.62 (dd, J1 = 9.2, J2 = 2.4, 1H), 6.67 (d, J = 9.2, 1H), 5.98 (s, 1H), 4.96 (t, J = 4.4, 1H), 4.82-4.76 (m, 1H), 4.19 (t, J = 7.5, 2H), 4.02-3.91 (m, 4H), 3.90-3.85 (m, 2H), 3.61-3.54 (m, 2H), 2.26-2.20 (m, 2H), 2.09-2.02 (m, 2H), 1.91-1.81 (m, 2H) |
| 1b-48 | Viscous liquid | δ8.39 (pseudo-d, J = 2.4, 1H), 7.62 (dd, J1 = 9.2, J2 = 2.4, 1H), 6.67 (d, J = 9.2, 1H), 5.97 (s, 1H), 4.83-4.76 (m, 1H), 4.59 (t, J = 5.0, 1H), 4.18-4.08 (m, 4H), 4.00-3.93 (m, 2H), 3.78-3.70 (m, 2H), 3.60-3.53 (m, 2H), 2.18-2.02 (m, 5H), 1.90-1.81 (m, 2H), 1.35 (pseudo-d, J = 13.2, 1H), |
| 1b-49 | Viscous liquid | δ8.40 (pseudo-d, J = 2.4, 1H), 7.62 (dd, J1 = 9.2, J2 = 2.4, 1H), 6.68 (d, J = 9.2, 1H), 6.02 (s, 1H), 4.81-4.76 (m, 1H), 4.15-4.10 (m, 2H), 4.00-3.93 (m, 2H), 3.62-3.55 (m, 2H), 2.19-2.03 (m, 6H), 1.90-1.82 (m, 2H) |

TABLE 61

| No. | Properties or Melting Points (° C.) | $^1$H-NMR data |
|---|---|---|
| 1b-50 | Viscous liquid | δ8.41 (pseudo-d, J = 2.4, 1H), 7.63 (dd, J1 = 8.8, J2 = 2.4, 1H), 6.58 (d, J = 8.8, 1H), 5.92 (s, 1H), 5.09-5.01 m, 1H), 4.75 (t, J = 5.5, 1H), 4.65 (br-s, 2H), 4.11 (d, J = 5.5, 2H), 3.67 (s, 6H), 2.24-2.13 (m, 4H), 1.94-1.88 (m, 2H), 1.82-1.75 (m, 2H) |
| 1b-51 | Viscous liquid | δ8.41 (pseudo-d, J = 2.4, 1H), 7.62 (dd, J1 = 8.8, J2 = 2.4, 1H), 6.68 (d, J = 8.8, 1H), 5.63 (s, 1H), 5.35 (t, J = 4.6, 1H), 5.10-5.00 (m, 1H), 4.64 (br-s, 2H), 4.13 (d, J = 4.6, 2H), 4.01-3.89 (m, 4H), 2.24-2.12 (m, 4H), 1.94-1.83 (m, 2H), 1.81-1.74 (m, 2H) |
| 1b-52 | 74.5-75.0 | δ8.39 (pseudo-d, J = 2.6, 1H), 7.62 (dd, J1 = 8.9, J2 = 2.6, 1H), 6.61 (d, J = 8.9, 1H), 6.03 (s, 1H), 4.79 (t, J = 5.5, 1H), 4.72 (br-s, 1H), 4.19-4.13 (m, 4H), 3.38 (s, 6H), 3.12 (d, J = 12.4, 2H), 2.61 (br-s, 2H), 2.00-1.96 (m, 2H), 1.62-1.56 (m, 2H) |
| 1b-53 | Viscous liquid | δ8.39 (pseudo-d, J = 2.4, 1H), 7.62 (dd, J1 = 9.0, J2 = 2.4, 1H), 6.61 (d, J = 9.0, 1H), 6.05 (s, 1H), 5.37 (t, J = 5.2, 1H), 4.73 (br-s, 1H), 4.18-4.13 (m, 4H), 4.01-3.89 (m, 4H), 3.12 (d, J = 12.4, 2H), 2.61 (br-s, 2H), 2.20-1.95 (m, 2H), 1.61-1.55 (m, 2H) |
| 1b-54 | Viscous liquid | δ8.40 (pseudo-d, J = 2.2, 1H), 7.62 (dd, J1 = 8.9, J2 = 2.4, 1H), 7.11-7.06 (m, 2H), 6.89-6.83 (m, 1H), 6.68 (d, J = 8.9, 1H), 5.76 (s, 1H), 5.36 (t, J = 4.4, 1H), 4.86-4.81 (m, 1H), 4.07 (d, J = 4.4, 2H), 4.01-3.94 (m, 2H), 3.89 (br-s, 4H), 3.64-3.57 (m, 2H), 2.12-2.06 (m, 2H), 1.95-1.86 (m, 2H) |

TABLE 61-continued

| No. | Properties or Melting Points (° C.) | $^1$H-NMR data |
|---|---|---|
| 1b-55 | Viscous liquid | δ8.39 (pseudo-d, J = 2.4, 1H), 7.61 (dd, J1 = 9.0, J2 = 2.4, 1H), 7.13-7.05 (m, 2H), 6.89-6.82 (m, 1H), 6.68 (d, J = 9.0, 1H), 5.75 (s, 1H), 5.36 (t, J = 4.4, 1H), 4.45-4.38 (m, 1H), 4.30-4.22 (m, 2H), 4.06 (d, J = 4.4, 2H), 3.89 (pseudo-s, 4H), 3.31-3.23 (m, 1H), 2.97-2.90 (m, 1H), 2.38-2.31 (m, 1H), 2.02-1.94 (m, 1H), 1.74-1.63 (m, 1H), 1.11 (d, J = 6.4, 3H) |

TABLE 62

| No. | Properties or Melting Points (° C.) | $^1$H-NMR data |
|---|---|---|
| 1b-56 | Viscous liquid | δ8.41 (pseudo-d, J = 1.7, 1H), 7.62 (dd, J1 = 8.5, J2 = 2.4, 1H), 7.08 (dd, J1 = 7.9, J2 = 2.2, 2H), 6.89-6.82 (m, 1H), 6.62 (d, J = 9.0, 1H), 5.76 (s, 1H), 4.80 (t, J = 5.4, 1H), 4.70 (s, 1H), 4.17 (dd, J1 = 12.9, J2 = 3.3, 2H), 4.03 (d, J = 5.5, 2H), 3.35 (s, 6H), 3.14 (d, J = 11.4, 2H), 2.65 (br-s, 2H), 2.05-2.00 (m, 2H), 1.63-1.59 (m, 2H) |
| 1b-57 | Viscous liquid | δ8.40 (pseudo-d, J = 2.4, 1H), 7.61 (dd, J1 = 8.8, J2 = 2.4, 1H), 6.55 (d, J = 8.8, 1H), 6.00 (s, 1H), 4.77-4.70 (m, 2H), 4.54 (br-s, 2H), 4.11 (d, J = 5.6, 2H), 3.36 (s, 6H), 2.33-2.28 (m, 2H), 2.20-2.13 (m, 2H), 2.10-2.01 (m, 4H) |
| 1b-58 | Viscous liquid | δ8.39 (pseudo-d, J = 2.2, 1H), 7.60 (dd, J1 = 8.9, J2 = 2.2, 1H), 6.54 (d, J = 8.9, 1H), 6.01 (s, 1H), 5.32 (t, J = 4.7, 1H), 4.73 (pseudo-t, J = 4.4, 1H), 4.54 (br-s, 2H), 4.14 (d, J = 4.7, 2H), 4.00-3.88 (m, 4H), 2.33-2.27 (m, 2H), 2.19-2.12 (m, 2H), 2.10-1.97 (m, 4H) |
| 1b-59 | Viscous liquid | δ8.39 (pseudo-d, J = 2.6, 1H), 7.62 (dd, J1 = 8.9, J2 = 2.6, 1H), 6.68 (d, J = 8.9, 1H), 5.98 (s, 1H), 5.82-5.71 (m, 1H), 5.12-5.05 (m, 2H), 4.82-4.75 (m, 1H), 4.09 (pseudo-t, J = 7.4, 2H), 3.99-3.92 (m, 2H), 3.63-3.55 (m, 2H), 2.63-2.56 (m, 2H), 2.10-2.02 (m, 2H), 1.92-1.83 (m, 2H) |
| 1b-60 | Viscous liquid | δ8.39 (pseudo-d, J = 2.4, 1H), 7.62 (dd, J1 = 8.8, J2 = 2.4, 1H), 6.68 (d, J = 8.8, 1H), 5.99 (s, 1H), 4.79-4.73 (m, 1H), 3.99-3.92 (m, 2H), 3.91 (d, J = 7.6, 2H), 3.62-3.55 (m, 2H), 2.10-2.02 (m, 2H), 1.99-1.82 (m, 3H), 1.38-1.27 (m, 4H), 0.88 (t, J = 7.5, 6H) |
| 1b-61 | 61.3-61.7 | δ8.39 (pseudo-d, J = 2.6, 1H), 7.62 (dd, J1 = 9.1, J2 = 2.6, 1H), 6.67 (d, J = 9.1, 1H), 5.97 (s, 1H), 4.79-4.74 (m, 1H), 4.05 (pseudo-t, J = 7.8, 2H), 3.99-3.92 (m, 2H), 3.63-3.55 (m, 2H), 2.10-2.02 (m, 2H), 1.91-1.82 (m, 2H), 1.76-1.69 (m, 2H), 1.69-1.58 (m, 1H), 0.95 (d, J = 6.5, 6H) |

TABLE 63

| No. | Properties or Melting Points (° C.) | $^1$H-NMR data |
|---|---|---|
| 1d-6 | Viscous liquid | δ8.41 (pseudo-d, J = 2.3, 1H), 7.64 (dd, J1 = 8.9, J2 = 2.3, 1H), 6.57 (d, J = 8.9, 1H), 5.61 (s, 1H), 4.60 (br-s, 2H), 4.41 (pseudo-t, J = 4.8, 1H), 4.03 (t, J = 7.3, 2H), 2.29-2.16 (m, 6H), 2.06 (pseudo-d, J = 14.5, 2H), 1.87-1.79 (m, 2H), 1.42-1.32 (m, 2H), 0.96 (t, J = 7.4, 3H) |
| 1d-37 | 65.4-66.0 | δ10.26 (br-s, 1H), 8.41 (pseudo-d, J = 2.6, 1H), 7.63 (dd, J1 = 8.9, J2 = 2.6, 1H), 6.57 (d, J = 8.9, 1H), 5.82 (s, 1H), 4.56 (pseudo-s, 3H), 2.26-2.03 (m, 8H) |
| 1d-38 | Viscous liquid | δ8.41 (pseudo-d, J = 2.4, 1H), 7.63 (dd, J1 = 9.0, J2 = 2.4, 1H), 6.57 (d, J = 9.0, 1H), 5.63 (s, 1H), 4.08 (t, J = 5.6, 1H), 4.59 (br-s, 2H), 4.42 (pseudo-t, J = 4.6, 1H), 4.12 (d, J = 5.6, 2H), 3.40 (s, 6H), 2.28-2.21 (m, 4H), 2.17-2.13 (m, 2H), 2.06 (pseudo-d, J = 14.8, 2H) |
| 1d-39 | Viscous liquid | δ8.41 (pseudo-d, J = 2.4, 1H), 7.64 (dd, J1 = 8.8, J2 = 2.4, 1H), 6.57 (d, J = 8.8, 1H), 5.64 (s, 1H), 5.31 (t, J = 4.4, 1H), 4.59 (br-s, 2H), 4.43 (pseudo-t, J = 4.6, 1H), 4.18 (d, J = 4.4, 2H), 3.99-3.89 (m, 4H), 2.31-2.20 (m, 4H), 2.19-2.13 (m, 2H), 2.07 (pseudo-d, J = 15.0, 2H) |
| 1d-40 | 185.6-186.1 | δ9.76 (br-s, 1H), 8.40 (pseudo-d, J = 2.4, 1H), 7.62 (dd, J1 = 8.8, J2 = 2.4, 1H), 7.09-7.05 (m, 2H), 6.83-6.76 (m, 1H), 6.56 (d, J = 8.8, 1H), 5.92 (s, 1H), 4.72 (br-s, 1H), 4.56 (br-s, 2H), 2.36-2.30 (m, 2H), 2.23-2.16 (m, 2H), 2.13-2.04 (m, 4H) |

TABLE 63-continued

| No. | Properties or Melting Points (° C.) | $^1$H-NMR data |
|---|---|---|
| 1d-41 | Viscous liquid | δ8.42 (pseudo-d, J = 2.4, 1H), 7.64 (dd, J1 = 8.8, J2 = 2.4, 1H), 7.26-7.21 (m, 2H), 6.75-6.68 (m, 1H), 6.58 (d, J = 8.8, 1H), 5.64 (s, 1H), 4.85 (t, J = 5.6, 1H), 4.59 (br-s, 2H), 4.46 (pseudo-t, J = 4.5, 1H), 4.12 (d, J = 5.6, 2H), 3.41 (s, 6H), 2.33-2.22 (m, 4H), 2.17-2.08 (m, 4H) |
| 1d-42 | 114.5-114.9 | δ8.42 (pseudo-d, J = 2.4, 1H), 7.64 (dd, J1 = 8.8, J2 = 2.4, 1H), 7.27-7.21 (m, 2H), 6.74-6.68 (m, 1H), 6.58 (d, J = 8.8, 1H), 5.65 (s, 1H), 5.36 (t, J = 4.6, 1H), 4.60 (br-s, 2H), 4.46 (pseudo-t, J = 4.5, 1H), 4.18 (d, J = 4.6, 2H), 4.02-3.90 (m, 4H), 2.34-2.23 (m, 4H), 2.18-2.14 (m, 4H) |

TABLE 64

| No. | Properties or Melting Points (° C.) | $^1$H-NMR data |
|---|---|---|
| 1e-3 | 93.1-93.3 | δ8.44 (pseudo-d, J = 2.4, 1H), 7.66 (dd, J1 = 8.9, J2 = 2.4, 1H), 6.61 (d, J = 8.9, 1H), 5.78 (s, 1H), 4.74-4.60 (m, 3H), 3.59(s, 3H), 2.25-2.13 (m, 4H), 1.92-1.77 (m, 4H) |
| 1e-6 | Viscous liquid | δ8.44 (pseudo-d, J = 2.3, 1H), 7.66 (dd, J1 = 8.9, J2 = 2.3, 1H), 6.60 (d, J = 8.9, 1H), 5.76 (s, 1H), 4.75-4.61 (m, 3H), 3.88 (t, J = 7.2, 2H), 2.26-2.14 (m, 4H), 1.91-1.77 (m, 4H), 1.75-1.60 (m, 2H), 1.29-1.18 (m, 2H), 0.86 (t, J = 7.4, 3H) |
| 1e-37 | Viscous liquid | δ8.53-8.50 (m, 1H), 8.41 (pseudo-d, J = 2.4, 1H), 7.78 (pseudo-t, J = 7.8, 1H), 7.62 (dd, J1 = 8.9, J2 = 2.4, 1H), 7.56 (d, J = 8.2, 1H), 7.28-7.24 (m, 1H), 6.58 (d, J = 8.9, 1H), 5.99 (s, 1H), 4.87-4.77 (m, 1H), 4.69 (br-s, 2H), 2.27-2.21 (m, 2H), 2.20-2.13 (m, 2H), 1.92-1.82 (m, 4H) |
| 1e-38 | 164.8-165.2 | δ9.70 (br-s, 1H), 8.43 (pseudo-d, J = 2.3, 1H), 7.65 (dd, J1 = 8.9, J2 = 2.3, 1H), 6.60 (d, J = 8.9, 1H), 5.87 (s, 1H), 4.86 (s, 1H), 4.67 (s, 2H), 2.21-2.15 (m, 4H), 1.90-1.78 (m, 4H) |
| 1e-39 | Viscous liquid | δ8.40 (pseudo-d, J = 2.4, 1H), 7.66 (dd, J1 = 8.8, J2 = 2.4, 1H), 6.60 (d, J = 8.8, 1H), 5.78 (s, 1H), 4.74-7.65 (m, 4H), 4.40 (d, J = 5.7, 2H), 3.29 (s, 6H), 2.22-2.16 (m, 4H), 1.88-1.80 (m, 4H) |
| 1e-40 | 142.6-143.0 | δ8.44 (pseudo-d, J = 2.4, 1H), 7.66 (dd, J1 = 8.8, J2 = 2.4, 1H), 6.60 (d, J = 8.8, 1H), 5.80 (s, 1H), 5.20 (t, J = 4.6, 1H), 4.75-4.66 (m, 3H), 4.04 (d, J = 4.6, 2H), 3.89-3.79 (m, 4H), 2.22-2.16 (m, 4H), 1.87-1.80 (m, 4H) |
| 1e-41 | 151.4-151.9 | δ9.67 (br-s, 1H), 8.43 (pseudo-d, J = 2.4, 1H), 7.64 (dd, J1 = 8.9, J2 = 2.4, 1H), 7.08 (d, J = 5.7, 2H), 6.82-6.76 (m, 1H), 6.60 (d, J = 8.9, 1H), 5.88 (s, 1H), 5.08 (s, 1H), 4.66 (s, 2H), 2.27-2.22 (m, 2H), 2.18-2.13 (m, 2H), 1.96-1.89 (m, 2H), 1.86-1.79 (m, 2H) |

TABLE 65

| No. | Properties or Melting Points (° C.) | $^1$H-NMR data |
|---|---|---|
| 1e-42 | 118.3-119.2 | δ8.44 (pseudo-d, J = 2.4, 1H), 7.66 (dd, J1 = 8.8, J2 = 2.4, 1H), 7.30-7.22 (m, 2H), 6.75-6.69 (m, 1H), 6.60 (d, J = 8.8, 1H), 5.80 (s, 1H), 4.75 (t, J = 5.7, 1H), 4.74-7.66 (m, 3H), 4.00 (d, J = 5.7, 2H), 3.31 (s, 6H), 2.25-2.17 (m, 4H), 1.91-1.82 (m, 4H) |
| 1e-43 | 131.0-131.9 | δ8.45 (pseudo-d, J = 2.4, 1H), 7.67 (dd, J1 = 8.8, J2 = 2.4, 1H), 7.30-7.23 (m, 2H), 6.75-6.68 (m, 1H), 6.61 (d, J = 8.8, 1H), 5.82 (s, 1H), 5.24 (t, J = 4.7, 1H), 4.78-4.69 (m, 3H), 4.04 (d, J = 4.7, 2H), 3.92-3.81 (m, 4H), 2.25-2.17 (m, 4H), 1.91-1.82 (m, 4H) |
| 1f-3 | 102.3-102.9 | δ8.40 (pseudo-d, J = 2.4, 1H), 7.64 (dd, J1 = 9.0, J2 = 2.4, 1H), 6.62 (d, J = 9.0, 1H), 5.84 (s, 1H), 4.45 (s, 1H), 4.23 (pseudo-dd, J1 = 12.9, J2 = 3.5, 2H), 3.68 (s, 3H), 3.09 (pseudo-d, J = 12.9, 2H), 2.65 (br-s, 2H), 2.00-1.92 (m, 2H), 1.72-1.62 (m, 2H) |
| 1f-6 | Viscous liquid | δ8.41 (pseudo-d, J = 2.4, 1H), 7.64 (dd, J1 = 9.0, J2 = 2.4, 1H), 6.62 (d, J = 9.0, 1H), 5.81 (s, 1H), 4.45 (s, 1H), 4.23 (pseudo-dd, J1 = 12.8, J2 = 3.4, 2H), 3.97 (t, J = 7.2, 2H), 3.19 (pseudo-d, J = 12.8, 2H), 2.65 (br-s, 2H), 1.98-1.90 (m, 2H), 1.83-1.72 (m, 2H), 1.71-1.63 (m, 2H), 1.38-1.22 (m, 2H), 0.93 (t, J = 7.4, 3H) |
| 1f-37 | 199.5-200.3 | δ10.35 (br-s, 1H), 8.40 (pseudo-d, J = 2.4, 1H), 7.64 (dd, J1 = 9.0, J2 = 2.4, 1H), 6.62 (d, J = 9.0, 1H), 5.94 (s, 1H), 4.56 (br-s, 1H), 4.20 (dd, J1 = 12.7, J2 = 3.4, 2H), 3.10 (d, J = 12.7, 2H), 2.64 (br-s, 2H), 2.00-1.90 (m, 2H), 1.67-1.60 (m, 2H) |

TABLE 65-continued

| No. | Properties or Melting Points (° C.) | $^{1}$H-NMR data |
|---|---|---|
| 1f-38 | 91.9-92.5 | δ8.40 (pseudo-d, J = 2.4, 1H), 7.64 (dd, J1 = 9.2, J2 = 2.4, 1H), 6.62 (d, J = 9.2, 1H), 5.83 (s, 1H), 4.77 (t, J = 5.7, 1H), 4.46 (br-s, 1H), 4.23 (dd, J1 = 12.9, J2 = 3.4, 2H), 40.7 (d, J = 5.7, 2H), 3.36 (s, 6H), 3.09 (d, J = 12.9, 2H), 2.65 (br-s, 2H), 1.99-1.95 (m, 2H), 1.68-1.62 (m, 2H) |

TABLE 66

| No. | Properties or Melting Points (° C.) | $^{1}$H-NMR data |
|---|---|---|
| 1f-39 | Viscous liquid | δ8.40 (pseudo-d, J = 2.6, 1H), 7.64 (dd, J1 = 8.9, J2 = 2.6, 1H), 6.62 (d, J = 8.9, 1H), 5.85 (s, 1H), 5.27 (t, J = 4.5, 1H), 4.47 (br-s, 1H), 4.23 (dd, J1 = 12.8, J2 = 3.2, 2H), 4.12 (d, J = 4.5, 2H), 3.97-3.87 (m, 4H), 3.09 (d, J = 12.8, 2H), 2.66 (br-s, 2H), 2.03-1.90 (m, 2H), 1.69-1.62 (m, 2H) |
| 1f-40 | 141.9-142.2 | δ8.40 (pseudo-d, J = 1.6, 1H), 7.64 (dd, J1 = 9.0, J2 = 2.4), 7.30-7.26 (m, 2H), 6.76-6.70 (m, 1H), 6.62 (d, J = 9.0, 1H), 5.84 (s, 1H), 4.81 (t, J = 5.6, 1H), 4.50 (s, 1H), 4.22 (dd, J1 = 13.1, J2 = 3.4, 2H), 4.07 (d, J = 5.7, 2H), 3.38 (s, 6H), 3.11 (d, J = 12.5, 2H), 2.68 (br-s, 2H), 2.01-1.98 (m, 2H), 1.68-1.63 (m, 2H) |
| 1f-41 | 183.3-184.8 | δ9.60 (br-s, 1H), 8.40 (s, 1H), 7.62 (dd, J1 = 9.0, J2 = 2.5, 1H), 7.08 (dd, J1 = 8.0, J2 = 2.0, 2H), 5.84-6.78 (m, 1H), 6.61 (d, J1 = 9.0, 1H), 5.98 (s, 1H), 4.73 (s, 1H), 4.18 (dd, J1 = 12.8, J2 = 3.1, 2H), 3.13 (d, J = 12.4, 2H), 2.66 (s, 2H), 2.01-1.99 (m, 2H), 1.64-1.59 (m, 1H) |
| 1g-3 | 113.2-113.5 | δ8.42 (pseudo-d, J = 2.4, 1H), 7.65 (dd, J1 = 9.0, J2 = 2.4, 1H), 6.63 (d, J = 9.0, 1H), 5.86 (s, 1H), 4.51 (t, J = 5.0, 1H), 3.96 (pseudo-dd, J1 = 12.5, J2 = 2.6, 2H), 3.70 (s, 3H), 3.35 (pseudo-d, J = 11.6, 2H), 2.59 (br-s, 2H), 1.90-1.85 (m, 2H), 1.78-1.71 (m, 2H) |
| 1g-6 | Viscous liquid | δ8.42 (pseudo-d, J = 2.4, 1H), 7.65 (dd, J1 = 9.0, J2 = 2.4, 1H), 6.62 (d, J = 9.0, 1H), 5.84 (s, 1H), 4.52 (t, J = 5.0, 1H), 3.99 (t, J = 7.2, 2H), 3.95 (pseudo-dd, J1 = 12.4, J2 = 2.4, 2H), 3.34 (pseudo-d, J = 11.4, 2H), 2.60 (br-s, 2H), 1.92-1.85 (m, 2H), 1.80-1.69 (m, 4H), 1.30-1.18 (m, 2H), 0.81 (t, J = 7.4, 3H) |

Formulation Example 1

Emulsifiable Concentrate 10 parts of each compound of the invention was dissolved in 45 parts of Solvesso 150 and 35 parts of N-methylpyrrolidone. To the solution was added 10 parts of an emulsifier (trade name: Sorpol 3005×, manufactured by Toho Kagaku Co., Ltd.). These ingredients were mixed by stirring to produce a 10% emulsifiable concentrate.

Formulation Example 2

Wettable Powder 20 parts of each compound of the invention was added to a mixture of 2 parts of sodium lauryl sulfate, 4 parts of sodium lignosulfonate, 20 parts of synthetic hydrous silicon oxide fine powder, and 54 parts of clay. These ingredients were mixed by stirring with a mixer to produce a 20% wettable powder.

Formulation Example 3

Granule 2 parts of sodium dodecylbenzenesulfonate, 10 parts of bentonite, and 83 parts of clay were added to 5 parts of each compound of the invention. These ingredients were thoroughly mixed by stirring. After addition of an appropriate amount of water, the mixture was further stirred. The mixture was granulated with a granulator and air-dried to produce 5% granules.

Formulation Example 4

Dust 1 part of each compound of the invention was dissolved in a suitable amount of acetone. To the solution were added 5 parts of synthetic hydrous silicon oxide fine powder, 0.3 parts of PAP (acidic isopropyl phosphate), and 93.7 parts of clay. These ingredients were mixed by stirring with a juice mixer. Acetone was removed therefrom by evaporation to produce a 1% dusting powder.

Formulation Example 5

Flowable 20 parts of each compound of the invention and 1.5 parts of sorbitan trioleate were mixed with 28.5 parts of an aqueous solution containing 2 parts of polyvinyl alcohol. The mixture was pulverized with a sand grinder (to a particle size of 3 microns or less). Thereto was added 40 parts of an aqueous solution containing 0.05 parts of xanthane gum and 0.1 parts of aluminium magnesium silicate, followed by addition of 10 parts of propylene glycol. These ingredients were mixed by stirring to produce a 20% suspension in water.

The compounds of the invention were tested as shown in Test Examples below to demonstrate that the compounds are useful as an active ingredient of miticides. The compounds of the invention are indicated by Compound Nos. shown in Tables 1 to 24.

Test Example 1

Test on Two-Spotted Spider Mites

A plastic cup (trade name: KP-120, manufactured by Konoike Plastic Co., Ltd., Iwata) was filled with tap water, and covered with a lid having a notch cut therein. A piece of non-woven fabric (4.5×5.5 cm) having a slit of about 4 cm in length, the slit being made parallel to the longer side of the fabric at a distance of 1 cm from the edge, was placed on the lid. The about 4-cm long, 1-cm wide portion of the fabric was suspended inside the plastic cup through the notch. A kidney bean leaf (about 3.5×4.5 cm) was placed on the sufficiently soaked non-woven fabric. Two-spotted spider mites (about twenty mites) were released on the leaf, and the leaf was placed in a thermostatic chamber (25±2° C., 16L8D). The next day, a miticidal formulation containing a compound of the invention (500 ppm) was prepared by adding an aqueous solution of Sorpol 355 (manufactured by Toho Kagagu Co., Ltd.) (100 ppm) to an acetone solution containing the compound of the invention. 4 ml of the miticidal formulation was sprayed over the leaf with a spray gun ("PB-308 Piece Bon", Olympos, Osaka; 1 kgf/cm$^2$). The leaf was air-dried and then placed in a thermostatic chamber. The mortality of the two-spotted spider mites was determined two days after the spraying.

As a result, a mortality of at least 50% was achieved by using the following compounds of the invention: Compound Nos. 1a-2, 1a-14 to 1a-19, 1a-24, 1a-28, 1a-45, 1a-46, 1a-50 to 1a-53, 1a-62, 1a-69, 1a-70, 1a-75 to 1a-77, 1a-79, 1a-81, 1a-99 to 1a-101, 1a-103, 1a-106 to 1a-108, 1a-126, 1a-127, 1a-145, 1a-173, 1a-174, 1a-200 to 1a-208, 1a-210 to 1a-214, 1a-216, 1a-221, 1a-223 to 1a-236, 1a-238, 1a-240 to 1a-242, 1a-247 to 1a-258, 1a-261 to 1a-282, 1a-288, 1a-297 to 1a-306, 1b-2, 1b-4, 1b-31 to 1b-50, 1b-52, 1b-53, 1b-56 to 1b-61, 1d-6, 1d-41, 1d-42, 1f-3, 1f-6, and 1f-38 to 1f-40.

Among these, a mortality of 100% was achieved by using the following compounds of the invention: Compound Nos. 1a-2, 1a-14 to 1a-19, 1a-24, 1a-28, 1a-45, 1a-46, 1a-50 to 1a-53, 1a-62, 1a-69, 1a-70, 1a-75 to 1a-77, 1a-81, 1a-99, 1a-100, 1a-106, 1a-108, 1a-126, 1a-127, 1a-173, 1a-174, 1a-200 to 1a-208, 1a-210 to 1a-214, 1a-216, 1a-224 to 1a-236, 1a-240 to 1a-242, 1a-247, 1a-249, 1a-251 to 1a-258, 1a-261 to 1a-282, 1a-297 to 1a-306, 1b-2, 1b-4, 1b-31 to 1b-41, 1b-43 to 1b-47, 1b-49, 1b-57, 1b-59 to 1b-61, 1d-6, 1d-41, 1d-42, 1f-3, 1f-6, and 1f-38 to 1f-40.

Test Example 2

Ovicidal Test on Two-Spotted Spider Mites

A plastic cup (trade name: KP-120, manufactured by Konoike Plastic Co., Ltd., Iwata) was filled with tap water, and covered with a lid having a notch cut therein. A piece of non-woven fabric (4.5×5.5 cm) having a slit of about 4 cm in length, the slit being made parallel to the longer side of the fabric at a distance of 1 cm from the edge, was placed on the lid. The about 4-cm long, 1-cm wide portion of the fabric was suspended inside the plastic cup through the notch. A kidney bean leaf (about 3.5×4.5 cm) was placed on the sufficiently soaked non-woven fabric. Female adult two-spotted spider mites (about 5 mites) were released on the leaf, and the leaf was placed in a thermostatic chamber (25±2° C., 16L8D). The next day, the female mites were removed, and 4 ml of a miticidal formulation containing a test compound (500 ppm), which was prepared according to Test Example 1, was sprayed over the leaf using a spray gun (PB-308 Piece Bon, Olympos, Osaka; 1 kgf/cm$^2$). The leaf was air-dried, and then placed in a thermostatic chamber. The ovicidal rate of the two-spotted spider mites was determined six days after the spraying.

As a result, an ovicidal rate of at least 50% was achieved by using the following compounds of the invention: Compounds Nos. 1a-2, 1a-14 to 1a-19, 1a-24, 1a-26, 1a-28, 1a-45, 1a-46, 1a-50, 1a-51, 1a-53, 1a-60, 1a-62, 1a-69, 1a-70, 1a-75 to 1a-77, 1a-81, 1a-99, 1a-100, 1a-106, 1a-108, 1a-126, 1a-127, 1a-173, 1a-174, 1a-200 to 1a-208, 1a-210 to 1a-214, 1a-216, 1a-221, 1a-223 to 1a-236, 1a-240, 1a-242, 1a-247 to 1a-258, 1a-261 to 1a-281, 1a-297 to 1a-306, 1b-4, 1b-31 to 1b-49, 1b-57 to 1b-61, 1d-6, 1d-41, 1d-42, 1f-3, 1f-6 and 1f-38 to 1f-40.

Among these, an ovicidal rate of 100% was achieved by using the following compounds of the invention: Compound Nos. 1a-15 to 1a-19, 1a-24, 1a-28, 1a-45, 1a-46, 1a-50, 1a-51, 1a-53, 1a-62, 1a-69, 1a-70, 1a-75 to 1a-77, 1a-99, 1a-100, 1a-106, 1a-108, 1a-127, 1a-173, 1a-174, 1a-200 to 1a-208, 1a-210 to 1a-214, 1a-216, 1a-224 to 1a-234, 1a-236, 1a-240, 1a-242, 1a-247, 1a-249, 1a-251 to 1a-254, 1a-256 to 1a-258, 1a-261 to 1a-277, 1a-297 to 1a-306, 1b-4, 1b-31 to 1b-41, 1b-43 to 1b-47, 1b-49, 1b-57, 1b-59 to 1b-61, 1d-6, 1d-41, 1f-3, 1f-6, and 1f-38 to 1f-40.

Test Example 3

Test on Citrus Red Mites

A plastic cup (trade name: KP-120, manufactured by Konoike Plastic Co., Ltd., Iwata) was filled with tap water, and covered with a lid having a notch cut therein. A piece of non-woven fabric (4.5×5.5 cm) having a slit of about 4 cm in length, the slit being made parallel to the longer side of the fabric at a distance of 1 cm from the edge, was placed on the lid. The about 4-cm long, 1-cm wide portion of the fabric was suspended inside the plastic cup through the notch. A *Citrus aurantium* leaf (3 cm×3 cm) was placed with the front side up on the sufficiently soaked non-woven fabric. To prevent drying and escape of mites, the leaf was covered with a filter paper (diameter: 5 cm, No. 2, Advantec Toyo Kaisha, Ltd.) having a hole of 2.4 cm in diameter, and surrounded by a tangle (Fujitangle). Thereafter, 10 female adult citrus red mites were released on the *Citrus aurantium* leaf on the cup. The next day, a miticidal formulation containing a compound of the invention (100 ppm) was prepared by adding an aqueous solution of Sorpol 355 (manufactured by Toho Kagagu Co., Ltd.) to an acetone solution containing the compound of the invention. 4 ml of the miticidal formulation was sprayed over the leaf with a spray gun ("PB-308 Piece Bon", Olympos, Osaka; 1 kgf/cm$^2$). The leaf was air-dried, and then placed in a thermostatic chamber (25±2° C., 16L8D). The mortality of the female adult citrus red mites was determined two days after the spraying.

In this Text Example, the following compounds of the invention were used as test compounds: Compound Nos. 1a-15 to 1a-19, 1a-28, 1a-45, 1a-51, 1a-62, 1a-70, 1a-75, 1a-76, 1a-99, 1a-100, 1a-106, 1a-108, 1a-127, 1a-173, 1a-174, 1a-200, 1a-201, 1a-203, 1a-206 to 208, 1a-213, 1a-224, 1a-226, 1a-228, 1a-266, 1a-267, 1a-297, 1a-298, 1a-301, and 1f-6. As a result, a mortality of 100% was achieved by all the test compounds of the invention.

Test Example 4

Test on Kanzawa Spider Mites

A plastic cup (trade name: KP-120, manufactured by Konoike Plastic Co., Ltd., Iwata) was filled with tap water, and covered with a lid having a notch cut therein. A piece of non-woven fabric (4.5×5.5 cm) having a slit of about 4 cm in length, the slit being made parallel to the longer side of the fabric at a distance of 1 cm from the edge, was placed on the lid. The 4-cm long, 1-cm wide portion of the fabric was suspended inside the plastic cup through the notch. A kidney bean leaf (3.5 cm×4.5 cm) was placed with the rear side up on the sufficiently soaked non-woven fabric. Thereafter, 20 female adult Kanzawa spider mites were released on the kidney bean leaf on the cup. The next day, 4 ml of a miticidal formulation containing a test compound (100 ppm), which was prepared according to Test Example 1, was sprayed over the leaf with a spray gun (PB-308 Piece Bon, Olympos, Osaka; 1 kgf/cre). The leaf was air-dried, and then placed in a thermostatic chamber (25±2° C., 16L8D). The mortality of the female adult Kanzawa spider mites was determined two days after the spraying.

In this Text Example, the following compounds of the invention were used as test compounds: Compound Nos. 1a-17, 1a-70, 1a-76, 1a-108, 1a-200, 1a-201, 1a-206 to 1a-208, 1a-210, 1a-224 to 1a-227, 1a-229, 1a-266, 1a-267, 1a-297, 1a-298 and 1a-301. As a result, a mortality of 100% was achieved by all the test compounds of the invention, except for Compound No. 1a-210 (mortality: 91%).

Comparative Test 1

Test on Citrus Rust Mites

A plastic cup (trade name: KP-120, manufactured by Konoike Plastic Co., Ltd., Iwata) was filled with tap water, and covered with a lid having a notch cut therein. A piece (4.5×5.5 cm) of non-woven fabric having a slit of about 4 cm in length, the slit being made parallel to the longer side of the fabric at a distance of 1 cm from the edge, was placed on the lid. The 4-cm long, 1-cm wide portion of the fabric was suspended inside the plastic cup through the notch. A *Citrus aurantium* leaf (3 cm×3 cm) was placed with the front side up on the sufficiently soaked non-woven fabric. To prevent drying and escape of mites, the leaf was covered with a filter paper (diameter: 5 cm, No. 2, Advantec Toyo Kaisha, Ltd.) having two holes of 10 mm in diameter. A leaf on which the citrus rust mites were bred was cut out into pieces with a cork borer (diameter: 2 mm), and the leaf pieces were placed with the front side up on the *Citrus aurantium* leaf on the non-woven fabric. The next day, the dry leaf pieces were removed. The movement of the rust mites was checked, and the mites that exhibited only slight movement to the *Citrus aurantium* leaf were eliminated. Subsequently, 4 ml of a miticidal formulation containing a test compound (100 ppm or 200 ppm), which was prepared according to Test Example 1, was sprayed over the leaf with a spray gun (PB-308 Piece Bon, Olympos, Osaka; 1 kgf/$cm^2$). The leaf was air-dried, and then placed in a thermostatic chamber (25±2° C., 16L8D). The mortality of the citrus rust mites was determined two days after the spraying.

In this Test Example, the following compounds of the invention were used as test compounds: Compound Nos. a-19, 1a-26, 1a-86, 1a-126, and 1e-3. For comparison, Compound 1-92 (Compound A), Compound 2-82 (Compound B), and Compound 5-97 (Compound C) described in WO 2005/095380 (Patent Document 1) were used.

TABLE 67

| Test Compound | | Insect mortality (%) 100 ppm | 200 ppm |
|---|---|---|---|
| Compounds of the Invention | 1a-19 | 100 | 94 |
| | 1a-26 | 100 | 67 |
| | 1a-86 | 100 | 80 |
| | 1a-126 | 100 | 88 |
| | 1e-3 | 95 | 75 |
| Comparative compounds | Compound A | 7 | 0 |
| | Compound B | 68 | 0 |
| | Compound C | 54 | 0 |

Compound A

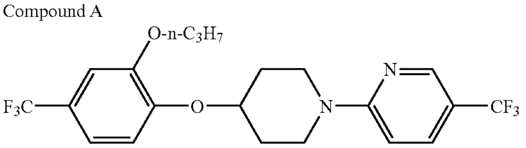

Compound B

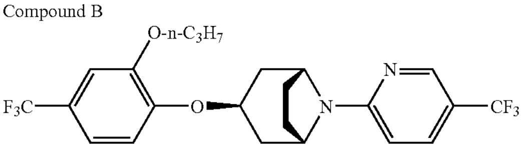

Compound C

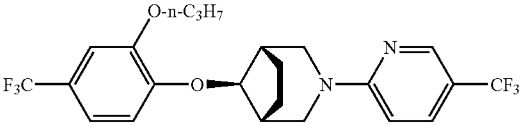

The invention claimed is:

1. An N-pyridylpiperidine compound, an N-oxide thereof, or a salt of either of the foregoing, the N-pyridylpiperidine compound being represented by Formula (1)

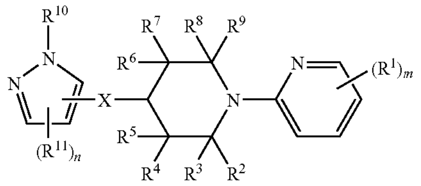

(1)

wherein $R^1$ is a halogen atom, a $C_{1-4}$ haloalkyl group, a cyano group, a nitro group, or a $C_{1-4}$ alkoxycarbonyl group;

$R^2$, $R^3$, $R^4$, $R^5$, $R^6$, $R^7$, $R^8$, and $R^9$ are each independently a hydrogen atom or a $C_{1-4}$ alkyl group;

each pair of $R^2$ and $R^8$, and $R^4$ and $R^6$ may join to form a $C_{1-4}$ alkylene group;

$R^{10}$ is a hydrogen atom; a $C_{1-20}$ alkyl group; a $C_{3-8}$ cycloalkyl group; a $C_{2-6}$ alkenyl group; a $C_{2-6}$ alkynyl group; a $C_{1-6}$ haloalkyl group; a $C_{2-6}$ haloalkenyl group; a $C_{1-6}$ alkylcarbonyl group; a $C_{1-6}$ alkoxycarbonyl group; a benzoyl group (optionally substituted on the phenyl group with one to five halogen atoms); a phenyl group (optionally substituted on the phenyl ring with one or more substituents each independently selected from the group consisting of halogen, $C_{1-4}$ alkyl, and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of optionally halogen-substituted $C_{3-8}$ cycloalkyl, cyano, nitro, formyl, $C_{1-6}$ alkoxy, $C_{1-4}$ haloalkoxy, benzyloxy, phenoxy, —CON($R^{12}$)($R^{13}$) (in which $R^{12}$ and $R^{13}$ are each independently a $C_{1-4}$ alkyl group or $R^{12}$ and $R^{13}$ may join to form a $C_{2-7}$ alkylene group), phenyl (optionally substituted on the phenyl ring with one or more halogen atoms), and a heterocyclic group (optionally substituted on the heterocyclic ring with one or more $C_{1-4}$ alkyl groups);

$R^{11}$ is a halogen atom, a $C_{1-6}$ alkyl group, a $C_{1-4}$ haloalkyl group, a $C_{1-4}$ hydroxyalkyl group, a $C_{1-4}$ alkoxycarbonyl group, a $C_{1-4}$ alkylcarbonyl group, a mono or di($C_{1-4}$ alkyl)aminocarbonyl group, a nitro group, a cyano group, a formyl group, —C($R^{14}$)═NO($R^{15}$) (in which $R^{14}$ is a hydrogen atom or a $C_{1-4}$ alkyl group, and $R^{15}$ is a hydrogen atom, a $C_{1-4}$ alkyl group, or a benzyl group), a phenyl group (optionally substituted on the phenyl ring with one or more substituents each independently selected from the group consisting of halogen, $C_{1-6}$ alkyl, $C_{1-4}$ haloalkyl, $C_{1-6}$ alkoxy, $C_{1-4}$ haloalkoxy, $C_{1-4}$ alkylthio, cyano, and nitro), or a heterocyclic group (optionally substituted on the heterocyclic ring with one or more substituents each independently selected from the group consisting of halogen, $C_{1-4}$ alkyl, and $C_{1-4}$ haloalkyl);

X is an oxygen atom, a sulfur atom, or —$SO_2$—;

m is an integer of 1 to 4, and when m is an integer of 2 or more, the $R^1$'s may be the same or different; and n is an integer of 1 or 2, and when n is 2, the two $R^{11}$'s may be the same or different.

2. An N-pyridylpiperidine compound, an N-oxide thereof, or a salt of either of the foregoing according to claim 1, wherein the N-pyridylpiperidine compound is represented by Formula (1) in which $R^1$ is a halogen atom, a $C_{1-4}$ haloalkyl group, a cyano group, or a nitro group.

3. An N-pyridylpiperidine compound, an N-oxide thereof, or a salt of either of the foregoing according to claim 2, wherein the N-pyridylpiperidine compound is represented by Formula (1) in which $R^{10}$ is a hydrogen atom; a $C_{1-20}$ alkyl group; a $C_{2-6}$ alkenyl group; a $C_{1-6}$ haloalkyl group; a $C_{1-6}$ alkylcarbonyl group; a $C_{1-6}$ alkoxycarbonyl group; a benzoyl group (optionally substituted on the phenyl group with one to five halogen atoms); a phenyl group (optionally substituted on the phenyl ring with one or more substituents each independently selected from the group consisting of halogen and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of formyl, $C_{1-6}$ alkoxy, phenyl group (optionally substituted on the phenyl ring with one or more halogen atoms), and a heterocyclic group (optionally substituted on the heterocyclic ring with one or more $C_{1-4}$ alkyl groups).

4. An N-pyridylpiperidine compound, an N-oxide thereof, or a salt of either of the foregoing according to claim 1, wherein the N-pyridylpiperidine compound is represented by Formula (1) in which $R^{11}$ is a halogen atom, a $C_{1-6}$ alkyl group, a $C_{1-4}$ haloalkyl group, a $C_{1-4}$ hydroxyalkyl group, a $C_{1-4}$ alkoxycarbonyl group, a formyl group, —C($R^{14}$)═NO($R^{15}$) (in which $R^{14}$ is a hydrogen atom, and $R^{15}$ is a hydrogen atom or a $C_{1-4}$ alkyl group), a phenyl group (optionally substituted on the phenyl ring with one or more substituents each independently selected from the group consisting of halogen, $C_{1-6}$ alkyl, $C_{1-4}$ haloalkyl, $C_{1-6}$ alkoxy, $C_{1-4}$ haloalkoxy, $C_{1-4}$ alkylthio, cyano, and nitro) or a heterocyclic group (optionally substituted on the heterocyclic ring with one or more halogen atoms).

5. An N-pyridylpiperidine compound, an N-oxide thereof, or a salt of either of the foregoing according to claim 1, wherein N-pyridylpiperidine compound is represented by Formula (1) in which X is an oxygen atom.

6. A method of producing an N-pyridylpiperidine compound, an N-oxide thereof, or a salt of either of the foregoing, the N-pyridylpiperidine compound being represented by Formula (1)

(1)

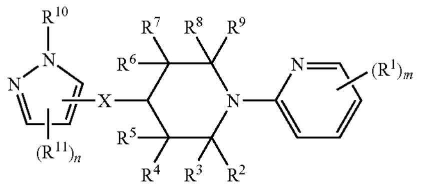

wherein $R^1$ is a halogen atom, a $C_{1-4}$ haloalkyl group, a cyano group, a nitro group, or a $C_{1-4}$ alkoxycarbonyl group;

$R^2$, $R^3$, $R^4$, $R^5$, $R^6$, $R^7$, $R^8$, and $R^9$ are each independently a hydrogen atom or a $C_{1-4}$ alkyl group;

each pair of $R^2$ and $R^5$, and $R^4$ and $R^6$ may join to form a $C_{1-4}$ alkylene group;

$R^{10}$ is a hydrogen atom; a $C_{1-20}$ alkyl group; a $C_{3-8}$ cycloalkyl group; a $C_{2-6}$ alkenyl group; a $C_{2-6}$ alkynyl group; a $C_{1-6}$ haloalkyl group; a $C_{2-6}$ haloalkenyl group; a $C_{1-6}$ alkylcarbonyl group; a $C_{1-6}$ alkoxycarbonyl group; a benzoyl group (optionally substituted on the phenyl group with one to five halogen atoms); a phenyl group (optionally substituted on the phenyl ring with one or more substituents each independently selected from the group consisting of halogen, $C_{1-4}$ alkyl, and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of optionally halogen-substituted $C_{3-8}$ cycloalkyl, cyano, nitro, formyl, $C_{1-6}$ alkoxy, $C_{1-4}$ haloalkoxy, benzyloxy, phenoxy, —CON($R^{12}$)($R^{13}$) (in which $R^{12}$ and $R^{13}$ are each independently a $C_{1-4}$ alkyl group, or $R^{12}$ and $R^{13}$ may join to form a $C_{2-7}$ alkylene group), phenyl (optionally substituted on the phenyl ring with one or more halogen atoms), and a heterocyclic group (optionally substituted on the heterocyclic ring with one or more $C_{1-4}$ alkyl groups);

$R^{11}$ is a halogen atom, a $C_{1-6}$ alkyl group, a $C_{1-4}$ haloalkyl group, a $C_{1-4}$ hydroxyalkyl group, a $C_{1-4}$ alkoxycarbonyl group, a $C_{1-4}$ alkylcarbonyl group, a mono or di($C_{1-4}$ alkyl)aminocarbonyl group, a nitro group, a cyano group, a formyl group, —$C(R^{14})$=$NO(R^{15})$ (in which $R^{14}$ is a hydrogen atom or a $C_{1-4}$ alkyl group, and $R^{15}$ is a hydrogen atom, a $C_{1-4}$ alkyl group, or a benzyl group), a phenyl group (optionally substituted on the phenyl ring with one or more substituents each independently selected from the group consisting of halogen, $C_{1-6}$ alkyl, $C_{1-4}$ haloalkyl, $C_{1-4}$ alkoxy, $C_{1-4}$ haloalkoxy, $C_{1-4}$ alkylthio, cyano, and nitro), or a heterocyclic group (optionally substituted on the heterocyclic ring with one or more substituents selected from the group consisting of halogen, $C_{1-4}$ alkyl, and $C_{1-4}$ haloalkyl);

X is an oxygen atom, a sulfur atom, or —$SO_2$—;

m is an integer of 1 to 4, and when m is two or more, the m $R^1$'s may be the same or different;

n is an integer of 1 or 2, and when n is 2, the two $R^{11}$'s may be the same or different;

the method comprising reacting a pyrazole compound represented by Formula (2)

(2)

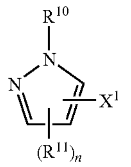

wherein $R^{10}$, $R^{11}$, and n are as defined above, $X^1$ is a halogen atom, a methanesulfonyloxy group, a trifluoromethanesulfonyloxy group, a p-toluenesulfonyloxy group, a methylthio group, a methanesulfonyl group, a hydroxy group, or a mercapto group with a piperidine compound represented by Formula (3)

(3)

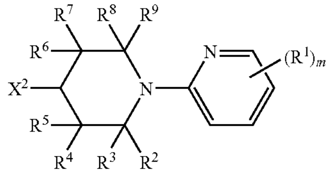

wherein $R^1$, $R^2$, $R^3$, $R^4$, $R^5$, $R^6$, $R^7$, $R^8$, $R^9$, and m are as defined above, and $X^2$ is a hydroxy group or a mercapto group.

7. A method of producing an N-pyridylpiperidine compound, an N-oxide thereof, or a salt of either of the foregoing, the N-pyridylpiperidine compound being represented by Formula (1)

(1)

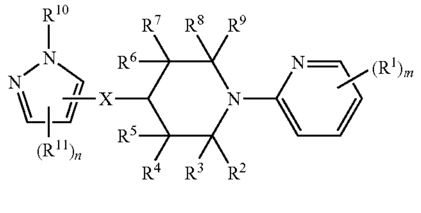

wherein $R^1$ is a halogen atom, a $C_{1-4}$ haloalkyl group, a cyano group, a nitro group, or a $C_{1-4}$ alkoxycarbonyl group;

$R^2$, $R^3$, $R^4$, $R^5$, $R^6$, $R^1$, $R^8$, and $R^9$ are each independently a hydrogen atom or a $C_{1-4}$ alkyl group;

each pair of $R^2$ and $R^8$, and $R^4$ and $R^6$ may join to form a $C_{1-4}$ alkylene group;

$R^{10}$ is a hydrogen atom; a $C_{1-20}$ alkyl group; a $C_{3-8}$ cycloalkyl group; a $C_{2-6}$ alkenyl group; a $C_{2-6}$ alkynyl group; a $C_{1-6}$ haloalkyl group; a $C_{2-6}$ haloalkenyl group; a $C_{1-6}$ alkylcarbonyl group; a $C_{1-6}$ alkoxycarbonyl group; a benzoyl group (optionally substituted on the phenyl group with one to five halogen atoms), a phenyl group (optionally substituted on the phenyl ring with one or more substituents each independently selected from the group consisting of halogen, $C_{1-4}$ alkyl, and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of halogen-substituted $C_{3-8}$ cycloalkyl, cyano, nitro, formyl, $C_{1-6}$ alkoxy, $C_{1-4}$ haloalkoxy, benzyloxy, phenoxy, —$CON(R^{12})(R^{13})$ (in which $R^{12}$ and $R^{13}$ are each independently a $C_{1-4}$ alkyl group, or $R^{12}$ and $R^{13}$ may join to form a $C_{2-7}$ alkylene group), phenyl (optionally substituted on the phenyl ring with one or more halogen atoms), and a heterocyclic group (optionally substituted on the heterocyclic ring with one or more $C_{1-4}$ alkyl groups);

$R^{11}$ is a halogen atom, a $C_{1-6}$ alkyl group, a $C_{1-4}$ haloalkyl group, a $C_{1-4}$ hydroxyalkyl group, a $C_{1-4}$ alkoxycarbonyl group, a $C_{1-4}$ alkylcarbonyl group, a mono or di($C_{1-4}$ alkyl)aminocarbonyl group, a nitro group, a cyano group, a formyl group, —$C(R^{14})$=$NO(R^{15})$ (in which $R^{14}$ is a hydrogen atom or a $C_{1-4}$ alkyl group, and $R^{15}$ is a hydrogen atom, a $C_{1-4}$ alkyl group, or a benzyl group), a phenyl group (optionally substituted on the phenyl ring with one or more substituents each independently selected from the group consisting of halogen, $C_{1-6}$ alkyl, $C_{1-4}$ haloalkyl, $C_{1-6}$ alkoxy, $C_{1-4}$ haloalkoxy, $C_{1-4}$ alkylthio, cyano, and nitro), or a heterocyclic group (optionally substituted on the heterocyclic ring with one or more substituents each independently selected from the group consisting of halogen, $C_{1-4}$ alkyl, and $C_{1-4}$ haloalkyl);

X is an oxygen atom, a sulfur atom, or —$SO_2$—; and m is an integer of 1 to 4, and when m is an integer of 2 or more, the m $R^1$s may be the same or different;

n is an integer of 1 or 2, and when n is 2, the two $R^{11}$s may be the same or different;

the method comprising reacting a pyrazole compound represented by Formula (4)

(4)

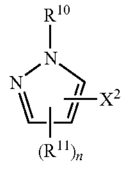

wherein $R^{10}$, $R^{11}$, and n are as defined above, and $X^2$ is a hydroxy group or a mercapto group with a piperidine compound represented by Formula (5)

(5)

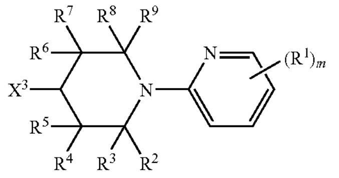

wherein $R^1$, $R^2$, $R^3$, $R^4$, $R^5$, $R^6$, $R^7$, $R^8$, $R^9$, and m are as defined above, and $X^3$ is a halogen atom, a methanesulfonyloxy group, a trifluoromethanesulfonyloxy group, a p-toluenesulfonyloxy group, a methylthio group, or a methanesulfonyl group.

8. A method of producing an N-pyridylpiperidine compound, an N-oxide thereof, or a salt of either of the foregoing, the N-pyridylpiperidine compound being represented by Formula (1)

(1)

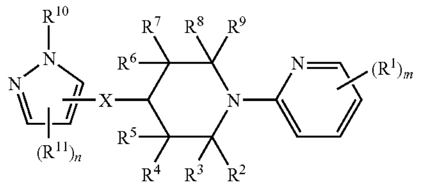

wherein $R^1$ is a halogen atom, a C haloalkyl group, a cyano group, a nitro group, or a $C_{1-4}$ alkoxycarbonyl group;

$R^2$, $R^3$, $R^4$, $R^5$, $R^6$, $R^7$, $R^8$, and $R^9$ are each independently a hydrogen atom or a $C_{1-4}$ alkyl group;

each pair of $R^2$ and $R^8$, and $R^4$ and $R^6$ may join to form a $C_{1-4}$ alkylene group;

$R^{10}$ is a hydrogen atom; a $C_{1-20}$ alkyl group; a $C_{3-8}$, cycloalkyl group; a $C_{2-6}$ alkenyl group; a $C_{2-6}$ alkynyl group; a $C_{1-6}$ haloalkyl group; a $C_{2-6}$ haloalkenyl group; a $C_{1-6}$ alkylcarbonyl group; a $C_{1-6}$ alkoxycarbonyl group; a benzoyl group (optionally substituted on the phenyl group with one to five halogen atoms), a phenyl group (optionally each independently substituted on the phenyl ring with one or more substituents selected from the group consisting of halogen atom, $C_{1-4}$ alkyl, and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of optionally halogen-substituted $C_{3-8}$ cycloalkyl, cyano, nitro, formyl, $C_{1-6}$ alkoxy, $C_{1-4}$ haloalkoxy, benzyloxy, phenoxy, —CON($R^{12}$)($R^{13}$) (in which $R^{12}$ and $R^{13}$ are each independently a $C_{1-4}$ alkyl group, or $R^{12}$ and $R^{13}$ may join to form a $C_{2-7}$ alkylene group), phenyl (optionally substituted on the phenyl ring with one or more halogen atoms), and a heterocyclic group (optionally substituted on the heterocyclic ring with one or more $C_{1-4}$ alkyl groups);

$R^{11}$ is a halogen atom, a $C_{1-6}$ alkyl group, a $C_{1-4}$ haloalkyl group, a $C_{1-4}$ hydroxyalkyl group, a $C_{1-4}$ alkoxycarbonyl group, a $C_{1-4}$ alkylcarbonyl group, a mono or di($C_{1-4}$ alkyl)aminocarbonyl group, a nitro group, a cyano group, a formyl group, —C($R^{14}$)═NO($R^{15}$) (in which $R^{14}$ is hydrogen or $C_{1-4}$ alkyl, and $R^{15}$ is hydrogen, $C_{1-4}$ alkyl, or benzyl), a phenyl group (optionally substituted on the phenyl ring with one or more substituents each independently selected from the group consisting of halogen, $C_{1-6}$ alkyl, $C_{1-4}$ haloalkyl, $C_{1-6}$ alkoxy, $C_{1-4}$ haloalkoxy, $C_{1-4}$ alkylthio, cyano, and nitro), or a heterocyclic group (optionally substituted on the heterocyclic ring with one or more substituents each independently selected from the group consisting of halogen, $C_{1-4}$ alkyl, and $C_{1-4}$ haloalkyl);

X is an oxygen atom, a sulfur atom, or —$SO_2$—;

m is an integer of 1 to 4, and when in is an integer of 2 or more, the in $R^1$'s may be the same or different;

n is an integer of 1 or 2, and when n is 2, the two $R^{11}$'s may be the same or different;

the method comprising reacting a piperidine compound represented by Formula (6)

(6)

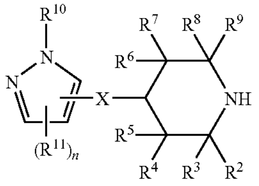

wherein $R^2$, $R^3$, $R^4$, $R^5$, $R^6$, $R^7$, $R^8$, $R^9$, $R^{10}$, $R^{11}$, X, and n are as defined above with a pyridine compound represented by Formula (7)

(7)

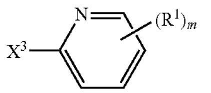

wherein $R^1$ and m are as defined above, and $X^3$ is a halogen atom, a methanesulfonyloxy group, a trifluoromethanesulfonyloxy group, a p-toluenesulfonyloxy group, a methylthio group, or a methanesulfonyl group.

9. An agricultural pest control agent comprising as an active ingredient the N-pyridylpiperidine compound, N-oxide thereof, or a salt of either of the foregoing of claim 1.

10. An agricultural pest control agent according to claim 9, which is a miticide.

11. An N-pyridylpiperidine compound, an N-oxide thereof, or a salt of either of the foregoing according to claim 1, wherein the N-pyridylpiperidine compound is represented by Formula (1) in which $R^{10}$ is a hydrogen atom; a $C_{1-20}$ alkyl group; a $C_{2-6}$ alkenyl group; a $C_{1-6}$ haloalkyl group; a $C_{1-6}$ alkylcarbonyl group; a $C_{1-6}$ alkoxycarbonyl group; a benzoyl group (optionally substituted on the phenyl group with one to five halogen atoms); a phenyl group (optionally substituted on the phenyl ring with one or more substituents each independently selected from the group consisting of halogen and $C_{1-4}$ haloalkyl); a heterocyclic group (optionally substituted on the heterocyclic ring with one or more substituents each independently selected from the group consisting of halogen, $C_{1-4}$ alkyl, $C_{1-4}$ haloalkyl, and optionally substituted heterocyclic groups); or a $C_{1-4}$ alkyl group substituted with one or more substituents each independently selected from the group consisting of formyl, $C_{1-6}$ alkoxy, phenyl group (optionally substituted on the phenyl ring with one or more halogen atoms), and a heterocyclic group (optionally substituted on the heterocyclic ring with one or more $C_{1-4}$ alkyl groups).

12. An agricultural pest control agent comprising as an active ingredient the N-pyridylpiperidine compound, N-oxide thereof, or a salt of either of the foregoing of claim 11.

13. An agricultural pest control agent according to claim 12, which is a miticide.

14. An agricultural pest control agent comprising as an active ingredient the N-pyridylpiperidine compound, N-oxide thereof, or a salt of either of the foregoing of claim 2.

15. An agricultural pest control agent according to claim 14, which is a miticide.

16. An agricultural pest control agent comprising as an active ingredient the N-pyridylpiperidine compound, N-oxide thereof, or a salt of either of the foregoing of claim 3.

17. An agricultural pest control agent according to claim 16, which is a miticide.

18. An agricultural pest control agent comprising as an active ingredient the N-pyridylpiperidine compound, N-oxide thereof, or a salt of either of the foregoing of claim 4.

19. An agricultural pest control agent according to claim 18, which is a miticide.

20. An agricultural pest control agent comprising as an active ingredient the N-pyridylpiperidine compound, N-oxide thereof, or a salt of either of the foregoing of claim 5.

21. An agricultural pest control agent according to claim 20, which is a miticide.

* * * * *